(12) United States Patent
Yin et al.

(10) Patent No.: US 9,834,439 B2
(45) Date of Patent: Dec. 5, 2017

(54) BIOMOLECULAR SELF-ASSEMBLY

(75) Inventors: Peng Yin, Brookline, MA (US); Niles A. Pierce, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 13/186,228

(22) Filed: Jul. 19, 2011

(65) Prior Publication Data

US 2012/0022243 A1    Jan. 26, 2012

Related U.S. Application Data

(60) Provisional application No. 61/366,091, filed on Jul. 20, 2010.

(51) Int. Cl.
*C07H 21/02* (2006.01)
*B82Y 15/00* (2011.01)

(52) U.S. Cl.
CPC .................................. *B82Y 15/00* (2013.01)

(58) Field of Classification Search
None
See application file for complete search history.

(56) References Cited

U.S. PATENT DOCUMENTS

| | | | |
|---|---|---|---|
| 4,714,680 A | 12/1987 | Civin | |
| 4,897,355 A | 1/1990 | Eppstein et al. | |
| 4,965,204 A | 10/1990 | Civin | |
| 5,057,410 A | 10/1991 | Kawasaki et al. | |
| 5,061,620 A | 10/1991 | Tsukamoto et al. | |
| 5,118,801 A | 6/1992 | Lizardi et al. | |
| 5,270,163 A | 12/1993 | Gold et al. | |
| 5,312,728 A | 5/1994 | Lizardi et al. | |
| 5,424,413 A | 6/1995 | Hogan et al. | |
| 5,459,127 A | 10/1995 | Felgner et al. | |
| 5,563,256 A | 10/1996 | Chakraborty et al. | |
| 5,579,793 A | 12/1996 | Gajewski et al. | |
| 5,643,741 A | 7/1997 | Tsukamoto et al. | |
| 5,677,136 A | 10/1997 | Simmons et al. | |
| 5,691,145 A | 11/1997 | Pitner et al. | |
| 5,716,827 A | 2/1998 | Tsukamoto et al. | |
| 5,750,397 A | 5/1998 | Tsukamoto et al. | |
| 5,928,913 A | 7/1999 | Efstathiou et al. | |
| 5,989,823 A | 11/1999 | Jayasena et al. | |
| 6,128,587 A | 10/2000 | Sjolander | |
| 6,130,047 A | 10/2000 | Nadeau et al. | |
| 6,242,246 B1 | 6/2001 | Gold et al. | |

(Continued)

FOREIGN PATENT DOCUMENTS

| | | |
|---|---|---|
| EP | 0 273 085 | 7/1988 |
| EP | 1 479 766 | 11/2004 |

(Continued)

OTHER PUBLICATIONS

Leontis. Chemistry Faculty Publications. 1995. Paper 33.*

(Continued)

*Primary Examiner* — Joseph G Dauner
(74) *Attorney, Agent, or Firm* — Knobbe, Martens, Olson & Bear, LLP

(57) ABSTRACT

The present invention relates generally to programming of biomolecular self-assembly pathways and related methods and constructs for self-assembly of prescribed two and three-dimensional structures.

12 Claims, 97 Drawing Sheets
(87 of 97 Drawing Sheet(s) Filed in Color)

(56) References Cited

U.S. PATENT DOCUMENTS

| | | | |
|---|---|---|---|
| 6,255,469 | B1 | 7/2001 | Seeman et al. |
| 6,261,783 | B1 | 7/2001 | Jayasena et al. |
| 6,264,825 | B1 | 7/2001 | Blackburn et al. |
| 6,361,944 | B1 | 3/2002 | Mirkin et al. |
| 6,361,945 | B1 | 3/2002 | Becker et al. |
| 6,485,965 | B1 | 11/2002 | Klatzmann et al. |
| 6,506,559 | B1 | 1/2003 | Fire et al. |
| 6,555,367 | B1 | 4/2003 | Spence et al. |
| 6,696,285 | B1 | 2/2004 | Mills, Jr. |
| 6,899,871 | B2 | 5/2005 | Kasahara et al. |
| 7,033,834 | B2 | 4/2006 | Valerio et al. |
| 7,632,641 | B2 | 12/2009 | Dirks et al. |
| 7,727,721 | B2 | 6/2010 | Pierce et al. |
| 7,960,357 | B2 | 6/2011 | Dirks et al. |
| 8,105,778 | B2 | 1/2012 | Dirks et al. |
| 8,124,751 | B2* | 2/2012 | Pierce et al. ............... 536/24.3 |
| 8,241,854 | B2 | 8/2012 | Yin et al. |
| 8,318,921 | B2 | 11/2012 | Pierce et al. |
| 8,478,543 | B2 | 7/2013 | Pierce |
| 8,497,364 | B2 | 7/2013 | Pierce et al. |
| 8,507,204 | B2 | 8/2013 | Pierce et al. |
| 8,658,780 | B2 | 2/2014 | Pierce et al. |
| 8,877,438 | B2 | 11/2014 | Yin |
| 8,962,241 | B2 | 2/2015 | Yin et al. |
| 8,962,582 | B2 | 2/2015 | Dirks et al. |
| 9,217,151 | B2 | 12/2015 | Yin et al. |
| 2001/0014445 | A1 | 8/2001 | Urnovitz |
| 2002/0051769 | A1 | 5/2002 | Zhang |
| 2002/0172950 | A1 | 11/2002 | Kenny et al. |
| 2003/0092162 | A1 | 5/2003 | Shankara et al. |
| 2003/0129611 | A1 | 7/2003 | Bao et al. |
| 2004/0009510 | A1 | 1/2004 | Seiwert et al. |
| 2004/0043386 | A1 | 3/2004 | Pray et al. |
| 2004/0126773 | A1 | 7/2004 | Beske et al. |
| 2004/0223953 | A1 | 11/2004 | Kung et al. |
| 2005/0089864 | A1 | 4/2005 | Li et al. |
| 2005/0112614 | A1 | 5/2005 | Cook |
| 2005/0233332 | A1 | 10/2005 | Collis |
| 2005/0239061 | A1 | 10/2005 | Marshall et al. |
| 2005/0260635 | A1 | 11/2005 | Dirks et al. |
| 2006/0035375 | A1 | 2/2006 | Head et al. |
| 2006/0088864 | A1 | 4/2006 | Smolke et al. |
| 2006/0228733 | A1 | 10/2006 | Pierce et al. |
| 2006/0234261 | A1 | 10/2006 | Pierce et al. |
| 2007/0072215 | A1 | 3/2007 | Seelig |
| 2007/0087334 | A1 | 4/2007 | Dirks et al. |
| 2007/0117109 | A1 | 5/2007 | Rothemund |
| 2008/0183958 | A1 | 7/2008 | Cheriton |
| 2008/0214488 | A1 | 9/2008 | Pierce et al. |
| 2009/0011956 | A1 | 1/2009 | Yin et al. |
| 2009/0123914 | A1 | 5/2009 | Erikson et al. |
| 2009/0197271 | A1 | 8/2009 | Kotlikoff et al. |
| 2009/0227774 | A1* | 9/2009 | Turberfield et al. ......... 530/358 |
| 2009/0247615 | A1 | 10/2009 | Pierce et al. |
| 2009/0311799 | A1 | 12/2009 | Sotzing et al. |
| 2010/0021901 | A1 | 1/2010 | Yin et al. |
| 2010/0021904 | A1 | 1/2010 | Pierce et al. |
| 2010/0035233 | A1 | 2/2010 | Yin et al. |
| 2010/0047926 | A1 | 2/2010 | Dirks et al. |
| 2011/0059064 | A1 | 3/2011 | Possani-Postay et al. |
| 2011/0104676 | A1 | 5/2011 | Pierce et al. |
| 2011/0287557 | A1 | 11/2011 | Zhang et al. |
| 2011/0288148 | A1 | 11/2011 | Pierce et al. |
| 2011/0288832 | A1 | 11/2011 | Pierce et al. |
| 2011/0313030 | A1 | 12/2011 | Dirks et al. |
| 2012/0021410 | A1 | 1/2012 | Yin et al. |
| 2012/0022244 | A1 | 1/2012 | Yin |
| 2012/0190835 | A1 | 7/2012 | Pierce et al. |
| 2012/0251583 | A1 | 10/2012 | Rothemund |
| 2014/0107983 | A1 | 4/2014 | Wolfe et al. |
| 2015/0004615 | A1 | 1/2015 | Pierce et al. |
| 2015/0154347 | A1 | 6/2015 | Wolfe et al. |

FOREIGN PATENT DOCUMENTS

| | | |
|---|---|---|
| EP | 1 634 890 | 3/2006 |
| EP | 2155770 | 5/2008 |
| EP | 2 055 781 | 5/2009 |
| EP | 1730161 | 9/2010 |
| EP | 193 1806 | 10/2011 |
| WO | WO 92/03464 | 3/1992 |
| WO | WO 94/01550 | 1/1994 |
| WO | WO 99/31276 | 6/1999 |
| WO | WO 01/40516 | 6/2001 |
| WO | WO 2005/098049 | 10/2005 |
| WO | WO 2006/002167 A2 | 1/2006 |
| WO | WO 2006/048025 | 5/2006 |
| WO | WO 2007/008276 | 1/2007 |
| WO | WO 2007/044727 | 4/2007 |
| WO | WO 2007/141809 A1 | 12/2007 |
| WO | WO 2007/148337 A2 | 12/2007 |
| WO | WO 2008/106658 | 2/2008 |
| WO | WO 2008/144562 | 5/2008 |
| WO | WO 2011/126996 | 4/2011 |

OTHER PUBLICATIONS

Shlyakhtenko et al. Nucleic Acids Research. 2000. 28(18): 3472-3477.*
Goodman. Science. 2005. 310(5754): 1661-1665.*
Ke et al. Nanoletters. 2009. 9(6): 2445-2447.*
Shlyakhtenko. Journal of Biomolecular Structure and Dynamics. 1994. 11(6): 1175-1189.*
Stuhmeier. Biochemistry. 1997. 36: 1350-13538.*
Zhang et al. PNAS. 2008. 105(31):10665-10669.*
Jonoska et al. Algorithmic Bioprocess. 2008. Springer Verlag.*
Bhatia et al. Angew. Chem. Int. Ed. 2009. 48:4134-4137.*
He et al. Nature. 2008. 452:198-201.*
Iluma et al. Science. 2014. 344(6179):65-69.*
U.S. Appl. No. 13/186,331, filed Jul. 2011, Yin et al.
U.S. Appl. No. 13/186,315, filed Jul. 2011, Yin et al.
Aagaard et al., "RNAi Therapeutics: Principles, Prospects and Challenges." *Advanced Drug Delivery Reviews* 59 (2007): 75-86.
Allan et al., "A Concise Total Synthesis of (-)-Quinocarcin via Aryne Annulation." *Journal of American Chemical Society* 130 (2008) 17270-17271.
Amarzguioui et al., "Rational design and in vitro and in vitro delivery of Dicer substrate siRNA,", Nature Protocols, vol. 1, No. 2, pp. 508-517, 2006.
Andronescu et al., "A New Algorithm for RNA Secondary Structure Design", J. Mol. Biol., vol. 336, pp. 607-624, 2004.
Asbury, C.L., "Kinesin: world's tiniest biped", Current Opinion in Cell Biology, vol. 17, pp. 89-97, 2005.
Barish, R.D.; Schulman, R.; Rothemund, P.W.K.; Winfree, E., "An Information-Bearing seed for nucleating algorithmic self assembly." Proceedings of the National Academy of Sciences 2009, 106, 6054.
Bates, M.; Huang, B.; Dempsey, G.T.; and Zhuang, X. "Multicolor super-resolution imaging with photo-switchable flurorescent probes." Science, 317: 1749-1759, 2007.
Behenna et al., "The Enantioselective Tsuji Allylation." *Journal of American Chemical Society* 126.46 (2004): 15044-15045.
Bloomfield et al., "Nucleic Acids: Structures, Properties, and Functions." *University Science Books*(2000).
Bois et al., "Topological constraints in nucleic acid hybridization kinetics", Nucleic Acids Research, vol. 33, No. 13, pp. 4090-4095, 2005.
Bolt et al., Differential Reactivities of the mono- and di-epoxide of 1,3-butadiene. *Toxicology* 113 (1996): 294-296.
Bumcrot et al., "RNAi Therapeutics: A Potential New Class of Pharmaceutical Drugs." *Nature Chemical Biology* 2.12 (Dec. 2006): 711-719.
Bushnell et al., "ProbeDesigner: for the design of probesets for branched DNA (bDNA) signal amplification assays," Bioinformatics, 15(5), pp. 348-355, 1999.
Butterfoss et al., Computer-Based Design of Novel Protein Structures, Annu. Rev. Biophys. Biomol. Struct., vol. 35, pp. 49-65, 2006.

(56) References Cited

OTHER PUBLICATIONS

Caltech News Release, "Caltech Scientists Create New Process to Program", Sep. 6, 2010.
Caplen, "RNAi as a gene therapy approach", Expert Opin. Biol. Ther., vol. 3, No. 4, pp. 575-586, 2003.
Castanotto et al., "The Promises and Pitfalls of RNA-Interface-Based Therapeutics." Nature 457 (Jan. 22, 2009):426-433.
Cerutti et al., "On the Origin and Functions of RNA-Mediated Silencing: From Protists to Man." Current Genetics 50 (2006) 81-99.
Check, "RNA to the rescue?", Nature, vol. 425, pp. 10-12, Sep. 4, 2003.
Chen, H.L.; Cheng, Q.; Goel, A.; Huang, M.D.' Espanes, P.M.d. "Invadable self-assembly: Combining robustness with efficiency." In Proceedings of the 15th annual ACM-SIAM Symposium on Discrete Algorithms (SODA); 2004.
Chen Y.; Liu, H.P.; Ye, T.; Kim, J.; Mao, C.D. "DNA-Directed Assembly of Single—Wall Carbon Nanotubes." J.Am. Chem. Soc. 2007,129.
Coburn et al., "siRNAs: a new wave of RNA-based therapeutics", Journal of Antimicrobial Chemotherapy, vol. 51, pp. 753-756, 2003.
Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.
Coleman et al., "Template-Directed Corss-Linking of Oligonucleotides: Site-Specific Covalent Modification of dG-N7 Within Duplex DNA." J. Org. Chem. 60 (1995): 6252-6253.
Collins et al., "A branched DNA signal amplification assay for quantification of nucleic acid targets below 100 molecules/ml," Nucleic Acids Res, 25(15), pp. 2979-2984, 1997.
Coppelli et al., "Oligonucleotides as Anticancer Agents: From the Benchside to the Clinic and Beyond", Current Pharmaceutical Design, vol. 11, pp. 2825-2840, 2005.
Cullen et al., "Genome-wide Screening for Gene Function Using RNAi in Mammalian Cells." Immunology and Cell Biology 83 (2005) 217-223.
Czauderna et al., "Structural Variations and Stabilising Modifications of Synthetic siRNAs in Mammalian Cells." Nucleic Acids Research 31.11 (2003): 2705-2716.
Definition for "substantial" from Merriam-Webster Online Dictionary. Downloaded from merriam-webster.com; downloaded on Mar. 5, 2008.
Dias et al., "Antisense Oligonucleotides: Basic Concepts and Mechanisms." Molecular Cancer Therapeutics 1 (Mar. 2002) 347-355.
Dietz, H.; Douglas, S.; Shih, W. "Folding DNA into Twisted and Curved Nanoscale Shapes." Science 2009, 325, 725-730.
Dirks et al., "An Algorithm for Computing Nucleic Acid Base-Pairing Probabilities Including Pseudoknots." Journal of Computational Chemistry 25.10 (2004): 1295-1304.
Dirks et al., "A Partition Function Algorithm for Nucleic Acid Secondary Structure Including Pseudoknots." Journal of Computational Chemistry 24.13 (2003) 1664-1677.
Dirks et al., "Paradigms for computational nucleic acid design," Nucleic Acids Research, vol. 32, No. 4, pp. 1392-1403, Oxford University Press, 2004.
Dirks et al., "Thermodynamic Analysis of Interacting Nucleic Acid Strands." SIAM Review 49.1 (2007): 65-88.
Dirks et al., "Triggered amplification by hybridization chain reaction," PNAS, vol. 101, No. 43, pp. 15275-15278, Oct. 26, 2004.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Douglas et al., "DNA-nanotube-induced alignment of membrane proteins for NMR structure determination", PNAS, vol. 104, No. 16, pp. 6644-6648, Apr. 17, 2007.
Douglas et al., "Self-assembly of DNA into nanoscale three-dimensional shapes", Nature, vol. 459, pp. 414-418, May 21, 2009.

Eckstein, F. "Phosphrothioate oligodeooxynucleotides: what is their origin and what is unique about them?" Antisense Nucleic Acid Drug Dev., 10:117-121, 2000.
Eddy, S.R. "Non-coding RNA genes and the modern RNA world." Nature Reviews, 2: 919-929, 2001.
Elbashir et al., "Functional anatomy of siRNAs for mediating efficient RNAi in Drosophila melanogaster embryo lysate", The EMBO Journal, vol. 20, No. 23, pp. 6877-6888, 2001.
Elghanian et al.,"Selective colorimetric detection of polynucleotides based on the distance-dependent optical properties of gold nanoparticles," Science, 277(5329), pp. 1078-1081, 1997.
Ellington et al., "In vitro selection of RNA molecules that bind specific ligands," Nature 346, pp. 818-822, 1990.
Elmén et al., "Locked Nucleic Acid (LNA) Mediated Improvements in siRNA Stability and Functionality." Nucleic Acids Research 33.1 (2005): 439-447.
Enquist et al.., "The Total Synthesis of ( - )-Cyanthiwigin F by Means of Double Catalytic Enantioselective Alkylation." Nature 453.7199 (Jun. 26, 2008) 1228-1231.
Extended European Search Report dated Apr. 22, 2010 in European Patent Application No. 06836249.0.
Extended European Search Report from Application No. 08755764.1, dated Nov. 7, 2011.
Feldkamp et al., "Rational Design of DNA Nanoarchitectures", Angew. Chem. Int. Ed., vol. 45, pp. 1856-1876, 2006.
Felgner, et al., "Nomenclature for Synthetic Gene Delivery Systems", Human Gene Therapy, vol. 8, pp. 511-512, Mar. 20, 1997.
Femino et al., "Visualization of Single Molecules of mRNA in Situ." Methods of Enzymology 361 (2003): 245-304.
Ferkol et al., "Gene Transfer into the Airway Epithelium of Animals by Targeting the Polymeric Immunoglobulin Receptor", J. Clin. Invest., vol. 95, pp. 493-502, Feb. 1995.
Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.
Ferreira et al., "The Palladium-Catalyzed Oxidative Kinetic Resolution of Secondary Alcohols with Molecular Oxygen." Journal of American Chemical Society 123.31 (2001): 7725-7726.
File history of U.S. Appl. No. 13/186,331.
File history of U.S. Appl. No. 13/186,315.
Final Office Action dated May 27, 2010 for U.S. Appl. No. 11/544,306.
Final Office Action dated Sep. 20, 2010 for U.S. Appl. No. 12/454,799.
Final Office Action dated Sep. 17, 2010 for U.S. Appl. No. 12/467,755.
Final Office Action dated Oct. 15, 2010 for U.S. Appl. No. 12/152,893.
Final Office Action dated Jul. 15, 2011 for U.S. Appl. No. 12/040,735.
Final Office Action dated Jul. 25, 2011 for U.S. Appl. No. 12/395,489.
Fire et al., "Potent and specific genetic interference by double-stranded RNA in Caenorhabditis elegans", Nature, vol. 391, pp. 806-811, Feb. 19, 1998.
Flamm et al., "RNA folding at elementary step resolution," RNA, vol. 6, pp. 325-338, 2000.
Friedrich et al., A Cellular Screening Assay to Test the Ability of PKR to Induce Cell Death in Mammalian Cells, Molecular Therapy, vol. 12, No. 5, pp. 969-975, Nov. 2005.
Friedrich et al., "RNA molecules as anti-cancer agents", Seminars in Cancer Biology, vol. 14, pp. 223-230, 2004.
Fu et al., "DNA Double-Crossover Molecules", Biochemistry, vol. 32, pp. 3211-3220, 1993.
Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.
Garg et al., "Development of an Enantiodivergent Strategy for the Total Synthesis of (+)- and (−)-Dragmacidin F from a Single Enantiomer of Quinic Acid." Journal of American Chemical Society 127 (2005) 5970-5978.

(56) References Cited

OTHER PUBLICATIONS

Garg et al., "A Ligand-free Solid-supported System for Sonogashira Couplings: Applications in Nucleoside Chemistry." *Chem. Commun.* (2005) 4551-4553.
Gilman et al., "The Biological Actions and Therapeutic Applications of the B-Chloroethyl Amines and Sulfides." *Science* 103.2675 (Apr. 5, 1946): 409-415.
Goodman, R.P.; Schaap, I.A.T.; Tardin, C.F.; Erben, C.M.; Berry, R.M.; Schmidt, C.F.; and Turberfield, A.K. "Rapid chiral assembly of rigid DNA blocks for molecular nanofabrication." Science, 310, 2005.
Green et al., "DNA Hairpins: Fuel for Autonomous DNA Devices", Biophysical Journal, vol. 91, pp. 2966-2975, Oct. 2006.
Hansma et al., "DNA Binding to Mica Correlates with Cationic Radius: Assay by Atomic Force Microscopy", Biophysical Journal, vol. 70, pp. 1933-1939, Apr. 1996.
Hashimoto et al., "Recent Progress in Diazirine-Based Photoaffinity Labeling." *Eur. J. Org. Chem.*(2008): 2513-2523.
Haugland RP. The Handbook: A Guide to Fluorescent Probes and Labeling Technologies. 10th Ed. Molecular Probes/Invitrogen; 2005.
Hearst et al., "Psoralen Photochemistry." *Ann.Rev. Biophys.Bioeng.* 10 (1981): 69-86.
Heidel, J.D., "Targeted, systematic non-viral delivery of small interfering RNA in vivo", Doctoral thesis, California Institute of Technology, pp. 1-128, 2005.
Hello, S.W. "Far-field optical nanoscopy." Science, 316: 1153-1158, 2007.
Herath et al., "Synthesis of Acrimarins from 1,3,5-Trioxygenated-9-acridone Derivatives." *Journal of Heterocyclic Chem.* 41 (2004): 23-28.
Higuchi et al. Selective regulation of mutant K-ras mRNA expression by photo-cross-linking antisense oligonucleotide. Nucleic Acids Symposium Series (2007) vol. 51 (1) pp. 443-444.
Hofacker et al., "Fast folding and comparison of RNA secondary structures," Monatshefte für Chemie, vol. 125, pp. 167-188, 1994.
Hokaiwado et al., "RNAi-based drug discovery and its application to therapeutics", IDrugs, vol. 11, No. 4, pp. 274-278, 2008.
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." *Cancer Research* 65.19 (Oct. 1, 2005): 8984-8992.
Hughes et al., "Double Labeling wit Fluorescence In Situ Hybridization in *Drosophila* Whole-Mount Embryos," BioTechniques, 24(4), pp. 530-532, 1998.
Huizenga et al., "A DNA Aptamer That Binds Adenosine and ATP." Biochemistry 34, pp. 656-665, 1995.
International Search Report and Written Opinion from PCT/US2005/009471, dated Mar. 8, 2006.
International Search Report and Written Opinion from PCT/US2008/055559, dated Sep. 3, 2008.
Iqbal et al., "A review of molecular recognition technologies for detection of biological threat agents", Biosensors & Bioelectronics, vol. 15, pp. 549-578, 2000.
Jagus et al., "PKR, apoptosis and cancer", The International Journal of Biochemistry & Cell Biology, vol. 31, pp. 123-138, 1999.
Jhaveri et al., "In vitro selection of signaling aptamers", Nature Biotechnology, vol. 18, pp. 1293-1297, Dec. 2000.
Judge et al., "Design of Noninflammatory Synthetic siRNA Mediating Potent Gene Silencing in Vivo." *Molecular Therapy* 13.3 (Mar. 2006): 494-505.
Judge et al., "Overcoming the Innate Immune Response to Small Interfering RNA", Human Gene Therapy, vol. 19, pp. 111-124, Feb. 2008.
Julian et al., "Biomimetic Approaches to Gas Phase Peptide Chemistry: Combining Selective Binding Motifs with Reactive Carbene Precursors to Form Molecular Mousetraps." *International Journal of Mass Spectrometry* 228 (2003): 851-864.
Julian et al., "Molecular Mousetraps: Gas-Phase Studies of the Covalent Coupling of Noncovalent Complexes Initiated by Reactive Carbenes Formed by Controlled Activation of Diazo Precursors." *Agnew. Chem.Int. Ed.* 42.9 (2003) 1012-1015.
Kadnikov et al., "Synthesis of Coumarins via Palladium—Catalyzed Carbonylative Annulation of Internal Alkynes by o-Iodophenols." *Organic Letters* 2.23 (2000): 3643-3646.
Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.
Kim et al., "Synthetic dsRNA Dicer substrates enhance RNAi potency and efficacy", Nature Biotechnology, vol. 23, No. 2, pp. 222-226, Feb. 2005.
Kim et al., "Strategies for Silencing Human Disease Using RNA Interference." *Nature Review Genetics* 8 (Mar. 2007) 173-184.
Kislauskis et al. "Isoform-specific 3'-untranslated Sequences Sort α-cardiac and β-cytoplasmic Actin Mesenger RNAs to Different ytoplasmic Compartments," The Journal of Cell Biology, 123(1), pp. 165-172, 1993.
Knorre et al., "Photoaffinity Labeling as an Approach to Study Supramolecular Nucleoprotein Complexes." *FEBS Letters* 433 (1998): 9-14.
Kobertz et al., "An Efficient Synthesis of a Furan-Side Furocoumarin Thymidine Monoadduct." *J. Org. Chem.* 62.8 (1997) 2630-2632.
Kobertz et al., "Solid-Phase Synthesis of Oligonucleotides Containing a Site-Specific Psoralen Derivative." *Journal of American Chemical Society* 119 (1997): 5960-5961.
Kobertz et al., "Total Synthesis of a Cis-Syn 2-Carbomethoxypsoralen Furan-Side Thymidine Monoadduct." *Journal of American Chemical Society* 118 (1996): 7101-7107.
Kosman, et al., "Multiplex Detection of RNA Expression in *Drosophila* Embryos," Science, 305, p. 846, 2004.
Kuzuya et al., "Six-Helix and Eight-Helix DNA Nanotubes Assembled from Half-Tubes", Nano Lett., vol. 7, No. 6, pp. 1757-1763, 2007.
Lacenere et al., "Effects of a Modified Dye-Labeled Nucleotide Spacer Arm on Incorporation by Thermophilic DNA Polymerases." *Nucleosides, Nucleotides, and Nucleic Acids* 25 (2006) 9-15.
Ladiges, et al., "Tissue specific expression of PKR protein kinase in aging B6D2F1 mice," Mechanisms of Ageing and Development, vol. 114, pp. 123-132, (2000).
Lawley et al., "DNA Adducts from Chemotherapeutic Agents." *Mutation Research—Fundamental and Molecular mechanisms of Mutagenesis* 355 (1996): 13-40.
Lawrence et al., "Highly Localized Tracks of Specific Transcripts within Interphase Nuclei Visualized by In Situ Hybridication," Cell, 57, pp. 493-502, 1989.
Layzer et al., "In Vivo Activity of Nuclease-Resistant siRNAs." *RNA* 10 (2004): 766-771.
Le et al., "DNA-Templated Self-Assembly of Metallic Nanocomponent Arrays on a Surface", Nano Lett., vol. 4, No. 12, pp. 2343-2347, 2004.
Lee, J.F., Hesselberth, J.R.; Meyers, L.A.; and Ellington, A.D. "Aptamer database." Nucleic Acids Research, 32: D95-100, 2004.
Lee et al., "A self-replicating peptide", Nature, vol. 382, pp. 525-528, Aug. 8, 1996.
Levsky et al., "Single-Cell Gene Expression Profiling," Science 297, pp. 836-840, 2002.
Levy et al., "Exponential growth by cross-catalytic cleavage of deoxyribozymogens", PNAS, vol. 100, No. 11, pp. 6416-6421, May 27, 2003.
Li, H.; LaBean, T.H.; Kenan, D.J. "Single-chain antibodies against DNA aptamers for use as adapter molecules on DNA tile arrays in nanoscale materials organization." Organic and Biomolecular Chemistry 2006, 3420-3426. 2006.
Li, Z, Trimble, M.J.; Brun, Y.V.; Jensen, G.J. "The structure of FtsZ filaments in vivo suggests a force-generating role in cell division." EMBO J.,26, pp. 4694-4708. 2007.
Lin et al., "DNA Tile Based Self-Assembly: Building Complex Nanoarchitectures", ChemPhysChem, vol. 7, pp. 1641-1647, 2006.
Liu et al., "A colorimetric lead biosensor using DNAzyme-directed assembly of gold nanoparticles," J. Am. Chem. Soc., 125(22), pp. 6642-6643, 2003.

(56) References Cited

OTHER PUBLICATIONS

Liu et al., "Approaching The Limit: Can One DNA Oligonucleotide Assemble into Large Nanostructures?", Angew. Chem. Int. Ed., vol. 45, pp. 1942-1945, 2006.
Liu et al., "DNA nanotubes self-assembled from triple-crossover tiles as templates for conductive nanowires", PNAS, vol. 101, No. 3, pp. 717-722, Jan. 20, 2004.
Macechko et al., "Comparison of Immunologic Amplification vs Enzymatic Deposition of Fluorochrome-conjugated Tyramide as Detection Systems for FISH," J Histochem Cytochem, 45(3), pp. 359-363, 1997.
Mahato et al., "Modulation of gene expression by antisense and antigene oligodeoxynucleotides and small interfering RNA", Expert Opin. Drug Deliv., vol. 2, No. 1, pp. 3-28. 2005.
Manche et al., "Interactions between Double-Stranded RNA Regulators and the Protein Kinase DAI", Molecular and Cellular Biology, vol. 12, No. 11, pp. 5238-5248, Nov. 1992.
Manoharan et al., "RNA Interference and Chemically Modified Small Interfering RNAs." Current Opinion in Chemical Biology 8 (2004): 570-579.
Mathieu et al., "Six-Helix Bundles Designed from DNA", Nano Lett., vol. 5, No. 4, pp. 661-665, 2005.
Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.
Meinhardt et al., "Wavelength-dependent Penetration Depths of Ultraviolet Radiation in Human Skin." Journal of Biomedical Optics 13.4 (Jul./Aug. 2008) 044030-1-044030-5.
Mitchell et al., "Self-Assembly of Chiral DNA Nanotubes", J. Am. Chem. Soc., vol. 126, pp. 16342-16343, 2004.
Mittelstadt, et al., "Interaction of human tRNA-dihydrouridine synthase-2 with interferon-induced protein kinase PKR," Nucleic Acids Research, vol. 36, No. 3, pp. 998-1008, (2008).
Mohr et al., "Catalytic Enantioselective Decarboxylative Protonation." Journal of American Chemical Society 128.35 (2006): 11348-11349.
Mohr et al., "Natural Products as Inspiration for the Development of Asymmetric Catalysis." Nature 455 (Sep. 18, 2008) 323-332.
Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292, American Chemical Society,.2002.
Naked Scientists (The): Science Radio & Science Podcasts, "RNA-away cancer cells", Sep. 12, 2010, http://www.thenakedscientists.com/HTML/content/news/news/2051/.
Noll et al., "Formation and Repair of Interstrand Cross-Links in DNA." Chemical Reviews 106.2 (2006) 277-301.
Noll et al., "Preparation of Interstrand Cross-Linked DNA Oligonucleotide Duplexes." Frontiers in Bioscience 9 (Jan. 1, 2004): 421-437.
Nutiu et al., "Structure-switching signaling aptamers," J. Am. Chem. Soc., vol. 125, pp. 4771-4778, American Chemical Society, 2003.
Office Action dated Feb. 4, 2010 in U.S. Appl. No. 12/152,893.
Office Action dated Apr. 1, 2010 in U.S. Appl. No. 12/467,755.
Office Action dated Apr. 16, 2010 in U.S. Appl. No. 12/454,799.
Office Action dated Dec. 16, 2010 for U.S. Appl. No. 12/395,489.
Office Action dated Mar. 10, 2011 in U.S. Appl. No. 12/454,743, filed May 22, 2009.
Office Action dated Mar. 17, 2011 for U.S. Appl. No. 12/611,875.
Office Action dated Oct. 14, 2011 for U.S. Appl. No. 12/454,743.
Opalinska et al., "Nucleic-Acid Therapeutics: Basic Principles and Recent Applications", Nature Reviews Drug Discovery, vol. 1, pp. 503-514, 2002.
Park, S.H.; Yin, P.; Liu, Y.; Reif, J.H.; LaBean, T.H.; Yan, H. "Programmable DNA Self-Assemblies for Nanoscale Organization of Ligands and Proteins." Nano Letters 2005, 5, 729-733.
Park et al., "Rapid Identification of Candida dubliniensis Using a Species-Specific Molecular Beacon", Journal of Clinical Microbiology, vol. 38, No. 8, pp. 2829-2836, 2000.
Park et al., "Three-Helix Bundle DNA Tiles Self-Assemble into 2D Lattice or 1D Templates for Silver Nanowires", Nano Lett., vol. 5, No. 4, pp. 693-696, 2005.
Paul et al., "A self-replicating ligase ribozyme", PNAS, vol. 99, No. 20, pp. 12733-12740, Oct. 1, 2002.
Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.
Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.
Pistona, D.W., and Gremersa, G.J. "Fluorescent protein FRET: the good, the bad and the ugly." Trends in Biochemical Sciences, 32, 2007.
Player et al., "Single-copy Gene Detection Using Branched DNA (bDNA)) In Situ Hybridization," J. Histochem & Cytochem, 49(5), pp. 603-611, 2001.
Pouton et al., "Key issues in non-viral gene delivery", Advanced Drug Delivery Reviews, vol. 46, pp. 187-203, 2001.
Qi et al., "Surface Transfer Doping of Diamond (100) by Tetrafluoro-tetracyanoquinodimethane", J. Am. Chem. Soc., vol. 129, pp. 8084-8085, 2007.
Qian et al., "Recent Developments in Signal Amplification Methods for In Situ Hybridization," Diagnostic Molecular Pathology, 12(1), pp. 1-13, 2003.
Qian, X., L. Jin, and R.V. Lloyd, In situ hybridization: basic approaches and recent development. The Journal of Histotechnology, 2004. 27(1): p. 53-67.
Rachofsky et al., "Probing structure and dynamics of DNA with 2-aminopurine: Effects of local environment on fluorescence," Biochemistry, vol. 40, pp. 946-956, 2001.
Raj et al., "Imaging Individual mRNA Molecules Using Multiple Singly Labeled Probes." Nature Methods 5.10 (Oct. 2008): 877-879.
Read et al., "Barriers to Gene Delivery Using Synthetic Vectors", Advances in Genetics, vol. 53, pp. 19-46, 2005.
Reif, J.H.; Sahu, S.; Yin, P. "Compact Error-Resilient Computational DNA tiling Assemblies." In Proc. $10^{th}$ International Meeting on DNA Computing; 2004.
Reif, J.H.; Sahu, S.; Yin, P. "Complexity of Graph Self-Assembly in Accretive Systems and Self-Destructible Systems." In Proc. $11^{th}$ International Meeting on DNA Computing; 2005.
Reynolds et al., "Rational siRNA Design for RNA Interference." Nature Biotechnology 22.3 (Mar. 2004) 326-330.
Rothemund, P.; Papadakis, J.; Winfree, E. "Algorithmic Self-Assembly of DNA Sierpinski Triangles." PLoS Biology 2004, 2, 2041-2053.
Rothemund et al., "Design and Characterization of Programmable DNA Nanotubes", J. Am. Chem. Soc., vol. 126, pp. 16344-16352, 2004.
Rothemund, P.W.K., "Folding DNA to creat nanoscale shapes and patterns", Nature, vol. 440, pp. 297-302, 2006.
Rothemund, P.W.K.; Winfree, E. "The Program-size complexity of self-assembled squares (extended abstract)." In Proceedings of the thirty-second annual ACM symposium on Theory of computing; ACM Press: 2000.
Sahu, S.; Yin, P.; Reif, J.H. "A Self-Assembly Model of Time-Dependent Glue Strength." In Proc. $11^{th}$ International meeting on DNA Computing; 2005.
Saunders et al., "Introduction of DNA into Bacteria." Methods in Microbiology 29 (1999): 3-49.
Schärer et al., "DNA Interstrand Crosslinks: Natural and Drug-Induced DNA Adducts that Induce Unique Cellular Responses." ChemBioChem 6 (2005): 27-32.
Scherer et al., "Approaches for the sequence-specific knockdown of mRNA", Nature Biotechnology, vol. 21, No. 12, pp. 1457-1465, 2003.

(56) References Cited

OTHER PUBLICATIONS

Schipani, Vanessa, "A targeted cancer therapy?" The Scientist, Sep. 7, 2010 blog post, http://www.the-scientist.com/blog/display/57674/.
Schulman et al., "Synthesis of crystals with a programmable kinetic barrier to nucleation", PNAS, vol. 104, No. 39, pp. 15236-15241, Sep. 25, 2007.
Schulte-Merker et al., "No tail (ntl) is the zebrafish homologue of the mouse T (Brachyury) gene." *Development* 120 (1994): 1009-1015.
Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.
Schweitzer et al., "Combining nucleic acid amplification and detection," Curr Opin Biotechnol, 12, pp. 21-27, 2001.
Seelig et al., "Catalyzed Relaxation of a Metastable DNA Fuel", Journal American Chemical Society, vol. 128, No. 37, pp. 12211-12220, 2006.
Seeman, "De Novo Design of Sequences for Nucleic Acid Structural Engineering", Journal of Biomolecular Structure & Dynamics, pp. 573-581, vol. 8, No. 3, 1990.
Seeman, "DNA in a material world", Department of Chemistry, New York University, Nature, vol. 421, pp. 427-431 (Jan. 23, 2003).
Seeman, "Nucleic acid junctions and lattices," J. Theor. Biol., vol. 99, pp. 237-247, Academic Press Inc. (London) Ltd., 1982.
Seeman, "Nucleic acid nanstructures and topology", Angew. Chem. Int. Ed. vol. 37, pp. 3220-3238 (1998).
Sekulic, A.; Hudson, C.C; Homme, J.L.; Yin, P.; Otterness, D.M.; Karnitz, L.M.; Abraham, R.T. A Direct Linkage between the Phosphoinositide 3-Kinase-AKT Signaling Pathway and the Mammalian Target of Rapamycin in Mitogen-stimulated and Transformed Cells. Cancer Research 2000, 60, 3504-3513.
Shah et al., "The Fries Isomerization of Acetyl and Benzoyl Esters of Umbelliferones." *J. Org. Chem.* 19 (1954): 1681-1685.
Sharma, J.; Chhabra, R.; Cheng, A.; Brownell, J.; Liu, Y.; Yan, H. "Control of Self-Assembly of DNA Tubules through Integration of Gold Nanoparticles" Science 2009, 112-116.
Sharma et al., "DNA-Tile-Directed Self-Assembly of Quantum Dots into Two-Dimensional Nanopatterns", Angew. Chem. Int. Ed., vol. 47, pp. 5157-5159, 2008.
Shih et al., "A 1.7-kilobase single-stranded DNA that folds into a nanoscale octahedron", Nature, vol. 427, pp. 618-621, Feb. 12, 2004.
Shir et al., "Inhibition of glioma growth by tumor-specific activation of double-stranded RNA-dependent dependent protein kinase PKR", Nature Biotechnology, vol. 20, pp. 895-900, Sep. 2002.
Silverman et al., "Oligonucleotide Probes for RNA-Targeted Fluorescence In Situ Hybridization." *Advances in Clinical Chemistry* 43 (2007): 79-115.
Silverman et al., "Quenched Autoligation Probes Allow Discrimination of Live Bacterial Species by Single Nucleotide Differences in rRNA." *Nucleic Acids Research* 33.15 (2005): 4978-4986.
Siolas et al., "Synthetic shRNAs as Potent RNAi Triggers." *Nature Biotechnology* 23.2 (Feb. 2005): 227-231.
Sokol et al., "Real time detection of DNA•RNA hybridization in living cells", Proc. Natl. Acad. Sci. USA, vol. 95, pp. 11538-11543, Sep. 1998.
Storhoff et al., "One-pot colorimetric differentiation of polynucleotides with single base imperfections using gold nanoparticles," J. Am. Chem. Soc., 120, pp. 1959-1964, 1998.
Sun et al., "Side Chain Chemistry Mediates Backbone Fragmentation in Hydrogen Deficient Peptide Radicals." *Journal of Proteome Research* 8 (2009) 958-966.
Supplementary European Search Report from PCT/US2005/009471, dated May 6, 2008.
Takei et al., "A Small Interfering RNA Targeting Vascular Endothelial Growth Factor as Cancer Therapeutics." *Cancer Research* 64. (May 15, 2004): 3365-3370.
Tani et al., "Synthesis and Structural Analysis of 2-Quinuclidonium Tetrafluoroborate." *Nature* 441 (Jun. 8, 2006) 731-734.
Thomas et al., "Photoaffinity Cross-Linking and RNA Structure Analysis." *Methods in Enzymology* 318 (2000) 136-147.
Thompson, N.L.; Lieto, A.M., and Allen, N.W. "Recent advances in fluorescence correlation spectroscopy." Curr. Opin.Struct. Biol., 12, 2002.
Tijsterman et al., "Dicers at RISC: The Mechanism of RNAi", Cell, vol. 117, pp. 1-3, 2004.
Tuerk et al., "Systematic Evolution of Ligands by Exponential Enrichment: RNA Ligands to Bacteriophage T4 DNA Polymerase," Science 249, pp. 505-510, 1990.
Turberfield, et al., "DNA fuel for free-running nanomachines," Physical Review Letters, vol. 90, No. 11, pp. 118102-1-118102-4, Mar. 21, 2003.
Turk, Greg and Levoy, Marc. "Zippered polygon meshes from range images." In SIGGRAPH, pp. 311-318, 1994.
Tyagi et al., "Molecular Beacons: Probes that Fluoresce upon Hybridization," Nature Biotechnology 14, pp. 303-308, 1996.
U.S. File History printed for U.S. Appl. No. 11/087,937, filed Mar. 22, 2005, entitled "Hybridization Chain Reaction".
U.S. File History for U.S. Appl. No. 12/611,875, filed Nov. 3, 2009, entitled "Hybridization Chain Reaction".
U.S. File History for U.S. Appl. No. 11/371,346, filed Mar. 7, 2006, entitled "Hybridization Chain Reaction Amplification for In Situ Imaging".
U.S. File History for U.S. Appl. No. 12/790,379, filed May 28, 2010, entitled "Hybridization Chain Reaction Amplification for In Situ Imaging".
U.S. File History for U.S. Appl. No. 11/371,347, filed Mar. 7, 2006, entitled "Colorimetric Readout of Hybridization Chain Reaction".
U.S. File History for U.S. Appl. No. 11/544,306, filed Oct. 6, 2006, entitled "PKR Activation via Hybridization Chain Reaction".
U.S. File History for U.S. Appl. No. 12/040,735, filed Feb. 29, 2008, entitled "Triggered RNAi".
U.S. File History for U.S. Appl. No. 12/152,893, filed May 16, 2008, entitled "A Versatile Nucleic Acid Hairpin Motif for Programming Biomolecular Self-Assembly Pathways".
U.S. File History for U.S. Appl. No. 12/395,489, filed Feb. 27, 2009, entitled "Triggered RNAi".
U.S. File History for U.S. Appl. No. 12/454,799, filed May 22, 2009, entitled "Compositions and Methods for Detecting Analytes".
U.S. File History for U.S. Appl. No. 12/467,755, filed May 18, 2009, entitled "Shielded Cross-Linking Probes".
U.S. File History for U.S. Appl. No. 12/454,743, filed May 22, 2009, entitled "Triggered RNAi".
U.S. File History for U.S. Appl. No. 13/186,331, filed Jul. 19, 2011, entitled "Self-Assembled Polynucleotide Structure".
U.S. File History for U.S. Appl. No. 13/186,315, filed Jul. 19, 2011, entitled "Triggered Molecular Geometry Based Bioimaging Probes".
Van De Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11), pp. 1249-1259, 1998.
Venkataraman et al., "An Autonomous Polymerization Motor Powered by DNA Hybridization." *Nature Nanotechnology* 2 (Aug. 2007): 490-494.
Venkataraman et al. "Selective Cell Death Mediated by Small Conditional RNAs", Proc Natl Acad Sci USA, early edition, approved Jul. 21, 2010, p. 1-6.
Vermeulen et al., "The contributions of dsRNA structure to Dicer specificity and efficiency", RNA, vol. 11, pp. 674-682, 2005.
Vodovozova et al., "Photoaffinity Labeling and Its Application in Structural Biology." *Biochemistry (Moscow)* 72.1 (2007): 1-20.
Volker, et al., "Conformational energetics of stable and metastable states formed by DNA triple repeat oligonucleotides: implications for triplet expansion diseases," PNAS, vol. 99, No. 23, pp. 14700-14705, Nov. 12, 2002.
Von Kiedrowski, "A Self-Replicating Hexadeoxynucleotide", Agnew. Chem. Int. Ed. Engl., vol. 25, No. 10, pp. 932-935, 1986.
Voorhoeve et al., "Knockdown Stands Up.:" *Trends in Biotechnology* 21.1 (Jan. 2003) 2-4.

(56) References Cited

OTHER PUBLICATIONS

Wagner et al., "Transferrin-Polycation Conjugates as Carriers for DNA Uptake into Cells", Proceedings of the National Academy of Sciences of the United States of America, vol. 87, pp. 3410-3414, May 1990.
Wassarman et al., "Psoralen Crosslinking of Small RNAs in vitro." *Molecular Biology Reports* 17 (1993): 143-151.
White et al., "The Catalytic Asymmetric Total Synthesis of Elatol." *Journal of American Chemical Society* 130.3 (2008): 810-811.
Wijen et al., "The in vivo Genetic Activity Profile of the Monofunctional Nitrogen Mustard 2-Chloroethylamine Differs Drastically from its Bifunctional Counterpart Mechlorethamine." *Carcinogenesis* 21.10 2000 1859-1867.
Wilkie et al., "Transcribed genes are localized according to chromosomal position within polarized *Drosophila* embryonic nuclei," Current Biology, 9, pp. 1263-1266, 1999.
Williams, B.R.G., "PKR; a sentinel kinase for cellular stress", Oncogene, vol. 18, pp. 6112-6120, 1999.
Willis, M.C., et al. Photocross-linking of 5-Iodouracil-Substituted RNA and DNA to Proteins. Science, 1993. 262: p. 1255-1257.
Winfree et al., "Design and self-assembly of two-dimensional DNA crystals", Nature, vol. 394, pp. 539-544, Aug. 6, 1998.
Winfree, E. Algorithmic Self-Assembly of DNA, Ph.D. thesis. Thesis, California Institute of Technology, 1998.
Winfree, E. "On the computational power of DNA annealing and ligation." Computation and Neural Systems, California Institute of Technology, May 25, 1995.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Yan et al., "DNA-Templated Self-Assembly of Protein Arrays and Highly Conductive Nanowires", Science, vol. 301, pp. 1882-1884, Sep. 26, 2003.
Yin et al., "Programming biomolecular self-assembly pathways", Nature, vol. 451, pp. 318-323, Jan. 17, 2008.
Yin, P.; Hartemink, "Theoretical and practical advances in genome halving." A.K. Bioinformatics 2005, 21, 869-879.
Yin, P.; Hariadi, R.; Sahu, S.; Choi, H.M.T.; Park, S.H.; :LaBean, T.H.; J.H. Reif, "Programming DNA Tube Circumferences." Science 2008, 321, 824-826.
Yin, P.; Yan, H.; Daniell, X.; Turberfield, A.J.; Reif, J. "A Unidirectional DNA Walker that Moves Autonomously along a Track." Angewandte Chemie International Edition 2004, 43, 4906-4911.
Yin, P.; Turberfield, A.J.; Reif, J.H. "Designs of Autonomous Unidirectional Walking DNA Devices." In Proc. 10th International Meeting on DNA computing; 2004.
Yoshimura et al., "Interstrand Photocrosslinking of DNA via p-carbamoylvinyl Phenol Nucleoside." *Bioorganic & Medicinal Chemistry Letters* 15 (2005): 1299-1301.
Yurke et al., "A DNA-fuelled molecular machine made of DNA", Letters to Nature, vol. 406, pp. 605-608 (Aug. 10, 2000).
Zadeh et al., "Software News and Updates NUPACK: Analysis and Design of Nucleic Acid Systems", Journal of Computational Chemistry, vol. 32, No. 1, pp. 170-173, 2011.
Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zhang et al., Targeted Gene Silencing by Small Interfering RNA-Based Knock-Down Technology, Current Pharmaceutical Biotechnology, vol. 5, pp. 1-7, 2004.
Zheng et al., "Activation of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zuker et al., "Optimal computer folding of large RNA sequence using thermodynamics and auxiliary information," Nucleic Acids Research, vol. 9, No. 1, pp. 133-147, 1981.
Notice of Allowance dated Apr. 4, 2013 for U.S. Appl. No. 13/363,022.
Notice of Allowance dated Feb. 20, 2013 for U.S. Appl. No. 12/395,489.
Notice of Allowance dated May 24, 2013 for U.S. Appl. No. 13/016,811.
Office Action dated Aug. 8, 2013 for U.S. Appl. No. 13/186,331.
Office Action dated Aug. 2, 2013 for U.S. Appl. No. 13/186,315.
Tyagi, et al., Multicolor Molecular Beacons for Allele Discrimination, Nature Biotechnology vol. 16, pp. 49-53, Jan. 1998.
Communication Article 94(3) EPC from Application No. 08755764.1, dated Nov. 7, 2012.
File History of U.S. Appl. No. 12/040,735.
Final Office Action dated Mar. 7, 2013 for U.S. Appl. No. 13/016,811.
Bath et al., "DNA nanomachines", Nature Nanotechnology, vol. 2, pp. 275-284, May 2007.
Bonnet et al. Thermodynamic basis of the enhanced specificity of structured DNA probes, Proc. Natl. Acad. Sci. USA vol. 96 (May 1999), pp. 6171-6176.
Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.
Evanko, "Hybridization chain reaction", Nature Methods, vol. 1, No. 3, pp. 186-187, Dec. 2004.
Gasparro et al., Site-specific targeting of psoralen photadducts with a triple helix-forming oligonuicleotide: characterization of psoralen monoadduct and crosslink formation. Nucleic Acids Research 22 (1994), pp. 2845-2852.
Jayasena, "Aptamers: An Emerging Class of Molecules That Rival Antiodies in Diagnostics", Clinical Chemistry, vol. 45, No. 9, pp. 1628-1650, 1999.
Li et al., A new class of homogenous nucleic acid probes based on specific displacement hybridization, Nucleic Acids Research, vol. 30, No. 2e5 (2002), pp. 1-9.
Peng et al., Facile SNP detection using bifunctional, cross-linking oligonucleotide probes, Nucleic Acids Research vol. 36 No. 5e31 (2008), pp. 1-7.
Piston et al., "Fluorescent protein FRET: the good, the bad and the ugly", Trends Biochem Sci., Sep. 2007, vol. 32, No. 9, pp. 407-414.
Seeman, et al., Nucleic Acid Nanostructures: Bottom Up Control of Geometry on the Nanoscale, Reports on Progress in Physics, 68 :237 (2005).
Shaner et al., "A guide to choosing fluorescent proteins", Nature Methods, vol. 2, No. 12, pp. 905-909, Dec. 2005.
Situma et al., "Immobilized molecular beacons: A new strategy using UV-activated poly(methyl methacrylate) surfaces to provide large fluorescence sensitivities for reporting on molecular association events." Analytical Biochemistry 363 (2007) 35-45.
Stemmer, et al, Single Step Assembly of a Gene and Entire Plasmid from Large Numbers of Oligodeoxyribonnucleotides. Gene, vol. 164, pp. 49-53 (1995).
Yurke, et al., "A DNA-fuelled molecular machine made of DNA" *Nature*, vol. 406, Aug. 10, 2000, pp. 605-608.
Final Office Action dated Jan. 22, 2014 for U.S. Appl. No. 13/186,331.
Office Action dated Apr. 2, 2014 for U.S. Appl. No. 12/467,755.
Office Action dated Nov. 9, 2010 for U.S. Appl. No. 12/040,735.
Office Action dated Jan. 27, 2014 for U.S. Appl. No. 13/186,315.
Office Action dated Feb. 27, 2014 for U.S. Appl. No. 12/454,799.
Office Action dated Jun. 25, 2014 for U.S. Appl. No. 13/136,315.
Notice of Allowance dated Jul. 1, 2014 for U.S. Appl. No. 13/183,331.
Office Action dated Jul. 2, 2014 for U.S. Appl. No. 13/154,989.
Office Action dated Aug. 1, 2014 for U.S. Appl. No. 12/454,799.
Choi et al., Nature Biotechnology 28(11): 1208-1214, 2010.

(56) References Cited

OTHER PUBLICATIONS

Dirks et al., Retraction for "Selective cell death mediated by small conditional RNAs" (which appeared in issue 39, Sep. 28, 2010 of Proc Natl Acad Sci USA), Proc Natl Acad Sci USA, Jan. 2, 2013 vol. 110, No. 1, p. 384.
Ha et al., Regulation of microRNA biogenesis, Nature Reviews Molecular Cell Biology 15, 509-524. Jul. 16, 2014.
Patel et al., Cancer Biology & Therapy 14: 8, 693-696; Aug. 2013.
Office Action dated Oct. 14, 2014 for U.S. Appl. No. 12/152,893.
Office Action dated Oct. 30, 2014 for U.S. Appl. No. 13/896,235.
Office Action dated Jan. 13, 2015 for U.S. Appl. No. 12/467,755.
Notice of Allowance dated Oct. 8, 2014 for U.S. Appl. No. 13/186,315.
Notice of Allowance dated Oct. 9, 2014 for U.S. Appl. No. 13/154,989.
Vieregg et al., "Selective Nucleic Acid Capture with Shielded Covalent Probes", J. Am. Chem. Soc., 2013, vol. 135, 9691-9699.
Vieregg et al., "Selective Nucleic Acid Capture with Shielded Covalent Probes—Supplemental Materials", J. Am. Chem. Soc., 2013, vol. 135, pp. S1-S52.
Final Office Action dated May 8, 2015 for U.S. Appl. No. 12/467,755.
Office Action dated May 5, 2015 for U.S. Appl. No. 12/454,799.
Office Action dated Aug. 27, 2015 in U.S. Appl. No. 12/467,755.
Notice of Allowance dated Jun. 26, 2015 for U.S. Appl. No. 12/152,893.
Johnston et al. Psoralen-DNA Photoreaction: Controlled Prodiction of Mono- and Diadducts with Nanosecond Ultraviolet Laser Pulses, New Series, vol. 197, pp. 906-908, 1997.
Supplemental Notice of Allowance dated Sep. 17, 2015 for U.S. Appl. No. 12/152,893.
An, C. I.; Trinh, V. B.; Yokobayashi, Y. "Artificial control of gene expression in mammalian cells by modulating RNA interference through aptamer-small molecule interaction" RNA 2006, 12, 710-716.
Beisel, C. L.; Bayer, T. S.; Hoff, K. G.; Smolke, C. D. "Model-guided design of ligand-regulated RNAi for programmable control of gene expression" Mol. Syst. Biol. 2008, 4, 224.
Beisel, C. L.; Chen, Y. Y.; Culler, S. J.; Hoff, K. G.; Smolke, C. D. "Design of small molecule-responsive microRNAs based on structural requirements for Drosha processing" Nucleic Acids Res. 2011, 39, 2981-2994.
Brummelkamp, T. R.; Bernards, R.; Agami, R. "A system for stable expression of short interfering RNAs in mammalian cells" Science 2002, 296, 550-553.
Dabby NL, Chen HL, Schaeffer JM, Winfree E. "The kinetics of toehold-mediated four-way branch migration." California Institute of Technology Thesis, Chapter 5 (2013), pp. 75-105.
Du QA, Thonberg H, Wang J, Wahlestedt C, Liang ZC (2005) A systematic analysis of the silencing effects of an active siRNA at all single-nucleotide mismatched target sites. Nucleic Acids Res 33:1671-1677.
Dunn JJ, Studier FW (1983) Complete nucleotide-sequence of bacteriophage-TY DNA and the locations of T7 genetic elements. J Mol Biol 166:477-535.
Hochrein et al., "Conditional Dicer Substrate Formation via Shape and Sequence Transduction with Small Conditional RNAs," *J. Am. Chem. Soc.* 2013, 135, 17322-17330.
Jinek M, Doudna JA (2009) A three-dimensional view of the molecular machinery of RNA interference. Nature 457:405-412.
Kumar D, An CI, Yokobayashi Y (2009) Conditional RNA interference mediated by allosteric ribozyme. J Am Chem Soc 131:13906-13907.
Kumar D, Kim SH, Yokobayashi Y (2011) Combinatorially inducible RNA interference triggered by chemically modified oligonucleotides. J Am Chem Soc 133:2783-2788.
Kurreck, J. Angew. "RNA interference: from basic research to therapeutic applications" Chem., Int. Ed. 2009, 48, 1378-1398.
Lee, S. K.; Kumar, P. "Conditional RNAi: towards a silent gene therapy" Adv. Drug Delivery Rev. 2009, 61, 650-664.

Lima W.F., Wu H.J., Nichols J.G., Sun H., Murray H.M., Crooke S.T. "Binding and cleavage specificities of human Argonaute2" J Biol Chem 284:26017-26028 (2009).
Masu, H.; Narita, A ; Tokunaga, T.; Ohashi, M.; Aoyama, Y.; Sando, S. Angew. "An activatable siRNA probe: trigger-RNA-dependent activation of RNAi function" Chem., Int. Ed. 2009, 48, 9481-9483.
McIntyre, G. J.; Yu, Y. H.; Lomas, M.; Fanning, G. C. "The effects of stem length and core placement on shRNA activity" BMC Mol. Biol. 2011, 12, 34.
Santalucia J. "A unified view of polymer, dumbbell, and oligonucleotide DNA nearest-neighbor thermodynamics" Proc Natl Acad Sci 95:1460-1465 (1998).
Serra M.J., Turner D.H., "Predicting thermodynamic properties of RNA" Methods Enzymol 259: 242-261 (1995).
Tuleuova, N.; An, C. I.; Ramanculov, E.; Revzin, A ; Yokobayashi, Y. "Modulating endogenous gene expression of mammalian cells via RNA-small molecule interaction" Biochem. Biophys. Res. Commun. 2008, 376, 169-173.
Wiznerowicz, M.; Szulc, J.; Trono, D. "Tuning silence: conditional systems for RNA interference" Nat. Methods 2006, 3, 682-688.
Xie, Z.; Liu, S. J.; Bleris, L.; Benenson, Y. "Logic integration of mRNA signals by an RNAi-based molecular computer" Nucleic Acids Res. 2010, 38, 2692-2701.
Zadeh, J. N.; Wolfe, B. R.; Pierce, N. A "Nucleic acid sequence design via efficient ensemble defect optimization" J. Comput. Chem. 2011, 32, 439-452.
Zhang, D. Y.; Seelig, G. "Dynamic DNA nanotechnology using strand-displacement reactions" Nat. Chem. 2011, 3, 103-113.
Final Office Action dated Jun. 25, 2014 for U.S. Appl. No. 13/186,315.
Final Office Action dated Jul. 2, 2014 for U.S. Appl. No. 13/154,989.
Final Office Action dated Aug. 1, 2014 for U.S. Appl. No. 12/454,799.
Final Office Action dated Aug. 29, 2014 for U.S. Appl. No. 12/467,755.
Final Office Action dated Feb. 4, 2016 for U.S. Appl. No. 12/467,755.
Final Office Action dated Nov. 25, 2015 for U.S. Appl. No. 12/454,799.
Stratagene Catalog. gene characterization kits. Stratagene Catalog, p. 39, 1988.
Office Action dated Jun. 22, 2012 for U.S. Appl. No. 13/363,022.
Final Office Action dated Dec. 10, 2012 for U.S. Appl. No. 13/363,022.
Notice of Allowance dated Jan. 15, 2013 for U.S. Appl. No. 13/363,022.
Office Action dated Sep. 20, 2012 for U.S. Appl. No. 13/016,811.
Notice of Allowance dated Oct. 23, 2013 for U.S. Appl. No. 13/016,811.
Office Action dated Jan. 30, 2014 for U.S. Appl. No. 13/154,989.
Andronescu, et al., "A New Algorithm for RNA Secondary Structure Design", Preprint submitted to Elsevier Science, pp. 1-32, Dec. 11, 2003.
Mathews, David H., et al, "22 predicting RNA secondary structure." Cold Spring Harbor Monograph Archive 43, pp. 631-657, 2006.
Zadeh, "Algorithms for nucleic acid sequence design." Doctoral Thesis [online[, orally defended Dec. 8, 2009 (Aug. 12, 2009), published May 25, 2010 (May 25, 2010), [Retrieved on Jun. 7, 2011], pp. 1-85, Retrieved from the Internet: <URL: http://resolver.caltech.edu/CaltechTHESIS:05112010-205335518>
Zadeh, "Algorithms for nucleic acid sequence design," Doctoral Thesis, defended Dec. 8, 2009; Abstract only [online]; downloaded from URL: http://thesis.library.caltech.edu/5801/ on Jul. 6, 2011.
Zadeh, J.N.; Wolfe, B.R.; Pierce, N. A "Nucleic acid sequence design via efficient ensemble defect optimization" J. Comput. Chem. 2011, 32, 439-452.
International Search Report and Written Opinion of the International Searching Authority for PCT/US11/31127, dated Oct. 31, 2011.
Office Action dated Jan. 5, 2017 for U.S. Appl. No. 14/033,081.

(56) References Cited

OTHER PUBLICATIONS

National Science Foundation, "These Cells Will Self-Destruct in Five . . . Four . . .", Press Release 10-160, pp. 1-3, dated Sep. 6, 2010, downloaded on Sep. 16, 2010.
Venkataraman et al. Abstract of "Selective Cell Death Mediated by Small Conditional RNAs", Proc Natl Acad Sci USA, early edition, http://www.pnas.org/content/early/2010/09/01/1006377107.abstract, Article published Sep. 20, 2010.
Final Office Action dated Feb. 7, 2017 for U.S. Appl. No. 14/320,479.
Office Action dated Oct. 12, 2016 for U.S. Appl. No. 14/320,479.
Office Action dated Feb. 22, 2017 for U.S. Appl. No. 14/497,070.
Response to Office Action filed on Jan. 12, 2017 in U.S. Appl. No. 14/320,479.
Restriction Requirement dated Feb. 23, 2006 in U.S. Appl. No. 11/087,937.
Office Action dated Apr. 27, 2006 in U.S. Appl. No. 11/087,937.
Office Action dated Mar. 1, 2007 in U.S. Appl. No. 11/087,937.
Office Action dated Aug. 23, 2007 in U.S. Appl. No. 11/087,937.
Office Action dated Mar. 25, 2008 in U.S. Appl. No. 11/087,937.
Office Action dated Sep. 26, 2008 in U.S. Appl. No. 11/087,937.
Office Action dated Apr. 30, 2008 in U.S. Appl. No. 11/371,347.
Office Action dated Dec. 3, 2008 in U.S. Appl. No. 11/371,347.
Office Action dated Mar. 26, 2008 in U.S. Appl. No. 11/371,346.
Office Action dated Oct. 16, 2008 in U.S. Appl. No. 11/371,346.
Office Action dated Mar. 20, 2009 in U.S. Appl. No. 11/371,346.
Office Action dated Sep. 29, 2009 in U.S. Appl. No. 11/371,346.
Office Action dated Sep. 21, 2011 in U.S. Appl. No. 12/790,379.
Office Action dated Feb. 8, 2008 in U.S. Appl. No. 11/544,306.
Office Action dated Oct. 15, 2008 in U.S. Appl. No. 11/544,306.
Office Action dated Mar. 19, 2009 in U.S. Appl. No. 11/544,306.
Office Action dated Sep. 2, 2009 in U.S. Appl. No. 11/544,306.
Office Action dated Dec. 24, 2009 in U.S. Appl. No. 11/544,306.
Office Action dated Sep. 19, 2012 in U.S. Appl. No. 12/395,489.
Office Action dated Jul. 2, 2012 in U.S. Appl. No. 13/079,747.
Notice of Allowance dated Apr. 25, 2017 in U.S. Appl. No. 14/320,479.
Notice to File Corrected Application Papers dated May 22, 2017 in U.S. Appl. No. 14/320,479.
Notice Regarding IDS dated May 25, 2017 in U.S. Appl. No. 14/320,479.
Interview Summary dated Jun. 21, 2017 in U.S. Appl. No. 14/320,479.
Interview Summary dated Mar. 29, 2017 in U.S. Appl. No. 14/033,081.

* cited by examiner

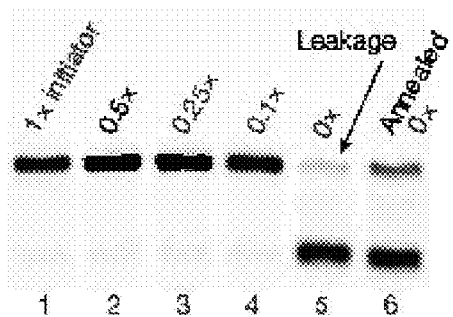
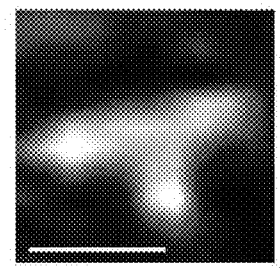
Figure 2c
Figure 2d
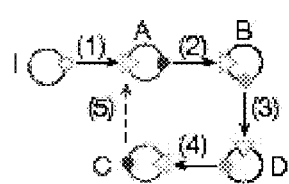
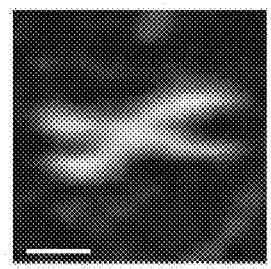
Figure 2e
Figure 2f

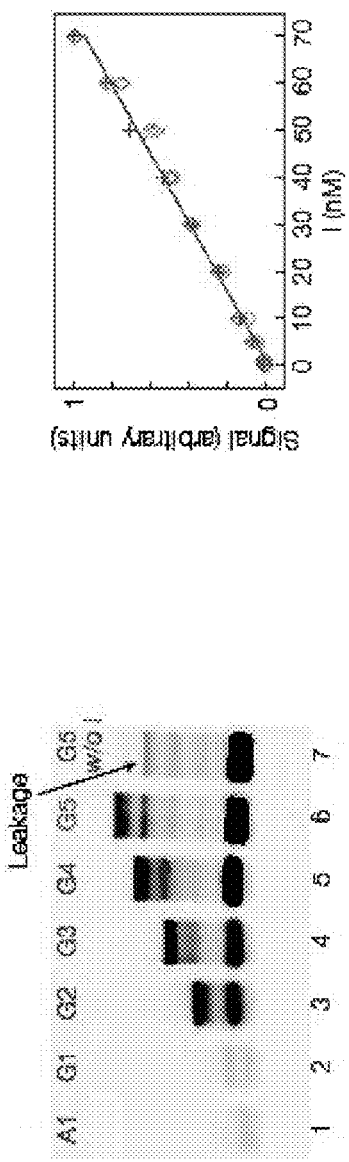
Figure 4c
Figure 4d
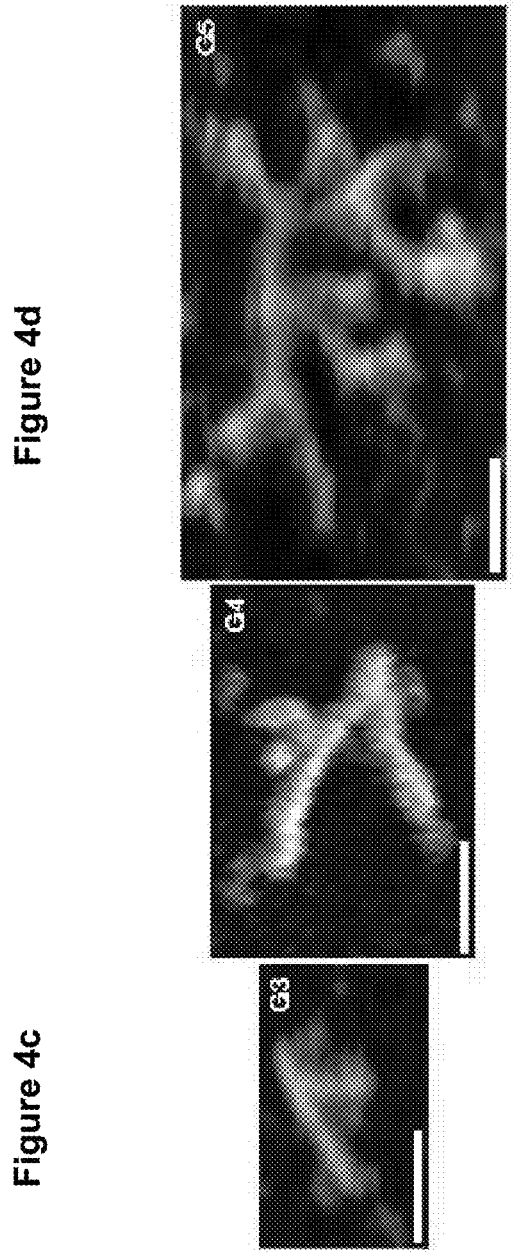
Figure 4e

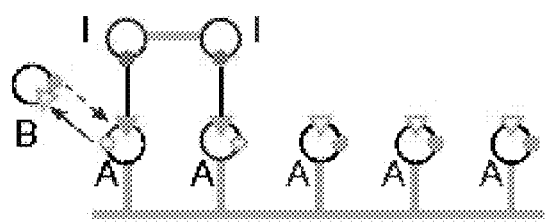
Figure 5a
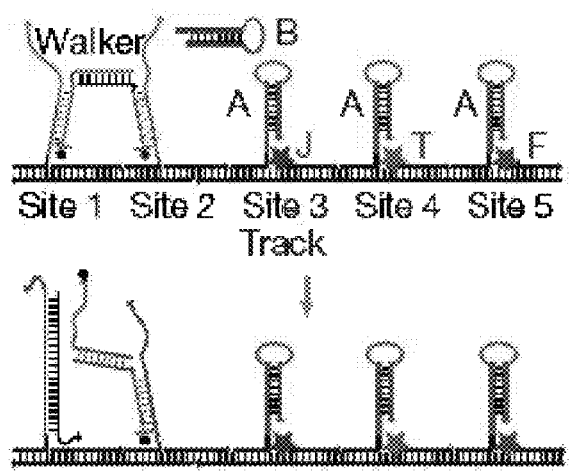
Figure 5b
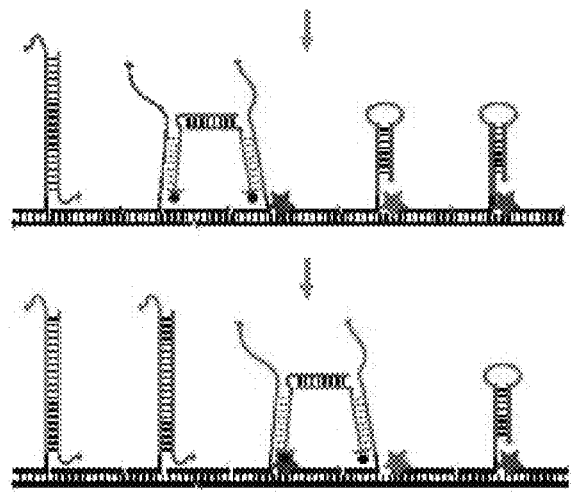

Figure 6a Target dynamic function: Catalytic formation of a 3-arm DNA junction (1) Pathway specifiation (2.1) Complementarity relationships (2.2) Clamping/padding    Figure 6c

(2.3) Dimensioning    Figure 6d

|a| = |b| = |c| = |x| = |y| = |z| = 6 nt (3) Sequence design    Figure 6e

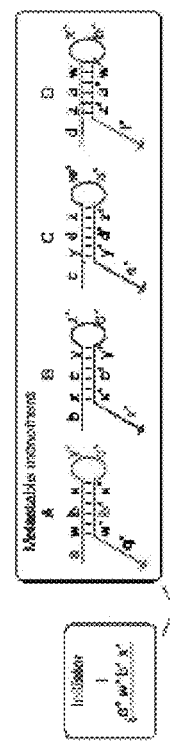
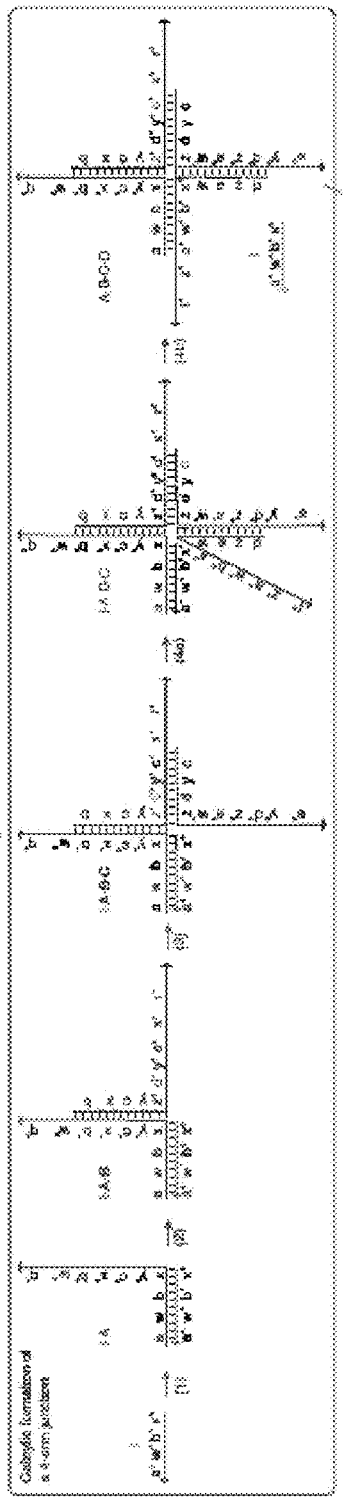
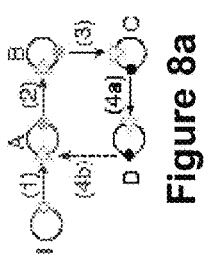
Figure 8a
Figure 8b
Figure 8c
Figure 8d initiator + monomers branched two-dimensional structure three-dimensional shape

........................................................................

initiator + monomers (A1, A2, A3, B1, B2, B3, C1, C2, and C3)

branched three-arm junction (A1 + A2 + A3)

tetrahedron (A1 + A2 + A3 + B1 + B2 + B3 + C1 + C2 + C3)

BIOMOLECULAR SELF-ASSEMBLY

REFERENCE TO RELATED APPLICATIONS

The present application claims priority to U.S. Provisional Application No. 61/366,091, filed Jul. 20, 2010, which is incorporated herein by reference in its entirety.

STATEMENT REGARDING FEDERALLY SPONSORED R&D

This invention was made with government support under grant #5P50HG004071 awarded by the NIH. The government has certain rights in the invention.

SEQUENCE LISTING IN ELECTRONIC FORMAT

The present application is being filed along with a Sequence Listing in electronic format. The Sequence Listing is provided as a file entitled CALTE_069_A Sequence_Listing.TXT, created on Jul. 19, 2011, which is 27,290 bytes in size. The information in the electronic format of the Sequence Listing is incorporated herein by reference in its entirety.

BACKGROUND

Field

The present invention relates generally to programming of biomolecular self-assembly pathways and related methods and constructs for self-assembly of prescribed three-dimensional structures and/or closed-loop two-dimensional structures.

Background

Molecular self-assembly, a fundamental process underlying the replication and regulation of biological systems, has emerged as an important engineering paradigm for nanotechnology. For example, molecular nanotechnology uses positionally-controlled mechanosynthesis guided by molecular systems. Molecular nanotechnology involves combining physical principles demonstrated by the molecular machinery of life, chemistry, and other nanotechnologies with the systems engineering principles found in modern macroscale factories.

In biological systems, self-assembling and disassembling complexes of proteins and nucleic acids bound to a variety of ligands perform intricate and diverse dynamic functions. Attempts to rationally encode structure and function into synthetic amino and nucleic acid sequences have largely focused on engineering molecules that self-assemble into prescribed target structures without explicit concern for transient system dynamics. See, Butterfoss, G. L. & Kuhlman, *Annu. Rev. Bioph. Biom.* 35, 49-65 (2006); Seeman, N.C., *Nature* 421, 427-431 (2003).

Current protocols for self-assembling synthetic DNA nanostructures often rely on annealing procedures to bring interacting DNA strands to equilibrium on the free energy landscape. Winfree et al., *Nature* 394, 539-544 (1998); Shih et al., *Nature* 427, 618-621 (2004); Rothemund, *Nature* 440, 297-302 (2006). Self-assembly in biology proceeds isothermally and assembly kinetics are often controlled by catalysts. To date, synthetic DNA catalysts have been used to control the kinetics of the formation of DNA duplex structures. Turberfield, A. J. et al., *Phys. Rev. Lett.* 90, 118102 (2003); Bois, J. S. et al., *Nucleic Acids Res.* 33, 4090-4095 (2005); Green, S. J. et al., *Biophys. J.* 91, 2966-2975 (2006); Seelig, G. et al., *J. Am. Chem. Soc.* 128, 12211-12220 (2006).

SUMMARY

In some embodiments, the present teachings provide methods and products pertaining to biomolecular self-assembly pathways. In some embodiments, the methods and products disclosed herein pertain to initiating and/or carrying out dynamic functions. In some embodiments, the methods and compositions disclosed herein are beneficial for providing, for example, without limitation, bio-markers and smart therapeutics that can detect a disease marker and activate a therapeutic biological pathway.

In some embodiments, a composition is provided. The composition can comprise a first hairpin monomer, a second hairpin monomer, and a third hairpin monomer, where upon binding of the first hairpin monomer to an initiator molecule, the first monomer, the second monomer, and the third monomer self-assemble in a set order and into a prescribed three-dimensional structure.

In some embodiments, the hairpin monomers comprise nucleic acid sequences such that the first hairpin monomer and the initiator molecule first assemble into a two-dimensional shape.

In some embodiments, the second and third hairpin monomers comprise a nucleic acid sequence such that they hybridize to the two-dimensional shape and transform it into a three-dimensional shape.

In some embodiments, the first hairpin monomers comprises a first domain comprising a first toehold and a first propagation region, where the first toehold is exposed such that it is available to hybridize to a portion of a first nucleic acid sequence complementary to the first domain, and where the first toehold is located at an end of the monomer; and a second domain comprising a second toehold, where the second toehold is hybridized to a portion of the first propagation region.

In some embodiments, the first nucleic acid sequence complementary to the first domain of the first hairpin monomer comprises a portion of the initiator molecule.

In some embodiments, the second toehold is configured to become available to hybridize to a second nucleic acid sequence of the second hairpin monomer if the first domain of the first hairpin monomer hybridizes to the initiator molecule.

In some embodiments, the second domain of the first hairpin monomer further comprises a second propagation region, where the second propagation region is complementary to a portion of the second hairpin monomer.

In some embodiments, the second toehold is configured to become available to initiate hybridization of the second propagation region to the portion of the second hairpin monomer if the first domain hybridizes to the first nucleic acid sequence complementary to the first domain.

In some embodiments, the second propagation region comprises a portion of a single stranded hairpin loop.

In some embodiments, a portion of the first propagation region and the second toehold comprise a portion of a duplex stem.

In some embodiments, the first toehold is single stranded.
In some embodiments, the composition further comprises the initiator molecule.

In some embodiments, a method for assembling a prescribed three-dimensional structure is provided. The method can comprise combining an initiator molecule, a first hairpin monomer, a second hairpin monomer, and a third hairpin monomer; and incubating the mixture under isothermal conditions such that the first hairpin monomer binds to the initiator molecule, which then allows for the second hairpin monomer to hybridize to the first hairpin monomer, which then allows for the third hairpin monomer to hybridize to the second hairpin monomer, thereby assembling the first, second, and third hairpin monomers into a prescribed three-dimensional structure.

In some embodiments, a method for assembling a prescribed closed structure is provided. The method can comprise combining an initiator molecule, a first hairpin monomer, and a second hairpin monomer; and incubating the mixture under isothermal conditions such that the first hairpin monomer and the initiator molecule hybridize, which then allows for the second hairpin monomer to hybridize to the first hairpin monomer, thereby assembling the initiator molecule, the first hairpin monomer, and the second hairpin monomer into a prescribed closed structure.

In some embodiments, the prescribed closed structure is a two-dimensional structure.

In some embodiments, the prescribed closed structure is a three-dimensional structure.

A portion of the disclosure provided herein is also provided in U.S. patent application Ser. No. 12/152,893, which is herein incorporated by reference in its entirety.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Several of the figures described herein are also provided in U.S. patent application Ser. No. 12/152,893, which is herein incorporated by reference, including without limitation for the purpose of providing color drawings.

FIGS. 2a-f generally depict catalytic self-assembly of three-arm and four-arm branched junctions. The small letters represent sequence segments. Letters marked with an asterisk (*) are complementary to the corresponding unmarked letter. a, Reaction graph for three-arm junctions. b, Secondary structure mechanism. c, Agarose gel electrophoresis demonstrating catalytic self-assembly for the three-arm system with 750-nM hairpins. d, AFM image of a three-arm junction. Scale bar: 10 nm. e, Reaction graph and f, AFM image for a four-arm junction. Scale bar: 10 nm.

FIGS. 4a-e generally depict triggered assembly of quantized binary molecular trees. a, Reaction graph. Multiple assembly arrows entering the same input port depict parallel processes on separate copies of the nodal species. b, Secondary structure mechanism. c, Agarose gel electrophoresis demonstrating triggered self-assembly. Lanes 1-6: the dominant reaction band shifts with the addition of each generation of hairpins. Subdominant bands are presumed to represent imperfect dendrimers. Lane 7: minimal conversion to reaction products in the absence of initiator. Hairpins A1, A2, B2 at 62.5 nM; the concentration doubles for each subsequent generation of hairpins. Initiator I at 50 nM. d, Linear relationship between amplification signal (putative G5 reaction product) and initiator for three independent experiments (cross, diamond, circle). e, AFM imaging of dendrimers for G=3, 4, and 5.

FIGS. 5a-f generally depict stochastic movement of a bipedal walker. a, Reaction graph. Bonds between output ports on I and input ports on A represent initial conditions. Static structural elements are depicted by grey line segments. b, Secondary structure mechanism depicting processive locomotion. c-f, Fluorescence quenching experiments measuring the proximity of the quenchers (black dots) on the walker feet to the fluorophores (colored stars) decorating the track. Fitted curves (solid) are used to determine the time at which the minimum fluorescence (maximum quenching) was observed (dashed vertical line) for each fluorophore. c, Bipedal walker with track labeled by fluorophores JOE (green star)→TAMRA (red)→FAM (blue) as in b. d, Monopedal walkers on the same track (JOE (orange star)→TAMRA (pale green)→FAM (pale blue)). e, Comparison of time scales for bipedal and monopedal walkers (eighteen traces per walker type: three fluorophores, six experiments). f, Bipedal walker with track labeled TAMRA (red star)→JOE (green)→FAM (blue).

FIGS. 6a-f generally depict the procedure for designing the catalytic e-arm junction system. a, the desired dynamic behavior: catalytic formation of a 3-arm DNA junction. b, Reaction graph for catalytic formation of a 3-arm DNA junction. c, Translation of the reaction graph to the secondary structure hairpin monomers. d, Addition of clamping and padding segments. e, Dimensioning. f, Sequence design. Green dot=A (adenine), blue dot=C (cytosine), black dot=G (guanine) and red dot=T (thymine).

FIGS. 8a-d depict catalytic formation of a 4-arm DNA junction. a, Reaction graph. Note: green output ports do not serve as initiators for any downstream reaction, and are omitted here for simplicity. b, Secondary structure schematic of the reaction. c, Agarose gel electrophoresis demonstrates the catalytic formation of the 4-arm junction. d, AFM images of two 4-arm junctions. Scale bar, 10 nm.

DETAILED DESCRIPTION

Figure 1A:
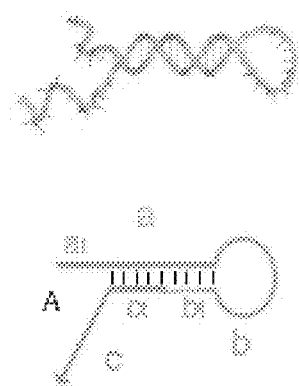
FIGS. 1a-f generally depict various aspects of one embodiment for programming biomolecular self-assembly pathways. a, secondary structure of a hairpin monomer. Colored lines represent strand domains; short black lines represent base pairs; arrowheads indicate 3' ends. The small letters represent sequence segments. b, Secondary structure mechanism illustrating assembly and disassembly reactions during catalytic duplex formation. Letters marked with an asterisk (*) are complementary to the corresponding unmarked letter. c, Abstraction of the motif A as a node with three ports (color/shade use is consistent with a). d, A reaction graph representing a molecular program executed schematically in b and e. e, Execution of the reaction graph of d. f, Hierarchical design process.

Various embodiments disclosed herein are generally directed towards programming biomolecular self-assembly pathways for dynamic functions as well as related methods and structures.

In some embodiments, the compositions and methods described herein pertain to hairpin monomers that are capable of self-assemble in a set order and thus into a prescribed three-dimensional structure. In some embodiments, the hairpin monomers self assemble into a prescribed two dimensional structure, such as a closed loop structure.

In some embodiments, the compositions and methods described herein pertain to structures that comprise a first hairpin monomer, a second hairpin monomer, and a third hairpin monomer, where upon binding of the first hairpin monomer to an initiator molecule, the first monomer, the second monomer, and the third monomer self-assemble in a set order and into a prescribed three-dimensional structure. This self-assembly can be performed under isothermal conditions and in a kinetically controlled manner, avoiding kinetic traps and permitting the environmental responsive assembly of complex molecular structures under in vivo conditions (e.g., in living cells).

A new approach to diverse molecular self-assembly pathways has been developed based on the rewiring of complementarity relationships between modular domains in a versatile hairpin motif. Monomer and polymer sequences can be encoded with the reaction pathways by which self-assembly occurs. In some embodiments, this allows them to perform dynamic functions without human intervention. By programming complementarity relationships between domains within the hairpin motif, systems can be engineered to exhibit a wide variety of dynamic behaviors. The modular programmability of the hairpin motif can be used to facilitate the conversion of conceptual dynamical system designs into physical molecular implementations, enabling new approaches to fabrication, amplification, and transport (see, Yin et al., Nature 451(7176), 318-322; Supplementary Information pages 1-49 (2008), which is incorporated herein by reference in its entirety).

The versatile hairpin motif can be used to implement a variety of dynamic functions through self-assembly pathways. In some embodiments, starting from a conceptual dynamic function, a molecular implementation can be realized in three steps: (1) pathway specification via a "reaction graph"; (2) translation of the reaction graph into a secondary structure mechanism using monomers having the hairpin motif ("hairpin monomers"); and (3) computational design of hairpin monomer primary sequences.

Methods and compositions for programming biomolecular self-assembly pathways for dynamic functions, including, without limitation, molecular programming of catalytic geometry, catalytic circuitry, non-catalytic geometry, non-catalytic circuitry, nucleated dendritic growth and autonomous locomotion are provided. In some embodiments, hairpin monomers to implement various dynamic functions are provided. In some embodiments, methods for designing hairpin monomers to implement dynamic functions are provided. In various embodiments, compositions and methods are provided for systems with catalytic geometry, catalytic circuitry, non-catalytic geometry, non-catalytic circuitry, nucleated dendritic growth or autonomous locomotion.

Figure 1B:
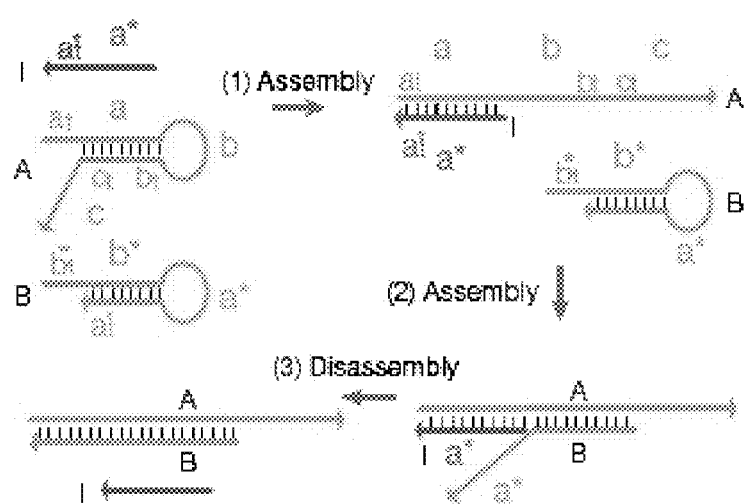
Figures 1C, 1D:
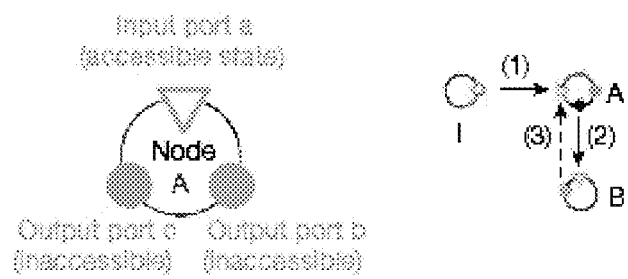
Figure 1E:
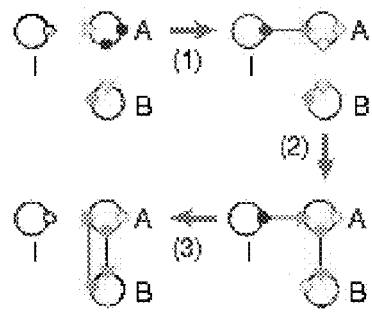
Figure 1F:
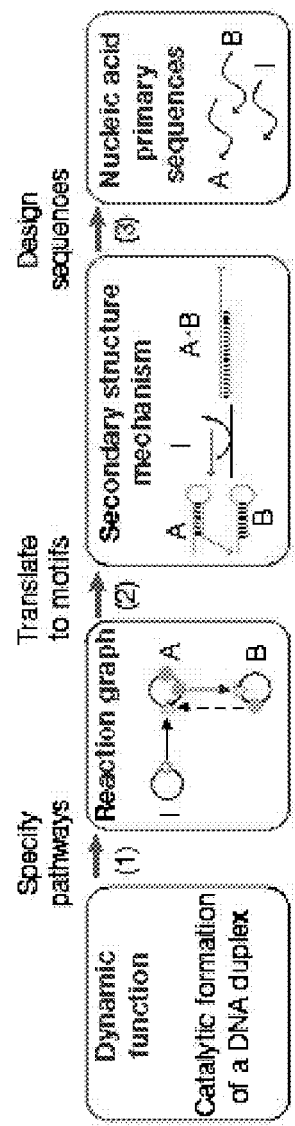

One embodiment for programming a biomolecular self-assembly pathway is summarized in FIG. 1f. As shown in FIG. 1f, beginning with the dynamic function of, for example, the catalytic formation of a DNA duplex, a reaction graph using nodal abstractions is specified (step (1)). Next, the reaction graph is translated into motifs. In particular, hairpin monomers are designed encompassing the second structure mechanism of the functions provided by the reaction graph (step (2)). Then the primary sequences of the hairpin monomers are designed (step (3)).

A schematic depiction of the secondary structure of a hairpin monomer, which embodies the versatile hairpin motif, according to various embodiments disclosed herein is shown in FIG. 1a. The hairpin monomer (A) shown in FIG. 1a comprises three concatenated domains, a, b, and c. In other embodiments, monomers can comprise two or more concatenated domains. In preferred embodiments, each domain has a nucleation site called a toehold. For example, in FIG. 1a the toeholds are denoted $a_t$, $b_t$, and $c_t$, respectively. Preferably, a domain further comprises a propagation region. In some embodiments, the propagation region can be the portion of a domain that is not the toehold. Typically, a hairpin monomer comprises at least one input domain, and at least one output domain. In some embodiments, the input domain can be an initiator binding domain. For example, in FIG. 1a, domain a of hairpin monomer A is an initiator binding domain. In some embodiments, an output domain can be an assembly domain or a disassembly domain. For example, in FIG. 1b, domain b of hairpin monomer A is an assembly domain, and in domain a* of hairpin monomer B is a disassembly domain.

Two basic reactions can be programmed using the hairpin motif, as illustrated for one possible example of catalytic duplex formation in FIG. 1b. The reaction in FIG. 1b utilizes two hairpin monomers, A and B, each having two concatenated domains, a and b. First, an assembly reaction (1) occurs when a single-stranded initiator I, containing an exposed toehold $a_t*$, nucleates at the exposed toehold $a_t$ of input domain a (also called the "initiator binding domain") of hairpin monomer A, initiating a branch migration that opens the hairpin. Hairpin output domains b and c, with newly exposed toeholds $b_t$ and $c_t$, can then serve as assembly initiators for other suitably defined hairpins, permitting cascading (e.g., in reaction (2), output domain b (an "assembly domain") of hairpin monomer A assembles with input domain b* (an "assembly complement domain") of hairpin monomer B, opening the hairpin). Second, a disassembly reaction (3) occurs when a single-stranded output domain a* of B (a "disassembly domain") initiates a branch migration that displaces the initiator I from A. In this example, I catalyzes the formation of duplex A•B via a prescribed reaction pathway.

To assist in programming more complex reaction pathways, a hairpin monomer can be abstracted as a node with input and output ports, with the state of the ports being indicated as either accessible or inaccessible. For example, the hairpin monomer of FIG. 1a can be abstracted as a node with three ports (FIG. 1c): a triangular input port and two circular output ports. The shade/color use for the nodal abstraction in FIG. 1c is consistent with FIG. 1a. The state of each port is either accessible (open triangle/circle) or inaccessible (solid triangle/circle), depending on whether the toehold of the corresponding hairpin domain is exposed or sequestered. Functional relationships between ports within a node are implicit in the definition of the nodal abstraction corresponding to a particular motif (e.g., for the node of FIG. 1c, the output ports flip to accessible states if the input port is flipped to an inaccessible state through an interaction with a complementary upstream output port).

Depicting assembly reactions by, for example, solid arrows and disassembly reactions by dashed arrows (each directed from an output port to a complementary input port of a different node), reaction pathways can be specified abstractly in the form of a reaction graph, representing a program to be executed by molecules such as, for example, nucleic acid molecules.

A reaction graph provides a simple representation of assembly (and disassembly) pathways that can be translated directly into molecular executables: nodes represent motifs, ports represent domains, states describe accessibility, arrows represent assembly and disassembly reactions between complementary ports. For example, the reactions depicted in the secondary structure mechanism of FIG. 1b are specified using a reaction graph in FIG. 1d. Conventions for the reaction graphs disclosed herein are provided below. The initial conditions for the program are described via the state (accessible or inaccessible) of each port in a reaction graph. FIG. 1e depicts the execution of this reaction graph through cascaded assembly and disassembly reactions. An assembly reaction is executed when ports connected by a solid arrow are simultaneously accessible.

The hairpin monomer functions as a modular programmable kinetic trap, and rewiring the connections between nodes in the reaction graph corresponds to rewiring the connections between kinetic traps in the underlying free energy landscape. In the physical systems, metastable hairpins are initially caught in engineered kinetic traps; the introduction of initiator molecules begins a chain reaction of kinetic escapes in which the hairpin species interact via programmed assembly and, optionally, disassembly steps to implement dynamic functions. Preferably, the time scale of metastability for kinetically trapped molecules is longer than the time scale relevant for the execution of the program.

As will be appreciated by one of skill in the art, the ability to design and implement biomolecular self-assembly (and disassembly) pathways can have great benefit, especially for engineering functional mechanical systems at the molecular scale. For example, the methods and compositions disclosed herein are beneficial for, inter alfa, smart materials (e.g., artificial drugs and self-healing structures), nanosensors (e.g., photosensors), nanofacturing, nanorobots (e.g., replicating nanorobots and medical nanorobots), utility fog, and phased-array optics. In some embodiments, methods and compositions disclosed herein are beneficial for providing, for example without limitation, smart therapeutics that can detect a disease marker (e.g., mutant mRNA known to cause cancer) and then activate a therapeutic biological pathway (e.g., kill the cancer cell leaving healthy cells untouched).

The above and additional embodiments are discussed in more detail below, after a brief discussion of the definitions some of the terms used in the specification.

DEFINITIONS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

A "self-assembly pathway" is a series of reactions autonomously executed by monomers in the formation of a polymer. The self-assembly pathway comprises assembly, or polymerization, of monomers. In some embodiments, the self-assembly pathway can also comprise one or more disassembly reactions.

The term "nucleic acid" refers to natural nucleic acids, artificial nucleic acids, analogs thereof, or combinations thereof. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

The term "hairpin" as used herein refers to a structure formed by intramolecular base pairing in a single-stranded polynucleotide ending in an unpaired loop (the "hairpin loop"). In various embodiments, hairpins comprise a hairpin loop protected by stems. For example, a hairpin can comprise a first stem region, a hairpin loop region, and a second stem region. The first and second stem regions can hybridize to each other and together form a duplex region. Thus, a stem region of a hairpin monomer is a region that hybridizes to a complementary portion of the same monomer to form the duplex stem of a hairpin.

The term "hairpin loop" refers to a single stranded region that loops back on itself and is closed by a single base pair.

"Interior loop" and "internal loop," are used interchangeably and refer to a loop closed by two base pairs. The closing base pairs are separate by single stranded regions of zero or more bases. A "bulge loop" is an interior loop where one of the separated single-stranded regions is zero bases in length and the other is greater than zero bases in length.

An "initiator" is a molecule that is able to initiate the polymerization of monomers. Preferred initiators comprise a nucleic acid region that is complementary to the initiator binding domain of a monomer.

"Monomers" as used herein refers to individual nucleic acid oligomers. Typically, at least two monomers are used in self-assembly pathways, although three, four, five, six or more monomers may be used. Typically each monomer comprises at least one domain that is complementary to at least a portion of one other monomer being used for the self-assembly pathway. Monomers are discussed in more detail below. In some embodiments, a monomer can have a hairpin motif. A monomer having a hairpin motif is referred to as a "hairpin monomer." In other embodiments, a monomer can be an initiator.

The term "domain" refers to a portion of a monomer comprising a sequence. Preferably, a domain of a hairpin monomer comprises a toehold and a propagation region. An "input domain" of a monomer refers to a domain that is configured to receive a signal which initiates a physical and/or chemical change, such as, a for example, a conformational change, of the monomer. Preferably, the signal is binding of a complementary sequence to the domain, typically beginning at the toehold. In some embodiments, an input domain can be an initiator binding domain, an assembly complement domain, or a disassembly complement domain. An "output domain" of a monomer refers to a domain that is configured to confer a signal. Preferably, the signal is binding of a complementary sequence to an input domain. In some embodiments, an output domain is configured to confer a signal to an input domain of another monomer. In some embodiments, an output domain can be, for example, an assembly domain, or a disassembly domain. In some embodiments, an output domain can be present in an initiator.

A first monomer in a self-assembly pathway preferably has an initiator binding or input domain (e.g., domain a of monomer A in FIG. 1a) that is complementary to a portion of an initiator. The initiator binding domain preferably has an exposed toehold. Binding of the initiator to the initiator binding domain initiates the self-assembly pathway. An initiator binding domain is an input domain.

A monomer preferably has at least one output domain (e.g., domain b of monomer A in FIG. 1a) that is complementary to an input domain of another monomer. An output domain on a hairpin monomer is preferably only available to interact with the input domain of the other monomer when a self-assembly pathway has been started by the initiator. For example, the assembly domain of a first monomer becomes available to hybridize to the assembly complement domain of a second monomer when the first monomer has already hybridized to at least a portion of an initiator, as discussed in more detail below.

The term "nucleate" as used herein means to begin a process of, for example, a physical and/or chemical change at a discrete point in a system. The term "nucleation" refers to the beginning of physical and/or chemical changes at discrete points in a system. In some embodiments, nucleation of a self-assembly reaction can occur by, for example, the hybridization of a portion of an initiator to an exposed toehold of a hairpin monomer.

The term "toehold" refers to nucleation site of a domain comprising a nucleic acid sequence designed to initiate hybridization of the domain with a complementary nucleic acid sequence. The secondary structure of a monomer may be such that the toehold is exposed or sequestered. For example, in some embodiments, the secondary structure of the toehold is such that the toehold is available to hybridize to a complementary nucleic acid (the toehold is "exposed," or "accessible"), and in other embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the hairpin of which it is a part of. When exposed, a toehold is configured such that a complementary nucleic acid sequence can nucleate at the toehold. In some embodiments, nucleation of a complementary nucleic acid sequence at an exposed toehold initiates branch migration that opens up the hairpin of a hairpin monomer.

A "propagation region" as used herein refers to a portion of a domain of a hairpin monomer that is configured to hybridize to a complementary nucleic acid sequence of another hairpin monomer once the toehold of the domain nucleates at an exposed toehold of the other hairpin monomer. The propagation region of a hairpin monomer is configured such that an available complementary nucleic acid sequence does not nucleate at the propagation region; rather, the propagation region hybridizes to a complementary nucleic acid sequence only after nucleation at the toehold of the same domain.

In some embodiments, monomers can be "metastable." That is, in the absence of an initiator they are kinetically disfavored from associating with other monomers comprising complementary regions.

As used herein, the terms "polymerization" and "assembly" are used interchangeably and refer to the association of two or more monomers, or one or more monomers and an initiator, to form a polymer. The "polymer" may comprise covalent bonds, non-covalent bonds or both. For example, in some embodiments three species of monomers can hybridize sequentially to form a polymer comprising a three-arm branched junction.

As used herein term "disassembly" refers to the disassociation of an initiator or at least one monomer from a polymer or another monomer. For example, polymers can disassemble from polymers, and monomers can disassemble from polymers.

As used herein "reaction graph" refers to a representation of assembly (and, optionally, disassembly) pathways that can be translated into molecular executables.

As used herein the terms "flip" and "switch" are used interchangeably and refer to a change from one state (e.g., accessible) to another state (e.g., inaccessible).

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or a by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

In some embodiments, "complementarity" can be perfect complementarity. In some embodiments, "complementarity" simply denotes that the sequences are complementary enough to allow for selective self-hybridization, and selective opening into the larger two or three dimensional structure, for a given purpose.

The term "closed structure" denotes that at least one structural element of a denoted nucleic acid structure has been closed to form, for example, a closed loop or other closed arrangement. Not all of the parts in the system need be closed. In some embodiments, the structure defines a closed volume structure, such as a three dimensional triangle, pyramid, cube, etc. In some embodiments, the arms of the self-assembled structure define a perimeter of the three-dimensional shape.

System Design

Starting from a conceptual dynamic function, molecular implementation of a self-assembly pathway can be realized in three steps as summarized in, for example, FIG. 1*f*.

Step 1: Pathway specification. In some embodiments, the pathway that implements a target dynamic function can be specified using a reaction graph, discussed in detail below. A reaction graph provides a simple representation of assembly (and disassembly) pathways that can be translated into molecular executables. For example, nodes in the reaction graph represent hairpin monomers, ports of the nodes represent domains, states of the ports describe accessibility, and arrows between the nodes represent assembly and disassembly reactions between complementary ports. An assembly reaction is executed when ports connected by a solid arrow are simultaneously accessible.

Step 2: Translation to motifs. The reaction graph can be directly translated to hairpin monomer secondary structures. In other words, hairpin monomer secondary structures can be modeled and designed based on the nodes and functional relationships represented in the reaction graph. For example, a node in a reaction graph can be translated into a hairpin monomer. The ports on the node can be translated into the domains of the hairpin monomer. More particularly, an input port on a node can be translated into an input domain of a hairpin monomer, and an output port can be translated into an output domain. The functional relationships between the nodes in the reaction graph can be translated into the functionality of the domains of the hairpin monomer. Initial dimensioning of the number of nucleotides in each segment can be performed using, for example, the NUPACK server, which models the behavior of strand species in the context of a dilute solution. Dirks et al., *SIMA Rev.* 49, 65-88 (2007). Several examples of hairpin monomer secondary structure design based on a reaction graph are provided below.

Step 3: Sequence design. The composition of the monomers is not limited to any particular sequences or number of bases, and is designed based on the particular dynamic function. A number of criteria can be used to design the monomers to achieve the desired properties. These include, for example and without limitation, sequence symmetry minimization, the probability of adopting the initiator secondary structure at equilibrium, the average number of incorrect nucleotides at equilibrium relative to the target structure, and hybridization kinetics. In some embodiments, primary sequences of the hairpin monomers can be designed by considering a suite of structures that punctuate the intended reaction pathway. In some embodiments, structures that explicitly preclude undesired off-pathway interactions (e.g., structures specifying the absence of an interaction between two strands that should not pair) are considered in designing the hairpin monomers.

In some embodiments, the sequences can be optimized computationally to maximize affinity and specificity for a desired structure by minimizing the average number of incorrectly paired bases at equilibrium (Dirks et al., *Nucleic Acids Research*, 32:1392-1403, 2004.) In some embodiments, the optimization can be performed primarily by computer software. (R. M. Dirks and N. A. Pierce. Nucleic acid sequence design software, unpublished. 2007. J. N. Zadeh and N. A. Pierce. Multi-objective nucleic acid sequence design software, unpublished. 2007.) In some embodiments, further manual optimization based on the same design metric can be performed for a subset of crucial target structures. Monomers are described in detail below. Several examples of hairpin monomer primary sequence design based on secondary structure are provided below.

The thermodynamic behavior of the sequences can be further analyzed using, for example, the NUPACK server (www.nupack.org). (Dirks et al., SIAM Rev, 49-65-88, 2007; Zadeh et al., NUPACK: a web-based tool for the analysis and design of nucleic acid systems. *In preparation*, 2007.) Stochastic kinetic simulation (Flamm et al., RNA, 6:325-338, 2000) can also be performed to confirm the absence of significant kinetic traps along the target reaction pathways. (J. M. Schaeffer and E. Winfree. Multi-stranded kinetic simulation software, unpublished).

The physical self-assembly pathway system components (e.g., hairpin monomers) can be prepared using standard methods, including, for example, commercially available nucleic acid synthesizers or obtained from commercial sources such as Integrated DNA Technologies (Coralville, Iowa). The monomers and polymers can be verified using, for example and without limitation, gel electrophoresis, bulk fluorescence quenching, or single-molecule atomic force microscopy (AFM), discussed below.

Reaction Graph Conventions

This section provides conventions for the reaction graphs described and depicted herein. Of course, as will be appreciated by those of skill in the art, reaction graphs representing the self-assembly pathways described herein can be prepared using conventions other than those described below to achieve the same results.

Initial conditions. The initial condition of the system is defined by the state of each port and the initial bonds between the ports. An initial bond between an output port and an input port implies that an assembly reaction has already occurred prior to the execution of the reaction graph (see, e.g., the bond between the output port of I and the input port of A in FIG. 5*a*).

Static structural elements. Static structural elements are depicted by gray line segments (e.g., the substrate of FIG. 5*a*) and are inert during execution of the reaction graph. These elements can be used to impose geometric constraints on the execution of the reaction graph (e.g., the rigid substrate and inextensible torso of the walker system).

Execution starting points. Execution begins with any solid arrow (assembly reaction) connecting two accessible ports. In a system lacking two accessible ports connected by a solid arrow, execution cannot begin (e.g., the removal of node I can prevent execution of the pathway).

Assembly reaction. An assembly reaction is depicted by a solid arrow that points from an input port to a complementary output port of a different node. An assembly reaction is executed when these two ports are simultaneously accessible. In the execution of an assembly reaction, a bond is formed between the two ports, they are flipped to their inaccessible states, and the internal logic of the node with the affected input port is applied to its output ports (e.g., for the present motif, the output ports are flipped to their accessible states). Multiple solid arrows entering the same input port depict parallel processes on separate copies of the nodal species (e.g., the input port of node A in FIG. 3*a* and the input ports of nodes A2-A5 and B2-B5 in FIG. 4*a*).

Figure 2A:
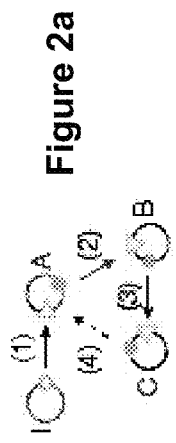

Disassembly reaction. A disassembly reaction is depicted by a dashed arrow that points from an input port to a complementary output port of a different node. Using nodal abstractions of the present hairpin motif, a disassembly arrow completes a disassembly cycle. For a cycle involving k nodes: input port 1∘blue output port 2→input port 3∘blue output port 4 . . . blue output port 2k→input port 1, where → denotes and assembly reaction, ⇢ denotes a disassembly reaction, and ∘ denotes the internal logical connection between two ports on the same node. For example, FIG. 1d contains a disassembly cycle for k=2: input port of A∘blue output of A→input port of B∘blue output port of B→input port of A. FIG. 2a contains a disassembly cycle for k=3: input port of A∘blue output of A→input port of B∘blue output port of B→input port of C∘blue output port of C→input port of A. In physical terms, the displacing strand and the strand to be displaced emanate as adjacent branches for a k-arm junction, allowing nucleation of the displacement branch migration (e.g., FIG. 2b). The special case of k=2 corresponds to standard toehold-mediate strand displacement (e.g., FIG. 1b, where the whole of domain b of hairpin A serves as the toehold). Yurke et al., *Nature* 406, 605-608 (2000).

A disassembly reaction is executed when the participating output port is accessible and the participating input port is inaccessible (using nodal abstractions of the present motif, a disassembly arrow completes a disassembly cycle implies that the participating output port can only become accessible after the participating input port becomes inaccessible).

In the execution of a disassembly reaction (e.g., FIG. 1e), the existing bond from an (inaccessible) output port to an (inaccessible) input port is replaced by a new bond to the displacing (accessible) output port; the states of both output ports are flipped.

Multiple dashed arrows entering the same input depict parallel disassembly cycles involving separate copies of the nodal species.

Reaction graphs can be extended beyond the present versatile motif by defining new nodal species that abstract the functional relationships between domains in other motifs. In some embodiments, the present hierarchical approach to rationally encoding dynamic function in nucleic acid sequences can be used in, for example, constructing a compiler for biomolecular function—an automated design process uses a modular conceptual system design as an input, and provides a set of biopolymer sequences that encode the desired dynamic system behavior as an output.

Nodal Abstractions

As discussed above, to assist in programming more complex reaction pathways, a hairpin monomer can be abstracted as a node with input and output ports, with the state of the ports being indicated as either accessible or inaccessible. For example, the hairpin monomer of FIG. 1a can be abstracted as a node with three ports (FIG. 1c): a triangular input port and two circular output ports. The color use for the nodal abstraction in FIG. 1c is consistent with FIG. 1a. The state of each port is either accessible (open triangle/circle) or inaccessible (solid triangle/circle), depending on whether the toehold of the corresponding hairpin domain is exposed or sequestered. Of course, the particular conventions used for the nodal abstractions can vary from those disclosed herein and achieve the same result. An initiator can also be abstracted as a node with an input port, with the state of the port being indicated as either accessible or inaccessible. In some embodiments, the node representing an initiator can be referred to as an initiator node. In some embodiments, the node representing an initiator can be referred to as an initiator node. In some embodiments, nodes can have multiple input ports and/or multiple output ports.

In the nodal abstractions, nodes represent hairpin monomers and initiators, ports represent domains, and the port states describe accessibility of the corresponding domains. For example, an input port represents an input domain, and an output port represents and output domain. In addition, an accessible port represents an exposed (accessible) domain, and an inaccessible port represents a sequestered (inaccessible) domain.

Functional relationships between ports within a node are implicit in the definition of the nodal abstraction corresponding to a particular motif (e.g., for the node of FIG. 1c, the output ports flip to accessible states if the input port is flipped to an inaccessible state through an interaction with a complementary upstream output port).

In some embodiments, nodal abstractions can be used in a reaction graph to model a dynamic function. Secondary structure mechanisms can then be modeled and designed based on the reaction graph. Hairpin monomer (and initiator) primary sequences can be designed from the secondary structure mechanisms.

Figure 36A:
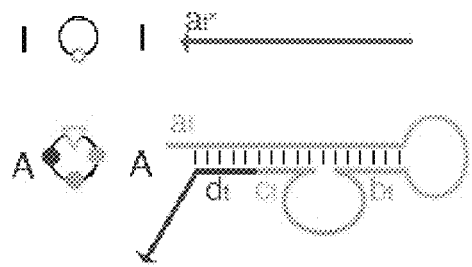
FIGS. 36a-c generally depict systems with multiple inputs and outputs. a, Node A has one initially accessible input port which controls three initially inaccessible output ports. b, Node A has an initially accessible pink input port and an initially inaccessible orange input port; these two input ports together control an initially inaccessible output port. c, In general, a node can have m inputs and n outputs.
Figure 36B:
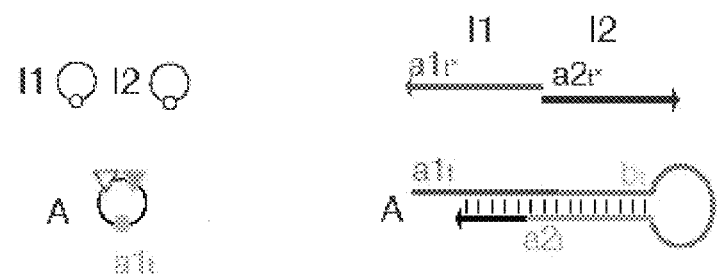
Figure 36C:

Nodes having multiple input and output ports are shown in FIGS. 36a-c. In FIG. 36a, node A has one initially accessible input port which controls three initially inaccessible output ports. It implements the molecular logic: if A's input is rendered inaccessible by the arrival of node I, then make all the three output ports accessible. The right panel depicts the molecular implementation using the hairpin motif. In FIG. 36a, toehold $a_t$ is initially accessible, while toeholds $b_t$, $c_t$, and $d_t$ are inaccessible. Initiator I can hybridize with A and opens the hairpin, rendering toeholds $b_t$, $c_t$, and $d_t$ accessible. In FIG. 36b, node A has an initially accessible pink input port and an initially inaccessible orange input port; these two input ports together control an initially inaccessible output port. It implements the molecular logic: if both of A's output ports are rendered inaccessible by the arrivals of nodes I1 and I2, then make the output port accessible. The right panel depicts the molecular implementation using the hairpin motif. In FIG. 36b, toeholds $a1_t$, is initially accessible; toehold $a2_t$ is initially inaccessible; toehold $b_t$ is initially inaccessible. Initiator I1 can hybridize with A, and renders $a2_t$ accessible; then the now accessible $a2_t$ can hybridize with I2, which opens the hairpin, rendering toehold $b_t$ accessible. Generally, a node can have m inputs and n outputs (FIG. 36c). In preferred embodiments, at least one of the input ports is initially accessible; all the output ports are initially inaccessible.

The node implements a prescribed molecular logic such that only a prescribed combination or combinations of suitable activators can activate a corresponding combination of output ports. For example, if and only upon hybridizing with initiators I1 AND (I2 OR I3) but NOT (I4 OR I5), activates output ports (O1 AND O2 AND O4).

Reaction Graphs

Self-assembly reaction pathways can be specified abstractly in the form of a reaction graph, representing a program to be executed by molecules such as, for example, nucleic acid molecules. A reaction graph provides a simple representation of assembly (and disassembly) pathways that can be translated directly into molecular executables: nodes represent hairpin monomers, ports represent domains, states describe accessibility, arrows represent assembly and disassembly reactions between complementary ports. For example, the reactions depicted in the secondary structure mechanism of FIG. 1b are specified using a reaction graph in FIG. 1d. Conventions for the reaction graphs disclosed herein are provided above.

The initial conditions for the program are described via the state of each port in a reaction graph. For example, FIG. 1e depicts the execution of this reaction graph through cascaded assembly and disassembly reactions. An assembly reaction is executed when ports connected by a solid arrow are simultaneously accessible. For example, for the initial conditions depicted in FIG. 1d, the program starts with the execution of reaction (1). Reaction 1 (assembly): In an assembly reaction (executed here by the accessible output port of I and the complementary accessible input port of A), a bond is made between the ports and they are flipped, or switched, to inaccessible states; the two output ports of A are flipped to accessible states (based on the internal logic of node A). Reaction 2 (assembly): A bond is made between the newly accessible blue output port of A and the complementary accessible input port of B and both ports are flipped to inaccessible states; the output port of B is flipped to the accessible state (based on the internal logic of node B). Reaction 3 (disassembly): In a disassembly reaction (executed here by the newly accessible output port of B, the inaccessible input port of A, and the inaccessible output port of I), the bond between the output port of I and the input port of A is displaced by a bond between the output port of B and the input port of A; the states of the two output ports are flipped. FIG. 1f summarizes the hierarchical design process starting from a conceptual dynamic function, a molecular implementation can be realized in three steps: (1) pathway specification via a reaction graph; (2) translation into secondary structure hairpin monomers; (3) computational design of hairpin monomer primary sequences.

Examples of reactions graphs are provided below and include reaction graphs for various dynamic functions, including: catalytic geometry, catalytic circuitry, non-catalytic geometry, non-catalytic circuitry, nucleated dendritic growth and autonomous locomotion.

Monomers

In some embodiments, the reaction graph can be used as a basis for modeling and designing a secondary structure mechanism using hairpin monomers. The reaction pathways by which self-assembly reactions occur are programmed within the primary sequences of the hairpin monomers.

A monomer having the hairpin motif (i.e., "hairpin monomers") typically has a hairpin structure having at least two distinct, concatenated domains. Typically, a hairpin monomer has at least one input domain and at least one output domain. In preferred embodiments, each domain comprises a nucleation site called a toehold and a propagation region. Preferably, the toehold of a first input domain is exposed and thus available to hybridize to a complementary nucleic acid of another molecule. Preferably, the propagation region of the second domain comprises at least a portion of a hairpin loop region of the hairpin monomer. In preferred embodiments, the toehold of the second domain is hybridized to a portion of the propagation region of the first domain and therefore sequestered in the duplex stem of the hairpin and unavailable to hybridize to a complementary nucleic acid of another molecule. Displacement of the propagation region of the first domain from the toehold of the second domain exposes the toehold such that is becomes available to hybridize with a complementary nucleic acid sequence of another nucleic acid, typically another monomer.

For example, in FIG. 1a, the monomer A comprises three concatenated domains, a, b and c. In FIG. 1a, domain a is an input domain, and domains b and c are output domains. In typical embodiments, a hairpin monomer comprises at least two distinct, concatenated domains. In some embodiments, a monomer can comprise two, three, four, five, six or more concatenated domains. Typically, a hairpin monomer has at least one input domain. In some embodiments, a hairpin monomer can have one, two, three, four, five, six or more input domains. In some embodiments in a hairpin monomer having more than one input domain, a first input domain toehold is exposed, and additional input domain toeholds are sequestered. In some embodiments, the sequestered input domain toeholds are sequestered by the duplex stem of the hairpin, and the corresponding domain propagation regions are located on bulge loops. Typically, a hairpin monomer can have one or two output domains. In some embodiments, a hairpin monomer can have one, two, three, four, five, six or more output domains. Typically, the toehold of an output domain is hybridized to a portion of a propagation region of an input domain and therefore sequestered. Displacement of the propagation region of the input domain from the toehold exposes the toehold such that is becomes available to hybridize with a complementary nucleic acid sequence of, generally, another monomer. In some embodiments, the hairpin monomer can have a second output domain. In some embodiments, the second output domain can comprise a single stranded region at an end of a hairpin monomer. For example, the second output domain can have a toehold which is hybridized to a portion of a propagation region of an input domain, and a single stranded propagation region.

Two or more distinct species of hairpin monomers are preferably utilized in a self-assembly pathway. Each monomer species typically comprises at least one domain that is complementary to a domain of another monomer species. However, the monomers are designed such that they are kinetically trapped and the system is unable to equilibrate in the absence of an initiator molecule that can disrupt the secondary structure of one of the monomers. Thus, the monomers are unable to polymerize in the absence of the initiator. Introduction of an initiator species triggers a self-assembly pathway resulting in formation of one or polymers. In some embodiments the polymer comprises only a first and second monomer species. In other embodiments, the polymers can comprise additional nucleic acids. In the examples below, two or more hairpin monomers polymerize in the presence of an initiator to begin a self-assembly pathway. The self-assembly pathways disclosed herein are discussed in more detail below and include, for example, pathways for: catalytic geometry, catalytic circuitry, non-catalytic geometry, non-catalytic circuitry, nucleated dendritic growth and autonomous locomotion. The self-assembly pathways typically result in formation of a polymer, such as, for example, a branched junction, an autocatalytic duplex, a binary molecular tree, or a bipedal walker.

A number of criteria can be used to design the monomers to achieve the desired properties. These include, for example and without limitation, sequence symmetry minimization, the probability of adopting the initiator secondary structure at equilibrium, the average number of incorrect nucleotides at equilibrium relative to the target structure, hybridization kinetics, and the silencing target sequence. The composition of the monomers is not limited to any particular sequences or number of bases, and is designed based on the particular dynamic function. In some embodiments, the composition of the monomers can be designed based on the reaction graph and corresponding secondary structure mechanism of a particular dynamic function Monomers can be synthesized using standard methods, including commercially available nucleic acid synthesizers or obtained from commercial sources such as Integrated DNA Technologies (Coralville, Iowa). In some embodiments, the monomers can be DNA monomers. In other embodiments, the monomers can be RNA monomers. In some embodiments, the monomers can be RNA-DNA hybrids. Examples of the formation of nucleic acid-based structures are provided in U.S. patent application Ser. No. 12/152,893, which is herein incorporated by reference in its entirety.

In some embodiments, at least two hairpin monomer species are utilized in a self-assembly pathway as illustrated in FIG. 1b. In the depicted embodiment, the monomers are denoted A and B. In FIG. 1b, monomer A comprises three concatenated domains: a, b and c, and monomer B comprises two concatenated domains, represented by b* and c*. Each domain comprises a toehold and a propagation region. In FIGS. 1a and b, each domain comprises a single sequence segment; however, a domain can comprise any number of sequence segments. In some embodiments, a domain can comprise a portion of a sequence segment. In FIGS. 1a and 1b, the small letters with a subscript t denote the toehold of the domain. For example in FIG. 1a, $a_t$ denotes the toehold of domain a. In other embodiments, a toehold can comprise one or more sequence segments, or a portion of a sequence segment. For the example shown in FIG. 1b, the portion of a domain that is not the toehold is referred to as the "propagation region." In FIG. 1b, the small letters represent sequence segments, and letters marked with an asterisk (*) are complementary to the corresponding unmarked letter.

In preferred embodiments, the first stem region of a monomer can hybridize to the second stem region of the monomer to form the hairpin structure. In some embodiments, in the absence of an initiator, the first and second stem regions of each monomer are generally hybridized to form a duplex region of the monomer. The monomers each preferably comprise a hairpin loop region and two "stems regions"—a first stem region and a second stem region that are complementary and together can form a duplex region.

In the embodiment depicted in FIG. 1b, an initiator I comprises an output domain comprising a* having an exposed toehold $a_t^*$. In the depicted embodiment, a first hairpin monomer A comprises an "initiator binding domain" (input domain a having an exposed toehold $a_t$) and a first "assembly domain" (output domain b having a sequestered toehold $b_t$). In the depicted embodiment, a second hairpin monomer B comprises a first "assembly complement domain" (input domain b* having an exposed toehold $b_t^*$ and a "disassembly domain" (output domain a* having a sequestered toehold $a_t^*$).

Assembly according to some embodiments of a self-assembly pathway having catalytic geometry is depicted in FIG. 1b (1) and (2). A domain a* of the initiator I and the initiator binding domain a of the first hairpin monomer A are typically substantially complementary. That is, the domain a* of the initiator I is able to hybridize to the initiator binding domain a of the first hairpin monomer A, here a portion of domain a.

The initiator preferably comprises an exposed toehold. In FIG. 1b, the initiator I comprises an exposed toehold $a_t^*$, which is a portion of the domain a*. Exposed toehold $a_t^*$ of the initiator is complementary to a domain a of a first hairpin monomer A. In some embodiments, the initiator binding domain of a first hairpin monomer can comprise an exposed toehold and at least a portion of the first stem region of the first hairpin monomer. For example, in the depicted figure, the first hairpin monomer A has an initiator binding domain a comprising the exposed toehold $a_t$ and a portion of the first stem region of A.

Preferably, upon hybridization of the initiator to the exposed toehold of the initiator binding domain of the first hairpin monomer, the second stem region is displaced from the first stem region. This opens the hairpin of the first hairpin monomer. For example, in FIG. 1b at (1), the initiator I nucleates at the exposed toehold $a_t^*$ of the first hairpin monomer A by pairing $a_t^*$ with $a_t$. This induces a strand displacement interaction resulting in the hybridization of the initiator I at domain a* to the initiator binding domain a of the first hairpin monomer A to form the first complex (I•A).

In FIG. 1b, the first complex (I•A) has a newly exposed single-stranded tail that comprises the assembly domain b of the first hairpin monomer A. Monomer A also has another domain, domain c having toehold $c_t$, which is newly exposed. The assembly domain b has a newly exposed toehold $b_t$.

In some embodiments, the assembly domain of a first hairpin monomer in the first complex can comprise a portion of the loop region and a portion of the second stem region of the first hairpin monomer. For example, in FIG. 1b, the assembly domain b of first hairpin monomer A comprises a portion of the loop region (the "propagation region" of b) and a portion of the second stem region of A (the toehold $b_t$). In the absence of an initiator, the first and second stem regions of the first hairpin monomer are generally hybridized to form a duplex domain of the first hairpin monomer, and the first assembly domain of the first hairpin monomer is generally not available for hybridization to another monomer.

Preferably, upon hybridization of a newly-exposed toehold of the assembly domain of the first hairpin monomer to the exposed toehold of the assembly complement domain of the second hairpin monomer, the second stem region is displaced from the first stem region. This opens the hairpin of the second hairpin monomer. For example, in FIG. 1b, the exposed toehold $b_t$ of first hairpin monomer A in the first complex I•A nucleates at the exposed toehold $b_t^*$ of the second hairpin monomer B by pairing segment $b_t$ with $b_t^*$(FIG. 1b at (2)). This induces a strand displacement interaction resulting in the hybridization of the first hairpin monomer A at the assembly domain b to the assembly complement domain b* of the second hairpin monomer B to form a second complex (I•A•B). In preferred embodiments, the exposed toehold of assembly complement domain of the second monomer is configured to nucleate at the newly exposed toehold of the assembly domain of the first monomer and not at the propagation region of the assembly domain of the first monomer. Preferably, the assembly complement domain of the second monomer the exposed toehold of assembly complement domain of the second monomer nucleates at the newly exposed toehold, thereby inducing a strand displacement interaction resulting in the hybridization of the assembly domain to the assembly complement domain.

In FIG. 1b, the second complex (I•A•B) has a newly exposed single-stranded tail that comprises the disassembly domain comprising the segment a* of the second hairpin monomer B.

In some embodiments, the disassembly domain of a second hairpin monomer can comprise a portion of the loop region and a portion of the second stem region of the third hairpin monomer. For example, in the depicted embodiment, the disassembly domain a* of second hairpin monomer B comprises the loop region and a portion of the second stem region of B. In the absence of an exposed second assembly domain, the first and second stem regions of the second hairpin monomer are generally hybridized to form a duplex domain of the second hairpin monomer, and the disassembly domain of the second hairpin monomer is generally not available for hybridization to another monomer.

In other embodiments, instead of a disassembly domain, the second monomer can have a second assembly domain complementary to a second assembly complement domain of a third hairpin monomer. Any number of additional hairpin monomer species having one or more assembly domains can be used in a self-assembly pathway depending on the dynamic function.

In some embodiments, disassembly of an initiator from a monomer or polymer can occur. In some embodiments, polymers can disassemble from polymers, and monomers can disassemble from polymers. For example, disassembly of an initiator from a polymer can occur as generally depicted in FIG. 1b (3). The second hairpin monomer can have a disassembly domain which is substantially complementary to the initiator binding domain of the first hairpin monomer. In the depicted embodiment, the disassembly domain of the second substrate monomer B comprises a segment a* that is complementary to initiator binding domain a of the first hairpin monomer of the first complex. The disassembly domain a* becomes accessible upon binding of the first assembly domain to the second hairpin monomer and opening of the hairpin of the second hairpin monomer (FIG. 1b (2)). Preferably, upon hybridization of a newly-exposed disassembly domain to the initiator binding domain of the first hairpin monomer, the initiator is displaced from the first hairpin monomer.

The system illustrated in FIGS. 1a-f and discussed above exhibits linear growth in response to initiator. However, in some embodiments, monomers can be designed to undergo triggered self-assembly into branched structures exhibiting quadratic growth or dendritic structures exhibiting exponential growth. See, Pierce et al., U.S. patent application Ser. No. 11/371,346, which is herein incorporated by reference in its entirety. In other embodiments, monomers can be designed to undergo autonomous locomotion of a bipedal walker, or other dynamic functions Exponential growth is limited by the available space such that it decreases to cubic amplification as the volume around the initiator fills. However, if chain reactions products are able to dissociate, exponential growth can be maintained until the supply of monomers is exhausted. In some embodiments, increasing the rate of polymer growth can enhance the ability to, for example detect the presence of low copy number target initiators, such as a single target molecule in a large test volume.

In some embodiments, the secondary structure is preferably such that the monomers are metastable under the reaction conditions in the absence of an initiator. In the presence of an initiator, the secondary structure of a first monomer changes such that it is able to hybridize to an exposed toehold of a second monomer species. This in turn leads to a change in the secondary structure of the second monomer, which is then able to continue the self-assembly pathway to form the desired structure.

Sequence segments of domains (for example, a, b, c, d, q, r, s, t, u, v, x, y and z as illustrated herein) are not limited to any particular sequences or number of bases, and are designed based on the particular dynamic function. In some embodiments, the primary sequence of the monomers can be designed based on the corresponding reaction graph and secondary structure mechanisms.

The length of the toeholds, propagation regions, hairpin loop regions, and stem regions of the monomers can be adjusted, for example to ensure kinetic stability in particular reaction conditions and to adjust the rate of polymerization in the presence of initiator. The hairpin loop regions are preferably between about 1 and about 100 nucleotides, more preferably between about 3 and about 30 nucleotides and even more preferably between about 4 and about 7 nucleotides. In some embodiment the hairpin loop regions of a pair of hairpin monomers can be about 6 nucleotides in length and the stems are about 18 nucleotides long.

The toeholds can be located at any site on a hairpin monomer. The length of the toeholds can be adjusted, for example to ensure kinetic stability in particular reaction conditions and to adjust the rate of polymerization in the presence of initiator. The toeholds are preferably between about 1 and about 100 nucleotides, more preferably between about 3 and about 30 nucleotides and even more preferably between about 4 and about 7 nucleotides. In some embodiment the toeholds of a pair of hairpin monomers can be about 6 nucleotides in length and the stems are about 18 nucleotides long.

Several methods are available to reduce spurious monomer polymerization in the absence of initiator for dynamic functions including those with both higher order growth schemes and linear growth schemes. These include helix clamping, helix lengthening and loop entropy ratchets. In helix clamping, the single stranded regions in one or more of the monomers are truncated at each end so that the helixes that they could potentially invade in other monomers are effectively clamped at the ends by bases that are not present in the single stranded regions. Experiments have shown that this can eliminate any spurious initiation. The amount of truncation that is effective to decrease or eliminate spurious initiation can be determined by routine experimentation. For example, control experiments can be performed using fluorescent gel electrophoresis time courses to monitor strand exchange between single stranded DNA and duplex DNA for different clamp lengths. Using spectrally distinct dyes for the initially single stranded DNA and for the two DNA species in the duplex allows independent monitoring of all species as strand exchange proceeds. These controls can provide a systematic basis for section of clamp dimensions.

In other embodiments utilizing hairpin monomers, loop entropy ratchets are used to reduce self-assembly in the absence of initiator. For example, in some embodiments, an initiator can open a hairpin monomer via a three-way branch migration. This reaction is reversible because the displaced strand is tethered in the proximity of the new helix. However, by increasing the length of the single-stranded loop, the entropy penalty associated with closing the loop increases. As a result, a longer loop will bias the reaction to proceed forward rather than returning to the uninitiated state. However, larger loops are more susceptible to strand invasion. To counter this effect and allow the use of larger loops, mismatches can be introduced between the loop sequences and the complementary regions of the other monomers. Again, the loop length and amount of mismatch that produces the desired reduction in non-specific self-assembly can be determined by the skilled artisan through routine experimentation.

Other refinements to the system stabilize the hairpin monomers to help prevent self-assembly in the absence of an initiator. This can be achieved, for example, via super-stable hairpin loop sequences (Nakano et al. *Biochemistry*

41:14281-14292 (2002), herein incorporated by reference in its entirety), with ostensible structural features that could further inhibit direct hybridization to the hairpin. In some embodiments, padding segments can be incorporated into the monomer to modulate the lengths of a hairpin monomer's sticky-end, stem, and loop regions, permitting more flexible dimensioning. In other embodiments hairpin loops are made to be self-complementary at their ends. This self-complementation "pinches" the hairpin loops, making them shorter. However, if the reactive exposed toeholds of each monomer are complementary to the hairpin loop regions on the opposite monomer, they will have a slight propensity to close up, thereby slowing down the reaction. This feature can be utilized if a slower reaction is desired. Completely self-complementary hairpins can also be used, for example if the monomer hairpins are forming dimers with interior loops that are more easily invaded than their hairpin counterparts.

In some embodiments, monomers can be derivitized with a compound or molecule, for example, to increase the molecular weight of the polymer resulting from execution of a self-assembly pathway. In some embodiments they can be derivitized at a location that does not interfere with their ability to hybridize. In some embodiments, the monomers comprise a protein-binding region, or other recognition molecule. In some embodiments, the monomers can contain a fluorophore, luminescent molecule, colorimetric compound or other component that allows the resulting polymers and/or the dynamic function to be visualized.

Reaction conditions are preferably selected such that hybridization is able to occur, including between the initiator and the exposed toehold of a first hairpin monomer, between the assembly domain of a first hairpin monomer and an available toehold of a second hairpin monomer, and between the disassembly domain of a second hairpin monomer and the initiator binding domain, between the first and second stem regions of the monomers themselves. At each step of monomer polymerization, energy is gained from the hybridization of the exposed toehold of the monomer. The reaction temperature does not need to be changed to facilitate the polymerization of hairpin monomers. That is, hairpin monomer polymerization or assembly or disassembly reactions are isothermic. They also do not require the presence of any enzymes.

Initiators

As discussed above, an initiator can be a molecule that is able to initiate the polymerization of monomers. Typically, an initiator comprises an output domain that is complementary to an initiator binding domain (which is an input domain) of a hairpin monomer. In some embodiments, a self-assembly pathway is initiated when an initiator interacts with an initiator binding domain of a hairpin monomer, which subsequently undergoes a change in secondary structure, leading to polymer formation. In some embodiments, an initiator can initiate formation of a branched junction, an autocatalytic duplex, a binary molecular tree, or a bipedal walker.

Initiators can be synthesized using standard methods, including commercially available nucleic acid synthesizers or obtained from commercial sources such as Integrated DNA Technologies (Coralville, Iowa). Synthesis is discussed in more detail below. In some embodiments, initiators are naturally-occurring molecules. In other embodiments, initiators could be already present in a system. For example, the initiator may comprise nucleic acid naturally present in a system. In such as system the polymerization of monomers may be used to detect the presence of an initiator.

In some embodiments, the initiator binding domain of a first hairpin monomer is preferably at least 80%, more preferably at least 90%, 95% or higher, complementary to at least a portion of an initiator. In preferred embodiments, the initiator binding domain is at least 2, 3, 4, 5, or 10 or more bases in length.

The initiator preferably comprises a nucleic acid or other molecule that is able to contact a hairpin monomer and initiate a self-assembly pathway. In some embodiments, the initiator comprises a toehold having a sequence that is complementary to a portion, such as, for example without limitation, an exposed toehold, of a monomer, that is available for hybridization with the initiator while the monomer is in its kinetically stable state. In some embodiments, the initiator also preferably comprises a sequence that is complementary to a portion of the monomer adjacent to the toehold such that hybridization of the monomer to the toehold causes a conformational change in the monomer. For example, as depicted in FIG. 1$b$, the initiator I may comprise a toehold a* complementary to the initiator binding domain a of a monomer A, where the initiator binding domain a comprises a toehold $a_t$ and a portion of a first stem region of the monomer adjacent to the toehold.

In various embodiments, an initiator can be, for example without limitation, an RNA molecule, such as a coding region of RNA, a non-coding region of RNA, a portion of an mRNA, or a microRNA. In other embodiments, an initiator can be, for example without limitation, a DNA molecule such as, for example, a coding strand of DNA, or an antisense DNA.

In some embodiments, the initiator binding domain of a hairpin monomer can be a recognition molecule that specifically binds an initiator molecule. When the initiator interacts with the recognition molecule, the hairpin monomer undergoes a conformational change and the self-assembly pathway is initiated.

Recognition molecules include, without limitation, polypeptides, antibodies and antibody fragments, nucleic acids, aptamers, and small molecules.

In some embodiments, an initiator is bound to an aptamer, and the aptamer makes the initiator available to interact with a first hairpin monomer when the aptamer binds to an appropriate target molecule. For example, the initiator binding domain of a first hairpin monomer can bind to an initiator which is bound to an aptamer specific for a target of interest.

Self-Assembly Pathways

Self-assembly pathways for a variety of different dynamic functions can be programmed via reaction graphs. The system illustrated in FIGS. 1$a$-$f$ and discussed above exhibits linear growth in response to initiator. However, a variety of different dynamic functions can be programmed using the methods disclosed herein. The programming of four different exemplary dynamic functions are generally described below: (1) catalytic formation of branched junctions, (2) autocatalytic duplex formation by a cross-catalytic circuit, (3) nucleated dendritic growth of a binary molecular tree, and (4) autonomous locomotion of a bipedal walker.

Catalytic Geometry

In some embodiments, the self-assembly pathway can be a pathway for catalytic formation of branched junctions. In some embodiments, a branched junction is formed in the presence of an initiator. The initiator may be, for example, any molecule in whose presence formation of a branch junction is desired. Initiators include, without limitation, polypeptides, such as antibodies and antibody fragments, nucleic acids, aptamers, and small molecules.

Compositions and methods are provided for catalyzing the formation of branched junctions. In some embodiments, the branched junction is a 3-arm, 4-arm or k-arm DNA junction (k≥3). For example, 3-arm DNA junctions are illustrated in Example 2, 4-arm DNA junctions are illustrated in Example 4, and k-arm junctions are illustrated in Example 6. The assembly and disassembly pathways for catalytic formation of a 3-arm DNA junction specified in the reaction graph of FIG. 2a are translated into the motif-based molecular implementation of FIG. 2b. The complementarity relationships between the segments of hairpins A, B, and C are specified (FIG. 2b, top) such that in the absence of initiator I, the hairpins are kinetically impeded from forming the three-arm junction that is predicted to dominate at equilibrium. In the reaction graph, this property is programmed by the absence of a starting point if node I is removed from the graph (i.e., no pair of accessible ports connected by an assembly arrow). The introduction of I into the system (FIG. 2b, bottom) activates a cascade of assembly steps with A, B, and C, followed by a disassembly step in which C displaces I from the complex, freeing I to catalyze the self-assembly of additional branched junctions. The design procedure for the catalytic 3-arm junction system shown in FIGS. 2a and b is described in detail below in the Examples section.

Figure 2B:
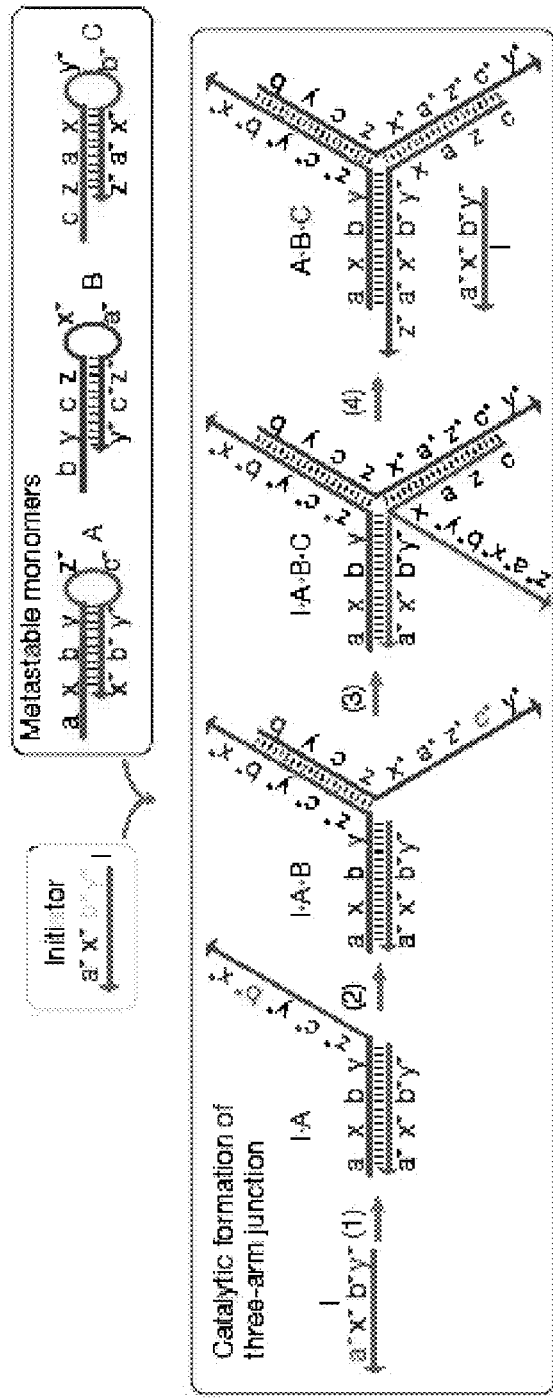

Each letter-labeled sequence segment shown in FIG. 2b is six nucleotides in length. However, as discussed above, sequence segments are generally not limited to any particular sequences or number of bases, and are designed based on the particular dynamic function. In FIG. 2b, the initially accessible toehold (a* for step (1)) or newly exposed toehold (b* for step (2); c* for step (3)) that mediates assembly reactions are labeled with purple letters.

In some embodiments, at least three hairpin monomers are utilized as illustrated in FIG. 2b to form a 3-arm junction. In FIG. 2b, the monomers are denoted A, B and C. The monomers each preferably comprise an exposed toehold (for example, toeholds having sequences a, b and c of A, B and C, respectively), a hairpin loop region at the opposite end of the exposed toehold, and two "stem regions," a first stem region and a second stem region, that together can form a duplex region. The small letters represent sequence segments. Letters marked with an asterisk (*) are complementary to the corresponding unmarked letter.

In preferred embodiments, the first stem region of a monomer can hybridize to the second stem region of the monomer to form the hairpin structure. For example, as shown in FIG. 2b, the monomer A comprises a first stem region comprising a sequence (x-b-y) that is able to hybridize to the second stem region (y*-b*-x*). In some embodiments, in the absence of an initiator, the first and second stem regions of each monomer are generally hybridized to form a duplex region of the monomer.

In the embodiment depicted in FIG. 2b, an initiator I comprises a domain comprising the sequence a*-x*-b*-y*. In the depicted embodiment, a first hairpin monomer A comprises an "initiator binding domain" (comprising the sequence a-x-b-y) and a first "assembly domain" (comprising the sequence z*-c*-y*-b*). Typically, the initiator binding domain is an input domain and the assembly domain is an output domain. In the depicted embodiment, a second hairpin monomer B comprises a first "assembly complement domain" (comprising the sequence b-y-c-z) and a second "assembly domain" (comprising the sequence x*-a*-z*-c*). In the depicted embodiment, a third hairpin monomer C comprises a second "assembly complement domain" (comprising the sequence c-z-a-x) and a "disassembly domain" (comprising the sequence y*-b*-x*-a*). In the depicted embodiment, the assembly and disassembly domains are output domains, and assembly complement domains are input domains.

Assembly according to some embodiments of a self-assembly pathway having catalytic geometry is depicted in FIG. 2b (1)-(3). An output domain (a*-x*-b*-y*) of the initiator I and the initiator binding domain (a-x-b-y) of the first hairpin monomer A are typically substantially complementary. That is, the domain (a*-x*-b*-y*) of the initiator I is able to hybridize to the initiator binding domain (a-x-b-y) of the first hairpin monomer A.

The initiator I preferably comprises an exposed toehold a*, which is a portion of the domain comprising the sequence a-x-b). Exposed toehold a* of the initiator is complementary to a sequence segment a of a first hairpin monomer A. In some embodiments, the initiator binding domain of a first hairpin monomer can comprise an exposed toehold and a portion of the first stem region of the initiator. For example in FIG. 2b, the first hairpin monomer A has an initiator binding domain a-x-b-y, where a is an exposed toehold, and x-b-y is portion of the first stem region of the first hairpin monomer A.

Preferably, upon hybridization of the initiator to the exposed toehold of the initiator binding domain of the first hairpin monomer, the second stem region is displaced from the first stem region. This opens the hairpin of the first hairpin monomer. For example in FIG. 2b, the initiator I nucleates at the exposed toehold a of the first hairpin monomer A by pairing segment a* with a (FIG. 2b at (1)). This induces a strand displacement interaction resulting in the hybridization of the initiator I at a domain a*-x*-b*-y* to the initiator binding domain a-x-b-y of the first hairpin monomer A to form the first complex (I•A).

In some embodiments, the first complex can have a newly exposed single-stranded tail that comprises a first assembly domain of the first hairpin monomer. For example, in FIG. 2b the first complex (I•A) has a newly exposed single-stranded tail that comprises the first assembly domain (comprising the sequence z*-c*-y*-b*) of the first hairpin monomer A. This first assembly domain has a newly exposed toehold (b*).

In some embodiments, the first assembly domain of a first hairpin monomer in the first complex can comprise a portion of the loop region and a portion of the second stem region of the first hairpin monomer. For example, in FIG. 2b, the first assembly domain of first hairpin monomer A comprises the sequence z*-c*-y*-b*, where z*-c* is a portion of the loop region and y*-b* is a portion of the second stem region of the first hairpin monomer A. In the absence of an initiator, the first and second stem regions of the first hairpin monomer are generally hybridized to form a duplex domain of the first hairpin monomer, and the first assembly domain of the first hairpin monomer is generally not available for hybridization to another monomer.

Preferably, upon hybridization of a newly-exposed toehold of the first assembly domain of the first hairpin monomer to the exposed toehold of the first assembly complement domain of the second hairpin monomer, the second stem region is displaced from the first stem region. This opens the hairpin of the second hairpin monomer. In the depicted embodiment, the exposed toehold b* of first hairpin monomer A in the first complex I•A nucleates at the exposed toehold b of the second hairpin monomer B by pairing segment b* with b (FIG. 2b at (2)). This induces a strand displacement interaction resulting in the hybridization of the first hairpin monomer A at the first assembly domain z*-c*- y*-b* to the first assembly complement domain b-y-c-z of the second hairpin monomer B to form a second complex (I•A•B).

In the depicted embodiment, the second complex (I•A•B) has a newly exposed single-stranded tail that comprises the second assembly domain (comprising the sequence x*-a*-z*-c*) of the second hairpin monomer B. This second assembly domain has a newly exposed toehold (c*).

In some embodiments, the second assembly domain of a second hairpin monomer can comprise a portion of the loop region and a portion of the second stem region of the second hairpin monomer. For example, in FIG. 2b, the second assembly domain of second hairpin monomer B comprises the sequence x*-a*-z*-c*, where x*-a* is a portion of the loop region and z*-c* is a portion of the second stem region of the second hairpin monomer In the absence of an exposed first assembly domain, the first and second stem regions of the second hairpin monomer are generally hybridized to form a duplex domain of the second hairpin monomer, and the second assembly domain of the second hairpin monomer is generally not available for hybridization to another monomer.

Preferably, upon hybridization of a newly-exposed toehold of the second assembly domain of the second hairpin monomer to the exposed toehold of the second assembly complement domain of the third hairpin monomer, the second stem region is displaced from the first stem region. This opens the hairpin of the third hairpin monomer. For example, in FIG. 2b the exposed toehold c* of second hairpin monomer B in the second complex I•A•B nucleates at the exposed toehold c of the third hairpin monomer C by pairing segment c* with c (FIG. 2b at (3)). This induces a strand displacement interaction resulting in the hybridization of the second hairpin monomer B at the second assembly domain x*-a*–z*-c* to the second assembly complement domain c-z-a-x of the third hairpin monomer C to form a third complex (I•A•B•C).

In FIG. 2b the third complex (I•A•B•C) has a newly exposed single-stranded tail that comprises the disassembly domain (comprising the sequence y*-b*-x*-a*) of the third hairpin monomer C. In some embodiments, the disassembly domain of the third hairpin monomer is complementary to a portion of the inhibitor binding domain of the first hairpin monomer.

In some embodiments, the disassembly domain of a third hairpin monomer can comprise a portion of the loop region and a portion of the second stem region of the third hairpin monomer. For example, in the depicted embodiment, the disassembly domain of third hairpin monomer C comprises the sequence y*-b*-x*-a* where y*-b* is a portion of the loop region and x*-a* is a portion of the second stem region of the third hairpin monomer. In the absence of an exposed second assembly domain, the first and second stem regions of the third hairpin monomer are generally hybridized to form a duplex domain of the third hairpin monomer, and the disassembly domain of the third hairpin monomer is generally not available for hybridization to another monomer.

In other embodiments for producing branched junctions with greater than 3 arms, instead of a disassembly domain, the third self-assembly has a third assembly domain complementary to a third assembly complement domain of a fourth hairpin monomer. For the formation of 3-arm branched junctions, preferably three hairpin monomers are used. For the formation of 4-arm branched junctions, preferably four hairpin monomers are used. For the formation of k-arm branched junctions (where k≥3), preferably k hairpin monomers are used. In some embodiments, the kth hairpin monomer can comprise a disassembly domain instead of a kth assembly domain.

In some embodiments, the disassembly domain of the kth hairpin monomer is exposed by the opening of the hairpin of the kth hairpin monomer. The kth hairpin monomer has a disassembly domain which is substantially complementary to the initiator binding domain of the first hairpin monomer. The exposed disassembly domain can bind the initiator binding domain of the first hairpin monomer, thereby displacing the initiator from the kth complex such that the initiator can be recycled to react with another first hairpin monomer.

Disassembly according to some embodiments of a self-assembly pathway having catalytic geometry is depicted in FIG. 2b (4). The third hairpin monomer C has a disassembly domain which is substantially complementary to the initiator binding domain of the first hairpin monomer A. In the depicted embodiment, the disassembly domain of the third substrate monomer C comprises a sequence y*-b*-x*-a* that is complementary to a sequence of the initiator binding domain a-x-b-y of the first hairpin monomer of the first complex (I•A) that becomes accessible upon binding of the second assembly domain to the third hairpin monomer and opening of the hairpin of the third hairpin monomer (FIG. 2b (3)). Preferably, upon hybridization of a newly-exposed disassembly domain of the third hairpin monomer to the initiator binding domain of the first hairpin monomer, the initiator is displaced.

In some embodiments, the number of arms of a branch junction depends on the number of hairpin monomer species in the self-assembly pathway. The number and sequences of the hairpin monomers can be designed to provide branched junction having a desired sequence. In some embodiments, the result of the self-assembly pathway can be a 3-arm, 4-arm or k-arm branched junction.

In some embodiments, after displacement by the disassembly domain of the kth hairpin monomer, the displaced initiator can be used in further self-assembly reactions.

In some embodiments, gel electrophoresis can be used to confirm that the hairpins assemble slowly in the absence of initiator and that assembly is dramatically accelerated by the addition of initiator (FIG. 2c). Disassembly of the initiator enables catalytic turnover as indicated by the nearly complete consumption of hairpins even at substoichiometric initiator concentrations. Lanes 1-4 of the gel in FIG. 2c show nearly complete conversion of hairpins to reaction products using stoichimetric or substoichiometric initiator I. In some embodiments, only minimal assembly is achieved by annealing the hairpin mixture, illustrating the utility of pathway programming for traversing free energy landscapes with kinetic traps that cannot be overcome by traditional annealing approaches. In FIG. 2c, minimal conversion is seen in the absence of initiator (lane 5), even with annealing (lane 6).

In some embodiments, direct imaging of the catalyzed self-assembly product (e.g., A•B•C) via atomic force microscopy (AFM) can be used to confirm the expected 3-arm junction morphology as shown in, for example, FIG. 2d.

In some embodiments, the reaction pathway can be extended to the catalytic self-assembly of k-arm junctions. FIGS. 2e and f show an example of catalytic self-assembly of a k-arm junction where k=4 in a reaction graph (FIG. 2e) and AFM image (FIG. 2f), respectively. A detailed example of the programming for the catalytic formation of a 4-arm junction is provided below in Example 4.

In some embodiments, the compositions and methods described herein are used to assemble a two-dimensional structure, such as a closed loop two-dimensional structure. In some embodiments, the two-dimensional structure is a closed loop two-dimensional shape. For example, in some embodiments, a triangle, square, rectangle, trapezoid, pentagon, hexagon, heptagon, octagon, nonagon, decagon, oval, or circle is assembled. In some embodiments, the compositions and methods described herein are used to assemble a three-dimensional structure. In some embodiments, the three-dimensional structure is a three-dimensional shape. For example, in some embodiments, a tetrahedron, cube, cuboid, octahedron, dodecahedron, icosahedron, bi-tetrahedron, wedge, square-based pyramid, triangular prism, hexagonal prism, cone, cylinder, or sphere is assembled or complex polygons with edges that range from 6 (tetrahedron) to 10,000.

Figure 72A:
FIGS. 72a-b depict flowcharts for a method of assembling a three-dimensional structure.
Figure 72A:
Figure 72B:
Figure 72B:

In some embodiments, the compositions and methods described herein are used to assemble a two-dimensional structure that is used to form a three-dimensional structure. For example, FIG. 72a demonstrates a method of forming a branched two-dimensional structure that is used to assemble a three-dimensional shape. FIG. 72b demonstrates a method of forming a branched three-arm junction in order to assemble a tetrahedron.

In some embodiments, the compositions and methods described herein comprise a plurality of branched junctions. For example, three-dimensional structures can comprise a plurality of k-arm junctions, where k is ≥3. In some embodiments, three-dimensional structures comprise a plurality of 3-arm, 4-arm, 5-arm, 6-arm, or other k-arm junctions, or a combination thereof. An example of a three-dimensional structure comprising a plurality of 3-arm DNA junctions is illustrated in FIG. 39d.

In some embodiments, a mixture of monomers is used to assemble a three-dimensional structure. In some embodiments, multiple mixtures are used to assemble a three-dimensional structure. For example, in some embodiments, a first mixture of monomers is used to form 3-arm junctions, and a second mixture of monomers is added to the three-arm junctions to form a three-dimensional structure.

By "three-dimensional structure" what is meant is that the structure has a component that structurally extends out of a plane. While it will be appreciated that long lengths of nucleic acids and even hairpin structures could be argued to be "three-dimensional structures", such structures are not encompassed within the term "three-dimensional" as used herein. Rather, what is meant is that the structure's arms (assuming them to be rigid) extends not only in a X and Y direction, but also in a direction Z, which is perpendicular to X and Y. That is not to say that the arm itself must be rigid or must be perpendicular, but that it extends in that perpendicular direction. In some embodiments, assuming the arms of the structure are rigid, a structure will be considered three-dimensional if it must extend in three dimensions. In some embodiments, a structure is three-dimensional when a single plane defined by the hairpin monomers cannot contain the structure. In some embodiments, a structure is three-dimensional when: the lengths of the hairpin monomers or nucleic acids define a first dimension, a second dimension that is at least partially perpendicular to the first dimension (e.g., a plane) and a third dimension, that is at least partially perpendicular to the first and second dimensions. As will be appreciated by those of skill in the art, the thickness of the hairpin monomer or nucleic acids themselves are not considered when determining whether or not a structure is three-dimensional, as the term is used herein.

In some embodiments, a first hypothetical line (X) down the length of a first hairpin monomer and a second hypothetical line (Y) down the length of a second hairpin monomer can define a first plane (e.g., limit and define a plane by X and Y). In such embodiments, a third hypothetical line (Z) down the length of a third hairpin monomer, where the first and second lines are perpendicular to the third line, can define the structure as being a three-dimensional structure. In many embodiments, more than three lengths or arms will be required to make the structure a rigid three dimensional structure (e.g., 6 arms or more for some embodiments.

Figure 37A:
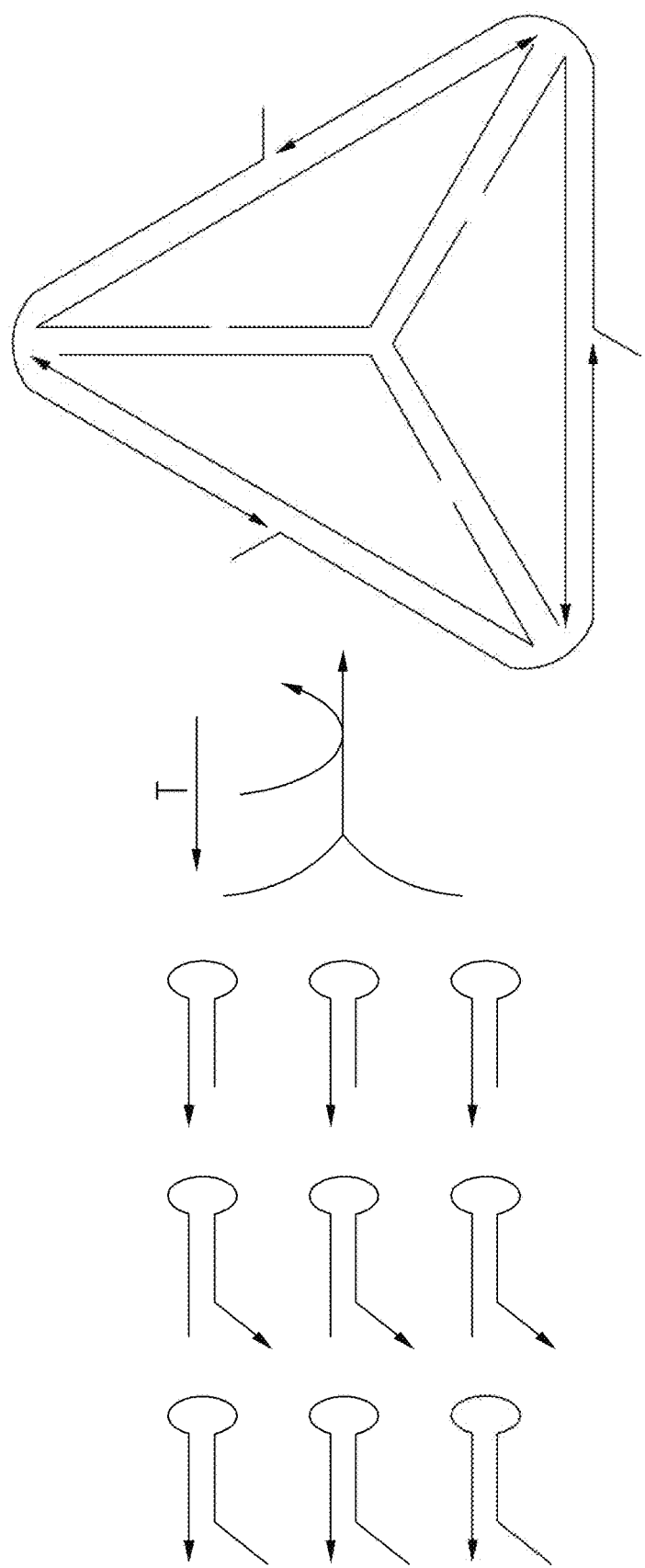
FIGS. 37a-c generally depict the catalytic formation of a DNA tetrahedron. a, Secondary structure schematic. b, Detailed growth pathway. c, Pathway summary.
Figure 37B:
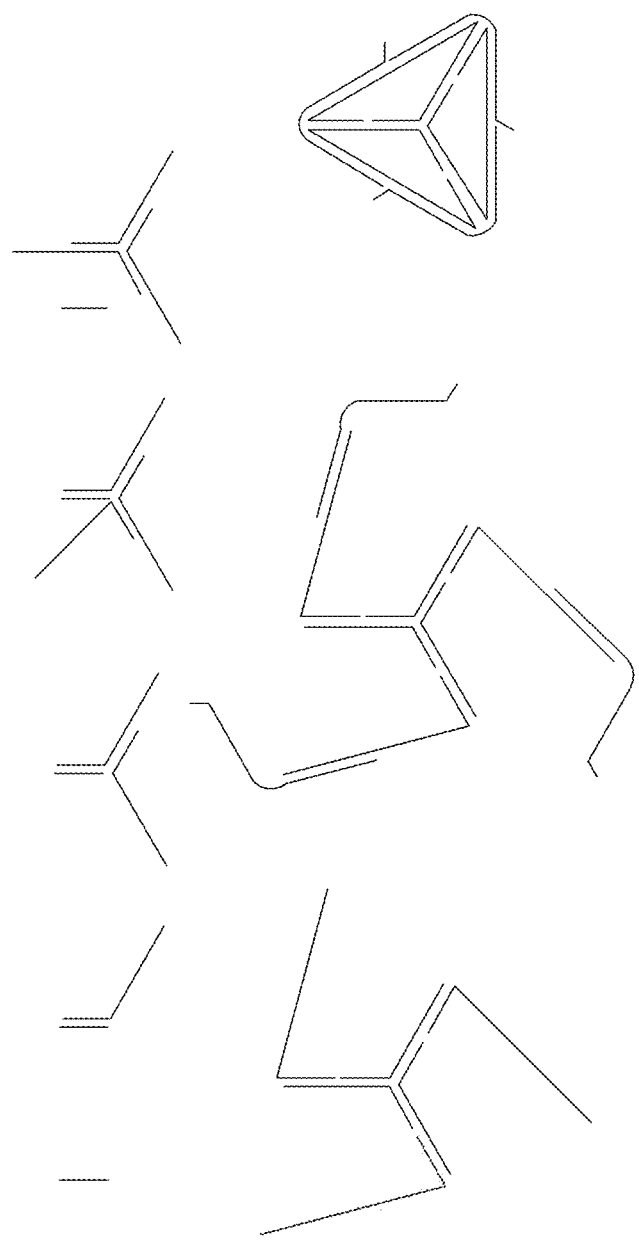
Figure 37C:
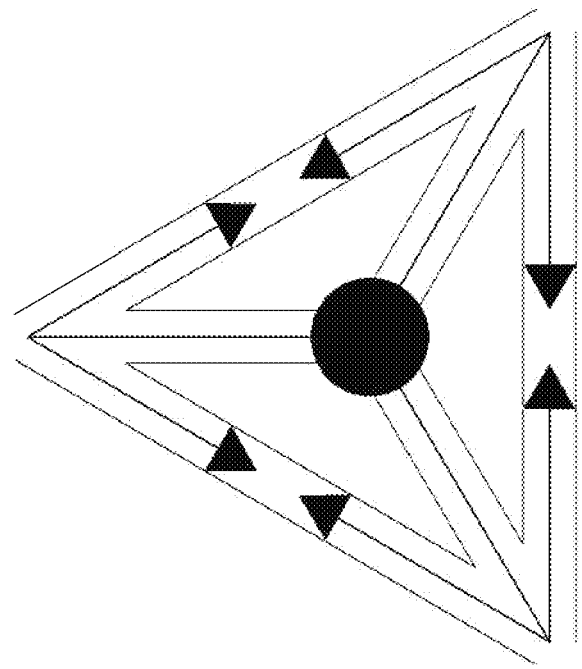
Figure 37C:
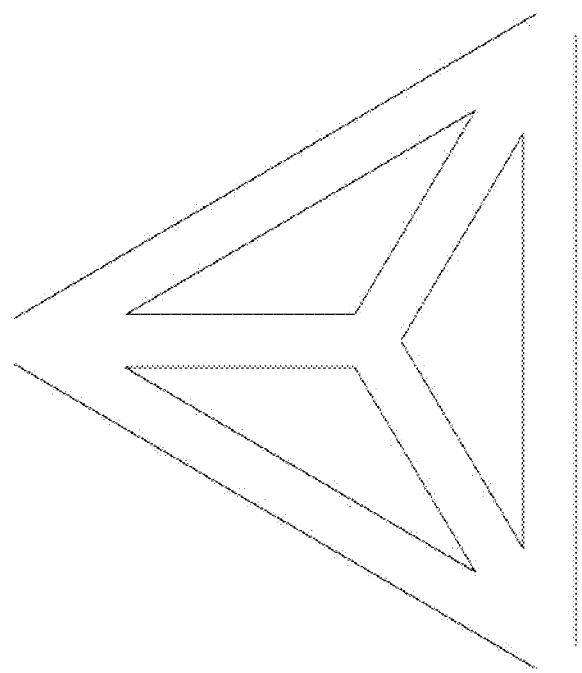

FIG. 37a illustrates the design schematic for a three-dimensional shape, using a tetrahedron as an example. In the absence of the trigger strand T, the nine hairpin species co-exist metastably. Introduction of the strand T triggers the hairpins to self-assemble autonomously and isothermally into a tetrahedron. The tetrahedron self-assembly pathway is generally depicted in FIGS. 37a-c.

Figure 38:
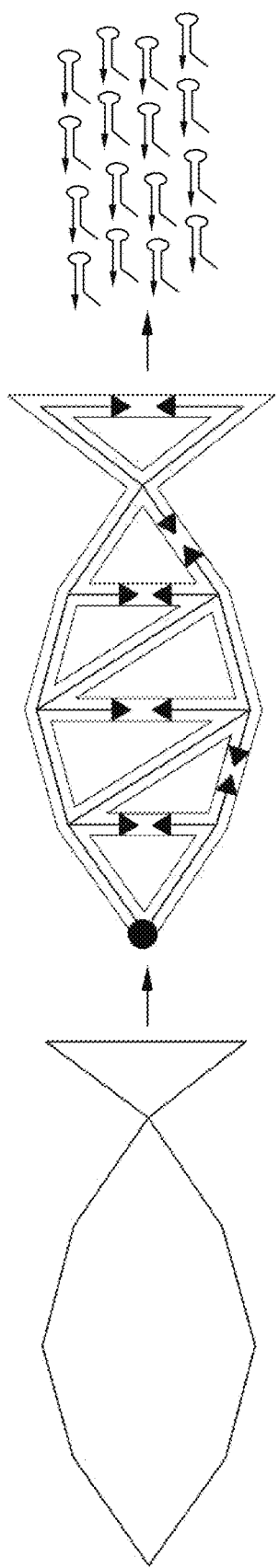
FIG. 38 generally depicts a design process for forming a two-dimensional structure. The red arrows depict the growth pathway that starts at the dot.

FIG. 38 describes the strategy for growing a predetermined two-dimensional shape. A triangular mesh can be generated to approximate the surface. A spanning tree can then be computed for the triangular mesh, further defining a growth pathway for the mesh. The growth pathway can then be encoded in DNA hairpin motifs. In the presence of a trigger strand, metastable DNA hairpins can self-assemble into the target structure following the specified kinetic pathway. This procedure can also be generalized to grow a three-dimensional shape by generating a wire-frame graph for the shape.

Some embodiments for assembly and/or disassembly pathways for catalytic formation of a tetrahedron comprising a plurality of 3-arm DNA junctions are illustrated in Example 18. The complementarity relationships between the segments of hairpins A1, A2, A3, B1, B2, B3, C1, C2, and C3 are specified (FIG. 39a) such that in the absence of initiator T, the hairpins are kinetically impeded from forming the junctions that are predicted to dominate at equilibrium. The introduction of T into the system activates a cascade of assembly steps for A1, A2, and A3, which includes a disassembly step in which A3 displaces T from the complex.

Figure 39A:
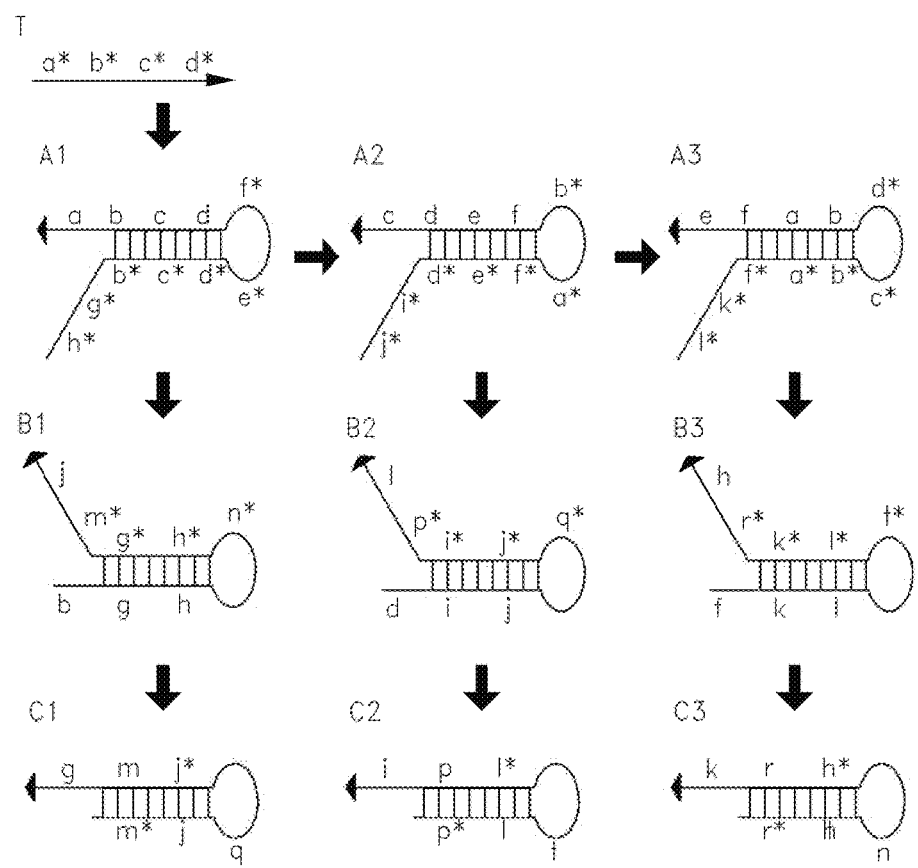
FIGS. 39a-d generally depict embodiments for the catalytic formation of a DNA tetrahedron. a, Initiator molecule and secondary structure of metastable hairpin monomers. b, Partial tetrahedral structure comprising the three-arm junction and connecting monomers. c, Partial tetrahedral structure comprising the three-arm junction and connecting monomers with partial binding of complementary segments. d, Partial tetrahedral structure comprising the three-arm junction and connecting monomers with full binding of complementary segments. The small letters represent sequence segments. Letters marked with an asterisk (*) are complementary to the corresponding unmarked letter.
Figure 39B:
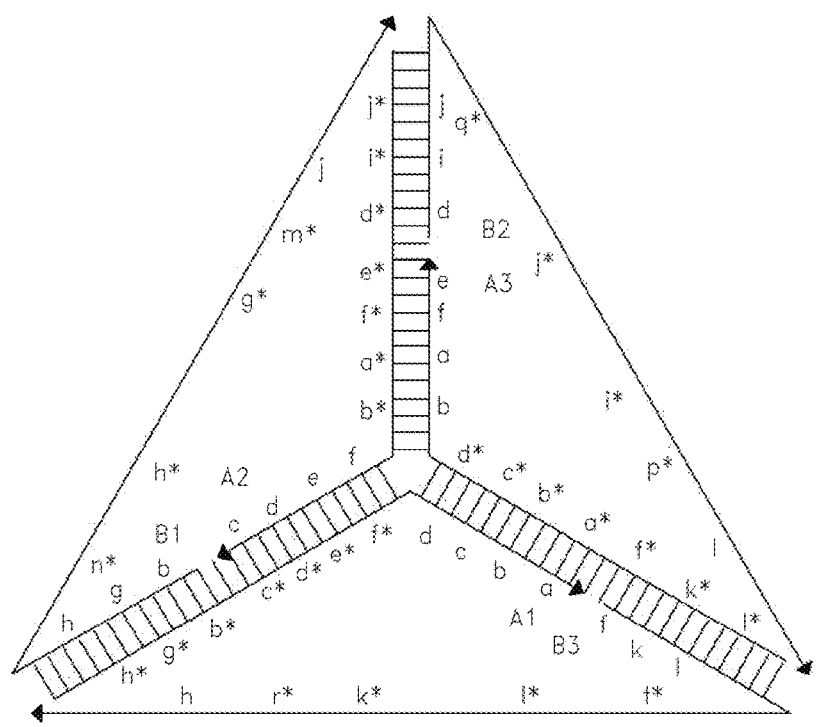
Figure 39C:
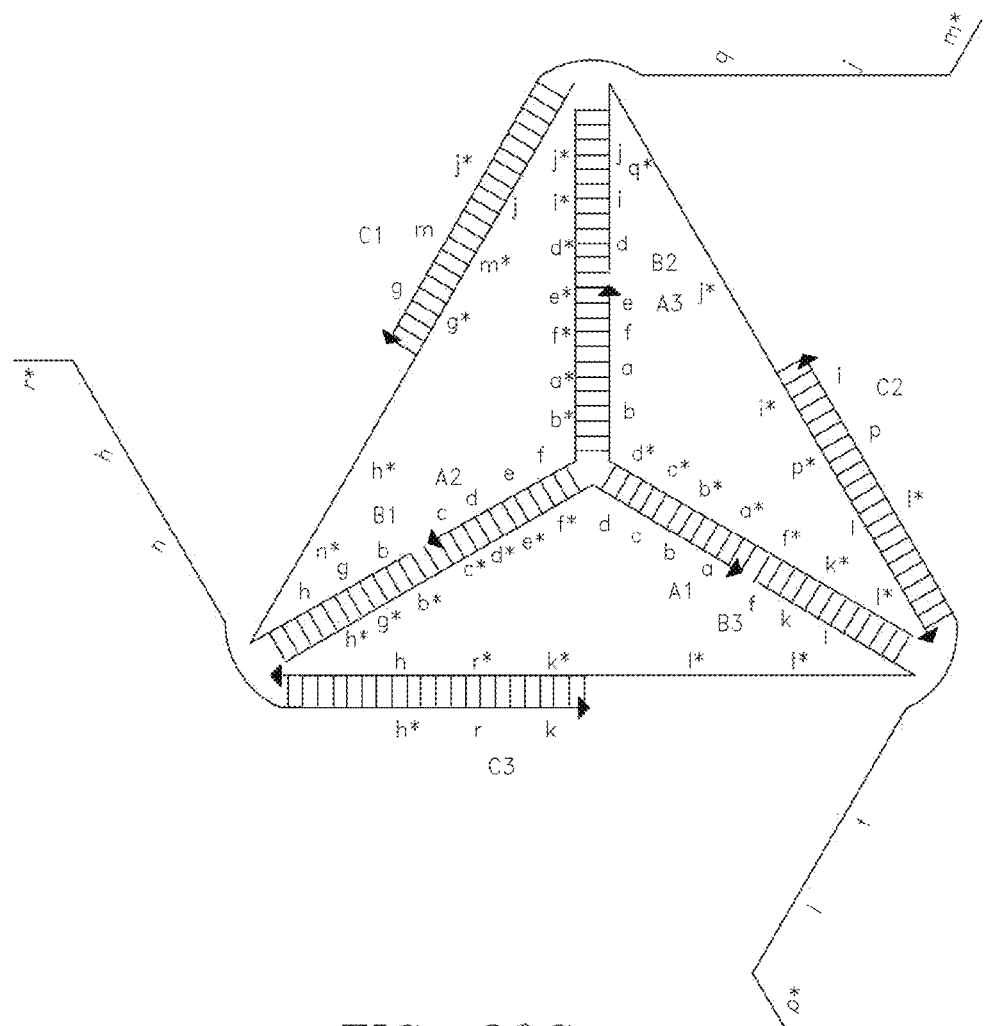
Figure 39D:
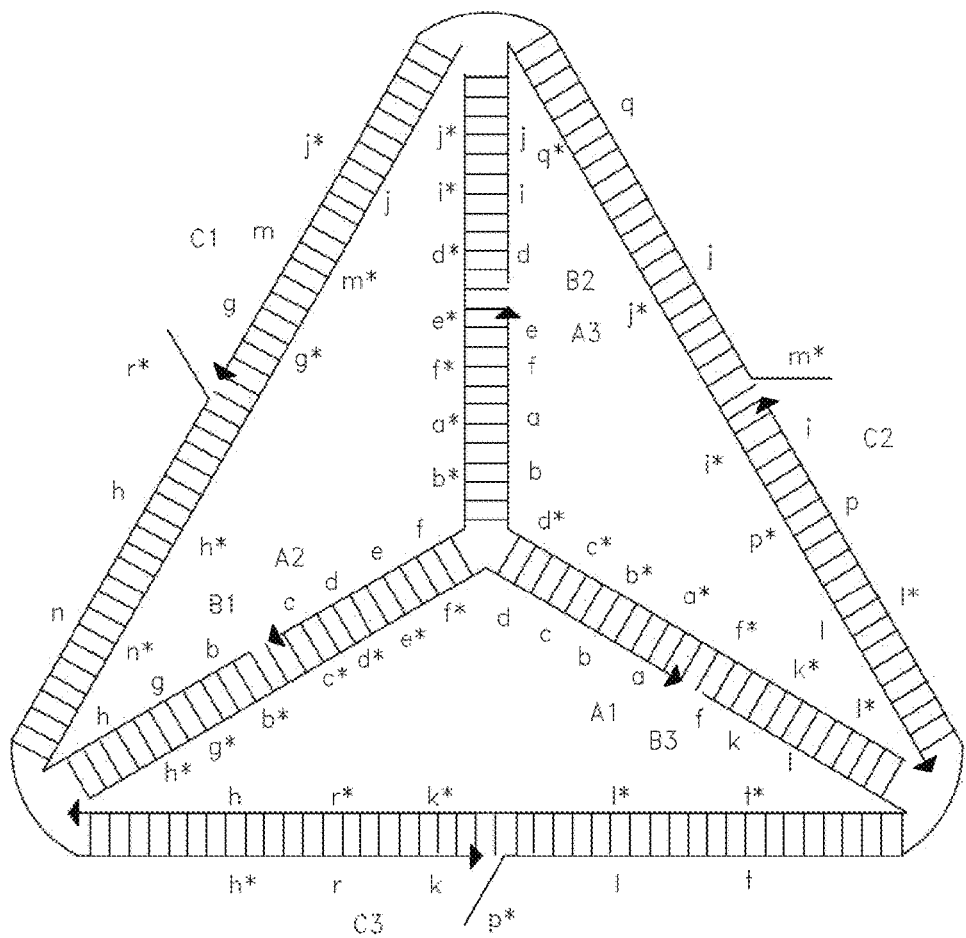

In some embodiments, at least nine hairpin monomers are utilized, as illustrated in FIGS. 39a-d and FIG. 40, to form a tetrahedron. In FIGS. 39a,-d, the monomers are denoted A1, A2, A3, B1, B2, B3, C1, C2, and C3. A1 binds to a target T, which exposes a region that is bound by A2, which in turn exposes a region that is bound by A3. A3 then binds to the region of A1 that was initially bound to the target. Opened hairpin A1 then binds and opens hairpin B1, which in turn binds and opens hairpin C1; opened hairpin A2 binds and opens hairpin B2, which in turn binds and opens hairpin C2; and opened hairpin A3 binds and opens hairpin B3, which in turn binds and opens hairpin C3. Finally, opened hairpin C1 binds to opened hairpin B2, opened hairpin C2 binds to opened hairpin B3, and opened hairpin C3 binds to opened hairpin B1.

In some embodiments, the monomers in FIG. 39 each comprise an exposed toehold (for example, toeholds having sequences a, c, e, b, d, f, g, i, and k of A1, A2, A3, B1, B2, B3, C1, C2, and C3, respectively), a hairpin loop region at the opposite end of the exposed toehold, and two "stem regions," a first stem region and a second stem region, that together can form a duplex region. The small letters represent sequence segments. Letters marked with an asterisk (*) are complementary to the corresponding unmarked letter.

In some embodiments, the first stem region of a monomer can hybridize to the second stem region of the monomer to form the hairpin structure. For example, as shown in FIG. 39a, the monomer A1 comprises a first stem region comprising a sequence (b-c-d) that is able to hybridize to the second stem region (b*-c*-d*). In some embodiments, in the absence of an initiator, the first and second stem regions of each monomer are generally hybridized to form a duplex region of the monomer.

In some embodiments, as depicted in FIG. 39a, an initiator T comprises a domain comprising the sequence a*-b*-c*-d*. In the depicted embodiment, a first hairpin monomer A1 comprises an "initiator binding domain" (comprising the sequence a-b-c-d), a first "assembly domain I" (comprising the sequence f*-e*-d*-c*), and a first "assembly domain II" (comprising the sequence b*-g*-h*). In the depicted embodiment, a second hairpin monomer A2 comprises a first "assembly complement domain" (comprising the sequence c-d-e-f), a second "assembly domain I" (comprising the sequence b*-a*-f*-e*), and a second "assembly domain II" (comprising the sequence d*-i*-j*). In the depicted embodiment, a third hairpin monomer A3 comprises a second "assembly complement domain" (comprising the sequence e-f-a-b), a "disassembly domain" (comprising the sequence d*-c*–b*-a*), and a third "assembly domain II" (comprising the sequence f*-k*-l*).

In the depicted embodiment, a fourth hairpin monomer B1 comprises a third "assembly complement domain" (comprising the sequence b-g-h), a fourth "assembly domain I" (comprising the sequence h*-n*), and a fourth "assembly domain II" (comprising the sequence g*-m*-j). In the depicted embodiment, a fifth hairpin monomer B2 comprises a fourth "assembly complement domain" (comprising the sequence d-l-j), a fifth "assembly domain I" (comprising the sequence q*-j*), and a fifth "assembly domain II" (comprising the sequence i*-p*-l). In the depicted embodiment, a sixth hairpin monomer B3 comprises a fifth "assembly complement domain" (comprising the sequence f-k-l), a sixth "assembly domain I" (comprising the sequence t*-l*), and a sixth "assembly domain II" (comprising the sequence k*-r*-h).

In the depicted embodiment, a seventh hairpin monomer C1 comprises a first "assembly complement domain I" (comprising the sequence g-m-j*) and a first "assembly complement domain II" (comprising the sequence q-j-m*). In the depicted embodiment, an eighth hairpin monomer C2 comprises a second "assembly complement domain I" (comprising the sequence i-p-l*) and a second "assembly complement domain II" (comprising the sequence t-l-p*). In the depicted embodiment, a ninth hairpin monomer C3 comprises a third "assembly complement domain I" (comprising the sequence k-r-h*) and a third "assembly complement domain II" (comprising the sequence n-h-r*).

In the depicted embodiment, the initiator binding domain is typically an input domain, and the assembly domains are typically output domains. In addition, in the depicted embodiment, the assembly and disassembly domains are typically output domains, and the assembly complement domains are typically input domains.

Assembly according to some embodiments of a self-assembly pathway having catalytic geometry is depicted in FIG. 39(b)-(d). An output domain (a*-b*-c*-d*) of the initiator T and the initiator binding domain (a-b-c-d) of the first hairpin monomer A1 are typically substantially complementary. That is, the domain (a*-b*-c*-d*) of the initiator T is able to hybridize to the initiator binding domain (a-b-c-d) of the first hairpin monomer A1.

The initiator T preferably comprises an exposed toehold a*, which is a portion of the domain comprising the sequence a*-b*-c*-d*. Exposed toehold a* of the initiator T is complementary to a sequence segment a of a first hairpin monomer A1. In some embodiments, the initiator binding domain of a first hairpin monomer can comprise an exposed toehold and a portion of the first stem region of the initiator. For example, in FIG. 39a, the first hairpin monomer A1 has an initiator binding domain a-b-c-d, where a is an exposed toehold, and b-c-d is portion of the first stem region of the first hairpin monomer A1.

Preferably, upon hybridization of the initiator to the exposed toehold of the initiator binding domain of the first hairpin monomer, the second stem region is displaced from the first stem region. This opens the hairpin of the first hairpin monomer. For example, in FIG. 39b, the initiator T nucleates at the exposed toehold a of the first hairpin monomer A1 by pairing segment a* with a. This induces a strand displacement interaction resulting in the hybridization of the initiator T at a domain a*-b*-c*-d* to the initiator binding domain a-b–c-d of the first hairpin monomer A1.

In the depicted embodiment, upon binding to a complementary monomer, several monomers have a newly exposed single-stranded tail that comprises an assembly domain. For example, monomer A2 has a newly exposed single-stranded tail that comprises the sequence b*-a*-f*-e* and d*-i*-j*. This assembly domain has newly exposed toeholds (e* and d*).

In some embodiments, the first complex can have a newly exposed single-stranded tail that comprises a first "assembly domain I" and a first "assembly domain II" of the first hairpin monomer. For example, as illustrated in FIG. 39b, the first hairpin monomer A1 develops a newly exposed single-stranded tail that comprises a first "assembly domain I" (comprising the sequence f*-e*-d*-c*) and a "first assembly domain II" (comprising the sequence b*-g*-h*). This first assembly domain has newly exposed toeholds (c* and b*).

In some embodiments, a first assembly domain of a first hairpin monomer can comprise a portion of the loop region and a portion of the second stem region of the first hairpin monomer. For example, in FIG. 39a, the first "assembly domain I" of first hairpin monomer A1 comprises the sequence f*-e*-d*-c*, where f*-e* is a portion of the loop region and d*-c* is a portion of the second stem region of the first hairpin monomer A1. In the absence of an initiator, the first and second stem regions of the first hairpin monomer are generally hybridized to form a duplex domain of the first hairpin monomer, and the first assembly domain of the first hairpin monomer is generally not available for hybridization to another monomer.

Preferably, upon hybridization of a newly-exposed toehold of the first "assembly domain I" of the first hairpin monomer to the exposed toehold of the first "assembly complement domain" of the second hairpin monomer, the second stem region is displaced from the first stem region. This opens the hairpin of the second hairpin monomer. In the depicted embodiment, the exposed toehold c* of first hairpin monomer A1 nucleates at the exposed toehold c of the second hairpin monomer A2 by pairing segment c* with c (FIG. 39b). This induces a strand displacement interaction resulting in the hybridization of the first hairpin monomer A1 at the first "assembly domain I" (i.e., f*-e*-d*-c*) to the first "assembly complement domain" (i.e., c-d-e-f) of the second hairpin monomer A2.

In some embodiments, the "second assembly domain I" of a second hairpin monomer can comprise a portion of the loop region and a portion of the second stem region of the second hairpin monomer. For example, in FIG. 39a, the second "assembly domain I" of second hairpin monomer A2 comprises the sequence b*-a*-f*-e*, where b*-a* is a portion of the loop region and f*-e* is a portion of the second stem region of the second hairpin monomer In the absence of an exposed first "assembly domain I," the first and second stem regions of the second hairpin monomer are generally hybridized to form a duplex domain of the second hairpin monomer, and the second "assembly domain I" of the second hairpin monomer is generally not available for hybridization to another monomer.

Preferably, upon hybridization of a newly-exposed toehold of the second assembly domain of the second hairpin monomer to the exposed toehold of the second "assembly complement domain" of the third hairpin monomer, the second stem region is displaced from the first stem region. This opens the hairpin of the third hairpin monomer. For example, in FIG. 39b, the exposed toehold e* of second hairpin monomer A2 nucleates at the exposed toehold e of the third hairpin monomer A3 by pairing segment e* with e (FIG. 39b). This induces a strand displacement interaction resulting in the hybridization of the second hairpin monomer A2 at the second "assembly domain I" (i.e., e*-f*-a*-b*) to the second assembly complement domain e-f-a-b of the third hairpin monomer A3.

In FIG. 39b, A3 has a newly exposed single-stranded tail that comprises the "disassembly domain" (comprising the sequence d*-c*-b*-a*) of the third hairpin monomer A3. In some embodiments, the "disassembly domain" of the third hairpin monomer is complementary to a portion of the inhibitor binding domain of the first hairpin monomer.

In some embodiments, the "disassembly domain" of a third hairpin monomer can comprise a portion of the loop region and a portion of the second stem region of the third hairpin monomer. For example, in the depicted embodiment, the disassembly domain of third hairpin monomer A3 comprises the sequence d*-c*-b*-a where d*-c* is a portion of the loop region and b*-a* is a portion of the second stem region of the third hairpin monomer. In the absence of an exposed second "assembly domain I," the first and second stem regions of the third hairpin monomer are generally hybridized to form a duplex domain of the third hairpin monomer, and the "disassembly domain" of the third hairpin monomer is generally not available for hybridization to another monomer.

Figure 40:
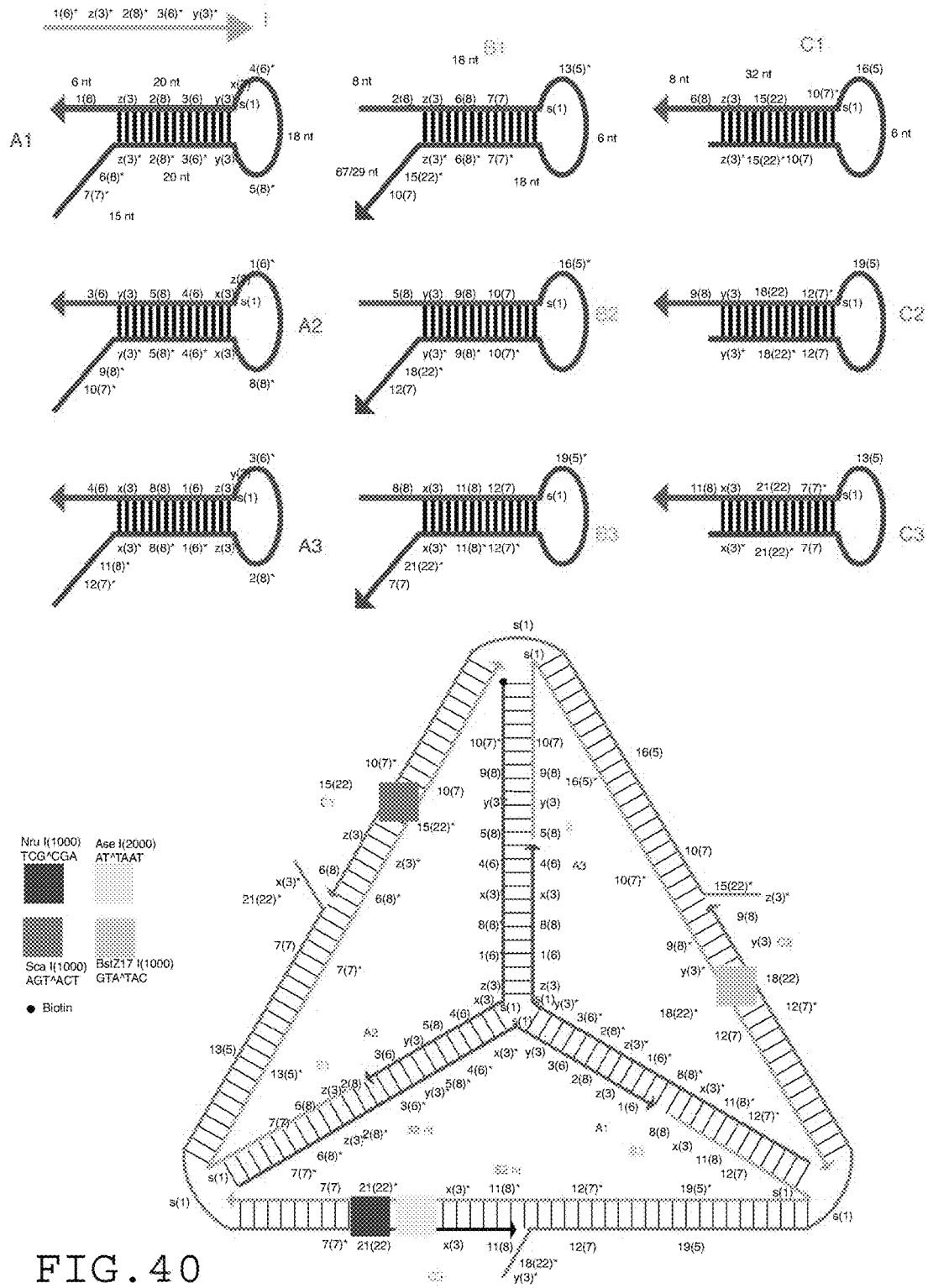
FIG. 40 generally depicts implementation details for the catalytic formation of a DNA tetrahedron. The number in the parenthesis depicts the number of bases for a particular fragment. For example, 1(6) refers to segment 1 which contains 6 bases; similarly, z(3)* refers to the segment z* that contains 3 bases, where * denotes complementarity.

FIG. 40 depicts another embodiment of the triggered tetrahedron formation, which is also discussed in detail in Example 19. In summary, the reaction system operates as follows: A1 hybridize to I, allowing A2 to bind to A1. A3 then displaces I and hybridizes to A1 and A2 (resulting a structure similar to the top right hand side of FIG. 37B). Following this, B1 hybridizes to A1, B2 hybridizes to A2, and B3 hybridizes to A3 (resulting in a structure similar to that depicted in 39B). Following this, C1 hybridizes to B1, C2 hybridizes to B2 and C3 hybridizes to B3 (resulting in a structure similar to 39C). A remaining part of C3 hybridizes to B1, a remaining part of C2 hybridizes to B3, and a remaining part of C1 hybridizes to B2, providing the structure shown in FIG. 40.

Catalytic Circuitry

In some embodiments, the self-assembly pathway can be a pathway for an autocatalytic system with exponential kinetics. Compositions and methods are provided for autocatalytic duplex formation by a cross-catalytic circuit. In some embodiments, the triggered exponential growth of cross-catalytic self-assembly pathway can be used in, for example, engineering enzyme-free isothermal detection methods. In sensing applications, self-replication can provide signal amplification for enzyme-free isothermal alternatives to polymerase chain reaction based on self-assembly reaction pathways.

Figure 3B:
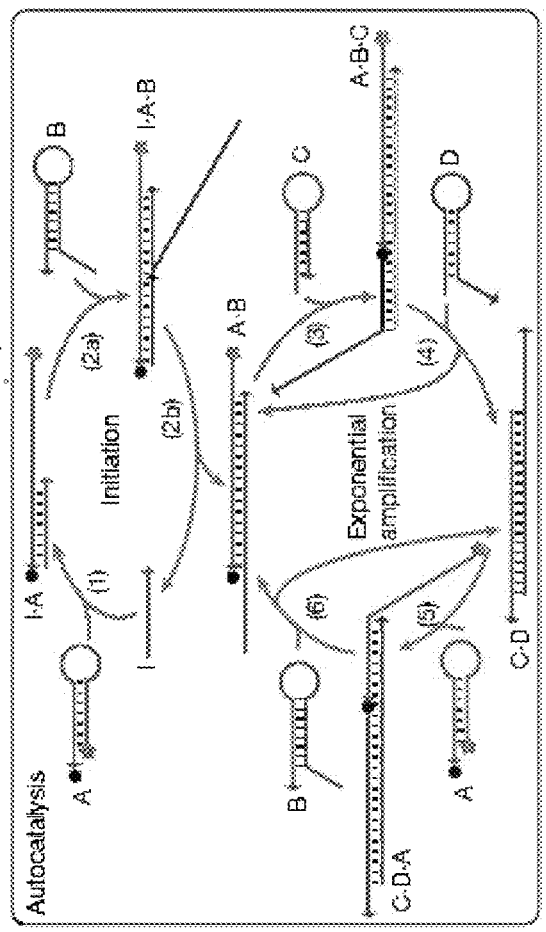
FIGS. 3a-c generally depict autocatalytic duplex formation by a cross-catalytic circuit with exponential kinetics. a, Reaction graph. Multiple assembly arrows entering the same input port depict parallel processes on separate copies of the nodal species. b, Secondary structure mechanism. c, System kinetics examined by fluorescence quenching. Formation of A-B is monitored by the increase in fluorescence resulting from increased spatial separation between the fluorophore resulting from increased spatial separation between the fluorophore (green star in b) and the quencher (black dot in b) at either end of A. Raw data for two independent reactions are displayed for each initiator concentration (20-nM hairpins). Single traces are shown for the controls containing only A and B or only A. Inset: linear fit of the 10% completion time against the logarithm of the relative concentration of I ($0.0003\times \leq [I] \leq 0.05\times$). High-concentration end points ($[I] \geq 0.1\times$) are excluded based on theoretical analysis; low-concentration end points ($[I] \leq 0.001\times$) are excluded because of signal poisoning by leakage.
Figure 3B:
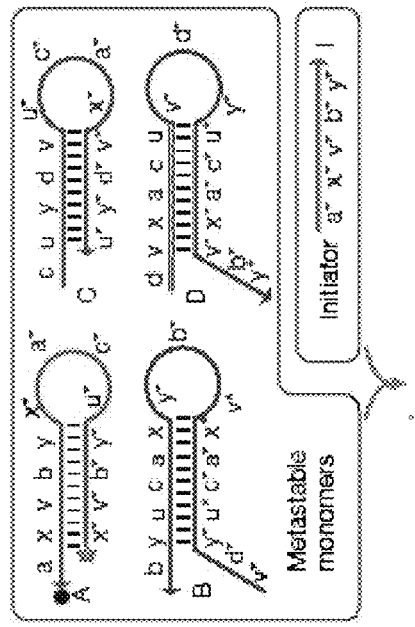
Figure 3A:
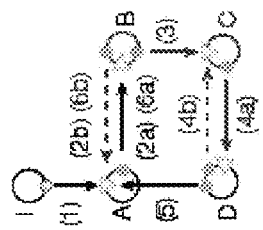

In some embodiments, programming of the cross-catalytic self-assembly pathways can be executed as shown in FIGS. 3a and b. The reaction graph of FIG. 3a generates an autocatalytic system with exponential kinetics. In the corresponding molecular implementation (FIG. 3b), four hairpin species, A, B, C, and D coexist metastably in the absence of initiator I (FIG. 3b, top). The initiator catalyzes the assembly of hairpins A and B to form duplex A•B (Steps 1-2, FIG. 3b, bottom), bringing the system to an exponential amplification stage powered by a cross-catalytic circuit: the duplex A•B has a single-stranded region that catalyzes the assembly of C and D to form C•D (Steps 3-4); C•D in turn has a single-stranded region that is identical to I and can thus catalyze A and B to form A•B (Steps 5-6). Hence, A•B and C•D form an autocatalytic set capable of catalyzing its own production. Disassembly (Steps 2b, 4b, and 6b) is fundamental to the implementation of autocatalysis and sterically uninhibited exponential growth.

Figure 3C:
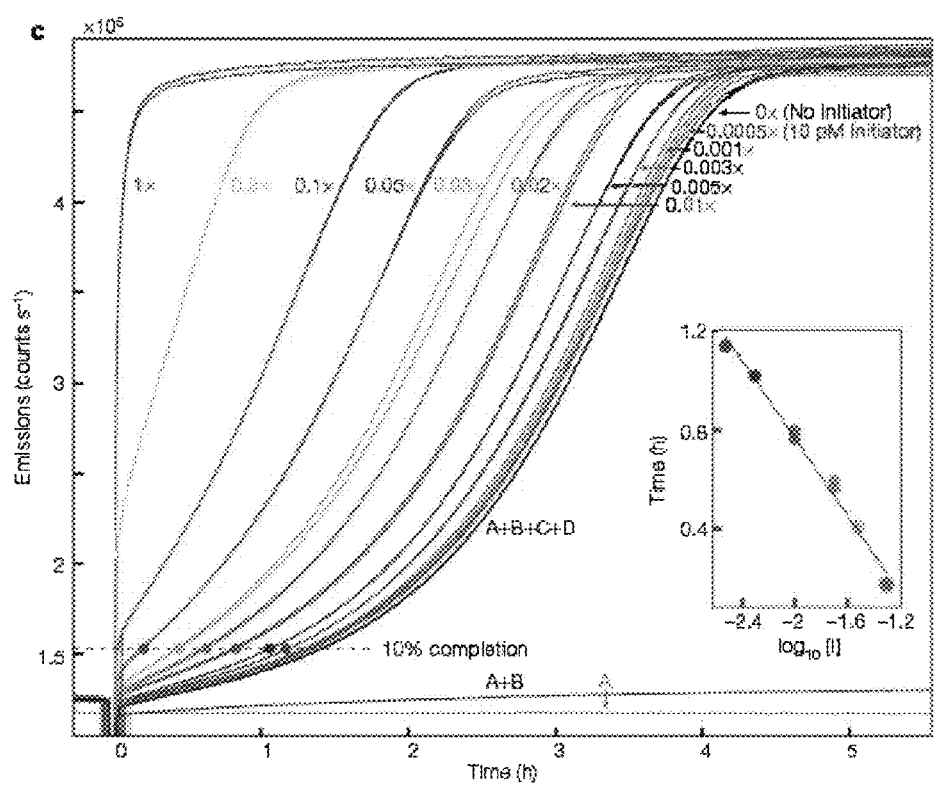

In some embodiments, each step in the reaction can be examined using, for example, native polyacrylamide gel electrophoresis to check for the expected assembly and disassembly behavior. System kinetics can be examined via a fluorescence quenching experiment (FIG. 3c). Spontaneous initiation in the absence of initiator reflects the finite time scale associated with the metastability of the hairpins and yields a sigmoidal time course characteristic of an autocatalytic system. As expected, the curve shifts to the left as the concentration of initiator is increased. A plot of 10% completion time against the logarithm of the concentration exhibits a linear regime, consistent with exponential kinetics and analytical modeling (FIG. 3c, inset). The minimal leakage of a system containing only A and B (labeled A+B in FIG. 3c) emphasizes that the sigmoidal kinetics of spontaneous initiation for the full system (A+B+C+D) are due to cross-catalysis.

The cross-catalytic self-assembly pathway demonstrates synthetic biomolecular autocatalysis (see, von Kiedrowski et al., *Angew. Chem. Int. Ed.* 25, 932-935 (1986); Paul et al., *Proc. Natl. Acad. Sci. USA* 99, 12733-12740 (2002); Levy, M. & Ellington, A. D., *Proc. Natl. Acad. Sci. USA* 100, 6416-6421 (2003); Lee et al., *Nature* 382, 525-528 (1996)) driven purely by the free energy of base-pair formation. Autocatalysis and exponential system kinetics can also be achieved via entropy-driven hybridization mechanisms.

A detailed example of one embodiment for programming catalytic circuitry is provided below in Example 7.

Nucleated Dendritic Growth

In some embodiments, the self-assembly pathway can be a pathway for nucleated dendritic growth. Compositions and methods for self-assembly pathways are provided in which nucleic acid monomers form dendrimers. In some embodiments, dendrimers are formed only upon detection of a target nucleation molecule. By growing to a prescribed size, such dendrimers can provide quantitative signal amplification with strength exponentially related to in the number of constituent species.

In some embodiments, methods and compositions disclosed herein can be used for in situ amplification in bioimaging applications, such as, for example, in bio-marker generation. The bio-marker can, for example, facilitate fluorescence imaging, molecule sorting, etc. See, Pierce et al., U.S. patent application Ser. No. 11/371,346, which is herein incorporated by reference in its entirety. For example, monomers disclosed herein can be used to self-assemble a fluorescent polymer tethered to a target mRNA to detect expression of the mRNA. In some embodiments, labeled hairpin monomers can self-assemble in the presences of an initiator into a dendrimer of a prescribed size, yielding quantized signal amplification with strength exponential in the number of components. In some embodiments, only the root hairpin monomer and its two child species depend on the sequence of the initiator; thus, the other monomers do not need to be redesigned for each target initiator.

Figure 4A:
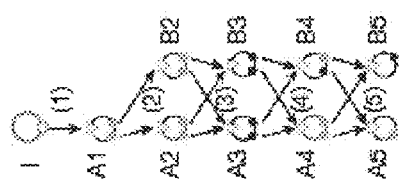
Figure 4B:
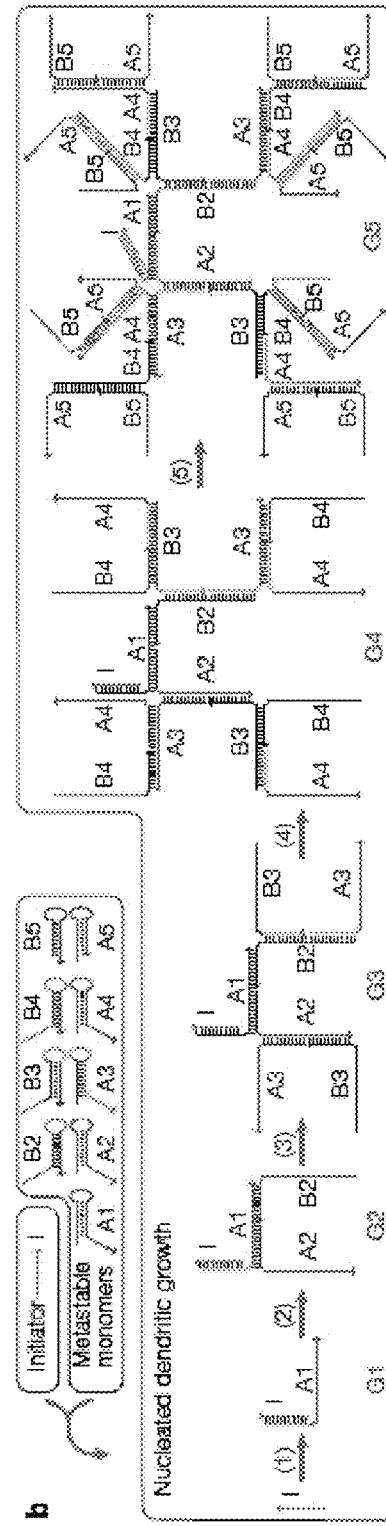

The molecular program in FIG. 4a depicts the triggered self-assembly of a binary molecular tree of a prescribed size. In the depicted embodiment, the reaction starts with the assembly of an initiator node I with a root node A1. Each assembled node subsequently assembles with two child nodes during the next generation of growth, requiring two new node species per generation. In the absence of steric effects, a G-generation dendrimer uses 2G-1 node species and yields a binary tree containing 2G-1 monomers, i.e., a linear increase in the number of node species yields an exponential increase in the size of the dendrimer product. FIG. 4b depicts the motif based implementation of the program depicted in FIG. 4a: Hairpins are metastable in the absence of initiator; the initiator I triggers the growth of a dendrimer with five generations of branching (G5).

In one embodiment, trees with G=1, 2, 3, 4, and 5 are constructed. The nucleated growth of the trees can be examined using, for example, native agarose gel electrophoresis. Band shifting demonstrates increasing dendrimer size with each generation of growth (FIG. 4c). FIG. 4d demonstrates that the concentration of dendrimer depends linearly on the concentration of the initiator in the system. Finally, AFM imaging of dendrimers for G=3, 4, and 5 reveals the expected morphologies (FIG. 4e). Measurements of the dendrimer segment lengths agree well with the design.

A detailed example of one embodiment for programming nucleated dendritic growth is provided below in Example 9.
Autonomous Locomotion In some embodiments, the self-assembly pathway can be a pathway for autonomous locomotion. In some embodiments, autonomous locomotion occurs in the presence of a catalyst. In some embodiments, autonomous locomotion occurs in the absence of a catalyst. Compositions and methods are provided for an autonomous enzyme-free bipedal DNA walker capable of stochastic locomotion along a DNA track. In some embodiments, the bipedal DNA walker system can mimic the bipedal motor protein, kinesin, which hauls intracellular cargo by striding along microtubules. Asbury et al., Curr. Opin. Cell Biol. 17, 89-97 (2005).

In some embodiments of a system for autonomous locomotion, the system comprises two species of "fuel" hairpin monomers, and a bipedal walker. In various embodiments, one species of fuel hairpin monomer ("track monomers") can be linearly arranged at regular intervals along substrate to form a track for a bipedal walker. In some embodiments, the substrate can comprise a nicked DNA duplex. Typically, the track monomers comprise an input domain and an output domain. A bipedal walker comprises two identical "walker legs" connected by a duplex torso (FIG. 5b). The walker legs comprise an output domain complementary to an input domain of the track monomers. The bipedal walker assembles with the track monomers. In the presence of the second fuel hairpin monomer assembles with a track monomer, which subsequently displaces from the bipedal walker. Typically, a second "fuel" hairpin monomer species comprises an input domain complementary to the output domain of the track monomer species, and an output domain complementary to the input domain of the track monomer species. The bipedal walker moves unidirectionally along the linear track by sequentially catalyzing the formation of a "track monomer-second fuel hairpin monomer" complex.

The molecular program in FIG. 5a depicts a self-assembly pathway the stochastic movement of a bipedal walker. Joined by a duplex torso, each of two identical walker legs, I, is capable of catalyzing the formation of waste duplex A•B from metastable fuel hairpins A and B via a reaction pathway in which I assembles with A, which assembles with B, which subsequently disassembles I from the complex. FIGS. 5a and b depict a reaction graph and corresponding molecular implementation for an exemplary bipedal walker. As shown in FIG. 5b, in some embodiments, the track can consist of five A hairpins arranged linearly at regular intervals along a nicked DNA duplex. In the presence of hairpin B, a subpopulation of walkers will move unidirectionally along the track by sequentially catalyzing the formation of A•B. Due to the one-dimensional arrangement of anchor sites, this processive motion occurs only for those walkers that exhibit a foot-over-foot gait by stochastically lifting the back foot at each step.

Figure 29A:
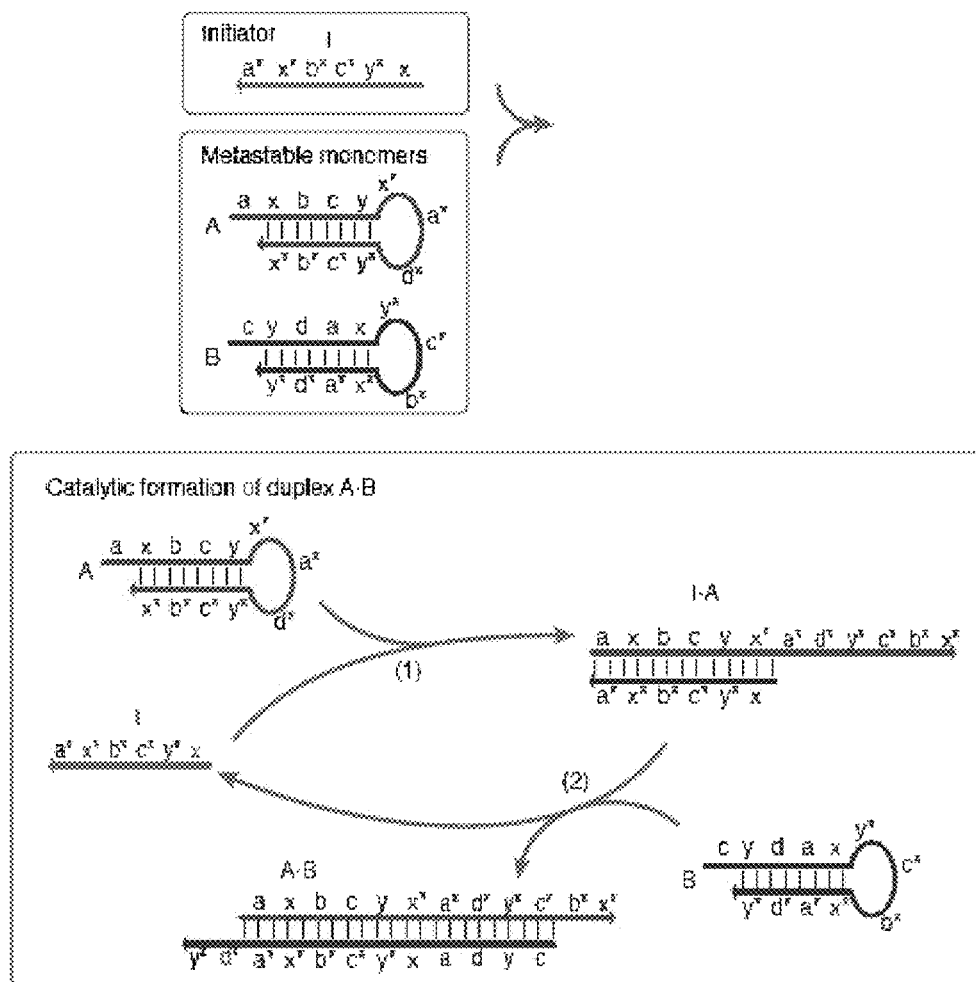
FIGS. 29a-b depict a fuel system for the walker system. a, Reaction schematic. b, Agarose gel electrophoresis demonstrates catalytic formation of the DNA duplex.

One embodiment of a fuel system for a walker system is shown in FIG. 29a. Hairpins A and B in co-exist metastably in the absence of catalyst I. Catalyst I catalyzes A and B to form duplex A•B. Step 1: the toehold a* of I nucleates at the toehold a of A, resulting in the opening of the hairpin A and the formation of the product I•A. Step 2: I•A, with c* newly exposed, opens hairpin B; B subsequently displaces I from A, producing waste product A•B.

Figure 5C:
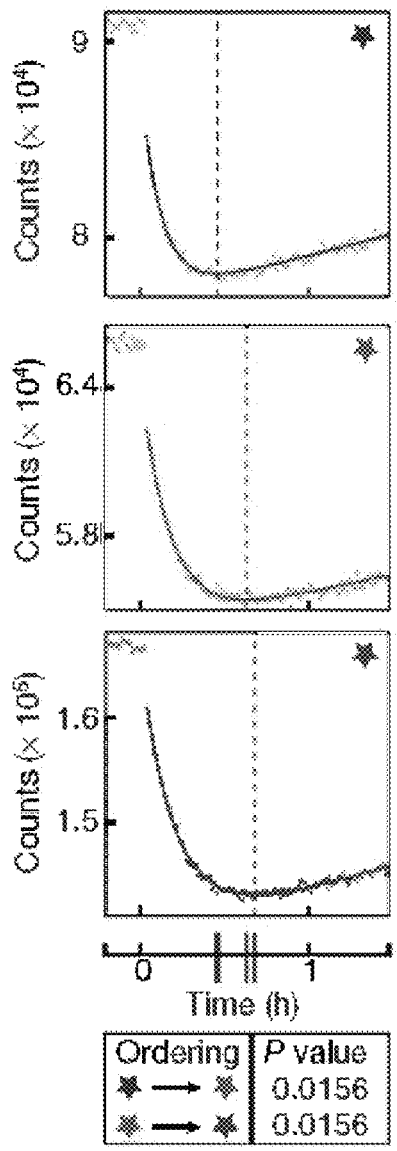

In some embodiments, walker locomotion can be investigated using a bulk fluorescence assay that tests whether there is a sub-population of walkers that locomotes processively through positions 3, 4, and 5, starting from an initial condition with legs anchored at positions 1 and 2. Quenchers are attached to the walker's legs and spectrally distinct fluorophores are positioned proximal to anchorages 3, 4, and 5. Consistent with processivity, the anticipated sequential transient quenching of the fluorophores at positions 3, 4, and 5 is observed (FIG. 5c).

Figure 5D:
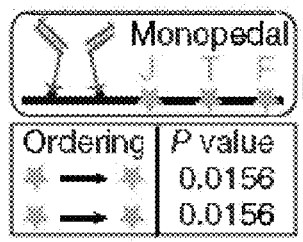
Figure 5E:
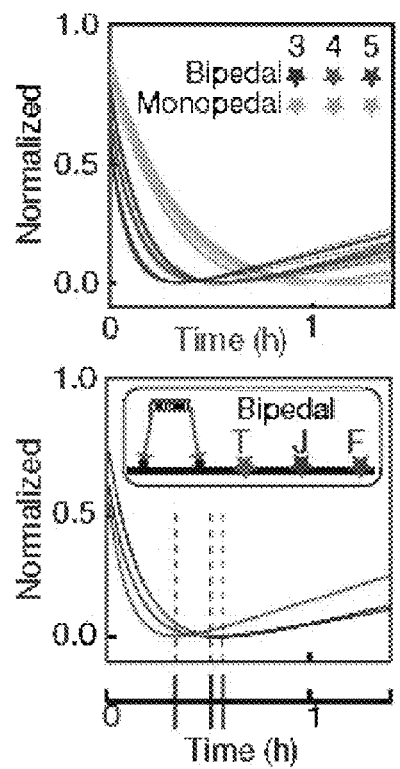

To rule out the possibility that this signal arises from non-processive walker diffusion through the bulk solution from one position to the next, monopedal walkers that lack a mechanism for achieving processivity can be used. In this case, the sequential transient quenching will no longer match the ordering of the fluorophores along the track (FIG. 5d) and the time scale for visiting any one of the three anchorages is longer than the time scale to visit all three anchorages for the bipedal system (FIG. 5e).

Figure 5F:
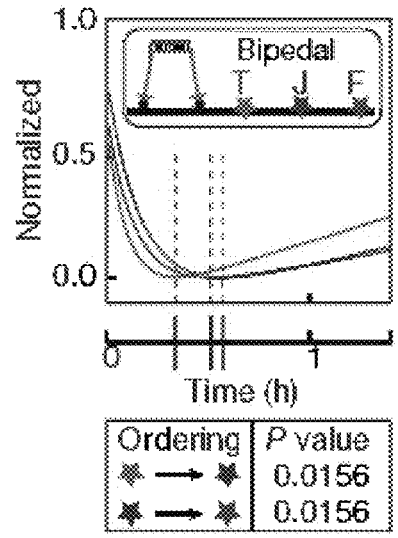

Additional control experiments show that this difference in time scales cannot be explained by the relative rates with which freely diffusing bipedal and monopedal walkers land on the track. As a further test of processivity for the bipedal walker, reordering the fluorophores along the track leads to the expected change in the ordering of the transient quenching (FIG. 5f).

A detailed example of one embodiment for programming autonomous locomotion is provided below in Example 11.
Pathway Analysis The hairpin monomers, polymers, self-assembly pathway reactions and dynamic functions can be analyzed by any of a variety of methods known in the art. For example, gel electrophoresis can be used to compare the hairpin monomers before and after the reaction. For example, an amount of each monomer species can be mixed and mixed with varying amounts of initiator and a control (e.g., reaction buffer only). The samples can be allowed to react for a suitable time, such as for example without limitation 2 hours. The annealed can be mixed with loading buffer mix was loaded into a gel. The gel can be run and the nucleic acid visualized under UV light. In some embodiments, the gel can be imaged using an imaging system such as, for example, an FLA-5100 imaging system (Fuji Photo Film Co., Ltd.).

In some embodiments, the hairpin monomers and polymers can be visualized using an atomic force microscope (AFM). For example, images can be obtained using a multimode scanning probe microscope, equipped with an Q-control module for analog AFMs. In some embodiments, samples can be first diluted in an appropriate buffer to achieve the desired sample density. The diluted sample can be applied onto the surface of freshly cleaved mica and allowed to bind. Supplemental $Ni^{++}$ can be added to increase the strength of DNA-mica binding. H. G. Hansma and D. E. Laney, *Biophysical Journal*, 70:1933-1939, 1996. Before placing the fluid cell on top of the mica puck, an additional amount of buffer can be added to the cavity between the fluid cell and the AFM cantilever chip to avoid bubbles.

In some embodiments, fluorescence data can be obtained for a walker system using, for example, a spectrofluorometer. For example, excitation and emission wavelengths were set to 394 nm and 517 nm (for FAM), 527 nm and 551 nm (for JOE), and 558 nm and 578 nm (for TAMRA), respectively, with 4 nm bandwidth. The assembly of the walker system is described above. In the experiments, an amount of the track and an amount of the bipedal walker can be used to assemble the system. In some embodiments, a sub-stoichiometric amount of walker can be used to ensure that no free-floating walker would bind to the hairpin monomer on the track. For the same reason, a sub-stoichiometric amount of monopedal walker can be used in the diffusion experiments. The assembled track can be introduced first to record the three fluorescence baselines of FAM, JOE, and TAMRA. The hairpin monomer is then introduced to start the walker's locomotion.

Compositions for Self-Assembly Pathways

Compositions and kits for self-assembly pathways are contemplated for use within the scope of the subject matter. In preferred embodiments, the compositions comprise a first hairpin monomer and a second hairpin monomer. In some embodiments, the compositions comprise a first hairpin monomer, a second hairpin monomer and a third hairpin monomer. In some embodiments, the compositions comprise a first hairpin monomer, a second hairpin monomer, a third hairpin monomer and a fourth hairpin monomer. Additional monomers can be included in some embodiments. In the presence of initiator, a self-assembly pathway is initiated causing the initiation of the desired dynamic function. In some embodiment, the dynamic function results in formation of a polymer. In some embodiments, in the presence of a catalyst, autonomous locomotion is initiated.

The compositions can also contain other components, such as, for example, accessory molecules that facilitate initiator recognition and aid the formation of polymers. Accessory molecules typically comprise nucleic acid molecules. In some embodiments, the accessory molecules are DNA helper strands that bind to regions flanking an initiator nucleic acid sequence. Preferably the accessory molecules are DNA helper strands that bind to regions flanking the binding site on an initiator.

Furthermore, the composition can comprise a carrier that facilitates the introduction of nucleic acids, such as, for example, nucleic acid monomers and accessory nucleic acid molecules, into a cell, such as a cell containing an initiator associated with a disease or disorder. Carriers for delivery of nucleic acids into cells are well known in the art and examples are described above.

In some embodiments, a computer program is provided that designs and/or aids in the design of the primary sequences of hairpin monomers. In some embodiments, a program can be used that specifies assembly and/or disassembly pathways for dynamic functions using nodal abstractions. In some embodiments, the program translates nodal abstractions into hairpin motifs. In some embodiments, the program designs primary sequences of hairpin monomers. In this manner, primary sequences for hairpin monomers for implementing a dynamic pathway can be provided by the program. In some embodiments, the program performs any of the methods described herein.

Molecular Compilers

Within the nucleic acid design community, it is common practice to specify a design as a set of one or more static target secondary structures. Seeman, *Nature* 421, 427-431 (2003). The sequences of the constituent strands are then typically designed by optimizing an objective function that captures some combination of affinity and/or specificity for the target structures. Seeman, *J. Biomol. Struct. Dyn.* 8, 573-581 (1990); Hofacker et al., *Chem. Mon.* 125, 167-188 (1994); Andronescu et al., *J. Mol. Biol.* 336, 607-624 (2004); Dirks et al., *Nucleic Acids Res.* 32, 1392-1403 (2004).

By contrast, dynamic function encoded in a self-assembly system can be designed by programming the reaction pathway of the system as described herein. The intended dynamic function is first specified using a reaction graph. The reaction graph is then implemented in terms of the present hairpin motif, and finally the molecular implementation is encoded in the primary sequences of a set of nucleic acid strands of the hairpin monomers. As such, the standardized hairpin motif and the reaction graph provide layers of abstraction that bridge the description of the dynamic behavior of the system and the set of nucleic acid primary sequences, which implement the target behavior.

In some embodiments, automating the process depicted in the reaction graph can provide a biomolecular compiler that can take the desired dynamic function as input, translate it first to a reaction graph, then to a motif-based molecular implementation, and subsequently into nucleic acid sequences that encode the intended dynamic function.

In some embodiments, a method for preparing hairpin monomers for carrying out a dynamic function is provided. In some embodiments, the method includes: providing an input, switching the state of a first input port on a first nodal abstraction from accessible to inaccessible, switching the state of a first output port on the first nodal abstraction from inaccessible to accessible; switching the state of a second input port on a second nodal abstraction from accessible to inaccessible and switching the state of the first output port on the first nodal abstraction from accessible to in accessible; and designing a first hairpin monomer based on the first nodal abstraction and a second hairpin monomer based on the second nodal abstraction, where the first and second hairpin monomers self-assemble in the presence of an initiator to perform the dynamic function. In some embodiments, a step of designing nucleic acid primary sequences for the first hairpin monomer and second hairpin monomer can be included in the method.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

System Synthesis

This example illustrates the synthesis and preparation of hairpin monomers.

Nucleic acid synthesis. Nucleic acid, such as, for example, DNA, can be synthesized and purified by various methods known in the art. In some embodiments, purified nucleic acid strands can be reconstituted in, for example, ultrapure water with resistance of at least 18MΩ. The concentrations of the nucleic acid solutions can then be determined by the measurement of ultraviolet absorption at 260 nm.

Hairpin synthesis. Each hairpin can be synthesized using a variety of methods known in the art. For example, in some embodiments, two nucleic acid pieces can be synthesized and ligated to produce the full hairpin. The ligation can be performed a suitable enzyme, such as, for example, T4 DNA ligase at suitable conditions. For example, the ligation can be performed at room temperature or 16° C. for at least two hours. Ligated strands can be further purified using, for example, denaturing polyacrylamide gel electrophoresis. The bands corresponding to the nucleic acid strands of expected sizes can be visualized by, for example, UV shadowing and excised from the gel. The nucleic acid strands can then be eluted and recovered by ethanol precipitation.

Monomer preparation. For preparation of monomers, concentrated nucleic acid strands can be diluted to suitable reaction conditions. Exemplary reaction conditions can be as follows: 50 mM $Na_2HPO_4$, 0.5 M NaCl, pH=6.8; or 20 mM Tris, pH=7.6, 2 mM EDTA, 12.5 mM $Mg^{++}$ (1×TAE/$Mg^{++}$ buffer). The hairpins are allowed to anneal under suitable conditions. For example, the hairpins can then annealed by, for example, heating for 5 minutes at 90° C., and then turning off the heating block to allow the system to cool to room temperature (requiring at least 2 hours).

Example 2

System Design Example: Catalytic Formation of 3-Arm Junction

This example illustrates the design procedure for the catalytic 3-arm junction system as presented in FIGS. 2a and b.

Figure 6B:
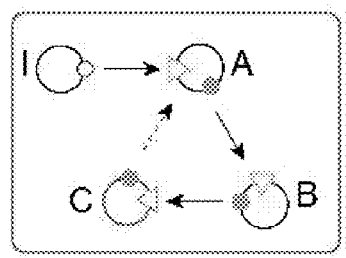
Figure 6B:
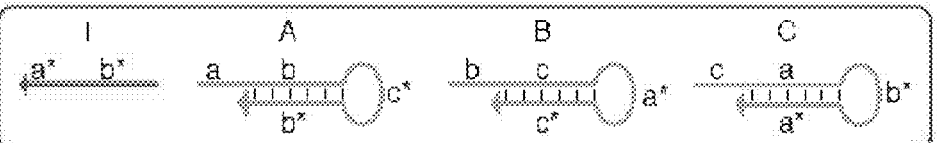
Figure 6B:
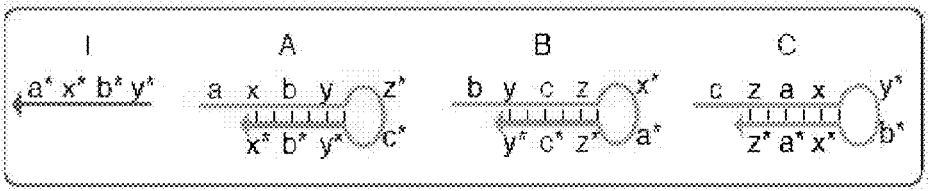

Step (1), Pathway specification. The desired dynamic behavior (FIG. 6a) is specified using a reaction graph (FIG. 6b).

Step (2.1), Basic molecular logic implementation. The reaction graph is implemented using the standard motif (FIG. 6c).

Step (2.2), Padding/clamping. The basic implementation (FIG. 6c) is modified by adding padding/clamping segments, i.e., segments x, y, z, x*, y* and z* in FIG. 6d. These segments serve two purposes. First, they serve as 'padding' segments to modulate the lengths of the hairpin's exposed toehold, stem, and loop, which permits more flexible dimensioning in the next step. Second, the segments serve as 'clamps' to decrease spurious 'leakage' reactions in the absence of the initiators. Consider un-clamped hairpin A and hairpin B in FIG. 6c. When the left-end of hairpin A's stem 'breathes,' the 3' end of the segment b* will be transiently exposed, revealing a partial toe-hold that is complementary to the toe-hold b of hairpin B. This transient toe-hold exposure would permit hairpin A and hairpin B to reach spuriously and form A•B (which would then react with C to form A•B•C). By contrast, the 'breathing' of the left end of the clamped hairpin A stem in FIG. S3d exposes x* instead of b* remains sequestered, discouraging spurious reaction between A and B that nucleates at b*.

Figure 6F:
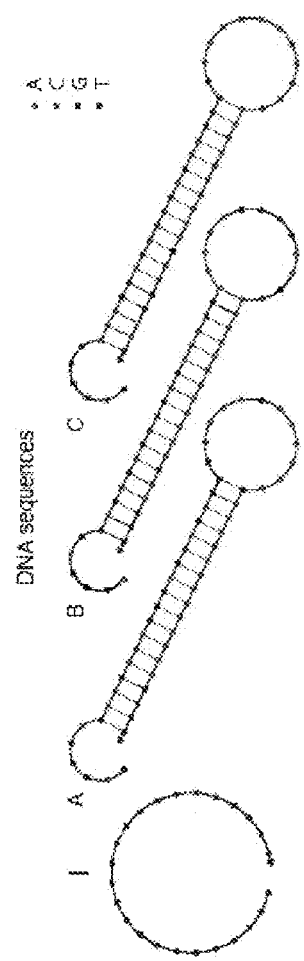

Step (2.3), Segment dimensioning. The purpose of segment dimensioning is to assign the length of each segment in terms of the number of nucleotides such that under specified conditions, the desired reaction can proceed smoothly while spurious reactions are suppressed. The NUPACK server (www.nupack.org) can be used for dimensioning. For the catalytic 3-arm junction system described here, assigning 6-nt to each segment (FIG. 6e) stabilizes critical structures in the reaction pathway in the context of a dilute solution of interacting nucleic acid strands. An exemplary sequence design is shown in FIG. 6f.

Step (3), Sequence design. Based on the criteria determined from implementing the reaction graph, primary sequences for the hairpin monomers are designed. The sequences are optimized computationally to maximize affinity and specificity for the formation of the 3-arm junction by minimizing the average number of incorrectly paired bases at equilibrium. The system is synthesized as described in Example 1. Verification of the system is carried out using gel and single-molecule AFM.

Example 3

Execution of the Reaction Graphs for Catalytic 3-Arm/4-Arm Junction Systems

Figure 7A:
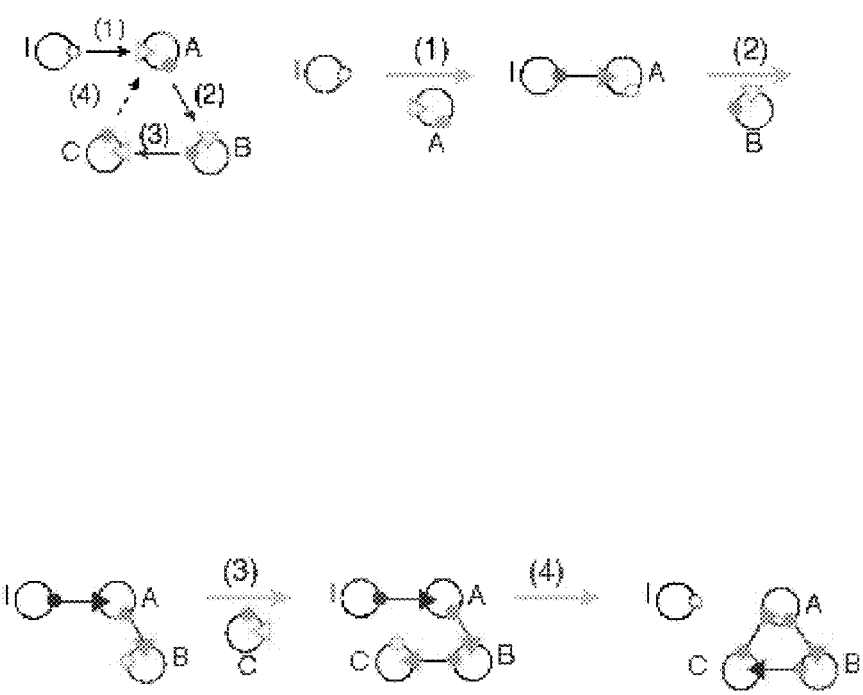
FIGS. 7a-b generally depict execution of the reaction graphs for catalytic 3-arm and 4-arm junction systems. a, Execution of the reaction graph for catalytic 3-arm junction systems. b, Execution of the reaction graph for catalytic 4-arm junction systems.

This example illustrates the step-by-step execution of the reaction graphs in FIGS. 2a and e. As shown in FIG. 7a, Reaction 1 (assembly), a bond is made between the accessible output port of I and the accessible input port of A and both ports are flipped to inaccessible states; the output port of A is flipped to the accessible state (based on the internal logic of node A). Reaction 2 (assembly): a bond is made between the newly accessible output port of A and the accessible input port of B and both ports are flipped to inaccessible states; the output port of B is flipped to the accessible state (based on the internal logic of node B). Reaction 3 (assembly): A bond is made between the newly accessible output port of B and the input port of C and both ports are flipped to inaccessible states; the output port of C is flipped to the accessible state (based on the internal logic of node C). Reaction 4 (disassembly): the bond between the inaccessible output port of I and the inaccessible input port of A is displaced by a bond between the newly accessible blue output port of C and the input port of A; the states of the two output ports are flipped.

Figure 7B:
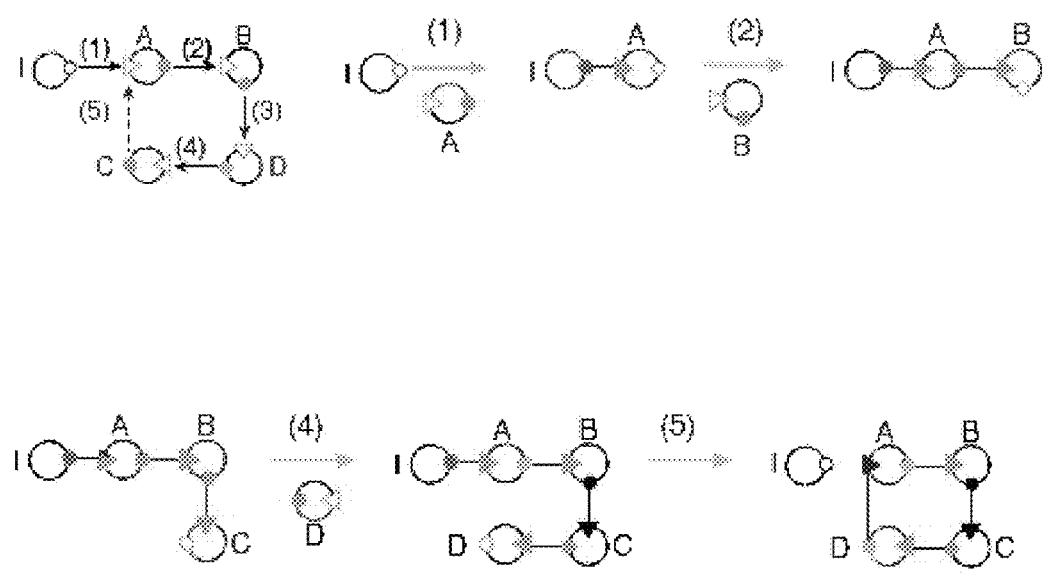

The reaction graph in FIG. 7a contains a k=3 disassembly cycle: input port of A∘blue output of A→input port of B∘blue output port of B→input port of C∘ blue output port of C→input port of A. The reaction graph in FIG. 7b contains a k=4 disassembly cycle: input port of A∘blue output of A→input port of B∘blue output port of B→input port of C∘blue output port of C→input port of D∘blue output port of D→input port of A.

Example 4

Catalytic Structure Formation: Catalytic Formation of a 4-Arm Junction

FIGS. 8a and b depict the reaction graph and reaction schematic for the catalytic formation of a 4-arm junction, respectively. In the absence of initiator I, hairpins A, B, C, and D are kinetically impeded from forming the 4-arm junction that is predicted to dominate at equilibrium. Introduction of I into the system (FIG. 8b, bottom) activates a cascade of assembly steps with A, B, C, and D followed by a disassembly step in which D displaces I from the complex, freeing I to catalyze the self-assembly of additional branched junctions. The lengths of segments q, q*, r, r*, s, s*, t, and t* are 18 nt; the lengths of the other segments are 6 nt. Hairpins A, B, C, and D are metastable in the absence of the initiator I. The initiator I catalyzes monomers A, B, C, and D to form a 4-arm DNA junction, as follows: (1) segment a* of I nucleates at the toehold a of hairpin A and initiates a strand displacement that results in the opening of hairpin A; (2) newly exposed b* of A nucleates at toehold b of B and results in the opening of B; (3) newly exposed c* of B nucleates at toehold c of C and results in the opening of C; (4a) newly exposed d* of C nucleates at d of hairpin D and results in the opening of D; (4b) D displaces I from A.

Lanes 1-5: A gel shifting assay validates each reaction step depicted in panel (b). Lanes 5-9: Effects of different concentrations of I (1×, 0.5×, 0.25×, 0.1×, and 0×) on the formation of A•B•C•D. 600 nM reactants were incubated at room temperature for 2 hours. Lane 10: A•B•C•D annealed over 2.5 hours (600 nM hairpin species heated at 95° C. for 5 minutes and cooled to room temperature over 2.5 hrs). The 2% agarose gel was prepared in 1×LB buffer (Faster Better Media, LLC) with 0.5 µg/ml ethidium bromide. The gels were run at 150 V for 30 min at room temperature and then visualized using UV transillumination. The hairpins used for these reactions did not contain the 3' tails (q*, r*, s*, and t*).

Native agarose gel electrophoresis (FIG. 8c) confirms that the hairpins assemble slowly in the absence of the initiator (Lane 9) and that assembly is dramatically accelerated by the addition of initiator (Lane 5). Disassembly of the initiator enables catalytic turnover as indicated by the nearly complete consumption of hairpins even at sub-stoichiometric initiator concentrations (Lanes 6-8). As in the 3-arm junction case, only minimal assembly is achieved by annealing the hairpin mixture (Lane 10).

AFM imaging of the catalyzed self-assembly product (augmented with strands that extend the duplex portion of each arm as described in the caption) reveals the expected 4-arm junction morphology (FIG. 8d). To assist in AFM imaging of the 4-arm junction, four strands (Ae, Be, Ce, and De) were incubated with the catalytically formed 4-arm junction A•B•C•D. Note that the duplex portion of the arms of the final structure A•B•C•D•Ae•Be•Ce•De are twice as long as the duplex portion of the arms of A•B•C-D. Two AFM images of A•B•C•D•Ae•Be•Ce•De are presented in FIG. 8d.

Example 5

AFM Image Analysis

Figure 9A:
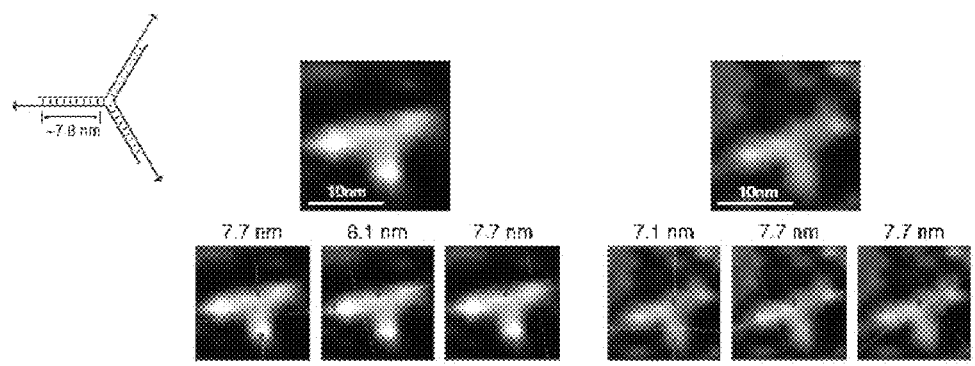
FIGS. 9a-b depict AFM measurements of the 3-arm (a) and 4-arm (b) junctions described in FIG. 2 and FIGS. 8a-d. The small images are screenshots of the measurement section files. The distance between the two arrows is listed above the image.
Figure 9B:
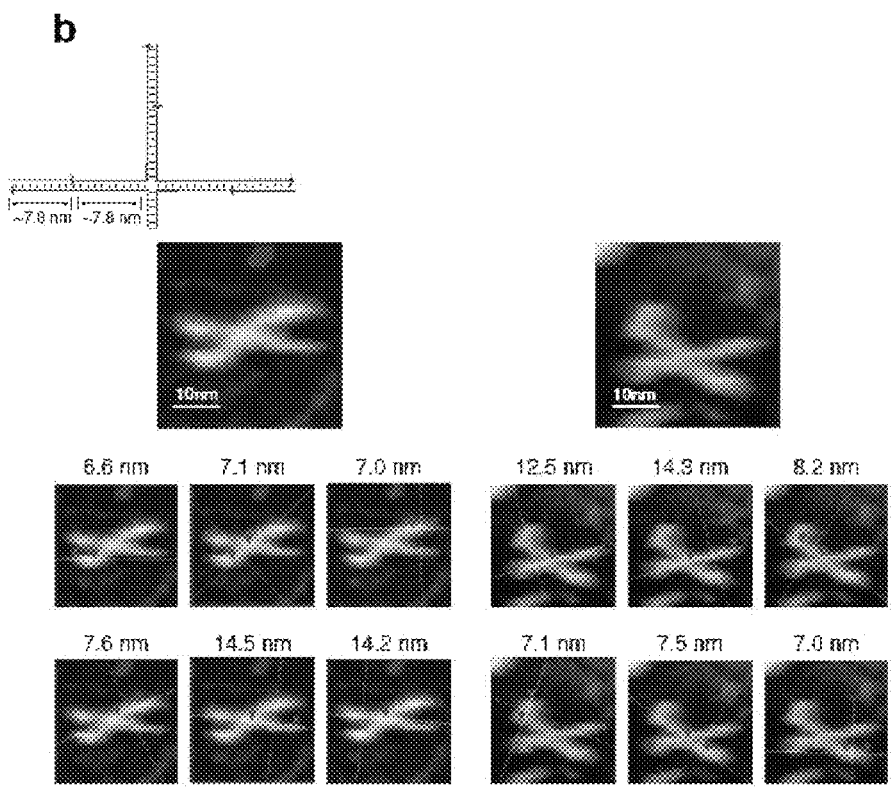
Figure 10A:
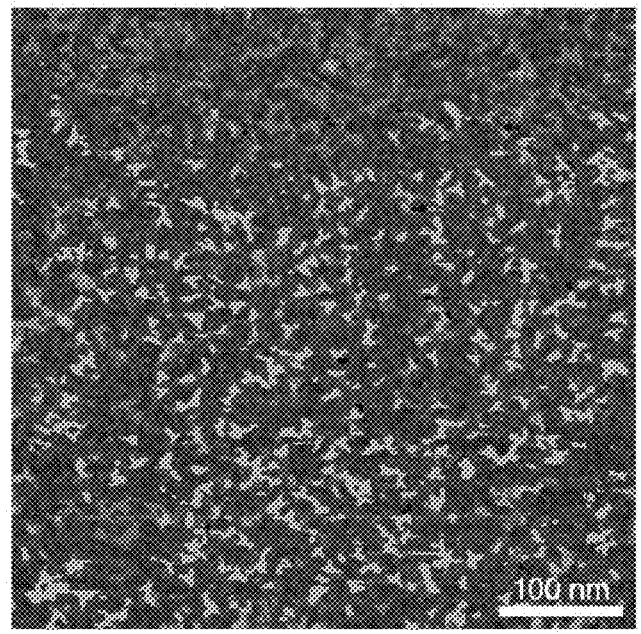
FIGS. 10a-b depict large-field-of-view AFM images of the 3-arm (a) and 4-arm (b) junction systems.
Figure 10B:
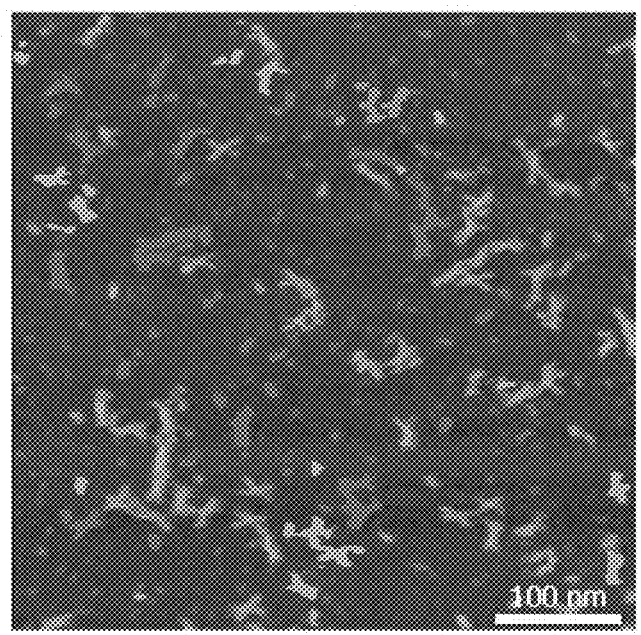

FIGS. 9a and b depict AFM image analysis of 3-arm/4-arm junctions. Using a B-DNA model where one helical turn contains 10.5 base pairs and measures 3.4 nm, the expected arm length for the 3-arm junction was calculated as follows: (24/10.5)×3.4 nm=7.8 nm. Similarly, the arm length for the 4-arm junction is calculated to be 7.8+7.8=15.6 nm. The measured lengths of the arms are roughly consistent with the calculated lengths. FIGS. 10a and b show AFM images with a larger field of view for 3-arm (a) and 4-arm (b) junctions.

Example 6

Design for the Catalytic Formation of a K-Arm Junction

Figure 11A:
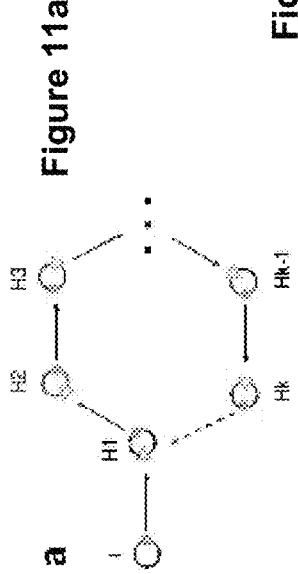
FIGS. 11a-b depict catalytic formation of a k-arm junction. a, Reaction graph. b, Reaction schematics.
Figure 11B:
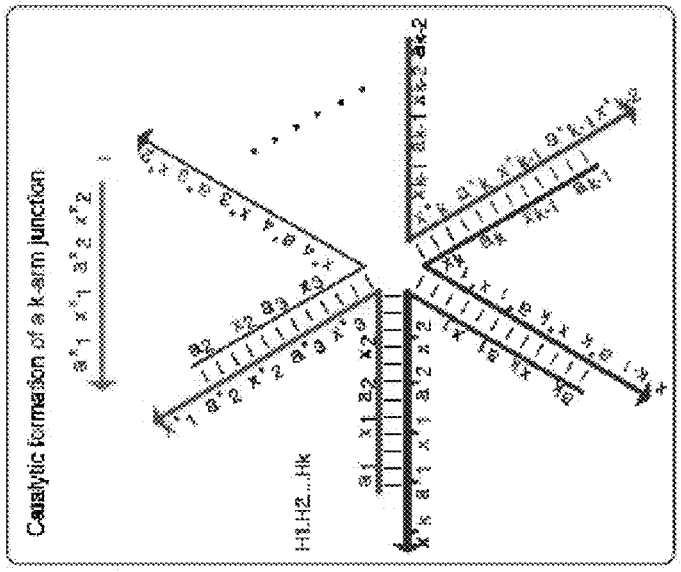
Figure 11B:
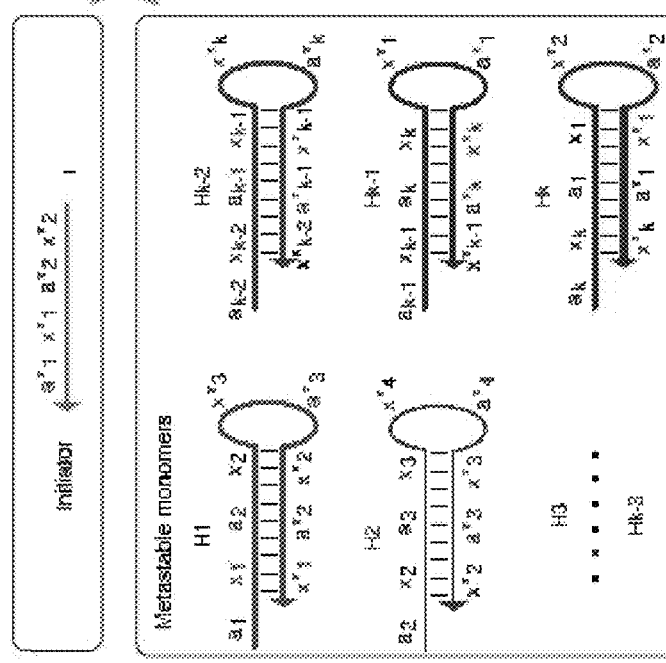

The catalytic system described in FIG. 2 and FIG. 8 can, in principle, be generalized to a system capable of the catalytic formation of a k-arm junction. FIGS. 11a and b describe the reaction graph and the secondary structure schematic for the catalytic formation of a k-arm junction. Hairpins $H_1, H_2, \ldots, H_k$ are metastable in the absence of the initiator I. The initiator I catalyzes monomers $H_1, H_2, \ldots, H_k$ to form a k-arm DNA junction.

Figure 12A:
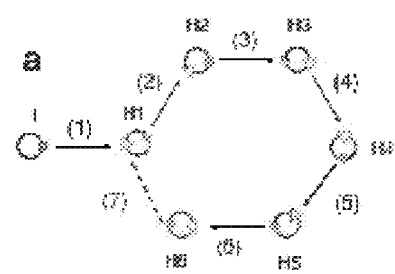
FIGS. 12a-c depict catalytic formation of a 6-arm junction. a, Reaction graph. b and c, Step-by-step reaction schematic.
Figure 12B:
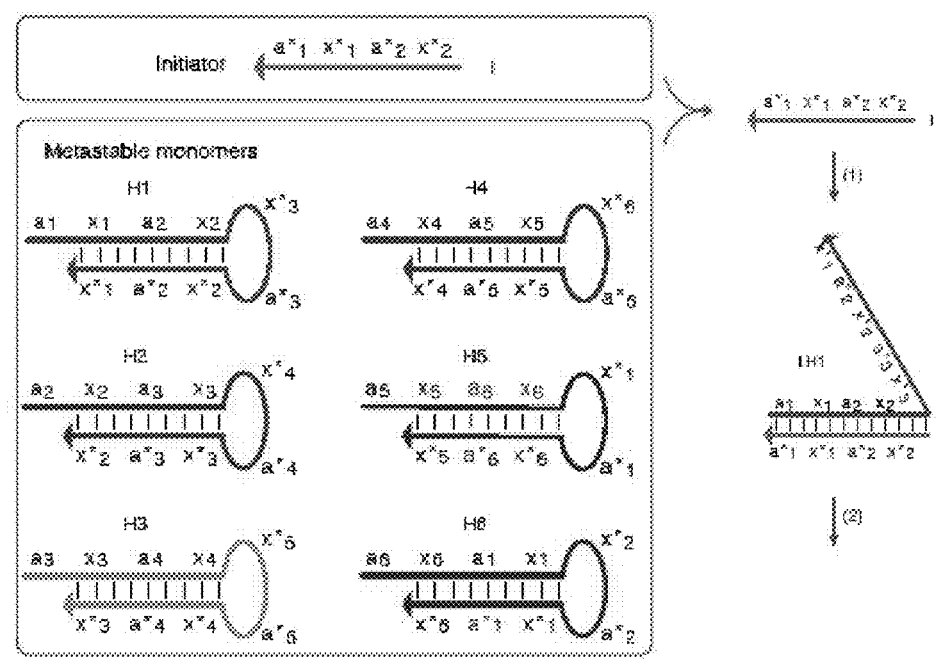
Figure 12C:
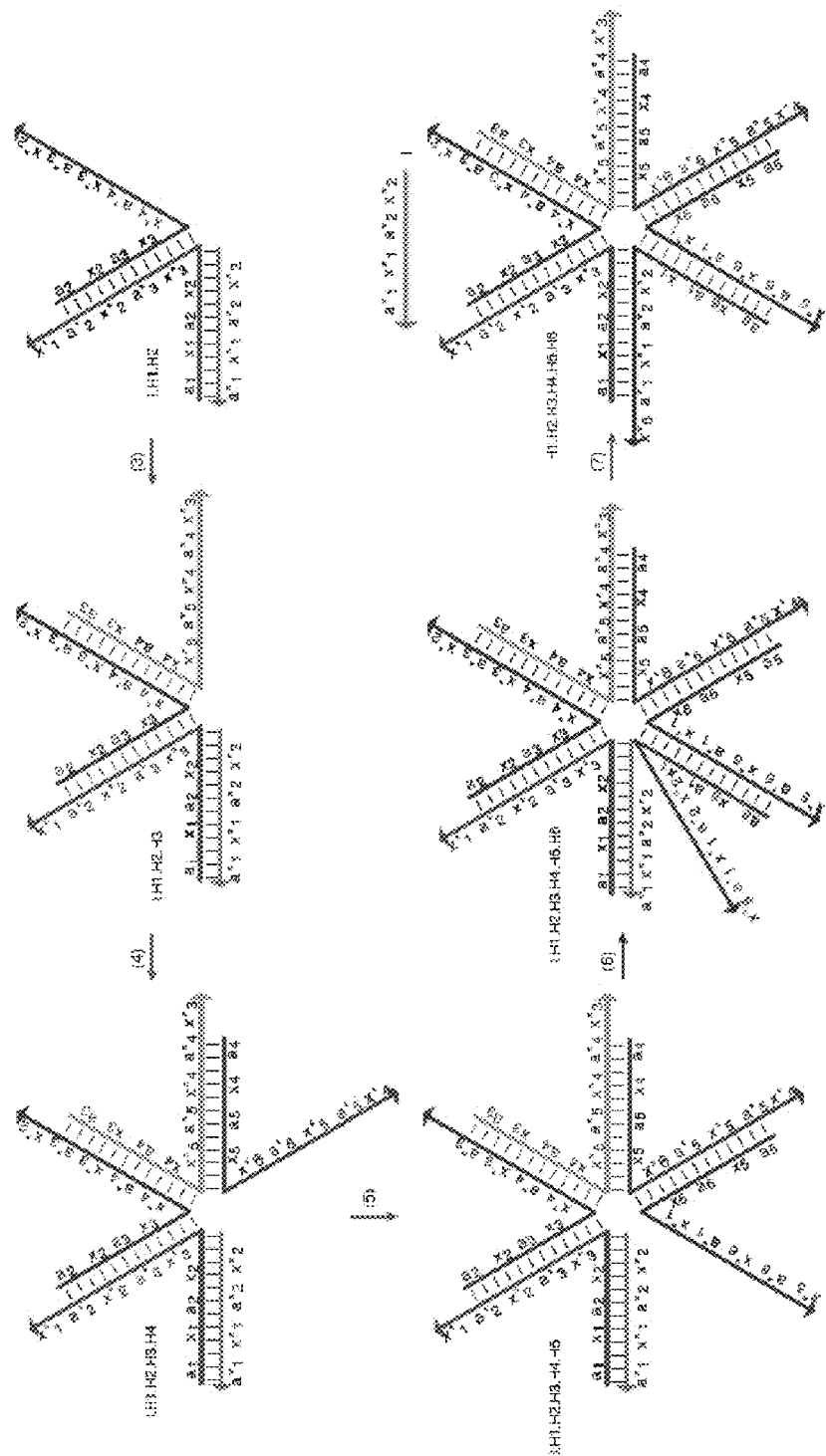

FIGS. 12a-c depict an example when k=6. In FIGS. 12b and c, hairpins $H_1, H_2, H_3, H_4, H_5$ and $H_6$ are metastable in the absence of the initiator I. The initiator I catalyzes monomers $H_1, H_2, H_3, H_4, H_5$ and $H_6$ to form a 6-arm DNA junction as follows. Step 1: segment $a^*_1$ of I nucleates at the toehold $a_1$ of hairpin $H_1$ and initiates a strand displacement that results in the opening of hairpin $H_1$. Step 2: the newly exposed $a^*_2$ of $H_1$ nucleates at the toehold $a_z$ of hairpin $H_2$ and opens hairpin $H_2$. Step 3: the newly exposed $a^*_3$ of $H_2$ nucleates at the toehold $a_3$ of hairpin $H_3$ and opens hairpin $H_3$. Step 4: the newly exposed $a^*_4$ of $H_3$ nucleates at the toehold $a_4$ of hairpin $H_4$ and opens hairpin $H_4$. Step 5: the newly exposed $a^*_5$ of $H_4$ nucleates at the toehold $a_5$ of hairpin $H_5$, and opens hairpin $H_5$. Step 6: the newly exposed $a^*_6$ of $H_5$, nucleates at the toehold $a_6$ of hairpin $H_6$ and opens hairpin $H_6$. Step 7: $H_6$ displaces I from $H_1$.

Example 7

Catalytic Circuitry

Figure 13:
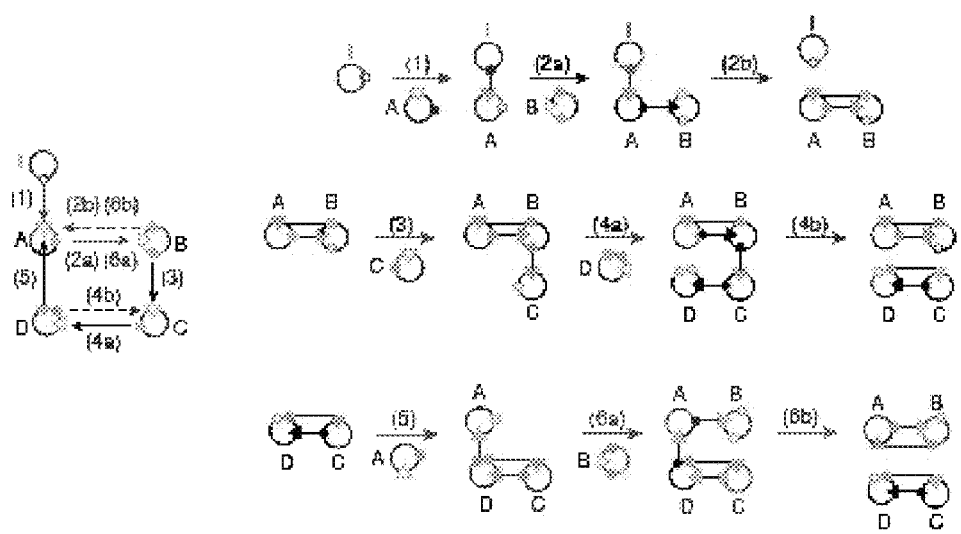
FIG. 13 depicts the execution of the reaction graph for the autocatalytic system of FIG. 3.

FIG. 13 describes the step-by-step execution of the reaction in FIG. 3a. The reaction starts at solid arrow (1) that connects the accessible output port of I and the accessible input port of A. Note that by convention, the two arrows entering the same input port of A depict parallel processes on separate copies of the nodal species.

Reaction 1 (assembly): A bond is made between the accessible output port of I and the accessible input port of A and both ports are flipped to inaccessible states; the output port of A is flipped to the accessible state (based on the internal logic of node A).

Reaction 2a (assembly): A bond is made between the newly accessible output port of A and the accessible input port of B and both ports are flipped to inaccessible states; the two output ports of B are flipped to accessible states (based on the internal logic of node B).

Reaction 2b (disassembly): The bond between the inaccessible output port of I and the inaccessible input port of A is displaced by a bond between the newly accessible blue output port of B and the input port of A; the states of the two output ports are flipped.

Reaction 3 (assembly): A bond is made between the newly accessible green output port of B and the accessible input port of C and both ports are flipped to inaccessible states; the output port of C is flipped to the accessible state (based on the internal logic of node C).

Reaction 4a (assembly): A bond is made between the newly accessible output port of C and the accessible input port of D and both ports are flipped to inaccessible states; the output ports of D are flipped to accessible states (based on the internal logic of node D).

Reaction 4b (disassembly): The bond between the inaccessible green output port of B and the inaccessible input port of C is displaced by a bond between the newly accessible blue output port of D and the input port of C; the states of the two output ports are flipped.

Reaction 5 (assembly): A bond is made between the newly accessible green output port of D and the accessible input port of A and both ports are flipped to inaccessible states; the output port of A is flipped to the accessible state (based on the internal logic of node A).

Reaction 6a (assembly): A bond is made between the newly accessible output port of A and the accessible input port of B and both ports are flipped to inaccessible states; the output ports of B are flipped to accessible states (based on the internal logic of node B).

Reaction 6b (disassembly): The bond between the inaccessible green output port of D and the inaccessible input port of A is displaced by a bond between the newly accessible blue output port of B and the input port of A; the states of the two output ports are flipped.

Figure 14:
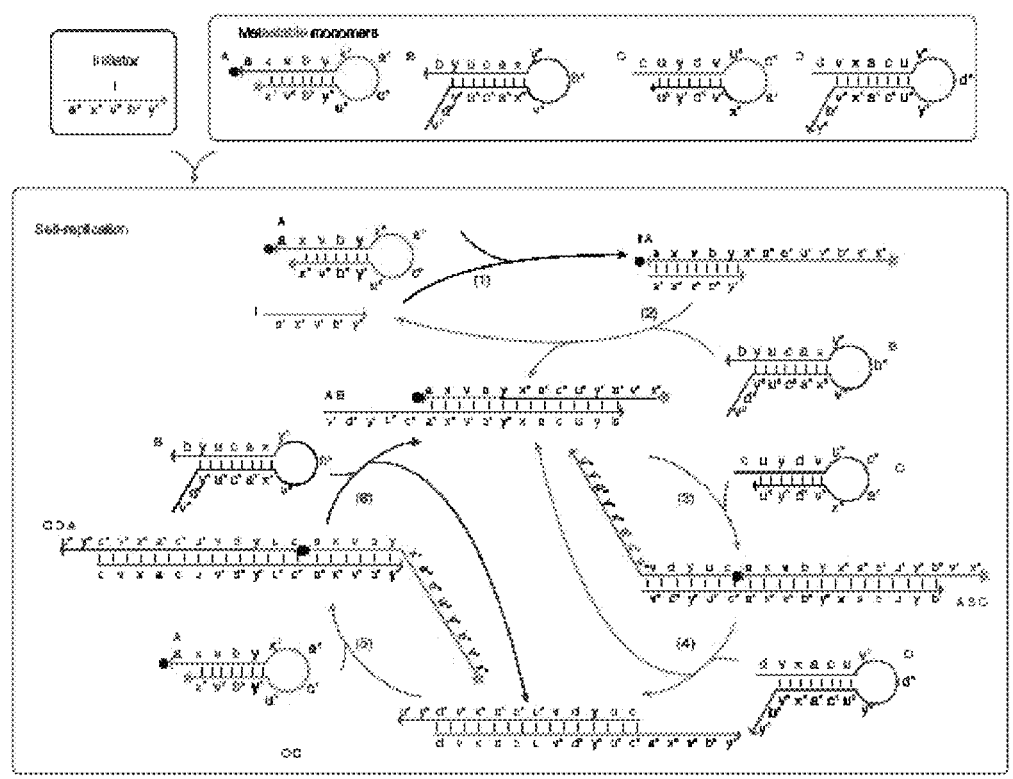
FIG. 14 depicts the detailed reaction schematic for the autocatalytic system of FIG. 3. The length of each segment is 6 nt. Green star, fluorophore; black dot, quencher.
Figure 15A:
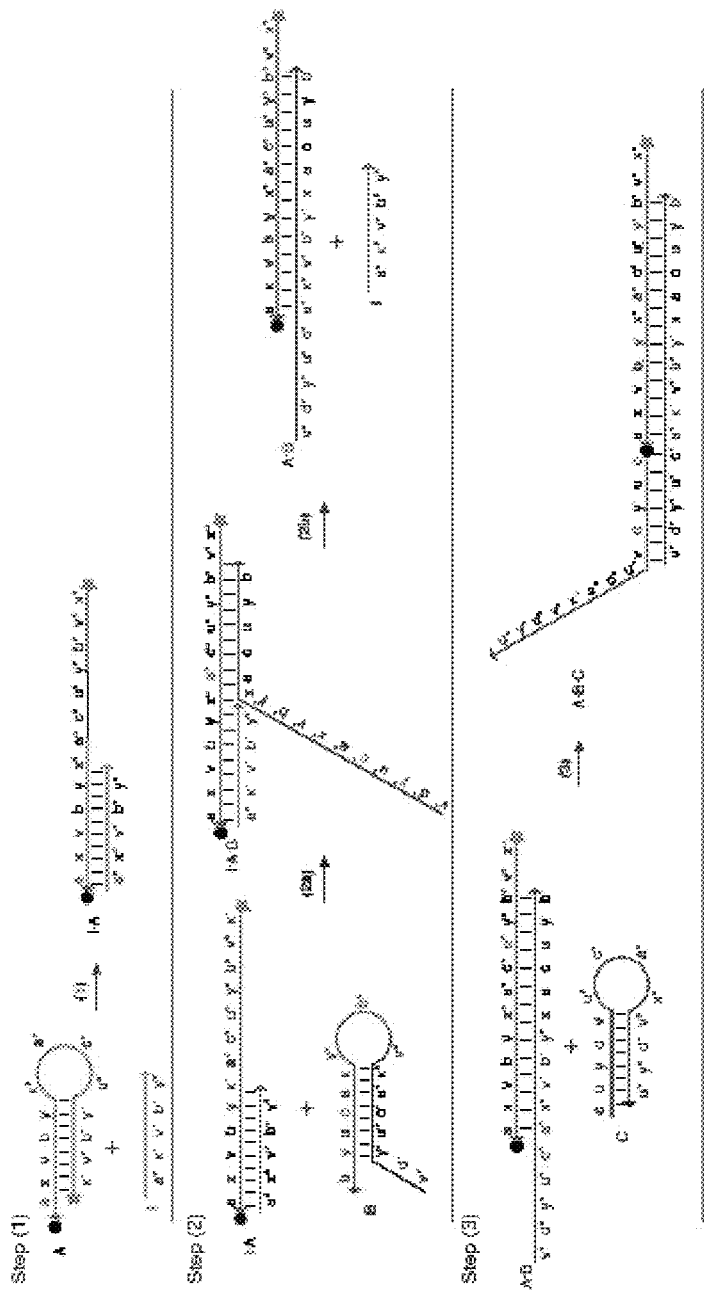
FIGS. 15a-c depict a step-by-step reaction schematic for the autocatalytic system of FIG. 3.
Figure 15B:
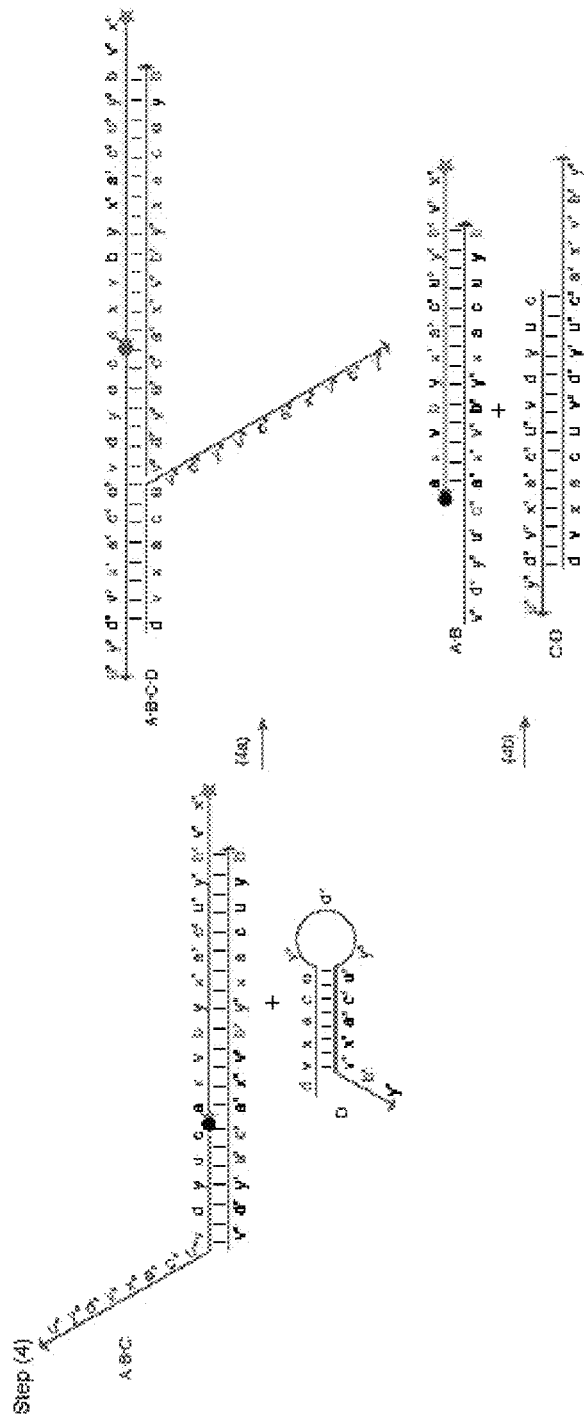
Figure 15C:
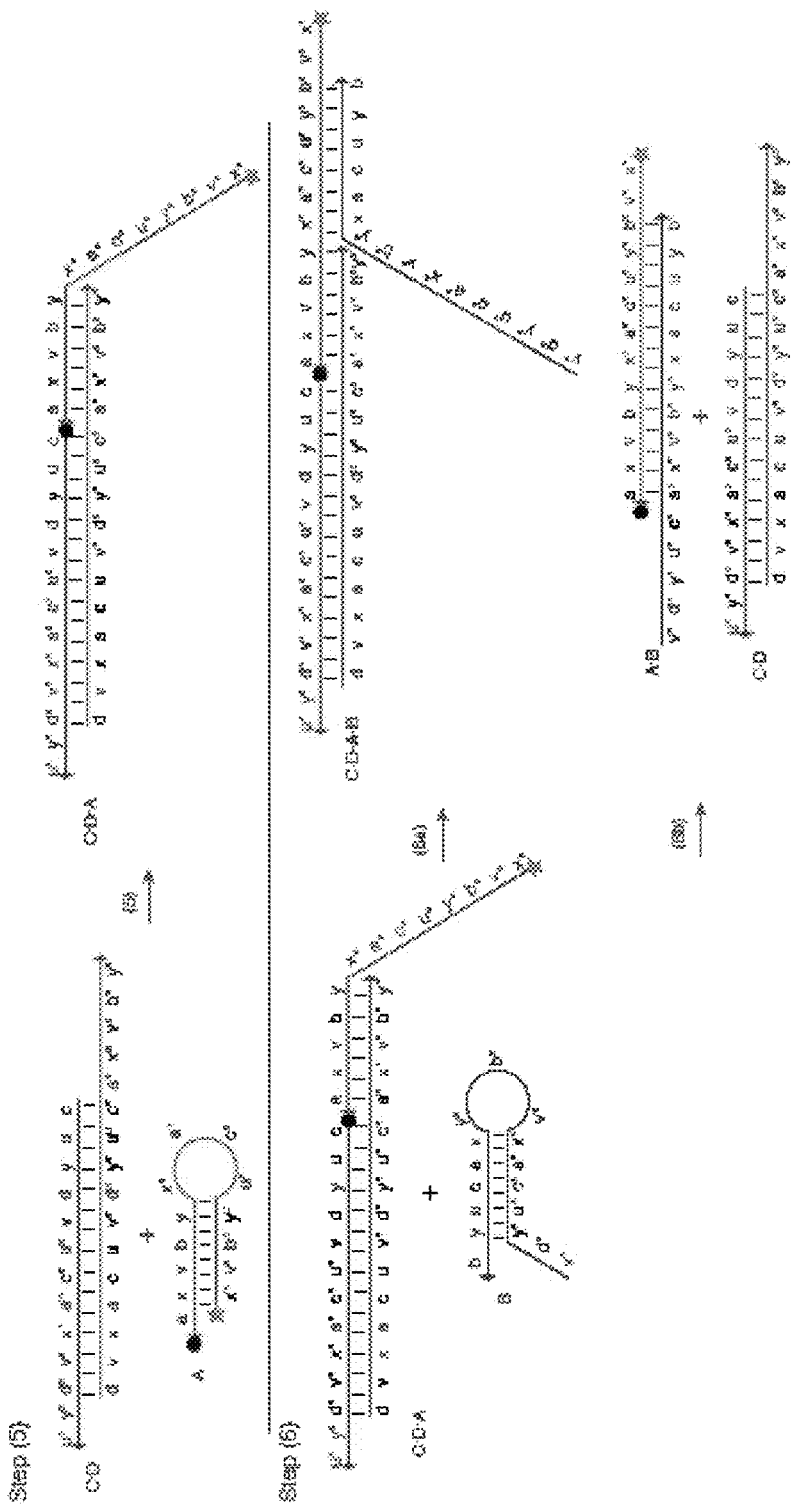

FIG. 14 describes the detailed reaction flow of the autocatalytic system described in FIG. 3. FIGS. 15a-c describe additional intermediate steps. Steps 1-2 are the initiation stage; steps 3-6 are the exponential amplification stage.

Step 1: the toehold a* of I nucleates at the toehold a of A, resulting in the opening of the hairpin and the formation of the product FA.

Step 2: FA, with b* newly exposed, opens hairpin B (step 2a); B subsequently displaces I from A (step 2b), producing A•B and bringing the system to the exponential amplification stage. The single-stranded tail (v*-d*-y*-u*-c*) of A•B next catalyzes C and D to form C•D (in steps 3 and 4).

Step 3: A•B, with c* newly exposed, opens hairpin C.

Step 4: A•B•C, with d* newly exposed, opens hairpin D (step 4a); D subsequently displaces C from B, separating A•B and C•D (step 4b). The single-stranded tail (a*-x*-v*-b*-y*) of C•D is identical to I and next catalyzes A and B to form A•B (in steps 5 and 6).

Step 5: C•D, with a* newly exposed, opens hairpin A.

Step 6: C•D•A, with b* newly exposed, opens B (step 6a); B subsequently displaces A from D, separating C•D and A•B (step 6b).

Figure 16A:
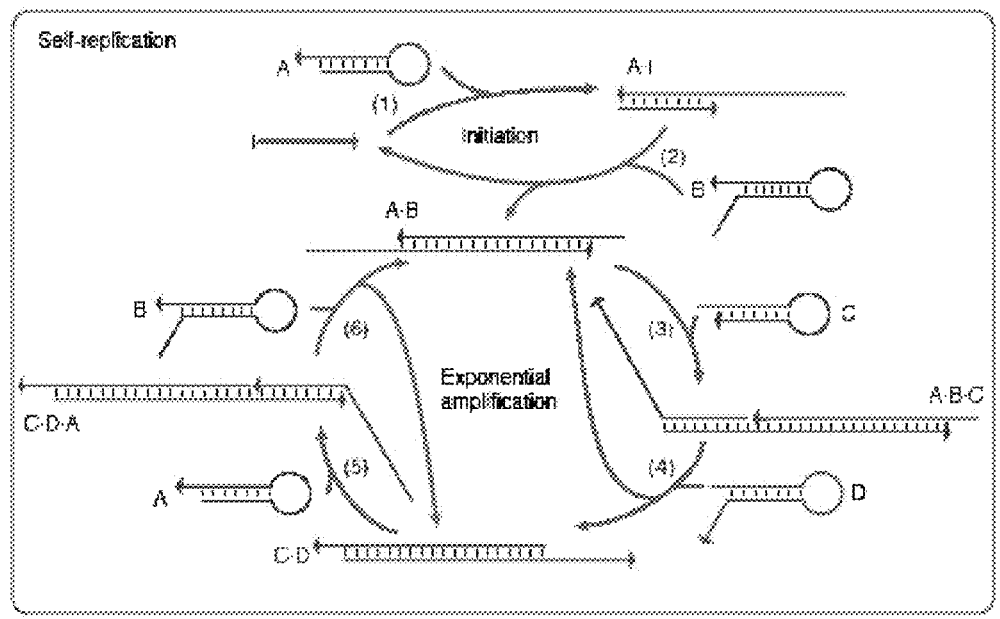
FIGS. 16a-b depict a reaction schematic and stepping gel for the autocatalytic system. a, Reaction schematic. b, Native polyacrylamide gel electrophoresis demonstrates the step-by-step reaction depicted in FIG. 3b. The symbol ( ) indicates annealing; + indicates 15 minute reaction at room temperature.

FIGS. 16a and b depict a stepping gel for the autocatalytic system. The hairpins used for these reactions were synthesized and purified by IDT DNA and used without further purification. The annealed samples were annealed at 2 μM reactant concentrations: heating at 95° C. for 5 minutes followed by cooling to room temperature over approximately 2.5 hours. The room temperature reactions were conducted with each reactant species at 1 μM concentration. Consider the sample, (AI)+B, in Lane 5. The sample was prepared by first annealing a mix containing 2 μM A and 2 μM I to produce (AI). Then 2 μM of (AI), at 2 μM concentration, was mixed with 2 μM of B at 2 μM concentration and allowed to react at room temperature for 15 minutes. Lanes 1 and 14 are 20-1000 by DNA ladders (Bio-Rad). The 5% native polyacrylamide gel was prepared in 1×TAE/Mg$^{++}$ buffer (20 mM Tris, pH=7.6, 2 mM EDTA, 12.5 mM Mg$^{++}$). The samples were loaded with 10% glycerol. The gel was run at 100 V for 90 minutes at room temperature, post-stained with 0.5 μg/mL ethidium bromide, and visualized by UV transillumination. The blue line delineates the boundary between two gels.

Figure 16B:
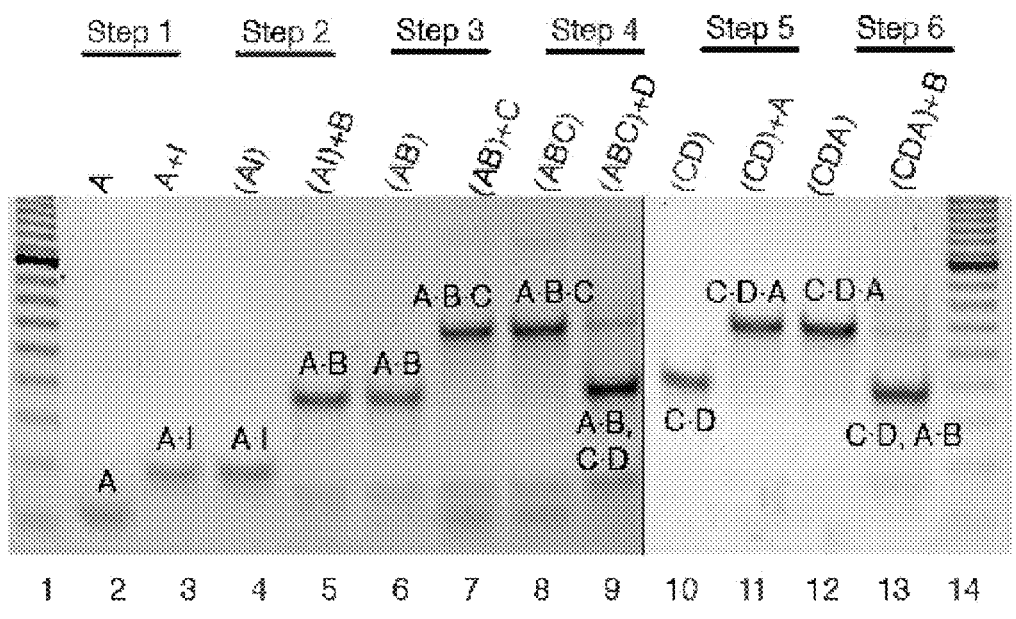

The autocatalytic system was validated on a step-by-step basis using native polyacrylamide gel electrophoresis (PAGE) (FIG. 16b):

Step 1. Hairpin A reacts with initiator I and produces a band that corresponds to product A•I (Lane 3), which migrates at about the same speed as the annealed product A•I (Lane 4), as expected.

Step 2. Annealed sample A•I reacts with hairpin B and produces a band that corresponds to product A•B (Lane 5), which migrates at about the same speed as the annealed product A•B (Lane 6), as expected.

Step 3. Annealed sample A•B reacts with hairpin C and produces a band that corresponds to product A•B•C (Lane 7), which migrates at about the same speed as the annealed product A•B•C (Lane 8), as expected.

Step 4. Annealed sample A•B•C reacts with hairpin D and produces a band that corresponds to product A•B and C•D (Lane 9), which migrates at about the same speed as the annealed product A•B (Lane 6) and the annealed product C•D (Lane 10), as expected.

Step 5. Annealed sample C•D reacts with hairpin A and produces a band that corresponds to product C•D•A (Lane 11), which migrates at about the same speed as the annealed product C•D•A (Lane 12), as expected.

Step 6. Annealed sample C•D•A reacts with hairpin B and produces a band that corresponds to product C•D and A•B (Lane 13), which migrates at about the same speed as the annealed product C•D (Lane 10) and the annealed product A•B (Lane 6), as expected.

System kinetic analysis and data analysis is described in Yin et al., *Nature* 451(7176), 318-322; Supplementary Information pages 1-49 (2008), which is incorporated herein by reference in its entirety.

Example 8

Nucleated Dendritic Growth

Figure 17:
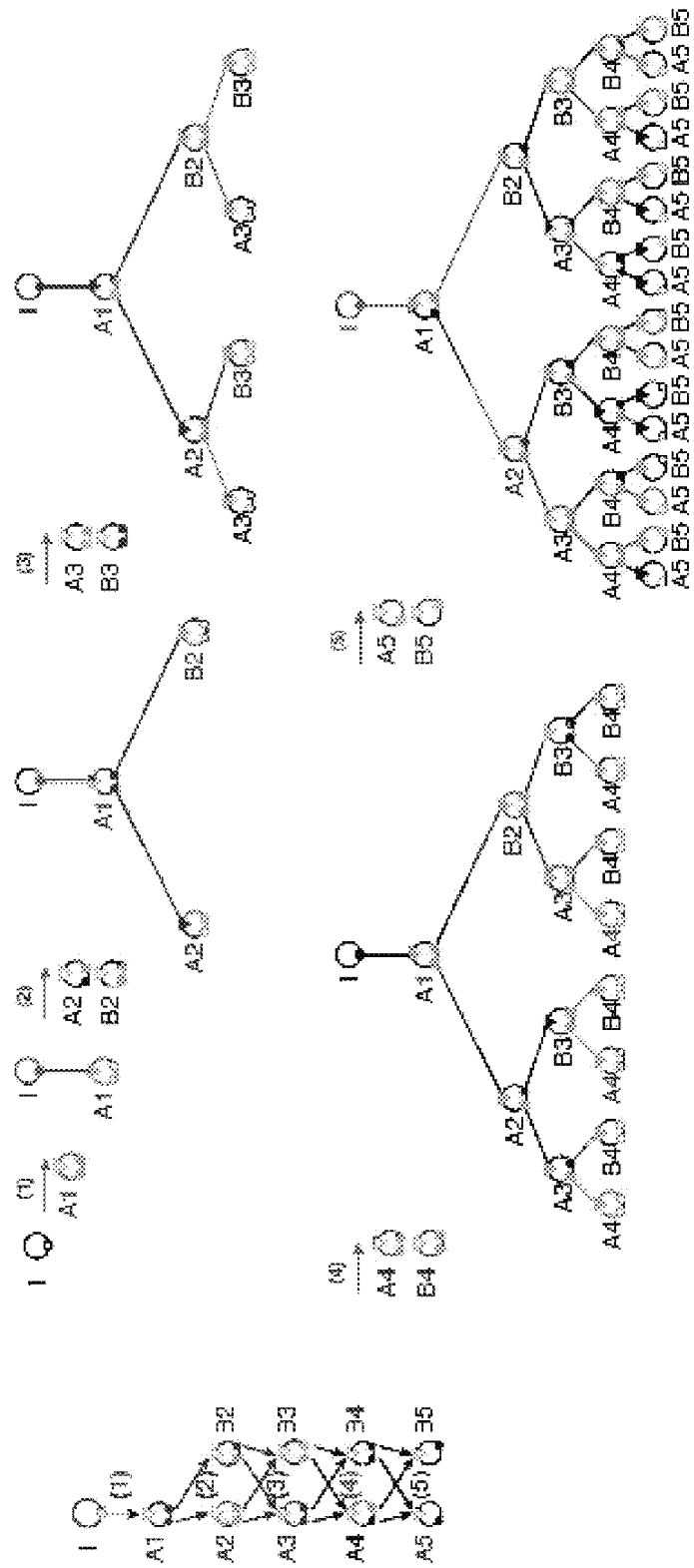
FIG. 17 depicts the execution of the reaction graph for the nucleated dendritic growth system.

FIG. 17 depicts the execution of the reaction graph of FIG. 4a. The multiple arrows entering the same input port depict parallel processes on separate copies of the nodal species. The parallel processes are not synchronized and hence it is possible, for example, that after A1 assembles with A2, the assembly of A2 with A3 occurs before the assembly of A1 with B2.

Figure 18:
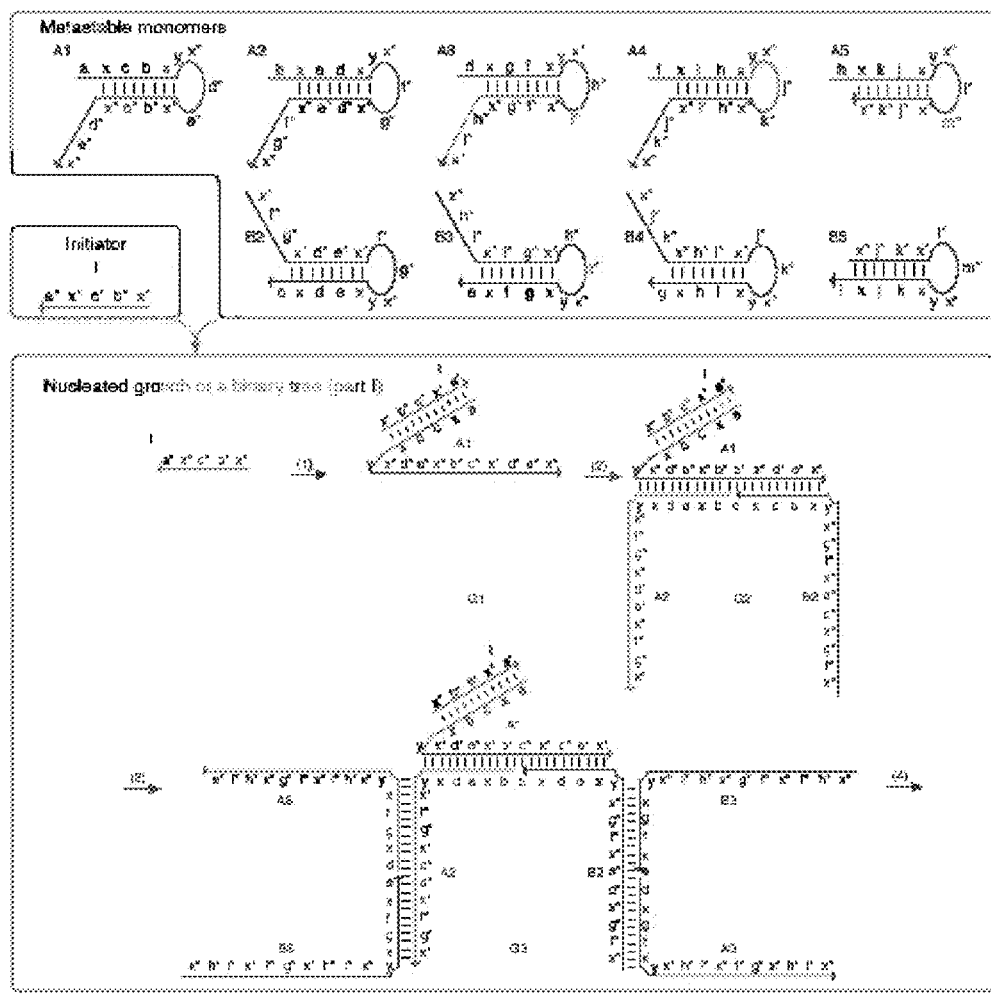
FIG. 18 depicts a reaction schematic of the nucleated dendritic growth system (part I). Step-by-step reaction schematic of the nucleated dendritic growth system, as described in FIG. 4. The lengths of segments x, x*, and y are 2 nt; the lengths of the other segments are 7 nt. The figure continues in FIG. 19.
Figure 19:
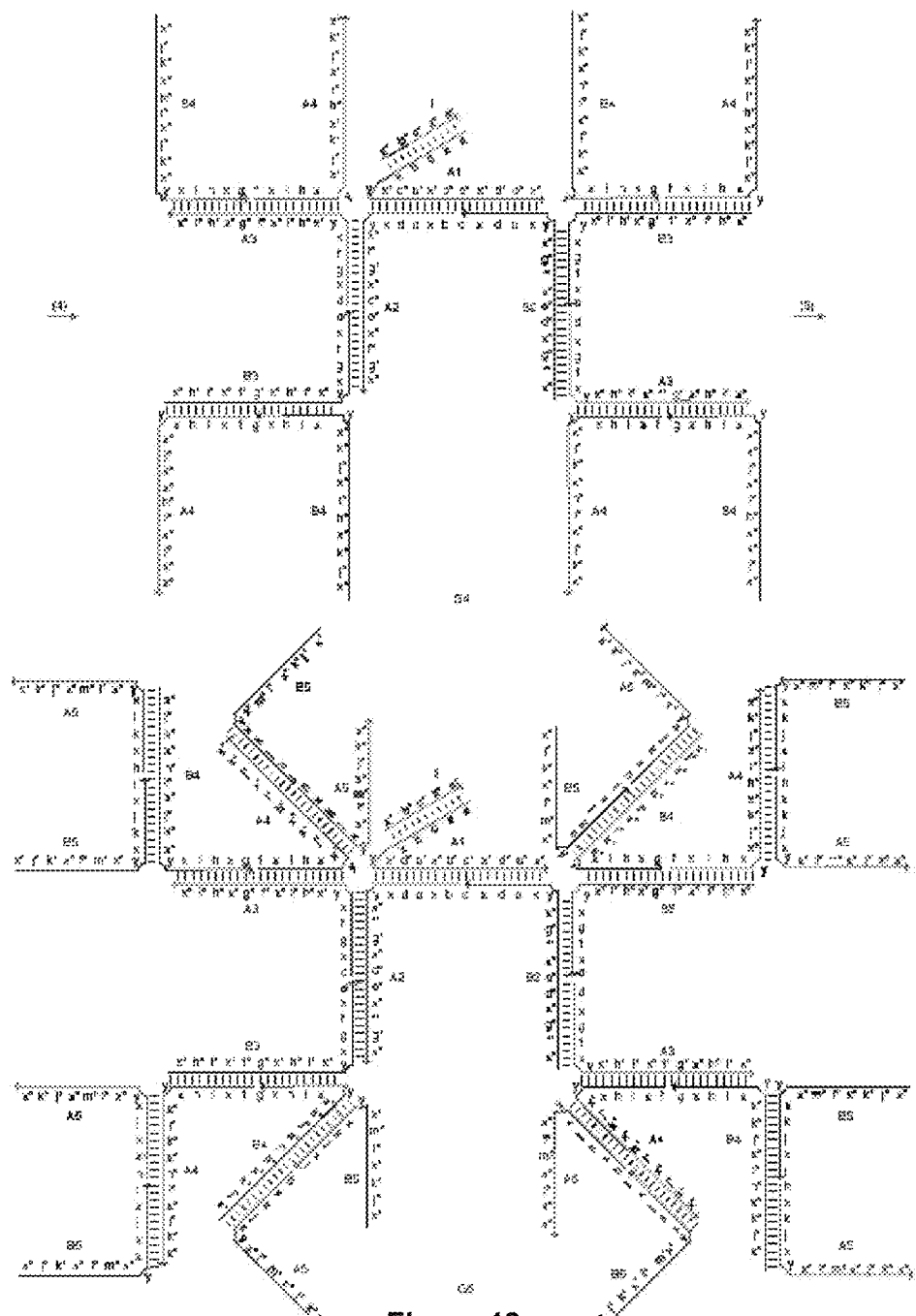
FIG. 19 depicts a reaction schematic of the nucleated dendritic growth system (part II). Step-by-step reaction schematic of the nucleated dendritic growth system, as described in FIG. 4. The figure continues from FIG. 9.

FIG. 18 and FIG. 19 present the detailed reaction schematic of the nucleated dendritic growth system described in FIG. 4. In the absence of the initiator I, hairpin monomers co-exist metastably. The initiator I triggers the system to self-assemble into a binary tree of a prescribed size.

Step 1: the toehold a* of the initiator I nucleates at the toehold a of hairpin A1, resulting in the opening of A1 and the formation of the first generation dendrimer, G1.

Step 2: A1, with b* and c* newly exposed, opens hairpins A2 and B2, producing the second generation dendrimer, G2. Note that now A2 and B2 reveal single-stranded tails of identical sequences.

Step 3: A2 and B2, with d* and e* newly exposed, open hairpins A3 and B3, producing G3.

Step 4: each copy of A3 and B3, with its newly exposed f* and g*, opens hairpins A4 and B4, producing G4.

Step 5: each copy of A4 and B4, with its newly exposed h* and i*, opens hairpins A5 and B5, producing G5.

Example 9

Quantitative Amplification Gel and AFM Image Analysis

Figure 20:
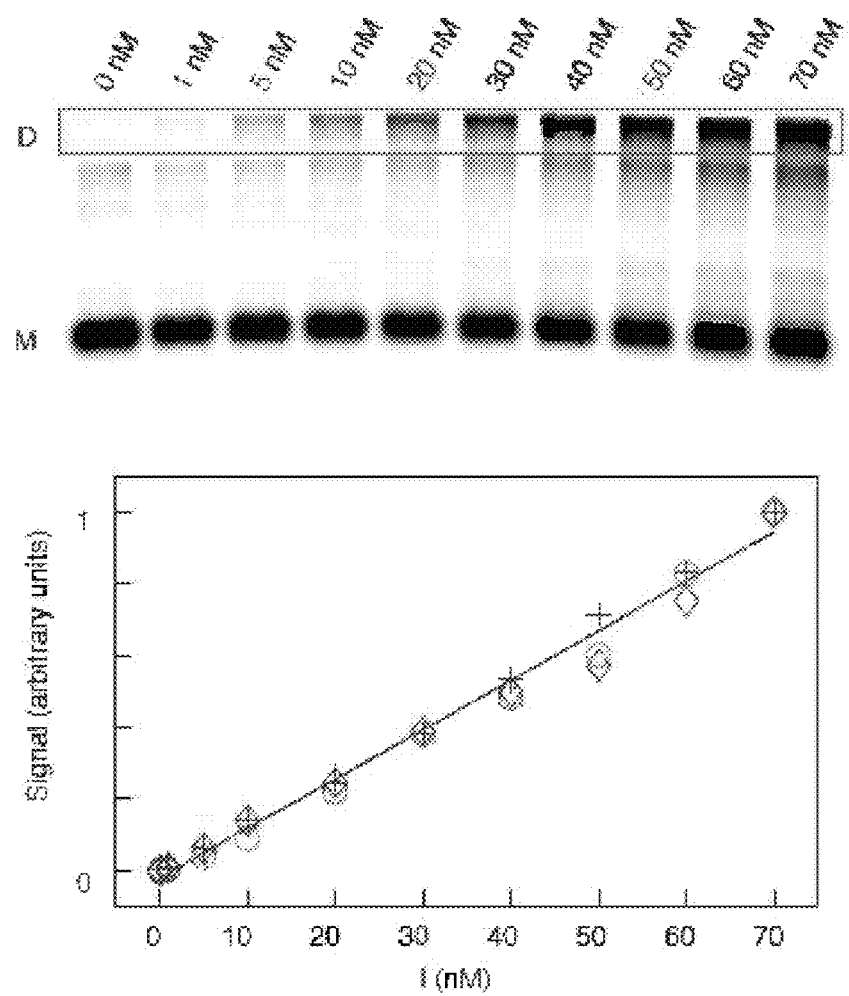
FIG. 20 depicts an agarose gel electrophoresis demonstrating quantitative amplification.

FIG. 20 demonstrates that the concentration of dendrimer depends linearly on the concentration of the initiator in the system. The top panel of FIG. 20 shows different concentrations of initiator incubated with all hairpin species (A1, A2, B2, 91 nM; the concentration doubles for each subsequent generation of hairpins). The gel shown in FIG. 20 is used to measure fluorescence emission from Cy5, which is used to label hairpin A1. In the figure, D denotes dendrimers; M denotes monomers. The bottom panel of FIG. 20 shows linear fit between the fluorescence signal of the dominant reaction product versus the concentration of initiator. Data from three independent experiments are denoted respectively by blue crosses, red diamonds, and green circles. Each set of data is normalized by the signal obtained at 70 nM initiator concentration.

Figure 21:
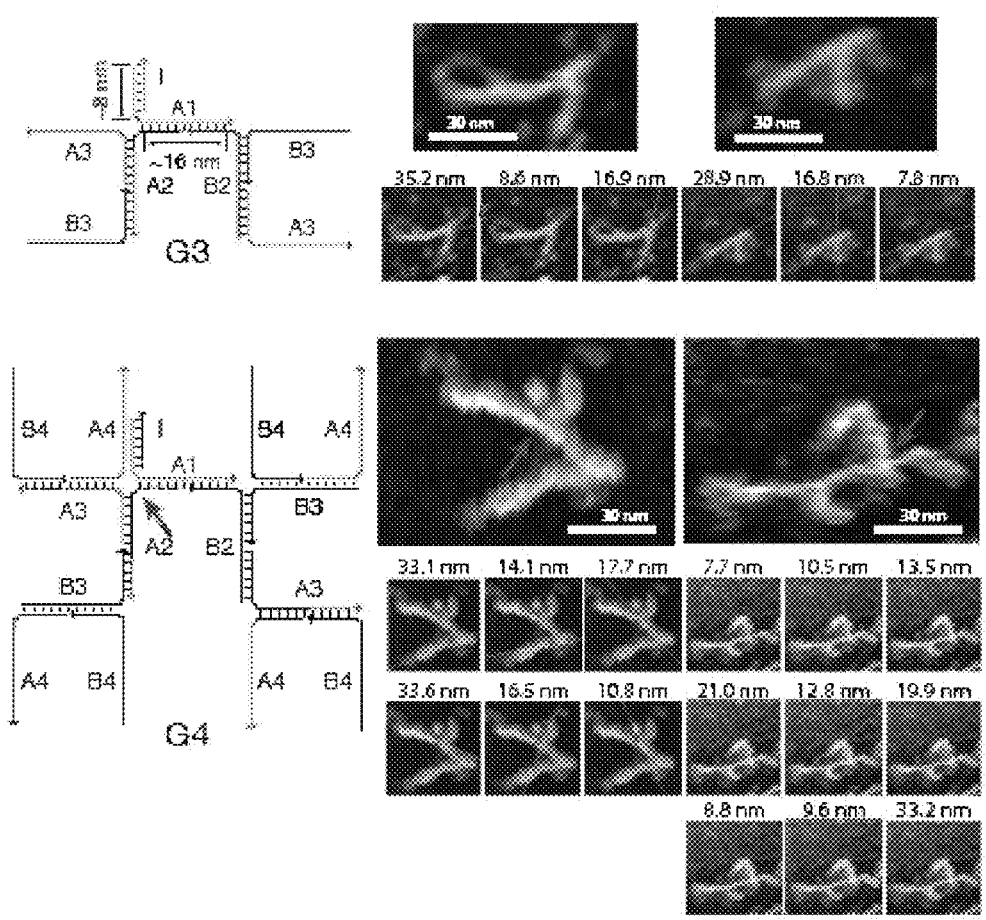
FIG. 21 depicts AFM measurements of the G3/G4 dendrimers.
Figure 22:
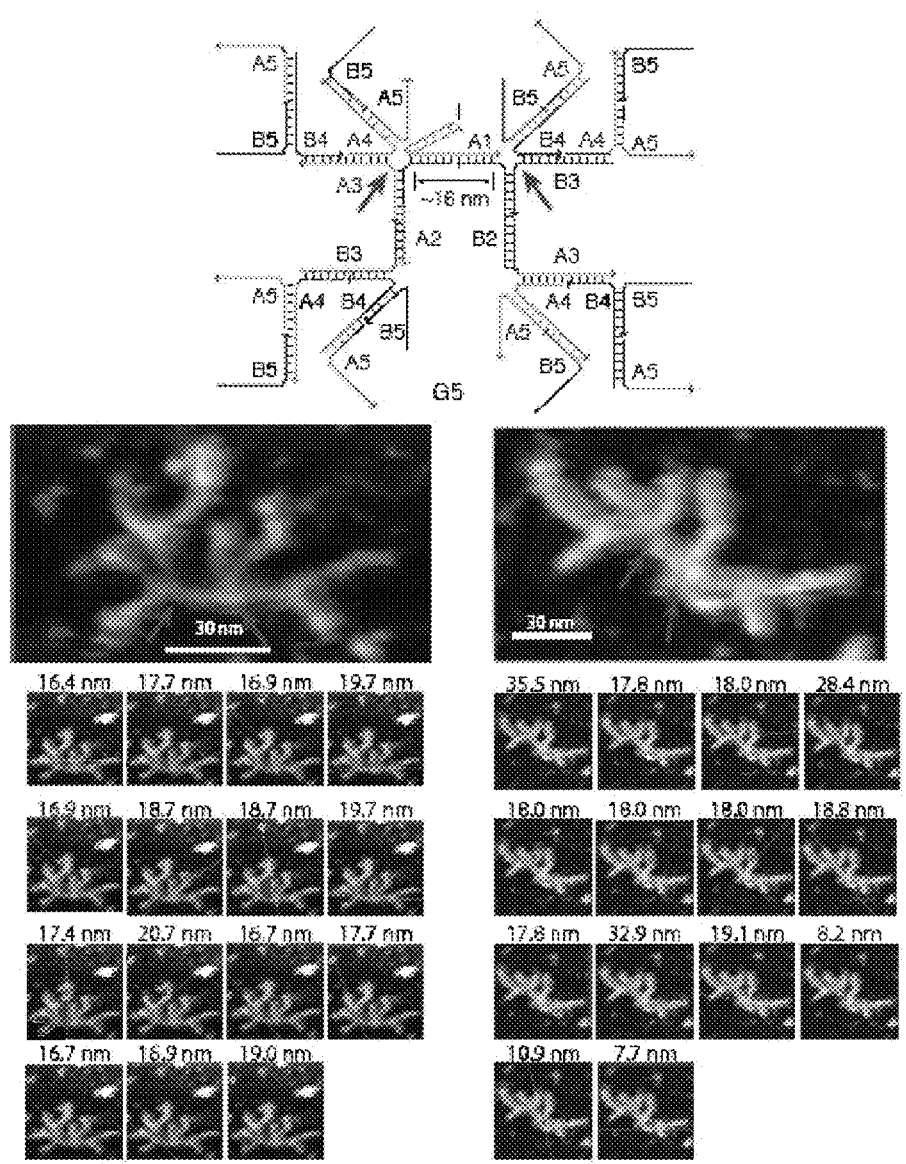
FIG. 22 depicts AFM measurements of the G5 dendrimers.
Figure 23:
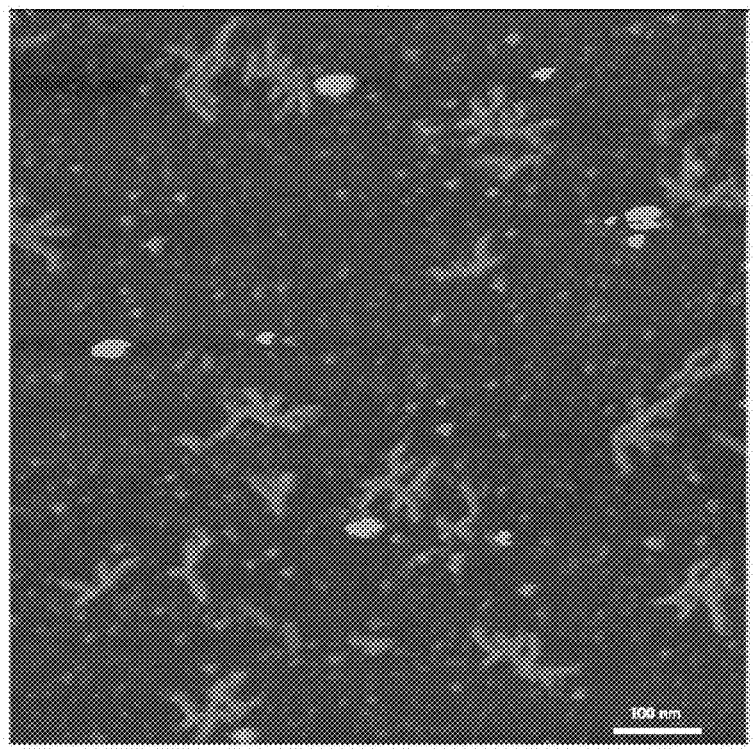
FIG. 23 depicts large-field-of-view AFM image of the G5 dendrimer system.

Using a B-DNA model where one helical turn contains 10.5 base pairs and measures 3.4 nm, we calculate the expected arm length for the duplex formed by A1 and I to be 25/10.5×3.4 nm=8.1 nm and the approximate length of all the other duplex segments to be 50/10.5×3.4 nm=16.2 nm. FIG. 21 shows the image analysis for G3 and G4 dendrimers. The small images are screenshots of the measurement section files. The distance between the two red arrowheads is listed above the image. The blue arrows point to the 4-arm junction in both the schematic and the images and help to relate the images to the schematic. FIG. 22 shows the image analysis for G5 dendrimers. The measured lengths of the arms are roughly consistent with the calculated lengths. In FIG. 22, the distance between the two red arrowheads is listed above the image. The blue arrows point to the 5-arm/4-arm junctions in both the schematic and the images and help to relate the images to the schematic. Note that the duplex A•I is not visible for the image in the left panel, likely due to damage during sample preparation or AFM scanning. FIG. 23 shows a large field-of-view AFM image of the G5 system. As seen by FIGS. 21-23, in most AFM images, only the duplex portions of the dendrimer are visible.

Example 10

Autonomous Locomotion

Figure 24A:
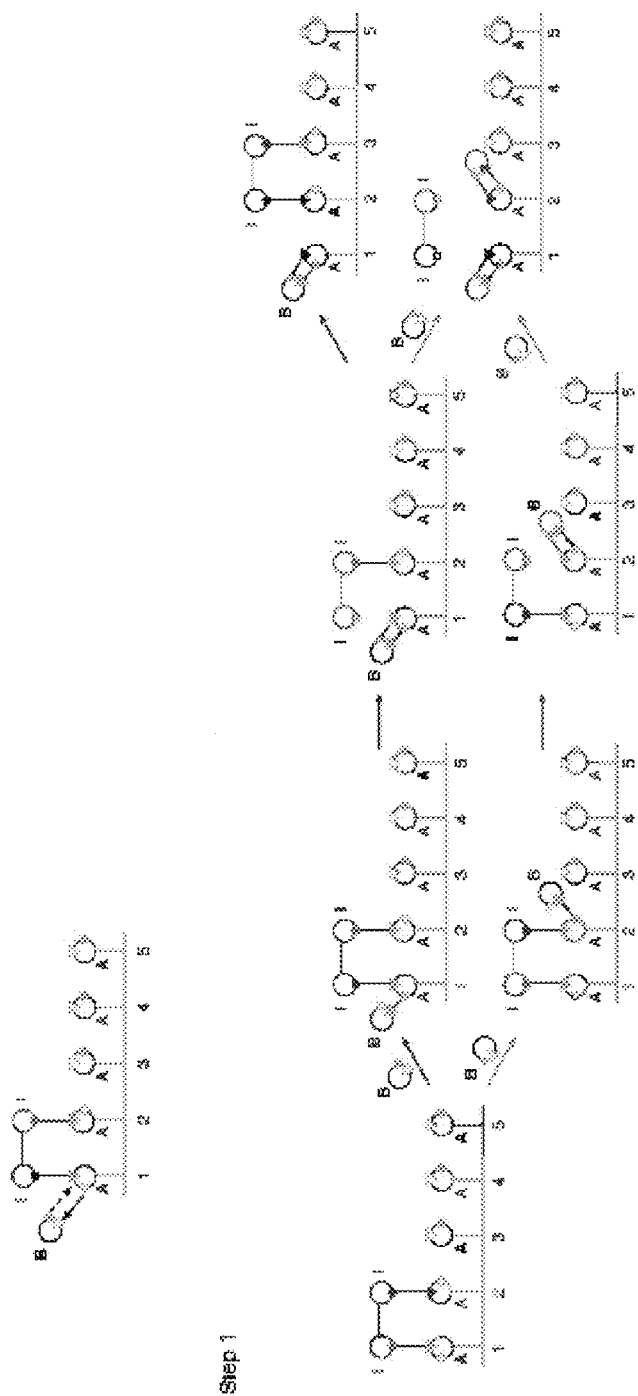
FIGS. 24a-b depict execution of the reaction graph for the autonomous walker system of FIG. 5.
Figure 24B:
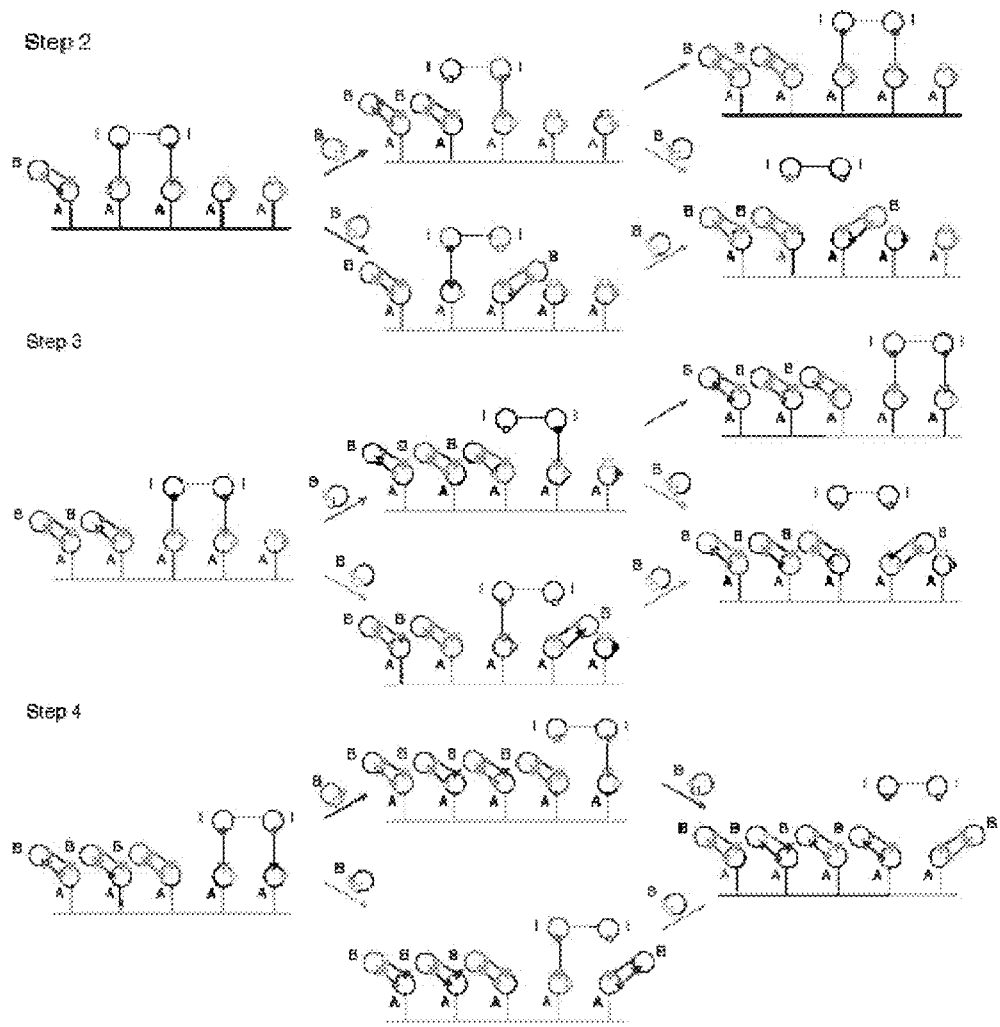

FIGS. 24a-b depicts the step-by-step execution of the reaction graph for the walker. In FIGS. 24a-b, the reaction steps corresponding to the processive sub-population of walkers are shown in purple. In the initial conditions prior to Step 1, the input ports of the A nodes at sites 1 and 2 are bound to the output ports of the I nodes on the bipedal walker. Execution begins with an assembly reaction between the accessible output port on either of these A nodes and the accessible input port on B. In the top route of Step 1, B assembles with A at site 1, resulting in the disassembly of the trailing I from A, which is then free to assemble with A at site 3, moving the walker one step down the track and bringing the system to Step 2. Alternatively, a B node could bind to A at site 2 prior to the assembly of I with A at site 3, resulting in the disassembly of the walker from the track. The walker could then diffuse through the bulk solution and re-attach to the same track or another track at any A monomer that has not yet been occupied. In the bottom route of Step 1, node B assembles with node A at site 2, resulting in the disassembly of the leading I from A. Due to geometric constraints (inextensible walker torso and rigid track backbone), the walker cannot attach to site 1 and site 3 simultaneously and hence will eventually detach from the track when a B node assembles with A at site 1. Similarly, in Step 2 and Step 3, processive stepping occurs stochastically for a sub-population of walkers. In Step 4, the walker will disassemble from track.

According to FIGS. 24a-b, the initial bond between the output port of I and the input port of A indicates that an assembly reaction has already occurred prior to the execution of the reaction graph. As noted above, static structural elements can impose geometrical constraints on the execution of the reaction graph. In the reaction graph depicted here, the gray structural elements represent a rigid track backbone and an inextensible walker torso; their relative dimensions imply that when one I node is attached to an A node on the track, the other I node can only interact with the A node to either side.

Figure 25:
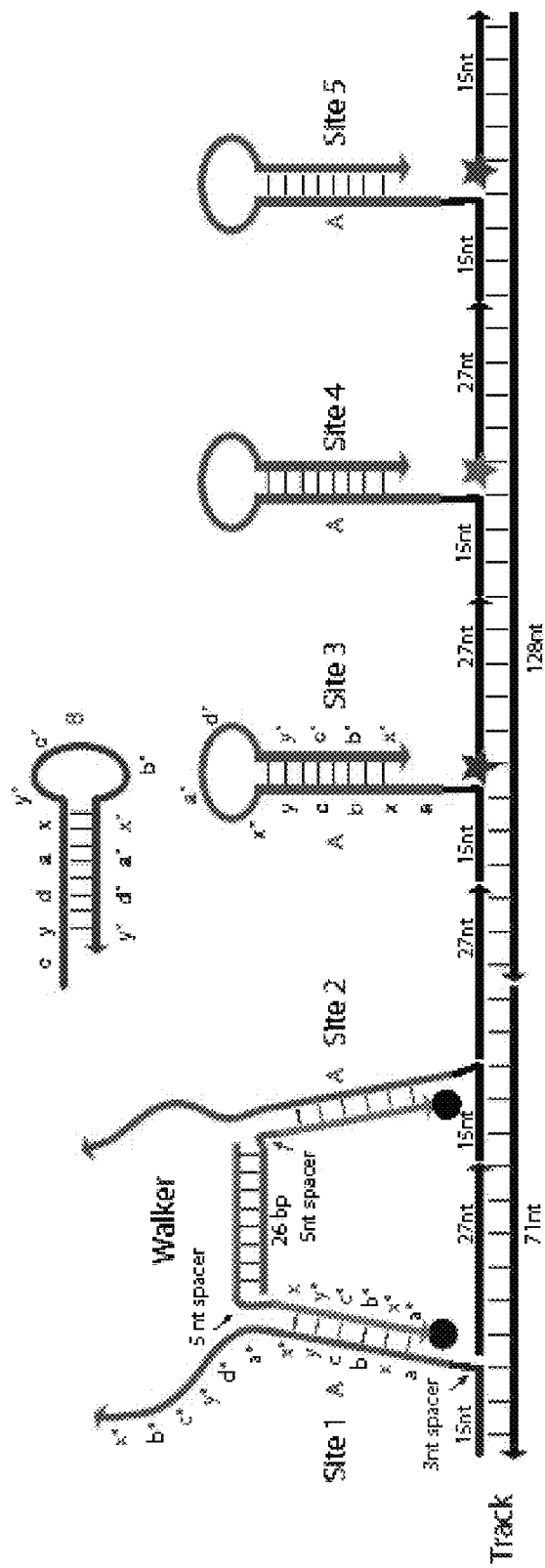
FIG. 25 depicts a secondary structure schematic of the walker system of FIG. 5. Stars represent fluorophores; black dots represent quenchers. The lengths of segments a, b, c, and d are 7 nt; the lengths of segments x and y are 2 nt.
Figure 26A:
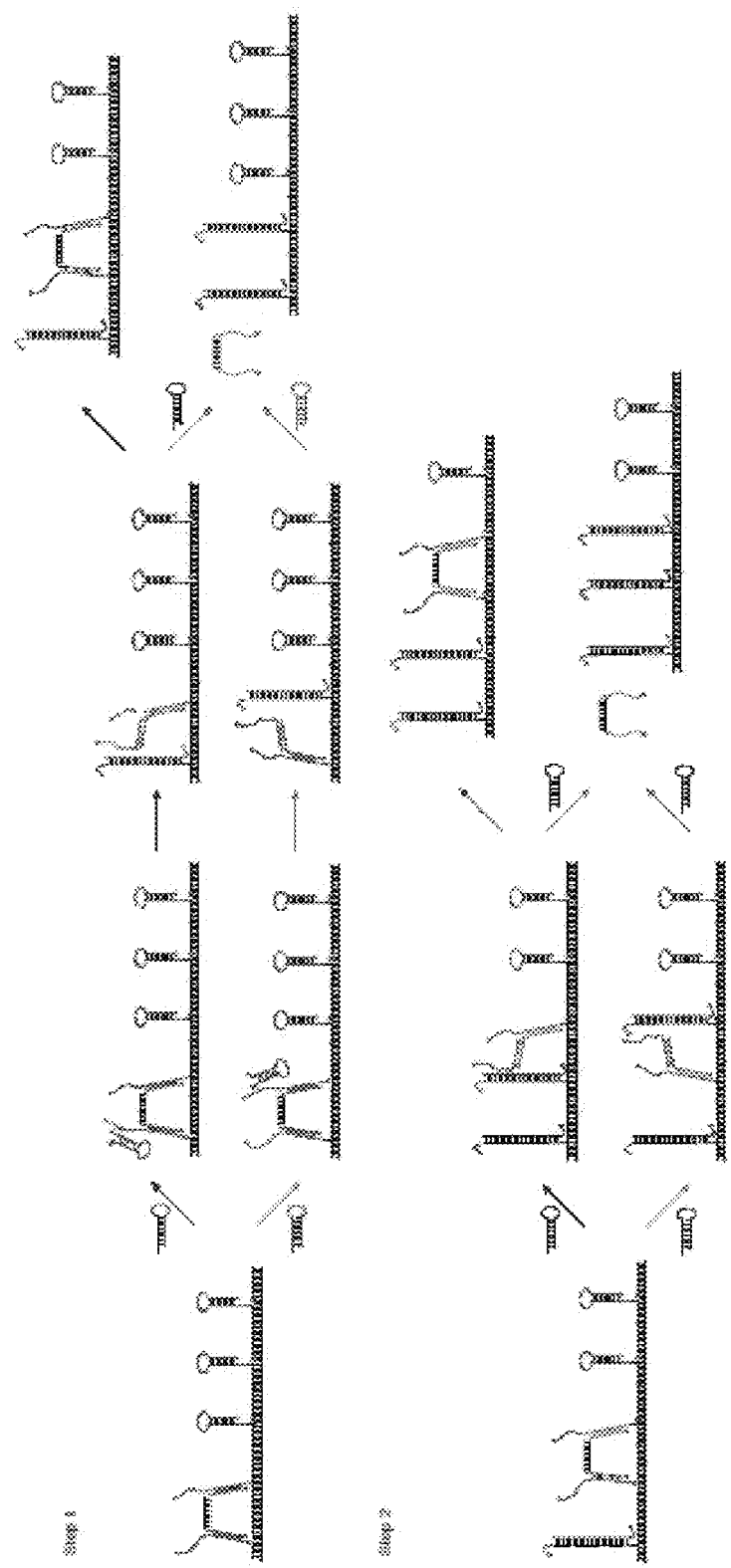
FIGS. 26a-b depict the step-by-step secondary structure schematic for the autonomous walker system of FIG. 5. Reaction arrows corresponding to the processive sub-population of walkers are shown in purple.
Figure 26B:
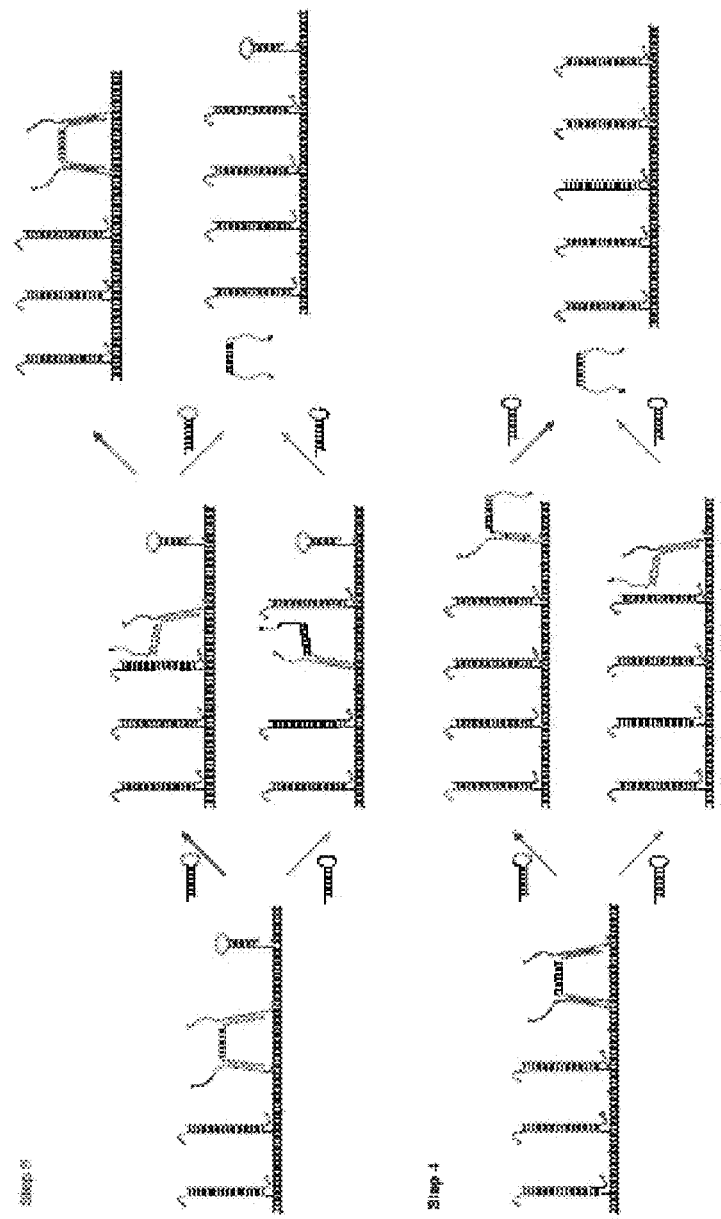
Figure 27A:
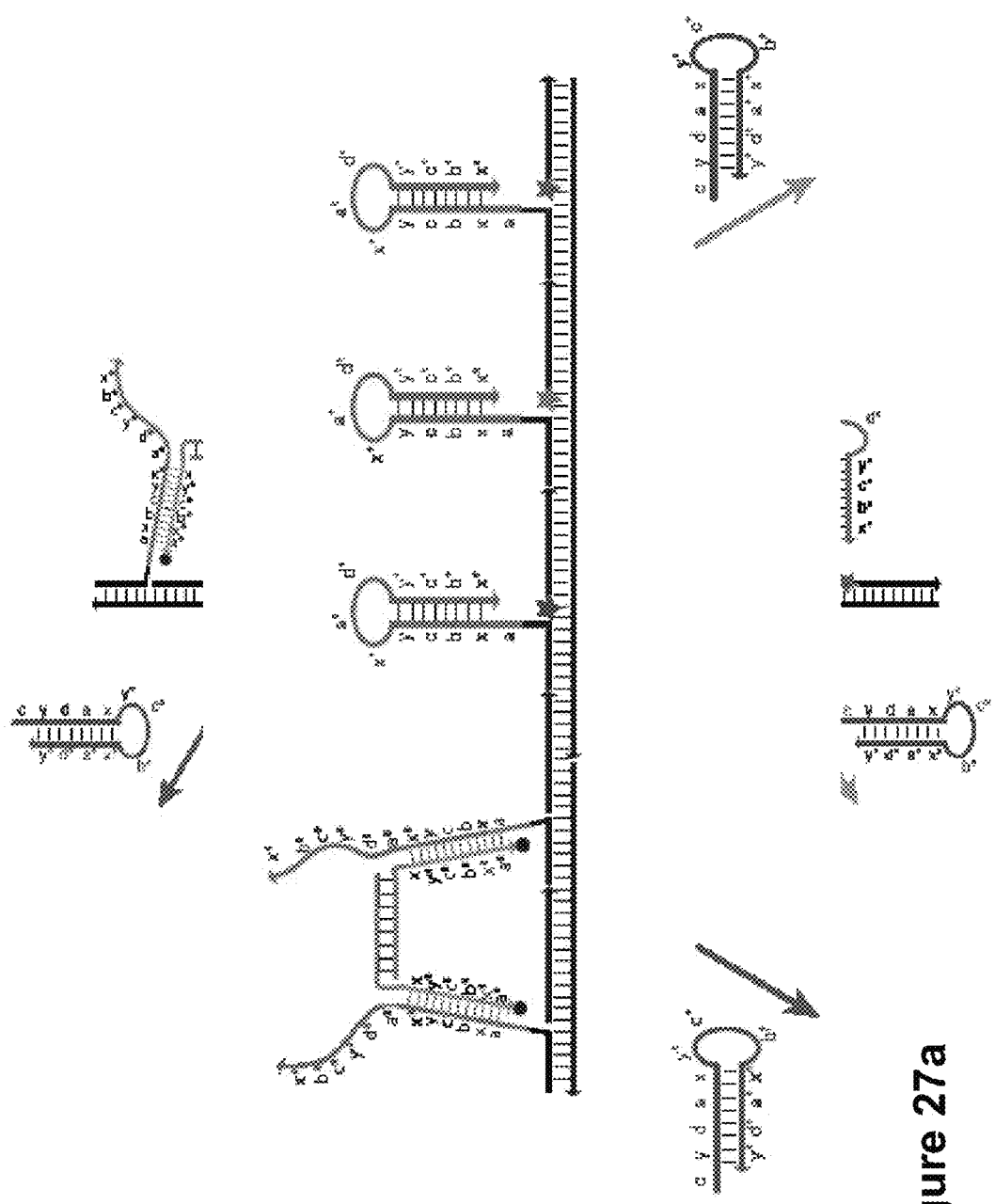
FIGS. 27a-d depict a detailed secondary structure schematic for step 1 of FIG. 26a. Reaction arrows corresponding to the processive sub-population of walkers are shown in purple.
Figure 27B:
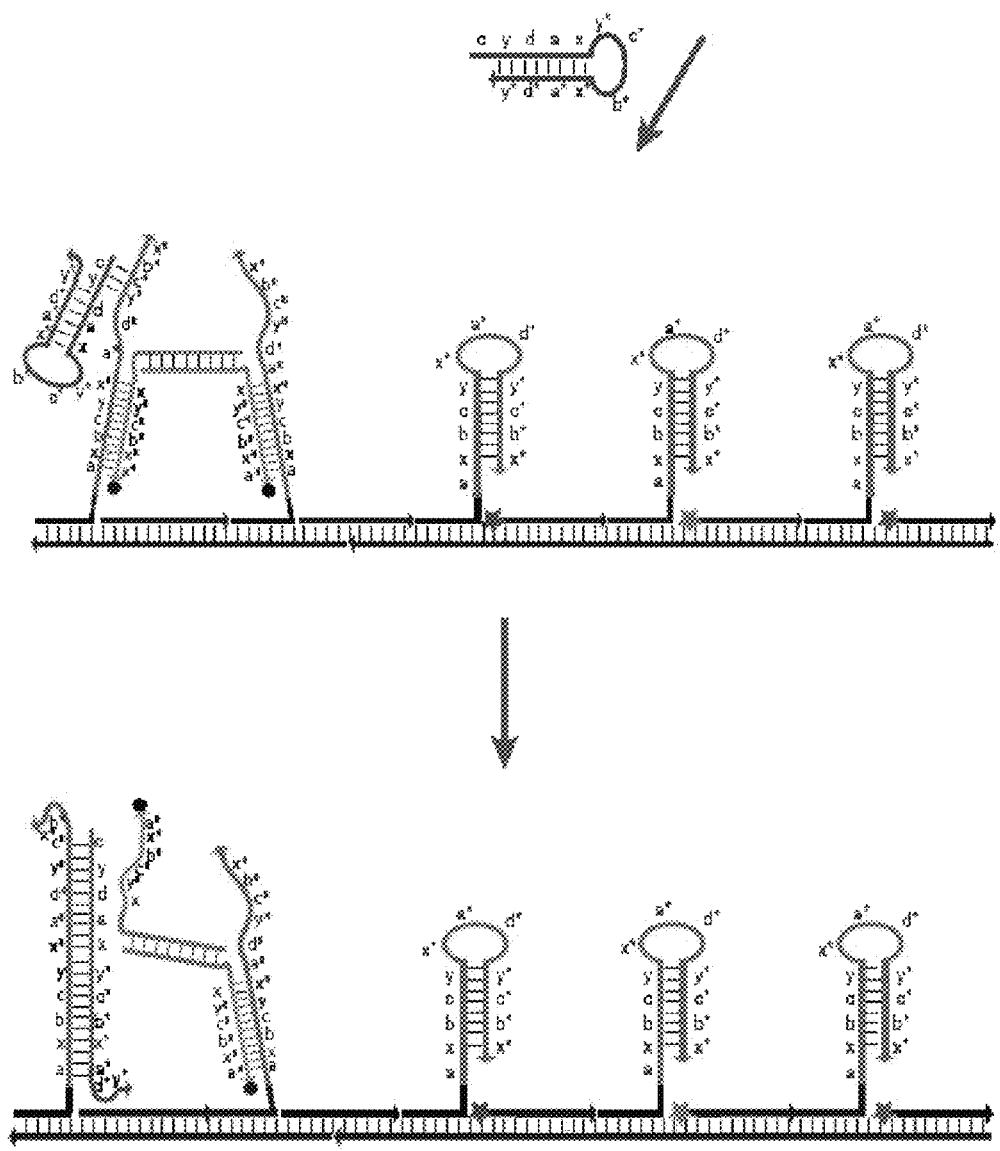
Figure 27C:
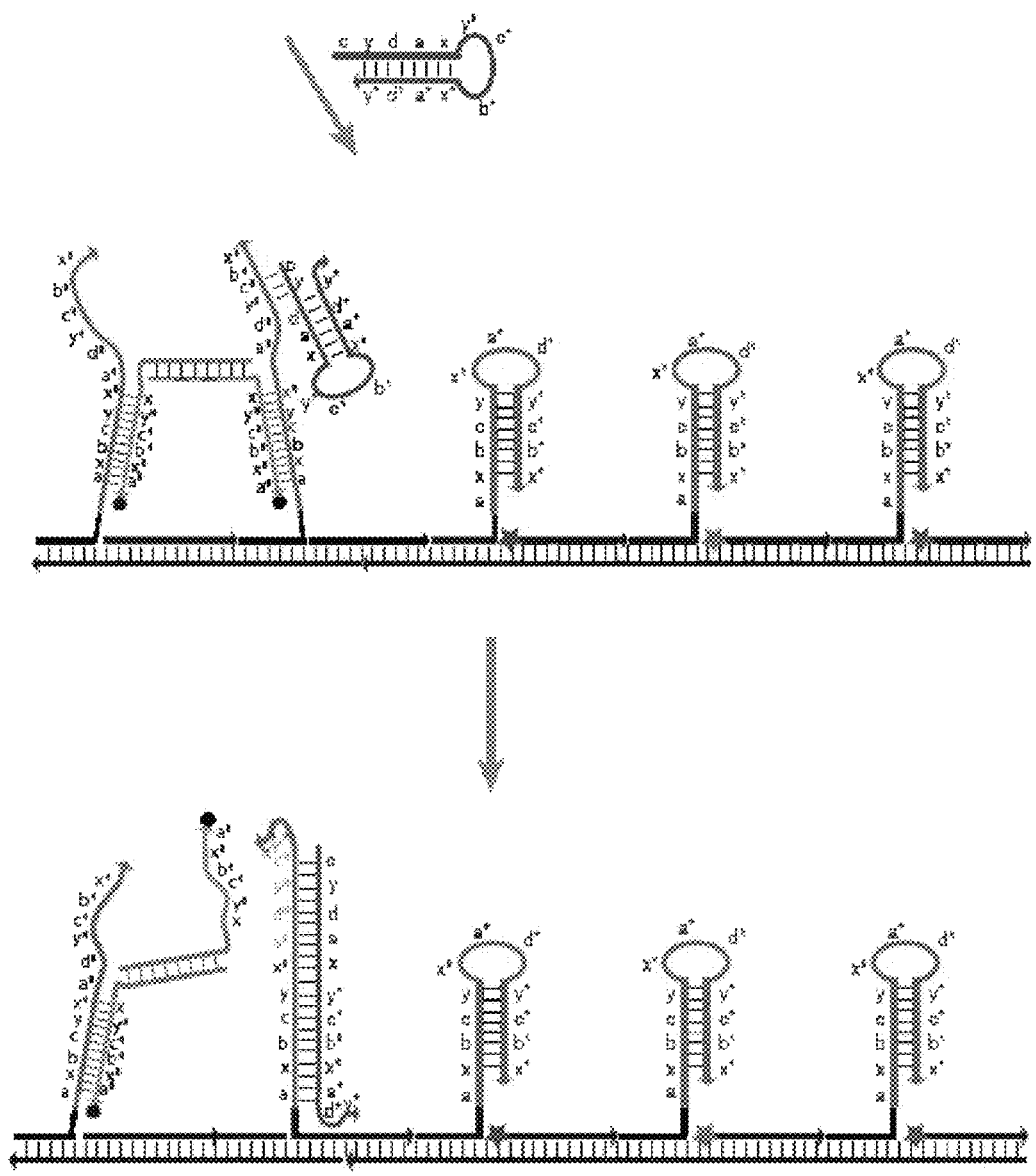
Figure 27D:
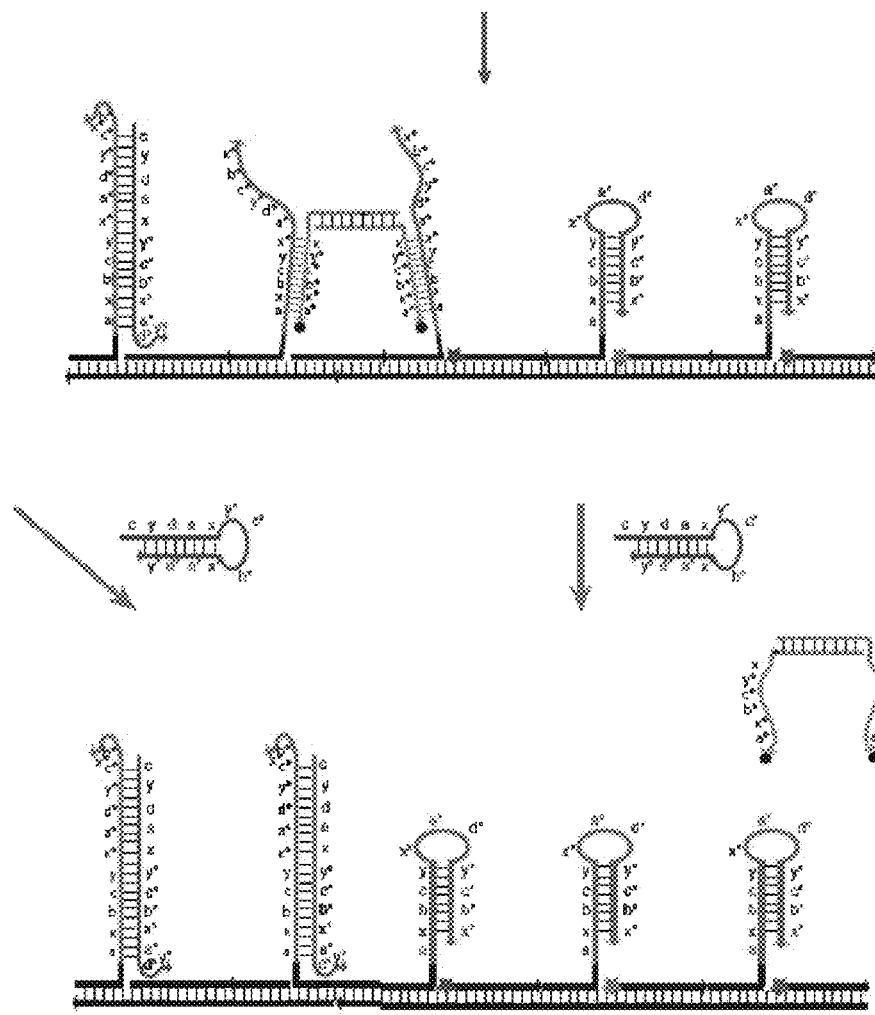

A secondary structure schematic of the walker system of FIG. 5 is shown in FIG. 25. FIGS. 26a-b depict the step-by-step secondary structure schematic corresponding to the reaction graph of FIGS. 24a-b. A more detailed view of Step 1 is shown in FIGS. 27a-d.

Figure 28A:
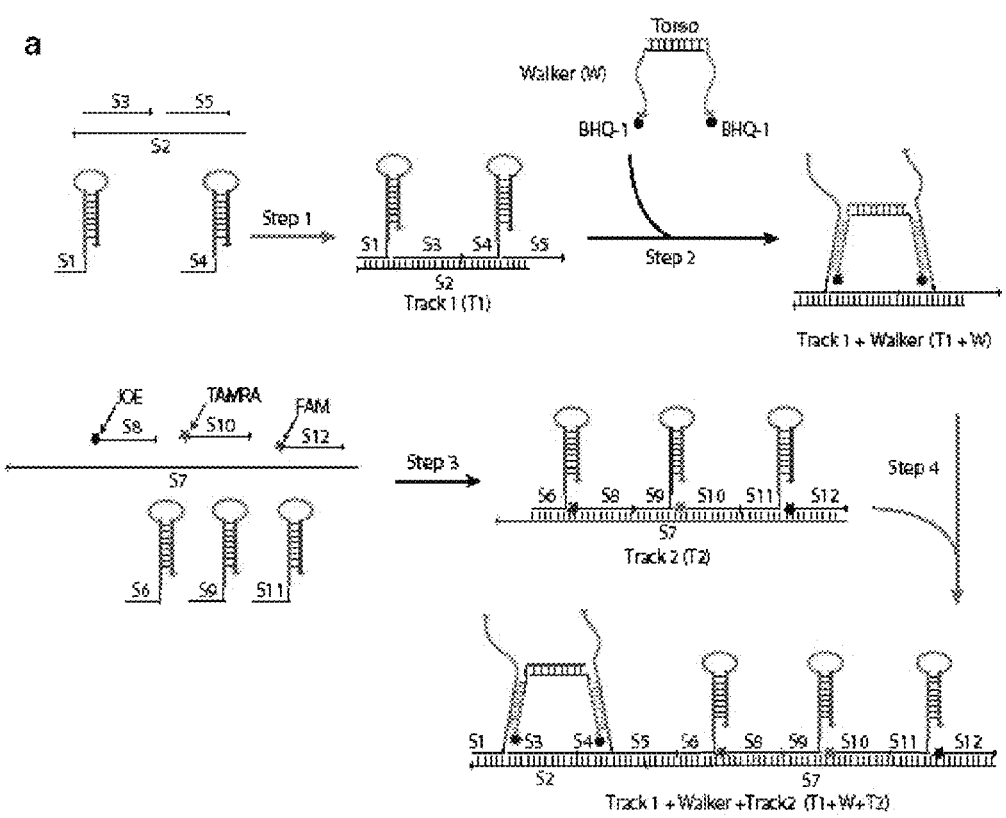
FIGS. 28a-b depict assembly of the walker system. a, Assembly procedure. b, Native agarose gel electrophoresis demonstrating the expected assembly of the system.

The walker system was assembled in four steps (FIG. 28a).

Step 0. The walker (W) was assembled by annealing strands W1-BHQ1 and W2-BHQ1 as follows: heat the mixture at 95° C. for 5 minutes and slowly cool to room temperature over the course of 4 hours.

Step 1. Hairpins S1 and S4 were mixed with track strands S2, S3, and S5, then annealed to produce Track 1 (T1) as follows: heat the system at 95° C. for 5 minutes; slowly cool to room temperature over the course of 4 hours.

Step 2. T1 and the pre-assembled walker (W) were incubated at room temperature for 2 hours to produce T1+W.

Step 3. Hairpins S6, S9, and S11 were mixed with track strands S7, S8, S10, and S12, then annealed to produce Track 2 (T2) as follows: heat the system to 95° C. for 5 minutes; slowly cool to room temperature over the course of 4 hours. For the bipedal and monopedal landing control experiments, the S7 track strand is replaced by S7 truncated so that T1 and T2 remain disjoint.

Step 4. T2 and T1+W were incubated at room temperature for 3 hours to produce the final system, T1+W+T2.

Figure 28B:
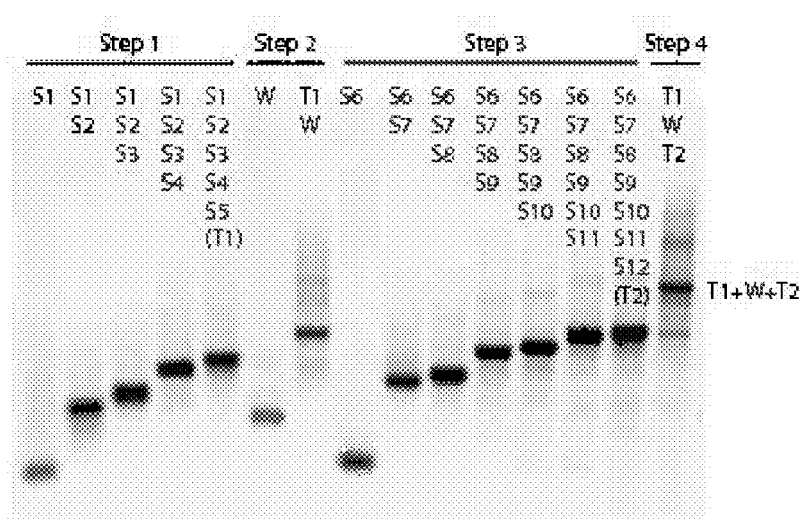

Native agarose gel electrophoresis demonstrates a band shifting pattern that confirms on a step-by-step basis the correct assembly of the walker system. (FIG. 28b). Samples were annealed and assembled in reaction buffer (4 mM $MgCl_2$, 15 mM KCl, and 10 mM Tris-HCl, pH=8.0) with all species at 0.5 μM. A 3% native agarose gel was prepared in 1×LB buffer (Faster Better Media, LLC). Samples were loaded with 2×SYBR Gold stain (Invitrogen) and 10% glycerol. The gel was run at 200 V for 40 minutes at room temperature and visualized using an FLA-5100 imaging system (Fuji Photo Film Co., Ltd.)

Example 11

Characterization of the Fuel System

This example describes the fuel system that powers the walker system, which is depicted in FIGS. 29a and b. Here, hairpins A and B co-exist metastably in the absence of catalyst I. Catalyst I catalyzes A and B to form duplex AB (FIG. 29a). Native gel electrophoresis (FIG. 29b) confirms that the hairpins assemble slowly in the absence of the initiator (Lane 7) and that the assembly is dramatically accelerated by the addition of initiator (Lane 3). Disassembly of the initiator enables catalytic turnover as indicated by the nearly complete consumption of hairpins even at substoichiometric initiator concentrations (Lanes 4-6).

Figure 29B:
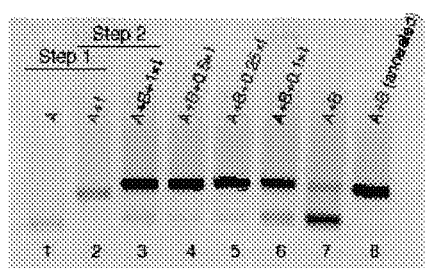

Agarose gel electrophoresis demonstrates catalytic formation of the DNA duplex (FIG. 29b). The hairpins were prepared in reaction buffer (4 mM MgCb, 15 mM KCl, and 10 mM Tris-HCl, pH=8.0) using a snap-cooling procedure: heating at 90° C. for 5 minutes and cooling on ice for 1 minute. The hairpins were allowed to equilibrate at room temperature for 30 minutes before use. Lanes 1-3: A gel shifting assay validates each reaction step depicted in panel (a). Lanes 3-7: Effects of different concentrations of I (1×, 0.5×, 0.25 x, 0.1×, and 0×) on the formation of A•B. Reactants were incubated at 1 µM at room temperature for 2 hours. Lane 8: A•B annealed over 2.5 hours (1 µM hairpin species heated at 95° C. for 5 minutes and cooled to room temperature over 2.5 hrs). Upon completion of the reaction, the samples were loaded with 5×SYBR Gold stain (Invitrogen) and 10% glycerol into a 2% native agarose gel, prepared with 1×LB buffer (Faster Better Media, LLC). The gel was run at 350 V for 10 minutes at room temperature and visualized using an FLA-5100 imaging system (Fuji Photo Film Co., Ltd.).

Fluorescence quenching experiments was carried out to investigate catalyst recovery, and is described, in Yin et al., Nature 451(7176), 318-322; Supplementary Information pages 1-49 (2008) at page 31-37, which is incorporated herein by reference in its entirety.

Example 13

Synthesis of DNA, Hairpins and Monomers

This example illustrates the synthesis of DNA, hairpins and monomers used in the Examples.

DNA was synthesized and purified by Integrated DNA Technologies. The purified DNA strands were reconstituted in ultrapure water (resistance of 18 MΩ-cm). The concentrations of the DNA solutions were determined by the measurement of ultraviolet light absorption at 260 nm.

Each hairpin was synthesized as two pieces which were then ligated to produce the full hairpin. The ligation was performed using T4 DNA ligase (New England Biolabs) at either room temperature or 16° C. for a minimum of two hours. Ligated strands were further purified using denaturing polyacrylamide gel electrophoresis. The bands corresponding to the DNA strands of expected sizes were visualized by UV shadowing and excised from the gel. The DNA strands were then eluted and recovered by ethanol precipitation. (3) Monomer preparation. The concentrated DNA strands were diluted to reaction conditions: 50 mM $Na_2HPO_4$, 0.5 M NaCl, pH=6.8 for species in FIG. 2 and FIG. S4; and 20 mM Tris, pH=7.6, 2 mM EDTA, 12.5 mM $Mg^{++}$ (1×TAE/$Mg^{++}$ buffer) for species in FIG. 3, FIG. S12, and FIG. 4. The hairpins were then annealed by heating for 5 minutes at 90° C., and then the heating block was turned off to allow the system to cool to room temperature (requiring at least 2 hours).

Figure 30:
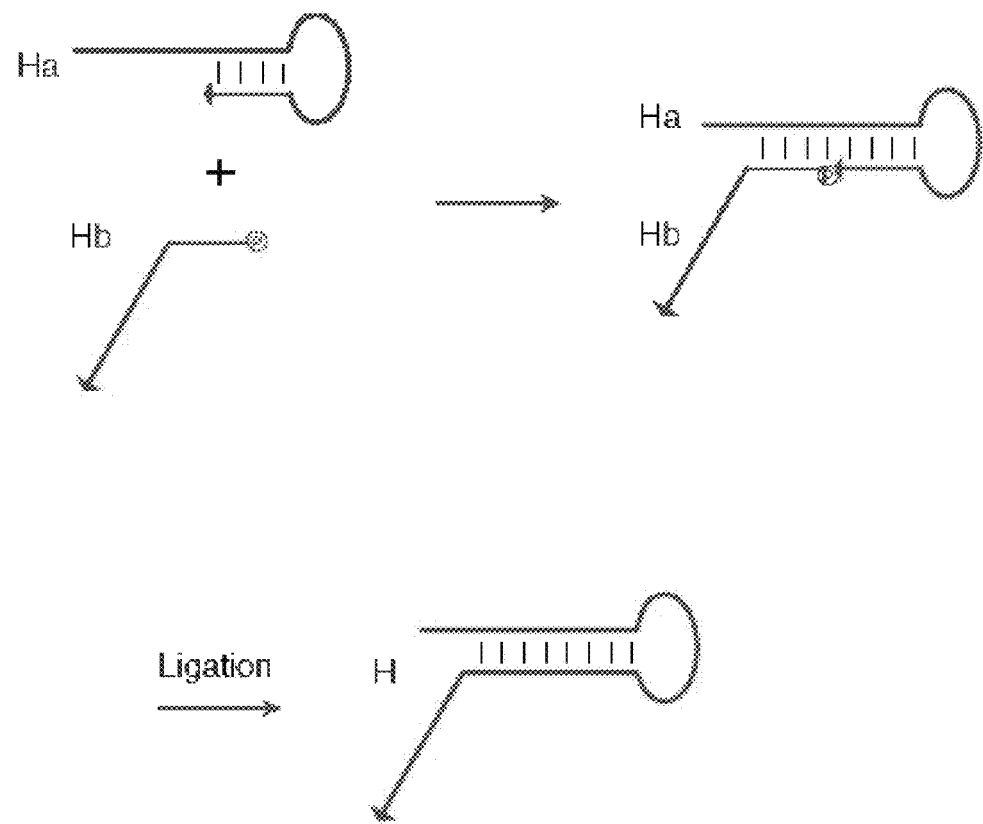
FIG. 30 depicts DNA hairpin synthesis by ligation. The circled P indicates a phosphate group, which is used for ligation by, for example, T4 ligase.
Figure 31:
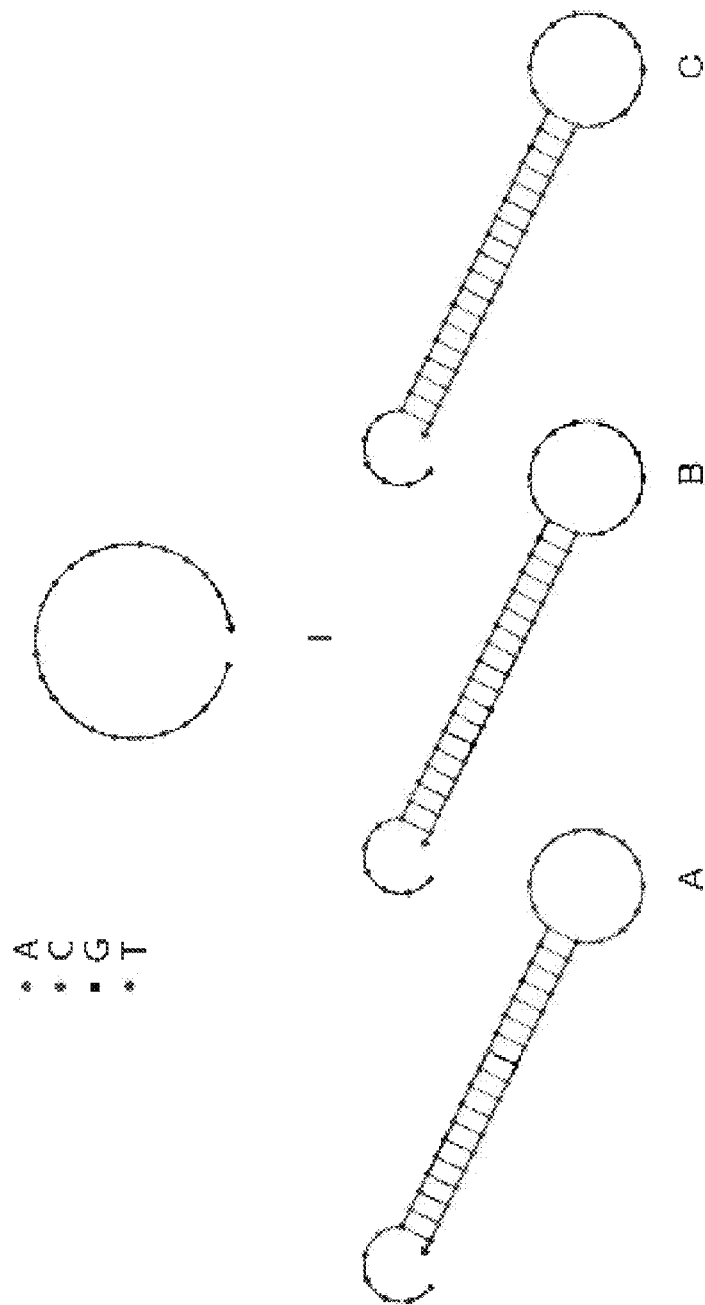
FIG. 31 depicts a schematic of DNA sequences and secondary structures for the catalytic 3-arm junction systems of FIG. 2.
Figure 32:
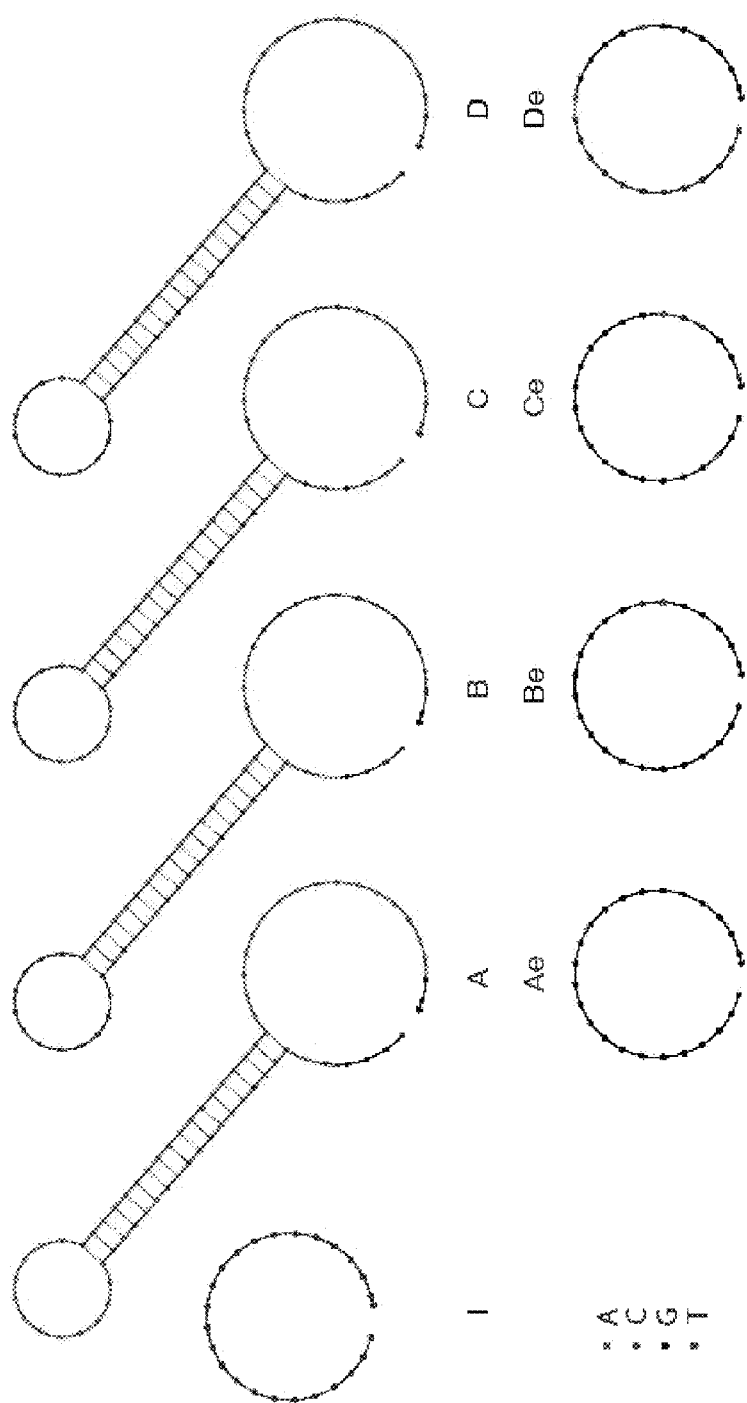
FIG. 32 depicts a schematic of DNA sequences and secondary structures for the catalytic 4-arm junction systems of FIG. 8.
Figure 33:
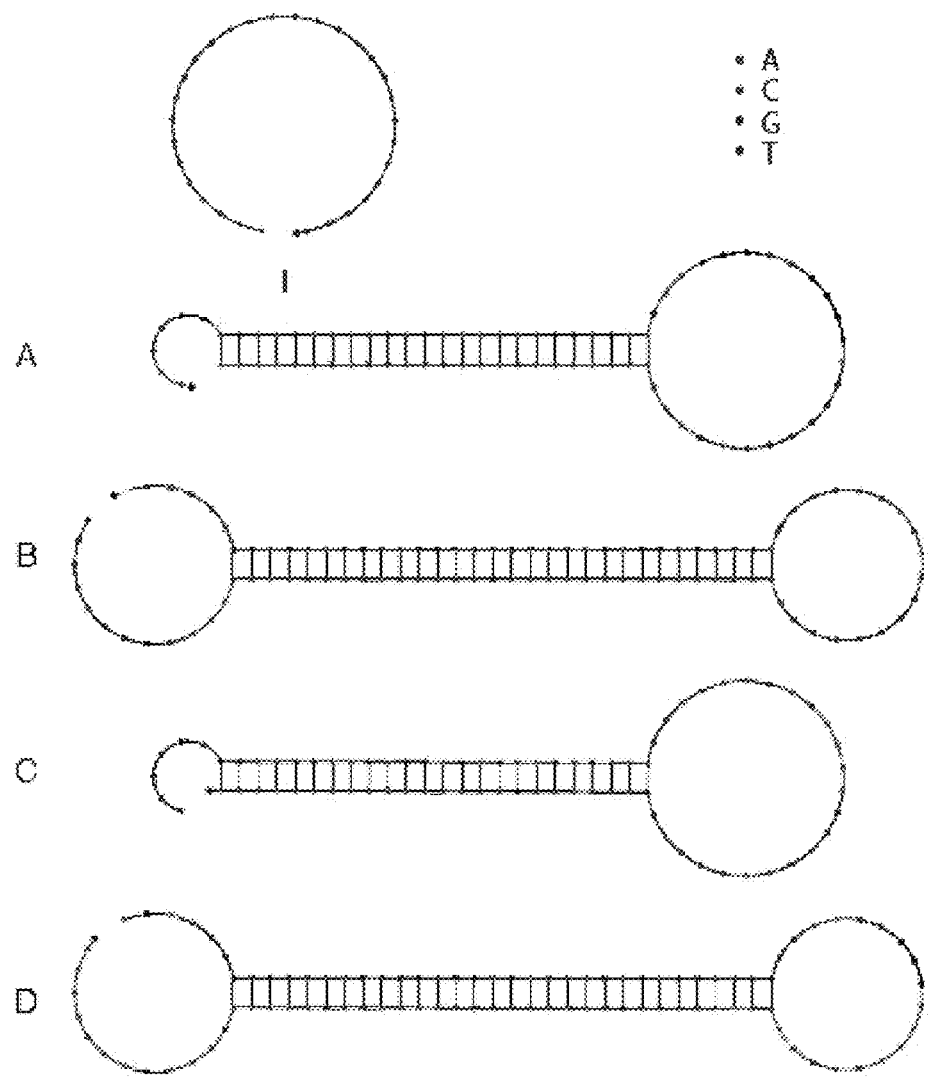
FIG. 33 depicts a schematic of DNA sequences and secondary structures for the autocatalytic system of FIG. 3.
Figure 34:
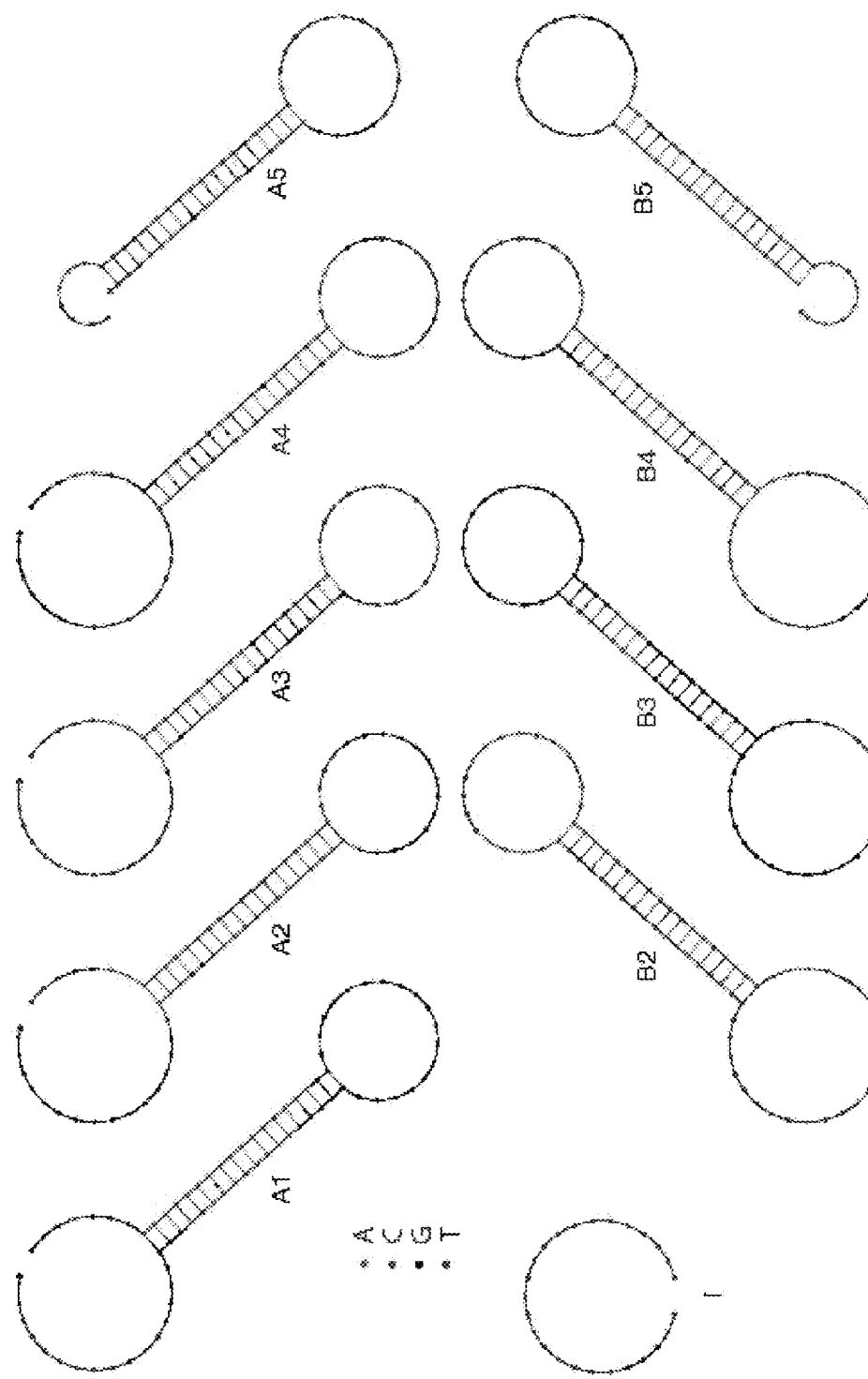
FIG. 34 depicts a schematic of DNA sequences and secondary structures for the nucleated dendritic growth system of FIG. 4.
Figure 35:
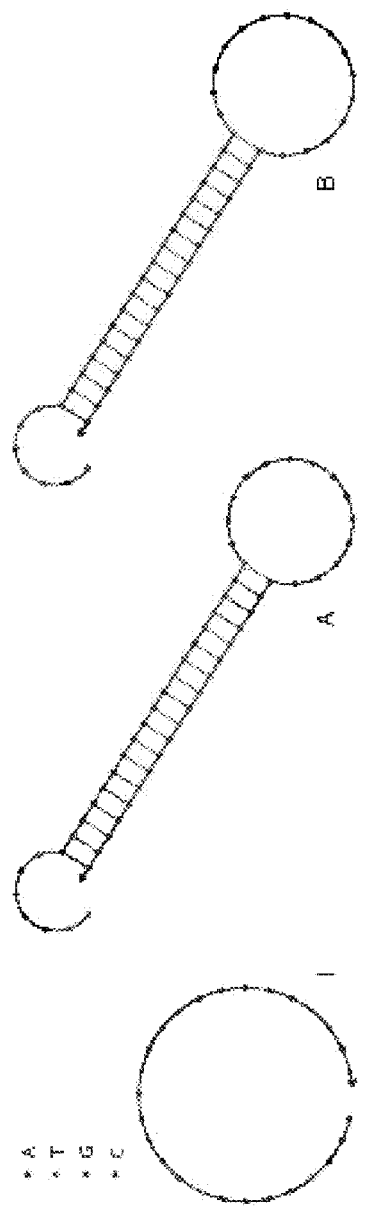
FIG. 35 depicts a schematic of DNA sequences and secondary structures for the fuels for the walker system of FIGS. 28a-b and 29a-b.

Commercially available synthetic single-stranded DNA oligos can be impure and contain incorrectly synthesized strands. The presence of such erroneous strands can contribute to leakage during self-assembly. In some embodiments, to improve strand purity and hence decrease system leakage, the following enzyme-based ligation method can be used to synthesize the hairpin monomers: two constituent segments of a hairpin are synthesized and purified separately and ligated to produce the full hairpin (FIG. 30). Significant reduction of system leakage in the ligation-based system is observed, as compared to the un-ligated system.

The observed error reduction may be attributed to the following two mechanisms. First, longer DNA strands contain more errors than shorter fragments, since the shorter fragments can be purified to a higher purity. Behlke et al., Tech. Rep., Integrated DNA Technologies (2005). As such, the two constituent segments contain fewer total errors than the full strand. Second, for T4 ligase mediated ligation of Ha and Hb, the successful ligation depends on the correct juxtaposition of the 5' end of fragment Hb with the 3' end of fragment Ha. This requirement provides an additional error reduction mechanism: DNA segments with errors in the regions adjacent to the nick position are not ligated successfully and are eliminated during the subsequent gel purification.

Example 14

Gel Electrophoresis

This example illustrates electrophoresis analysis of the self-assembly systems.

For the gel in FIG. 2c, 12 µL of each 3 µM hairpin species were mixed by pipetting. 6 µL of this master mix was aliquoted into 5 separate tubes. To these tubes were added 2 µL of either 3 µM I (Lane 1), 1.5 µM I (Lane 2), 0.75 µM I (Lane 3), 0.3 µM I (Lane 4), or 1× reaction buffer (50 mM $Na_2HPO_4$, 0.5 M NaCl, pH=6.8) (Lane 5) to reach a total reaction volume of 8 µL. The samples were then mixed by pipetting and allowed to react for 2.5 hours at room temperature. The annealed reaction (Lane 6), prepared 0.5 hour in advance, was made by mixing 2 µL of each hairpin with 2 µL of the 1× reaction buffer, and then annealing as described in monomer preparation. A 2% native agarose gel was prepared for use in 1×LB buffer (Faster Better Media, LLC). 1 µL of each sample was then mixed with 1 µL of 5×SYBR Gold loading buffer: 50% glycerol/50% $H_2O$/SYBR Gold (Invitrogen) and loaded into the gel. The gel was run at 350 V for 10 minutes at room temperature and imaged using an FLA-5100 imaging system (Fuji Photo Film Co., Ltd.).

For the gel in FIG. 4c, hairpins were annealed at the following concentrations: A1, A2, B2, A3, and B3 at 1 µM; A4 and B4 at 2 µM; A5 and B5 at 4 µM. The initiator I was prepared at 800 nM. The following sample mixtures were prepared: Lane 1, A1; Lane 2, I+A1; Lane 3, I+A1+A2+B2; Lane 4, I+A1+A2+B2+A3+B3; Lane 5, I+A1+A2+B2+A3+B3+A4+B4; Lane 6, I+A1+A2+B2+A3+B3+A4+B4+A5+B5; Lane 7, A1+A2+B2+A3+B3+A4+B4+A5+B5. Here, I, A1, A2, and B2 were added at 1 µL; A3, B3, A4, B4, A5, and B5 at 2 µL. 1× reaction buffer (20 mM Tris, pH=7.6, 2 mM EDTA, 12.5 mM $Mg^{++}$) was added to bring the total volume of each sample to 16 µL. The samples were mixed by pipetting and allowed to react for 2 hours at room temperature. A 1% native agarose gel was prepared in 1×LB buffer. 8 µL of each sample were added to 2 µL 5×SYBR Gold loading buffer. 8 µL of the sample/loading-buffer mix were then loaded into the gel. The gel was run at 350 V for 10 minutes at room temperature and then imaged using an FLA-5100 imaging system. For the reactions in FIG. 4d, the hairpins were mixed to reach the following final concentration: A1-Cy5, A2, B2, 100 nM; A3, B3, 200 nM; A4, B4, 400 nM; A5, B5, 800 nM. 9 µL of this mix were then aliquoted into 10 separate tubes. To these tubes was added either 1×TAE/$Mg^{++}$ reaction buffer or the initiator I to give the indicated final concentration of I and a final volume of 11 µL. The samples were mixed by pipetting and then allowed to react for 1 hour at room temperature. The sample was then mixed with 5×LB loading buffer (Faster Better Media, LLC) to reach 1× loading buffer concentration (8 µL sample, 2 µL loading buffer). The sample/loading buffer mix was loaded into a 1% native agarose gel prepared in 1×LB buffer. The gel was run at 350 V for 10 minutes at room temperature and then imaged and quantified using an FLA-5100 imaging system. The experiments were performed with 10 µM inert 25-nt poly-T carrier strands in the reaction solution.

Example 15

AFM Imaging

This example illustrates AFM imaging of the self-assembly systems.

AFM images were obtained using a multimode scanning probe microscope (Veeco Instruments Inc.), equipped with a Q-Control module for analog AFM systems (Atomic Force F&E GmbH). The images were obtained in liquid phase under tapping mode using DNP—S oxide sharpened silicon nitride cantilevers (Veeco Instruments Inc.). Samples were first diluted in 1×TAE/Mg$^{++}$ buffer to achieve the desired imaging density. A 20 µL drop of 1×TAE/Mg$^{++}$ and a 5 µL drop of sample were applied to the surface of freshly cleaved mica and allowed to bind for approximately 2 minutes. Supplemental 15-30 mM Ni$^{++}$ was added to increase the strength of DNA-mica binding. Before placing the fluid cell on top of the mica puck, an additional 15-20 µL of 1×TAE/Mg$^{++}$ buffer was added to the cavity between the fluid cell and the AFM cantilever chip to avoid bubbles.

Example 16

Fluorescence Experiments

This example illustrates fluorescence experiments with the self-assembly systems.

Catalytic circuitry. Fluorescence data were obtained using a QM-6/2005 steady state spectrofluorometer (Photon Technology International), equipped with a Turret 400™ four-position cuvette holder (Quantum Northwest) and 3.5 mL QS quartz cuvettes (Hellma GmbH & Co. KG). The temperature was set to 25° C. The excitation and emission wavelengths were set to 520 nm (2 nm bandwidth) and 540 nm (4 nm bandwidth), respectively. For the experiments in FIG. 3c, hairpin monomers, A, B, C, and D, and initiator, I, were prepared separately as described above. 40 µL 1 µM A were added to 1800 µL 1×TAE/Mg$^{++}$ buffer and mixed by rapid pipetting 8 times using a 1 mL tip. The baseline signal was recorded for ~16 minutes. Then 40 µL of 1 µM B, C, and D, and the appropriate concentration of I (or 1×TAE/Mg$^{++}$ buffer in the case of 0×I) were added to the cuvette (to reach the target concentrations described in FIG. 3c) and mixed by rapid pipetting 8 times using a 1 mL tip. The control with 20 nM A alone was monitored continuously. The final volume was 2 mL for all experiments. The experiments were performed with 10 µM inert 25-nt poly-T carrier strand in the individual hairpin and initiator stock solutions and ~1 µM inert 25-nt poly-T carrier strands in the final reaction solution.

Autonomous locomotion. Fluorescence experiments were performed at 21° C. using the same spectrofluorometer as above. Two 3.5 mL QS quartz cuvettes (Hellma GmbH & Co. KG) were used in each set of experiments. Excitation and emission wavelengths were set to 492 nm and 517 nm (for FAM), 527 nm and 551 nm (for JOE), and 558 nm and 578 nm (for TAMRA), respectively, with 4 nm bandwidths. The assembly of the walker system is described above. Hairpin B was snap cooled in the reaction buffer (4 mM MgCl$_2$, 15 mM KCl, and 10 mM Tris-HCl, pH=8.0): heating at 95° C. for 90 seconds, rapid cooling at room temperature, allowed to sit at room temperature for 30 minutes before use. The system was assembled using 4 nM track and 3.5 nM bipedal walker. A sub-stochiometric amount of walker was used to ensure that no free-floating walker would bind to hairpin A on the track. For the same reason, sub-stoichiometric monopedal walker (7 nM) was used in the diffusion experiments. The final concentration of hairpin B was 20 nM, which was equimolar with the five A hairpins on the track (5×4 nM=20 nM). The assembled track was first introduced to record the fluorescence baselines for FAM, JOE, and TAMRA. Hairpin B was then introduced and mixed 100 times by rapid pipetting to start walker locomotion.

Example 17

DNA Sequences

The DNA sequences for the systems described in the Examples are presented both as secondary structure schematics in FIGS. 31-35 and as text sequences annotated with segment names.

For each hairpin sequence X, the two segments that are ligated to produce X are indicated as Xa and Xb. Strand modifications are indicated as follows:

5' phosphorylation: /5Phos/;
3' 6-carboxyfluorescein: /36FAM/;
5' 6-carboxyfluorescein: /56FAM/;
5' 6-carboxy-4', 5'dichloro-2',7'-dimethoxyfluorescein (NHS Ester): /5JOEN/;
5' tetrachlorofluorescein: /5STET/;
5' carboxytetramethylrhodamine (NHS Ester): /5TMRN/;
3' black hole quencher-1: /3BHQ_1/

Catalytic 3-arm junction system. The sequences are listed below as text sequences annotated with segment names.

```
A: a-x-b-y-z*-c*-y*-b*-x*
GCTTGA-GATGTT-AGGGAG-TAGTGC-TCCAAT-CACAAC-GCACTA-CTCCCT-AACATC    (SEQ ID NO: 1)

Aa:
GCTTGAGATGTTAGG                                                    (SEQ ID NO: 2)

Ab:
/5Phos/GAGTAGTGCTCCAATCACAACGCACTACTCCCTAACATC                     (SEQ ID NO: 3)

B: b-y-c-z-x*-a*-z*-c*-y*
AGGGAG-TAGTGC-GTTGTG-ATTGGA-AACATC-TCAAGC-TCCAAT-CACAAC-GCACTA    (SEQ ID NO: 4)
```

-continued

```
Ba:
AGGGAGTAGTGCGTT                                              (SEQ ID NO: 5)

Bb:
/5Phos/GTGATTGGAAACATCTCAAGCTCCAATCACAACGCACTA               (SEQ ID NO: 6)

C: c-z-a-x-y*-b*-x*-a*-z*
GTTGTG-ATTGGA-GCTTGA-GATGTT-GCACTA-CTCCCT-AACATC-TCAAGC-TCCAAT (SEQ ID NO: 7)

Ca:
GTTGTGATTGGAGCT                                              (SEQ ID NO: 8)

Cb: /5Phos/TGAGATGTTGCACTACTCCCTAACATCTCAAGCTCCAAT           (SEQ ID NO: 9)

I: y*-b*-x*-a*
GCACTA-CTCCCT-AACATC-TCAAGC                                  (SEQ ID NO: 10)
```

Catalytic 4-arm junction system. The sequences are listed below as text sequences annotated with segment names.

```
A: a-w-b-x-y*-c*-x*-b*-w*-q*
GCTTGA-GATGTT-AGGGAG-TAGTGC-TCCAAT-CACAAC-GCACTA-CTCCCT-AACATC- (SEQ ID NO: 11)

AACCACCACCAACCACCC

Aa:
GCTTGAGATGTTAGGGAGTAGTGCTCCAATCACAACGCACTACTCC              (SEQ ID NO: 12)

Ab:
/5Phos/CTAACATCAACCACCACCAACCACCC                           (SEQ ID NO: 13)

B: b-x-c-y-x*-d*-y*-c*-x*-r*
AGGGAG-TAGTGC-GTTGTG-ATTGGA-ACTCAT-CTACCG-TCCAAT-CACAAC-GCACTA- (SEQ ID NO: 14)

ACAACACACACAAACCAC

Ba:
AGGGAGTAGTGCGTTGTGATTGGAACTCATCTACCGTCCAATCAC              (SEQ ID NO: 15)

Bb:
/5Phos/AACGCACTAACAACACACACAAACCAC                          (SEQ ID NO: 16)

C: c-y-d-z-w*-a*-z*-d*-y*-s*
GTTGTG-ATTGGA-CGGTAG-ATGAGT-AACATC-TCAAGC-ACTCAT-CTACCG-TCCAAT- (SEQ ID NO: 17)

ATCCTTCCCTTCCTCTCC

Ca:
GTTGTGATTGGACGGTAGATGAGTAACATCTCAAGCACTCATCTAC             (SEQ ID NO: 18)

Cb:
/5Phos/CGTCCAATATCCTTCCCTTCCTCTCC                          (SEQ ID NO: 19)

D: d-z-a-w-x*-b*-w*-a*-z*-t*
CGGTAG-ATGAGT-GCTTGA-GATGTT-GCACTA-CTCCCT-AACATC-TCAAGC-ACTCAT- (SEQ ID NO: 20)

TCTCTTCTTCTCTTCTTC

Da:
CGGTAGATGAGTGCTTGAGATGTTGCACTACTCCCTAACATCTCAA             (SEQ ID NO: 21)

Db:
/5Phos/GCACTCATTCTCTTCTTCTCTTCTTC                          (SEQ ID NO: 22)

I: x*-b*-w*-a*
GCACTA-CTCCCT-AACATC-TCAAGC                                (SEQ ID NO: 23)

Ae: q-w
GGGTGGTTGGTGGTGGTT-GATGTT                                  (SEQ ID NO: 24)

Be: r-x
GTGGTTTGTGTGTGTTGT-TAGTGC                                  (SEQ ID NO: 25)
```

```
Ce: s-y
GGAGAGGAAGGGAAGGAT-ATTGGA                                                (SEQ ID NO: 26)

De: t-z
GAAGAAGAGAAGAAGAGA-ATGAGT                                                (SEQ ID NO: 27)
```

Autocatalytic system. The sequences are listed below as text sequences annotated with segment names.

```
A: x*-v*-b*-y*-u*-c*-a*-x*-y-b-v-x-a
ACAACT-GAACAC-GTTAGA-CCACTT-CCATCC-TCGCAA-ATCTCC-ACAACT-AAGTGG-TCTAAC-   (SEQ ID NO: 28)

GTGTTC-AGTTGT-GGAGAT

Aa-TET:
/5TET/TT-ACAACTGAACACGTTAGACCACTTCCATCCTCGCAAATCTCCACAACTAAGTGGTCTAAC   (SEQ ID NO: 29)

Ab-BHQ1:
/5Phos/GTGTTCAGTTGTGGAGAT/3BHQ_1/                                        (SEQ ID NO: 30)

B: v*-d*-y*-u*-c*-a*-x*-v*-b*-y*-x-a-c-u-y-b
GAACAC-TGCTCT-CCACTT-CCATCC-TCGCAA-ATCTCC-ACAACT-GAACAC-GTTAGA-CCACTT-   (SEQ ID NO: 31)

AGTTGT-GGAGAT-TTGCGA-GGATGG-AAGTGG-TCTAAC

Ba:
GAACACTGCTCTCCACTTCCATCCTCGCAAATCTCCACAACTGAACACGTTAGACCACTTAGTTGTGGAGATTTG (SEQ ID NO: 32)

CGA

Bb:
/5Phos/GGATGGAAGTGGTCTAAC                                                (SEQ ID NO: 33)

C: c-u-y-d-v-u*-c*-a*-x*-v*-d*-y*-u*
TTGCGA-GGATGG-AAGTGG-AGAGCA-GTGTTC-CCATCC-TCGCAA-ATCTCC-ACAACT-GAACAC-   (SEQ ID NO: 34)

TGCTCT-CCACTT-CCATCC

Ca:
TTGCGAGGATGGAAGTGGAGAGCAGTGTTCCCATCCTCGCAAATCTCCACAACTGAACACTGCTCTCC    (SEQ ID NO: 35)

Cb:
/5Phos/ACTTCCATCC                                                        (SEQ ID NO: 36)

D: d-v-x-a-c-u-v*-d*-y*-u*-c*-a*-x*-v*-b*-y*
AGAGCA-GTGTTC-AGTTGT-GGAGAT-TTGCGA-GGATGG-GAACAC-TGCTCT-CCACTT-CCATCC-   (SEQ ID NO: 37)

TCGCAA-ATCTCC-ACAACT-GAACAC-GTTAGA-CCACTT

Da:
AGAGCAGTGTTCAGTTGTGGAGATTTGCGAGGATGGGAACACTGCTCTCCACTTCCATCCTCGCAAATCTCC (SEQ ID NO: 38)

Db:
/5Phos/ACAACTGAACACGTTAGACCACTT                                          (SEQ ID NO: 39)

I: a*-x*-v*-b*-y*
ATCTCC-ACAACT-GAACAC-GTTAGA-CCACTT                                       (SEQ ID NO: 40)
```

Nucleated dendritic growth system. The sequences are listed below as text sequences annotated with segment names. A1b-Cy5 (together with A1a) is used to synthesize Cy5 labeled hairpin A1.

```
A1: a-x-c-b-x-y-x*-d*-e*-x*-b*-c*-x*-d*-e*-x*
CAAACTC-TT-ATCTATC-TCTGCCA-TT-TT-AA-TGCAATG-TCACGGT-AA-TGGCAGA-GATAGAT-AA- (SEQ ID NO: 41)

TGCAATG-TCACGGT-AA

A1a:
CAAACTCTTATCTATCTCTGCCATTTTAATGCAATGTCACGGTAATGGCAGA                     (SEQ ID NO: 42)

A1b:
/5Phos/GATAGATAATGCAATGTCACGGTAA                                          (SEQ ID NO: 43)
```

```
A1b-Cy5:
/5Phos/GATAGATAATGCAATGTCACGGTAA-TT/3Cy5sp/                                    (SEQ ID NO: 44)

A2: b-x-e-d-x-y-x*-f*-g*-x*-d*-e*-x*-f*-g*-x*
TCTGCCA-TT-ACCGTGA-CATTGCA-TT-TT-AA-GCTACAG-GACTACG-AA-TGCAATG-TCACGGT-AA-     (SEQ ID NO: 45)
GCTACAG-GACTACG-AA

A2a:
TCTGCCATTACCGTGACATTGCATTTTAAGCTACAGGACTACGAATGCAATG                          (SEQ ID NO: 46)

A2b:
/5Phos/TCACGGTAAGCTACAGGACTACGAA                                              (SEQ ID NO: 47)

A3: d-x-g-f-x-y-x*-h*-i*-x*-f*-g*-x*-h*-i*-x*
CATTGCA-TT-CGTAGTC-CTGTAGC-TT-TT-AA-GTATCAG-ATCGCCG-AA-GCTACAG-GACTACG-AA-     (SEQ ID NO: 48)
GTATCAG-ATCGCCG-AA

A3a:
CATTGCATTCGTAGTCCTGTAGCTTTTAAGTATCAGATCGCCGAAGCTACAG                          (SEQ ID NO: 49)

A3b:
/5Phos/GACTACGAAGTATCAGATCGCCGAA                                              (SEQ ID NO: 50)

A4: f-x-i-h-x-y-x*-j*-k*-x*-h*-i*-x*-j*-k*-x*
CTGTAGC-TT-CGGCGAT-CTGATAC-TT-TT-AA-TGACCAA-ACCACCT-AA-GTATCAG-ATCGCCG-AA-     (SEQ ID NO: 51)
TGACCAA-ACCACCT-AA

A4a:
CTGTAGCTTCGGCGATCTGATACTTTTAATGACCAAACCACCTAAGTATCAG                          (SEQ ID NO: 52)

A4b:
/5Phos/ATCGCCGAATGACCAAACCACCTAA                                              (SEQ ID NO: 53)

A5: h-x-k-j-x-y-x*-l*-m*-x*-j*-k*-x*
CTGATAC-TT-AGGTGGT-TTGGTCA-TT-TT-AA-CTCCACT-CCTACTC-AA-TGACCAA-ACCACCT-AA      (SEQ ID NO: 54)

A5a:
CTGATACTTAGGTGGT                                                              (SEQ ID NO: 55)

a5b:
/5Phos/TTGGTCATTTTAACTCCACTCCTACTCAATGACCAAACCACCTAA                          (SEQ ID NO: 56)

B2: x*-f*-g*-x*-d*-e*-x*-f*-g*-x*-y-x-e-d-x-c
AA-GCTACAG-GACTACG-AA-TGCAATG-TCACGGT-AA-GCTACAG-GACTACG-AA-TT-TT-ACCGTGA-     (SEQ ID NO: 57)
CATTGCA-TT-ATCTATC

B2a:
AAGCTACAGGACTACGAATGCAATG                                                     (SEQ ID NO: 58)

B2b:
/5Phos/TCACGGTAAGCTACAGGACTACGAATTTTACCGTGACATTGCATTATCTATC                   (SEQ ID NO: 59)

B3: x*-h*-i*-x*-f*-g*-x*-h*-i*-x*-y-x-g-f-x-e
AA-GTATCAG-ATCGCCG-AA-GCTACAG-GACTACG-AA-GTATCAG-ATCGCCG-AA-TT-TT-CGTAGTC-     (SEQ ID NO: 60)
CTGTAGC-TT-ACCGTGA

B3a:
AAGTATCAGATCGCCGAAGCTACAG                                                     (SEQ ID NO: 61)

B3b:
/5Phos/GACTACGAAGTATCAGATCGCCGAATTTTCGTAGTCCTGTAGCTTACCGTGA                   (SEQ ID NO: 62)

B4: x_j_k*-x*-h*-i*-x*-j*-k*-x*-y-x-i-h-x-g
AA-TGACCAA-ACCACCT-AA-CTCCACT-CCTACTC-AA-TT-TT-AGGTGGT-TTGGTCA-TT-CGGCGAT      (SEQ ID NO: 63)

B5a:
AATGACCAAACCACCTAACTCCACTCCTACTCAATTTTAGGTGGT                                 (SEQ ID NO: 64)

B5b:
/5Phos/TTGGTCATTCGGCGAT                                                       (SEQ ID NO: 65)

I: x*-b*-c*-x*-a*
AA-TGGCAGA-GATAGAT-AA-GAGTTTG                                                 (SEQ ID NO: 66)
```

Fuel for the walker system. The sequences are listed below as text sequences annotated with segment names.

```
A: z-x-b-c-y-x*-a*-d*-y*-c*-b*-x*
AAGTAGT-GATTGAGCG-TGATGAA-TG-TC-ACTACTT-CAACTCG-CA-TTCATCA-CGCTCAA-TC  (SEQ ID NO: 67)

Aa:
AAGTAGTGATTGAGCGTGATGAATGTCACTACTTCAACTCGCATTCATC                      (SEQ ID NO: 68)

Ab:
/5Phos/ACGCTCAATC                                                       (SEQ ID NO: 69)

B: c-y-d-a-x-y*-c*-b*-x*-a*-d*-y*
TGATGAA-TG-CGAGTTG-AAGTAGT-GA-CA-TTCATCA-CGCTCAA-TC-ACTACTT-CAACTCG-CA (SEQ ID NO: 70)

Ba:
TGATGAATCCGAGTTGAAGTAGTGACATTCATCACGCTCAATCACTACT                      (SEQ ID NO: 71)

Bb:
/5Phos/TCAACTCGCA                                                       (SEQ ID NO: 72)

I: x-y*-c*-b*-x*-a*
GA-CA-TTCATCA-CGCTCAA-TC-ACTACTT                                        (SEQ ID NO: 73)

I-FAM:
GACATTCATCACGCTCAATCACTACTT/36FAM                                       (SEQ ID NO: 74)
```

Walker system. Sequence B is the same as described above for fuel for the walker system. W1s is used as a splint strand for ligating strands W1a and W1b to produce W1; W2s is used as a splint strand for ligating strands W2a and W2b to produce W2.

```
S1:
GGTAGTTCTAGGCAGCTGAAGTAGTGATTGAGCGTGATGAATGTCACTACTTCAACTCGCATTCATCACGCTCAA (SEQ ID NO: 75)
TC

S1a:
GGTAGTTCTAGGCAGCTGAAGTAGTGATTGAGCGT                                     (SEQ ID NO: 76)

S1b:
/5Phos/GATGAATGTCACTACTTCAACTCGCATTCATCACGCTCAATC                       (SEQ ID NO: 77)

S2:
TCATAGGCACCGTCAGACAGGATAGAGCAGTGCATAGATAGTCATAGCCTTGGACCTGCCTAGAACTACC  (SEQ ID NO: 78)

S3:
GTCCAAGGCTATGACTATCTATGCACT                                             (SEQ ID NO: 79)

S4:
GCTCTATCCTGTCTGCTGAAGTAGTGATTGAGCGTGATGAATGTCACTACTTCAA                 (SEQ ID NO: 80)
CTCGCATTCATCACGCTCAATC

S4a:
GCTCTATCCTGTCTGCTGAAGTAGTGATTGAGCGT                                     (SEQ ID NO: 81)

S4b:
/5Phos/GATGAATGTCACTACTTCAACTCGCATTCATCACGCTCAATC                       (SEQ ID NO: 82)

S5:
ACGGTGCCTATGACATGGTACTCAGCT                                             (SEQ ID NO: 83)

S6:
GCTCGTATCTGGTCGCTGAAGTAGTGATTGAGCGTGATGAATGTCACTACTTCAA                 (SEQ ID NO: 84)
CTCGCATTCATCACGCTCAATC

S6a:
GCTCGTATCTGGTCGCTGAAGTAGTGATTGAGCGT                                     (SEQ ID NO: 85)

26b:
/5Phos/GATGAATGTCACTACTTCAACTCGCATTCATCACGCTCAATC                       (SEQ ID NO: 86)

S7:
CGTAAGTCGCAGAGTATGCCATTGCCTCATCAGCGTAGCATCGAGATCTAAGTTA                 (SEQ ID NO: 87)
```

```
                                    -continued
GTAACTCTGGCAGCCTGGTAGAGCGAGCCTATCGTCCTGATGTACGACCAGATAC

GAGCAGCTGAGTACCATG

S7truncated:
CGTAAGTCGCAGAGTATGCCATTGCCTCATCAGCGTAGCATCGAGATCTAAGTTA          (SEQ ID NO: 88)

GTAACTCTGGCAGCCTGGTAGAGCGAGCCTATCGTCCTGATGTACGACCAGATAC

GAGC

S8-TMR:
/5TMRN/TACATCAGGACGATAGGCTCGCTCTAC                               (SEQ ID NO: 89)

S8-JOE:
/5JOEN/TACATCAGGACGATAGGCTCGCTCTAC                               (SEQ ID NO: 90)

S9:
CAGGCTGCCAGAGTTCTGAAGTAGTGATTGAGCGTGATGAATGTCATACTTCAAC          (SEQ ID NO: 91)

TCGCATTCATCACGCTCAATC

S9a:
CAGGCTGCCAGAGTTCTGAAGTAGTGATTGAGCGT                              (SEQ ID NO: 92)

S9b:
/5Phos/GATGAATGTCACTACTTCAACTCGCATTCATCACGCTCAATC                (SEQ ID NO: 93)

S10-TMR:
/5TMRN/ACTAACTTAGATCTCGATGCTACGCTG                               (SEQ ID NO: 94)

S10-JOE:
/5JOEN/ACTAACTTAGATCTCGATGCTACGCTG                               (SEQ ID NO: 95)

S11:
ATGAGGCAATGGCATTAGAAGTAGTGATTGAGCGTGATGAATGTCACTACTTCAA          (SEQ ID NO: 96)

CTCGCATTCATCACGCTCAATC

S11a:
ATGAGGCAATGGCATTAGAAGTAGTGATTGAGCGT                              (SEQ ID NO: 97)

S11b:
/5Phos/GATGAATGTCACTACTTCAACTCGCATTCATCACGCTCAATC                (SEQ ID NO: 98)

S12-FAM:
/56FAM/ACTCTGCGACTTACG                                           (SEQ ID NO: 99)

W1:
TTGCCTCGTATCCTAACCGAACGGACTCCAGGACATTCATCACGCTCAATCACTA          (SEQ ID NO: 100)

CTT

W1a:
TTGCCTCGTATCCTAACCGAACGGACTCC                                    (SEQ ID NO: 101)

W1b:
AGGACATTCATCACGCTCAATCACTACTT /BHQ-1/                            (SEQ ID NO: 102)

W1s:
CGTGATGAATGTCCTGGAGTCCGTTCGGTT                                   (SEQ ID NO: 103)

W2:
GTCCGTTCGGTTAGGATACGAGGCAATCCAGGACATTCATCACGCTCAATCACTA          (SEQ ID NO: 104)

CTT

W2a:
GTCCGTTCGGTTAGGATACGAGGCAATCC                                    (SEQ ID NO: 105)

W2b:
AGGACATTCATCACGCTCAATCACTACTT/BHQ-1/                             (SEQ ID NO: 106)

W2s:
CGTGATGAATGTCCTGGATTGCCTCGTATC                                   (SEQ ID NO: 107)
```

Example 18

Catalytic Formation of a DNA Tetrahedron

FIGS. 39a-d depict the reaction schematic for the catalytic formation of a tetrahedron. In the absence of initiator T, hairpins A1, A2, A3, B1, B2, B3, C1, C2, and C3 were metastable. In the presence of initiator T, the hairpins were catalyzed by T to form a tetrahedron.

Initiator T first catalyzed A1, A2, and A3 to form a three-arm junction, resulting in the opening of hairpins A1, A2, and A3. Opened hairpin A1 interacted with and opened hairpin B1, which then opened hairpin C1. In a similar fashion, opened hairpin A2 caused hairpin B2 to open, which then opened hairpin C2; and opened hairpin A3 caused hairpin B3 to open, which then opened hairpin C3. Finally, opened hairpin C1 hybridized with opened hairpin B2; opened hairpin C2 hybridized with opened hairpin B3; and opened hairpin C3 hybridized with opened hairpin B1—completing the catalytic formation of the tetrahedrons.

More specifically, initiator T catalyzed monomers A1, A2, A3, B1, B2, B3, C1, C2, and C3 to form a tetrahedron as follows: (1) segment a* of T nucleated at the toehold a of hairpin A1 and initiated a strand displacement that resulted in the opening of hairpin A1; (2) newly exposed c* of A1 nucleated at toehold c of A2 and resulted in the opening of A2; (3a) newly exposed e* of A2 nucleated at toehold e of A3 and resulted in the opening of A3; (3b) D displaced T from A; (4) segment b of B1 nucleated at b* of hairpin A1 and initiated a strand displacement that resulted in the opening of hairpin B1; (5) segment d of B2 nucleated at d* of hairpin A2 and initiated a strand displacement that resulted in the opening of hairpin B2; (6) segment f of B3 nucleated at of hairpin A3 and initiated a strand displacement that resulted in the opening of hairpin B3; (7) segment g of C1 nucleated at g* of hairpin b1 and initiated a strand displacement that resulted in the opening of hairpin C1; (8) segment i of C2 nucleated at i* of hairpin B2 and initiated a strand displacement that resulted in the opening of hairpin C2; (9) segment k of C3 nucleated at k* of hairpin B3 and initiated a strand displacement that resulted in the opening of hairpin C3; (10) segment m* of C1 nucleated at m of B2; (11) segment p* of C2 nucleated at p of B3; and (12) segment r* of C3 nucleated at r of B1, thereby completing the formation of the tetrahedrons.

Example 19

Formation of a DNA tetrahedron with Restriction Sites

FIG. 40 outlines another example of a DNA tetrahedron, using the following exemplary sequences:

I:
(SEQ ID NO: 108)
TACTTCATCGATCGCTCCAAATCACA

A1:
(SEQ ID NO: 109)
ATAGTCTCCACAACAATCGATCGCTCCAAATCACAAGGTCAACAAACAGC

ACATGTGATTTGGAGCGATCGATGAAGTA

A2:
(SEQ ID NO: 110)
TCTTCTCTAACCCAAACAAGGTCAACAAACAGCACAATCTCACTACTTCA

TCAGTGCTGTTTGTTGACCTTGTGATTTG

A3:
(SEQ ID NO: 111)
TTCTATACTCCTTCACACAATCTCACTACTTCATCGATCGCTCCAAATCA

CAAGATGAAGTAGTGAGATTGTGCTGTTT

B1:
(SEQ ID NO: 112)
GAGCGATCGATTGTTGTGGAGACTATAGAAATATAGTCTCCACAACAATC

AGTACTACAACAAACAAACACCGAGAAGA

B2:
(SEQ ID NO: 113)
GTTGACCTTGTTTGGGTTAGAGAAGAACTAAATCTTCTCTAACCCAAACA

GTATACCATCAGAAACGATATCTATAGAA

B3:
(SEQ ID NO: 114)
GTGAGATTGTGTGAAGGAGTATAGAAATGGGCTTCTATACTCCTTCACAC

ATTAATTCGCGACCAAACCAACAGACTAT

C1:
(SEQ ID NO: 115)
ATCAGTACTACAACAAACAAACACCGAGAAGATTTAGATCTTCTCGGTGT

TTGTTTGTTGTAGTACTGATTGTTGTGG

C2:
(SEQ ID NO: 116)
ACAGTATACCATCAGAAACGATATCTATAGAAGCCCAATTCTATAGATAT

CGTTTCTGATGGTATACTGTTTGGGTTA

C3:
(SEQ ID NO: 117)
CACATTAATTCGCGACCAAACCAACAGACTATATTTCAATAGTCTGTTGG

TTTGGTCGCGAATTAATGTGTGAAGGAG

The reaction system operated as follows: A1 hybridized to I, allowing A2 to bind to A1. A3 then displaced I and hybridized to A1 and A2 (resulting a structure similar to the top right hand side of FIG. 37B). Following this, B1 hybridized to A1, B2 hybridized to A2, and B3 hybridized to A3 (resulting in a structure similar to that depicted in 39B). Following this, C1 hybridized to B1, C2 hybridized to B2 and C3 hybridized to B3 (resulting in a structure similar to 39C). A remaining part of C3 hybridized to B1, a remaining part of C2 hybridized to B3, and a remaining part of C1 hybridized to B2, and provided the structure shown in FIG. 40.

Figure 41:
FIG. 41 depicts a gel shifting assay used to validate each reaction step depicted in FIG. 39.

The system depicted in FIG. 40 was experimentally verified. A gel shifting assay validated the addition of each monomer to form the tetrahedron (FIG. 41). 100 nM reactants were incubated at room temperature for 16 hours. An agarose gel was prepared in 1×LB buffer (Faster Better Media, LLC). The gels were at room temperature and then visualized using UV transillumination.

The gel shifting assay confirmed that the hairpins assembled slowly in the absence of the initiator (Lane 13), and that assembly was accelerated by the addition of the initiator (see, e.g., Lane 10). Only minimal assembly was achieved by annealing the hairpin mixture (Lane 14).

In addition to the above, the structure of the present DNA tetrahedron included restriction sites, so as to allow further verification and examination of the structure produced. As shown in FIG. 40, the edges of the tetrahedron included designed enzyme restriction sites, which are depicted as colored squares. For example, the Sca I site is depicted as a magenta square.

Figure 42:
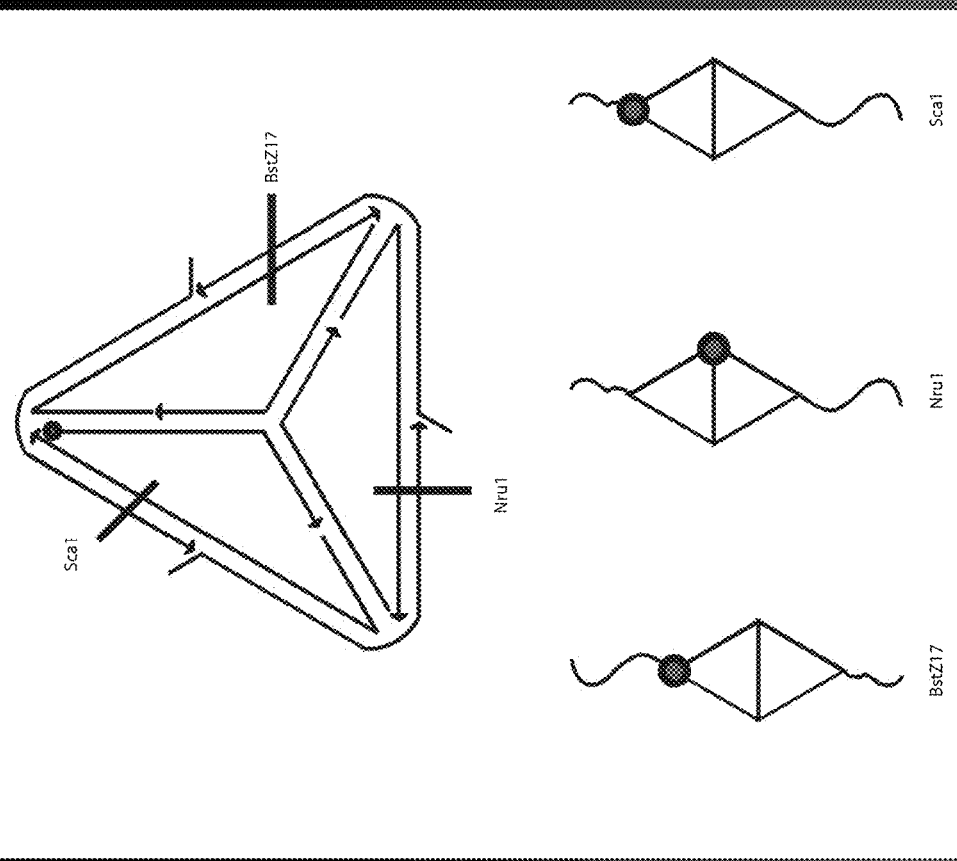
FIG. 42 depicts molecular dissection schemes for analyzing tetrandedrons.
Figure 43:
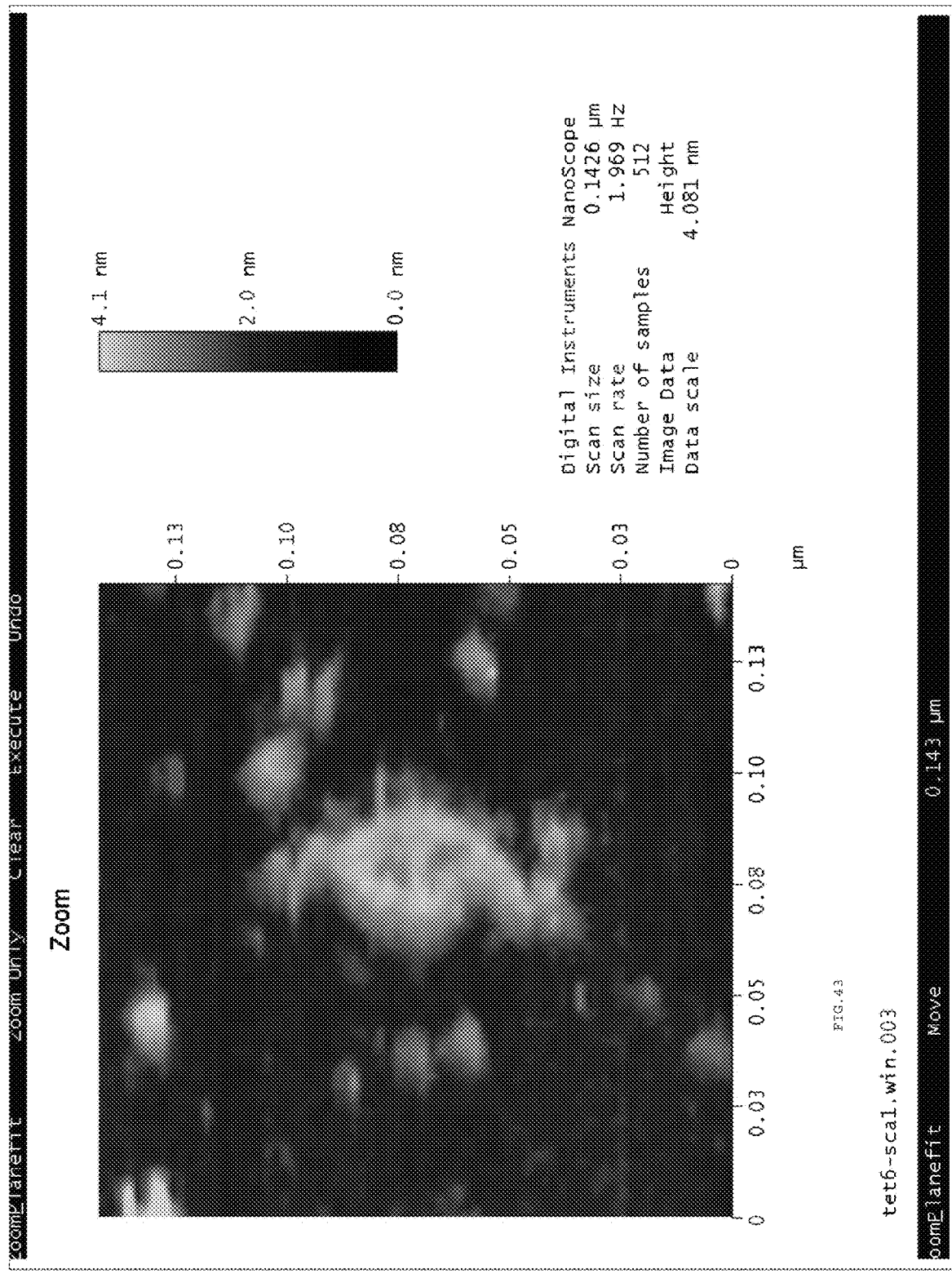
FIGS. 43-71 depict AFM images of tetrahedrons.
Figure 44:
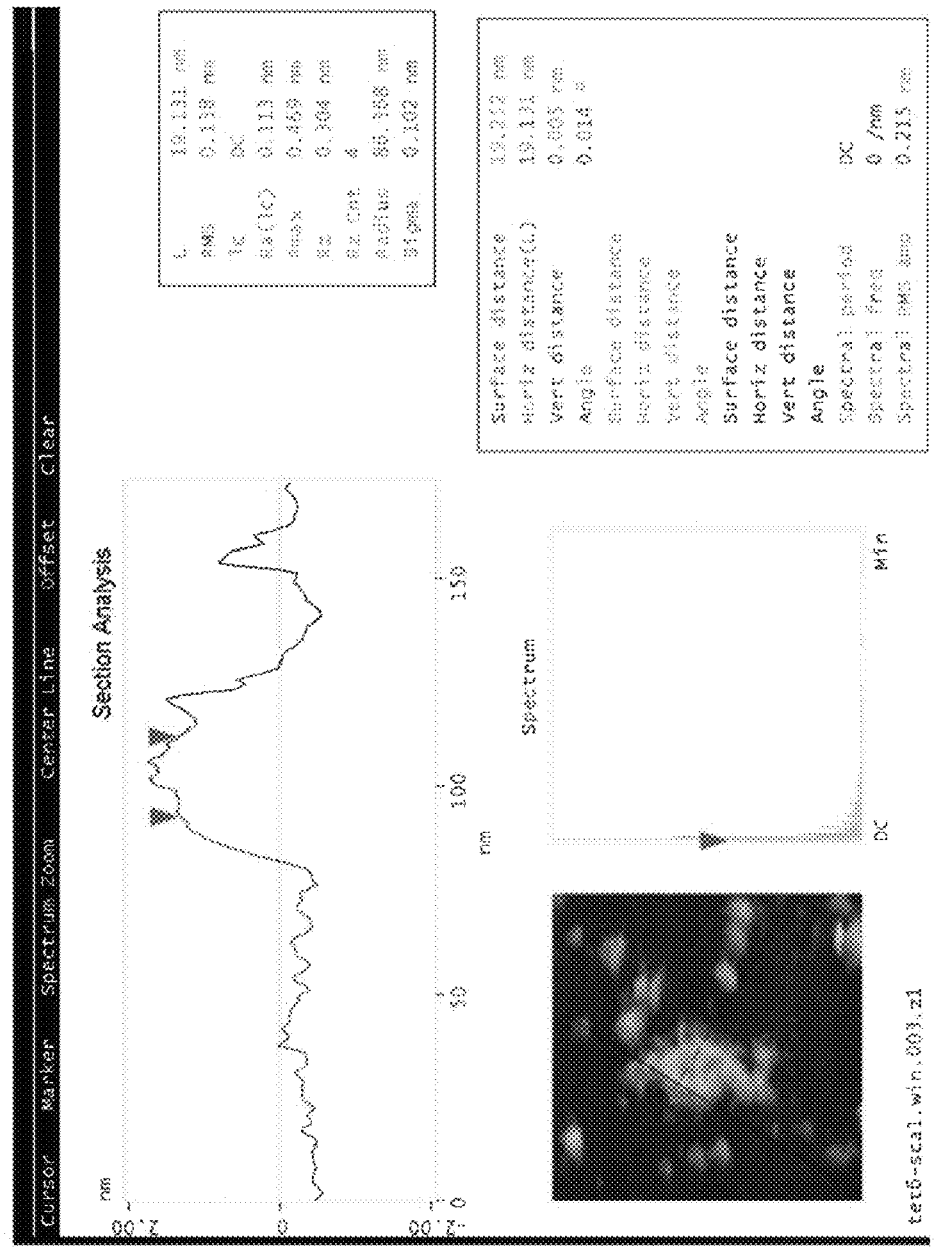
Figure 45:
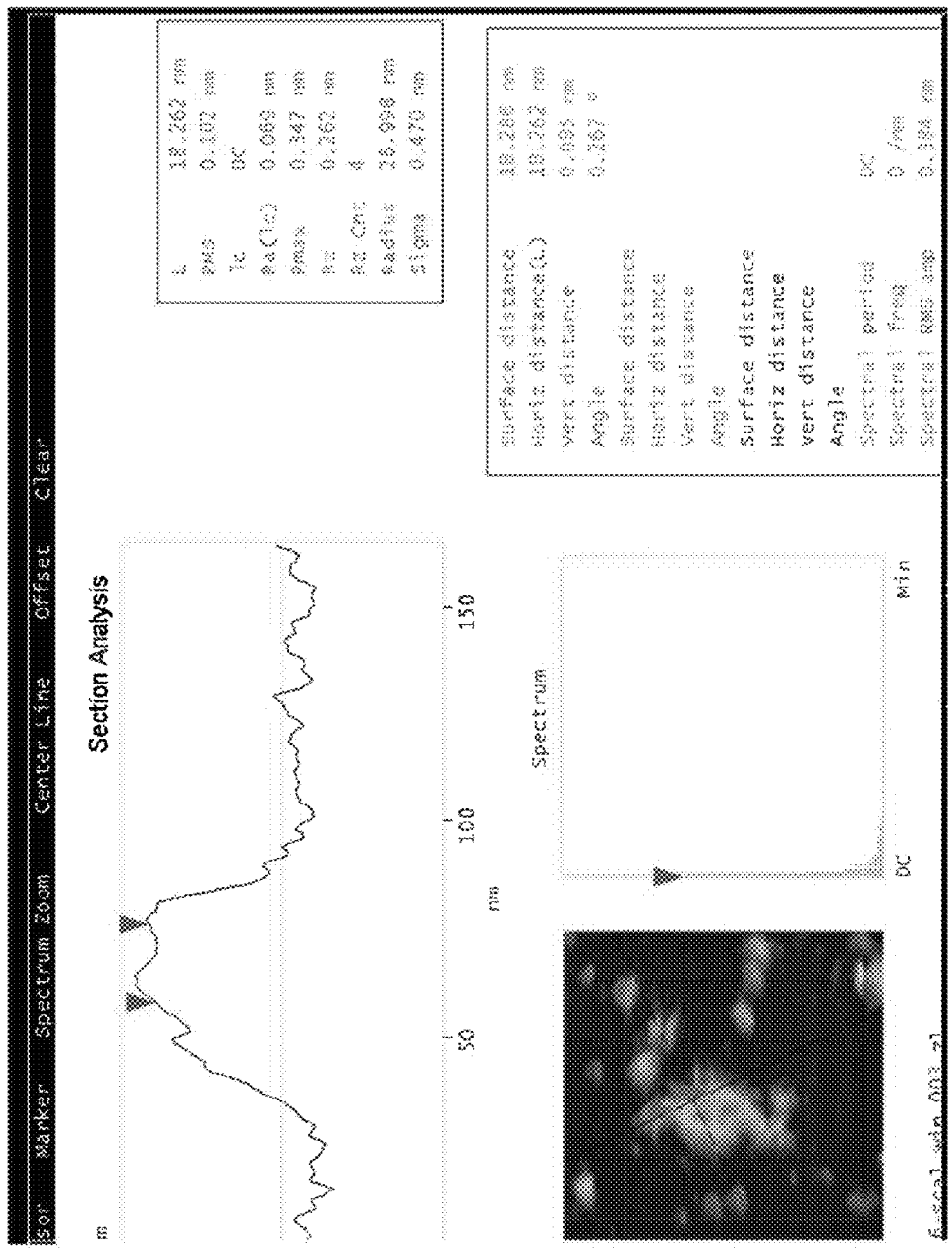
Figure 46:
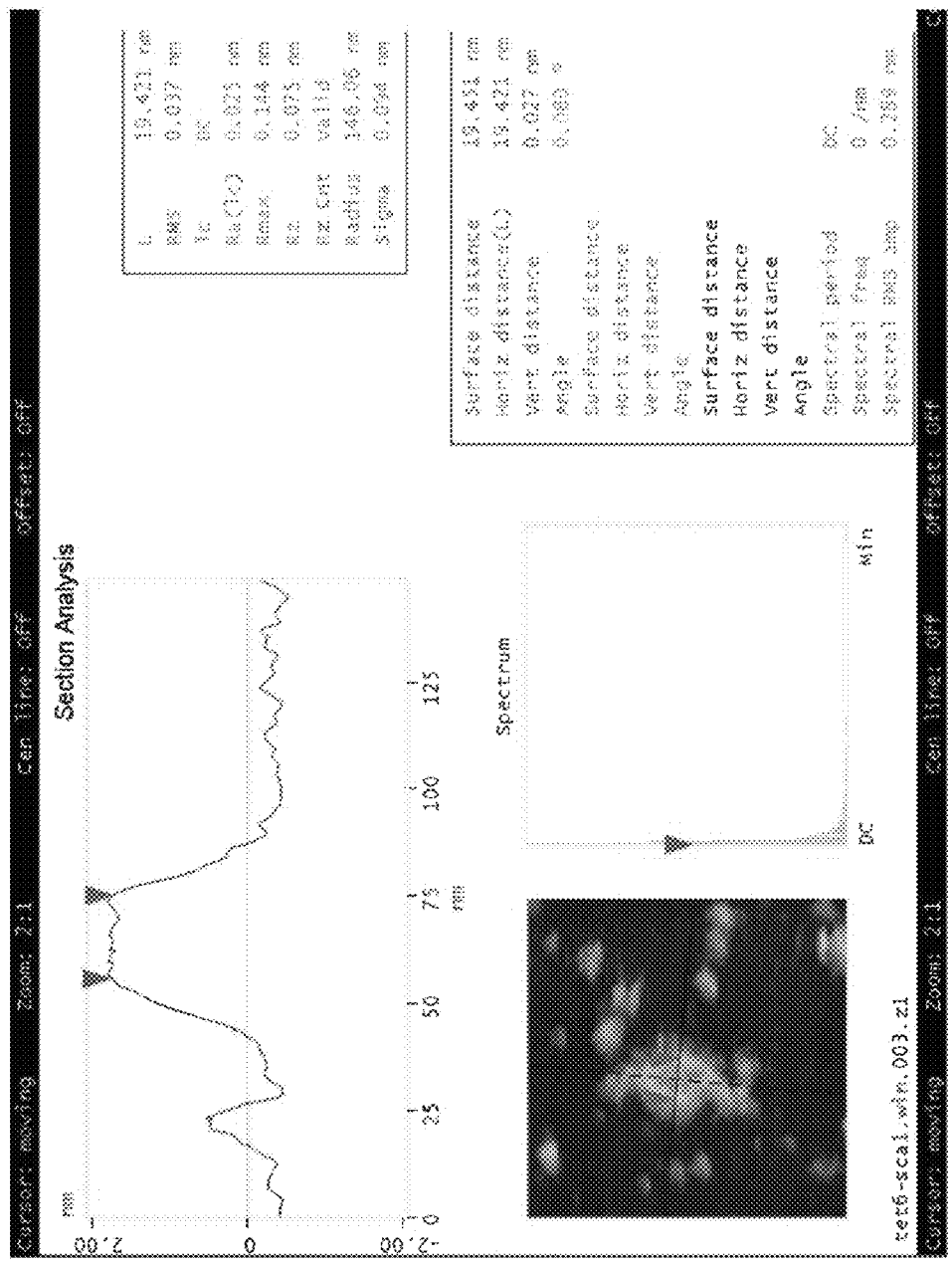
Figure 47:
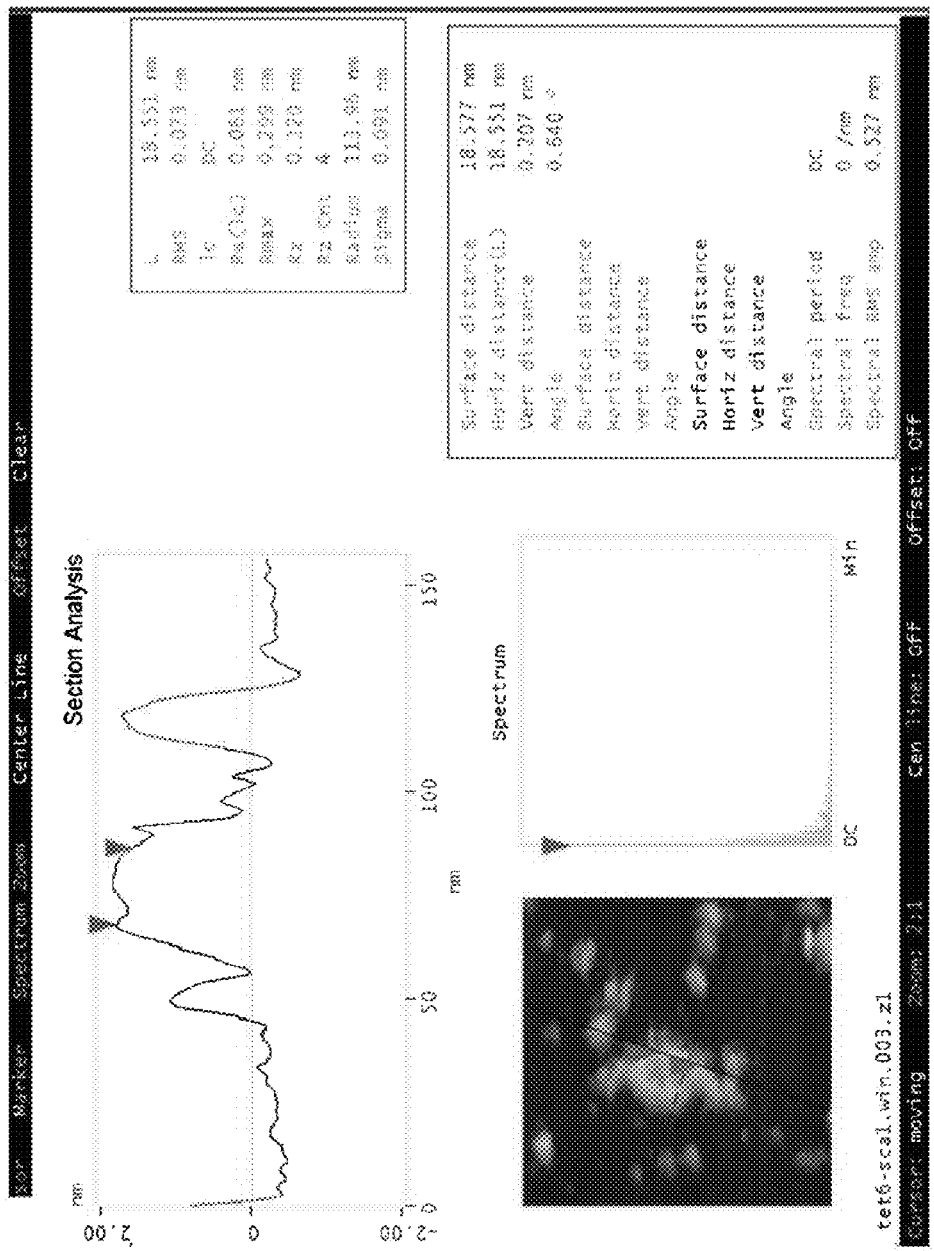
Figure 48:
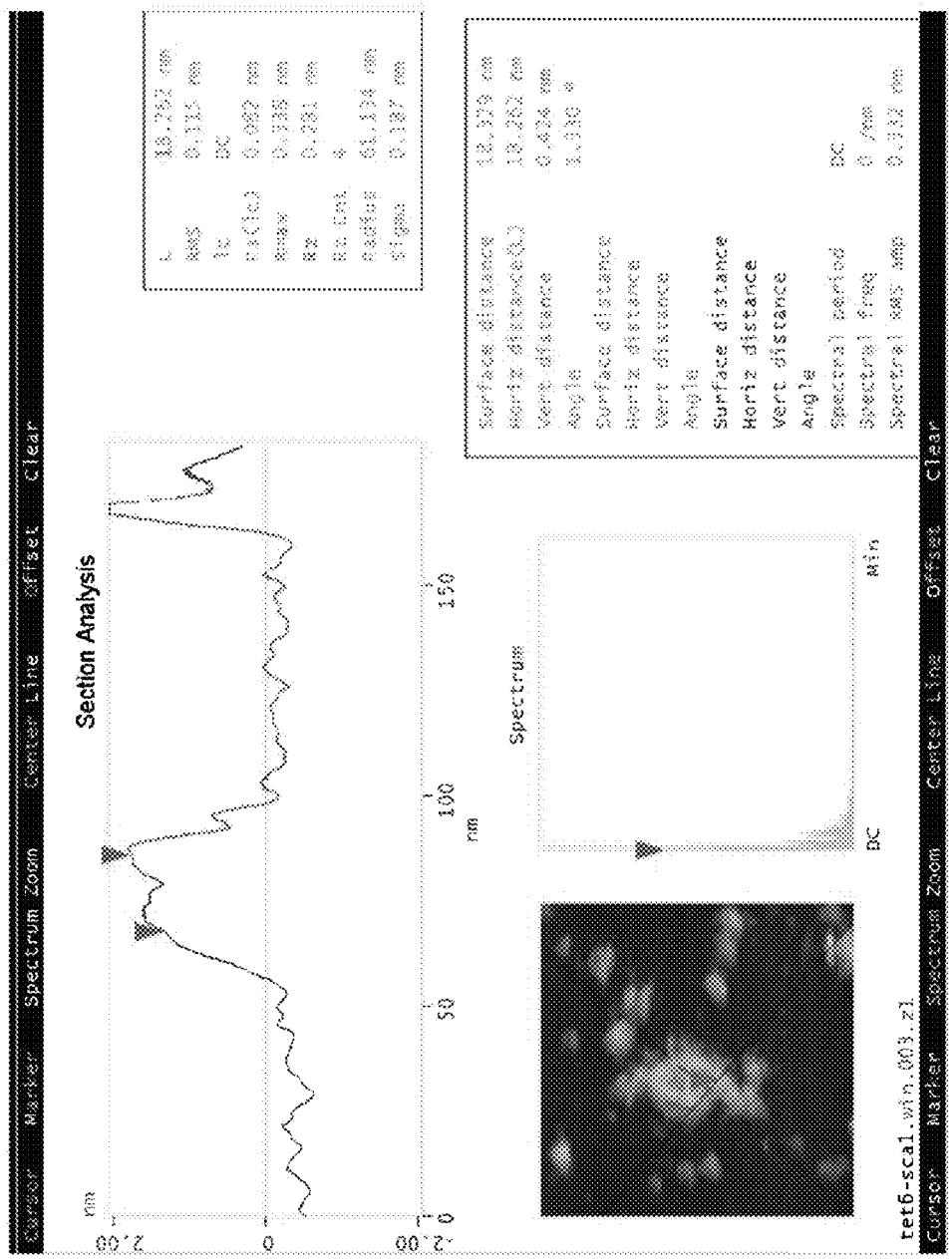
Figure 49:
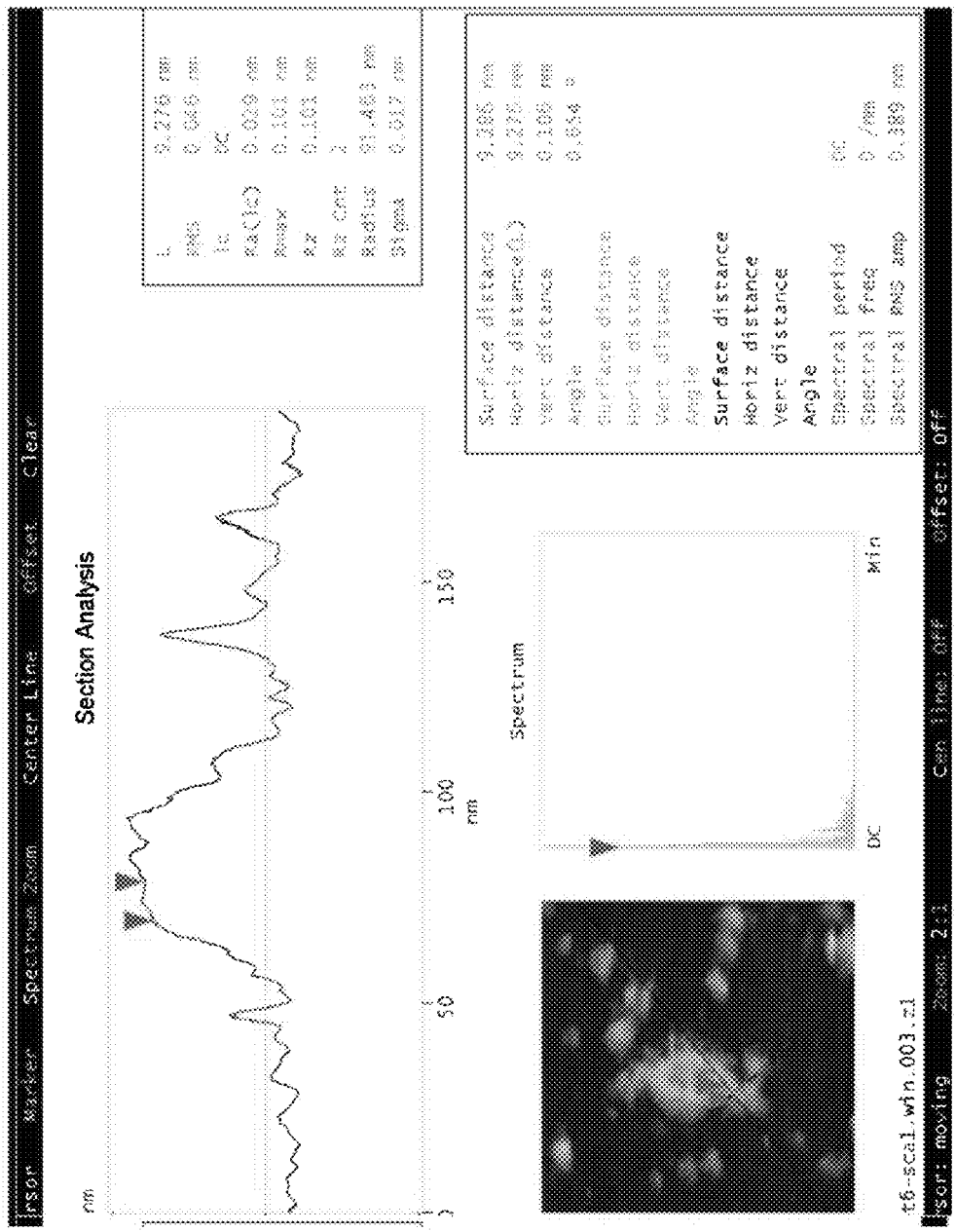
Figure 50:
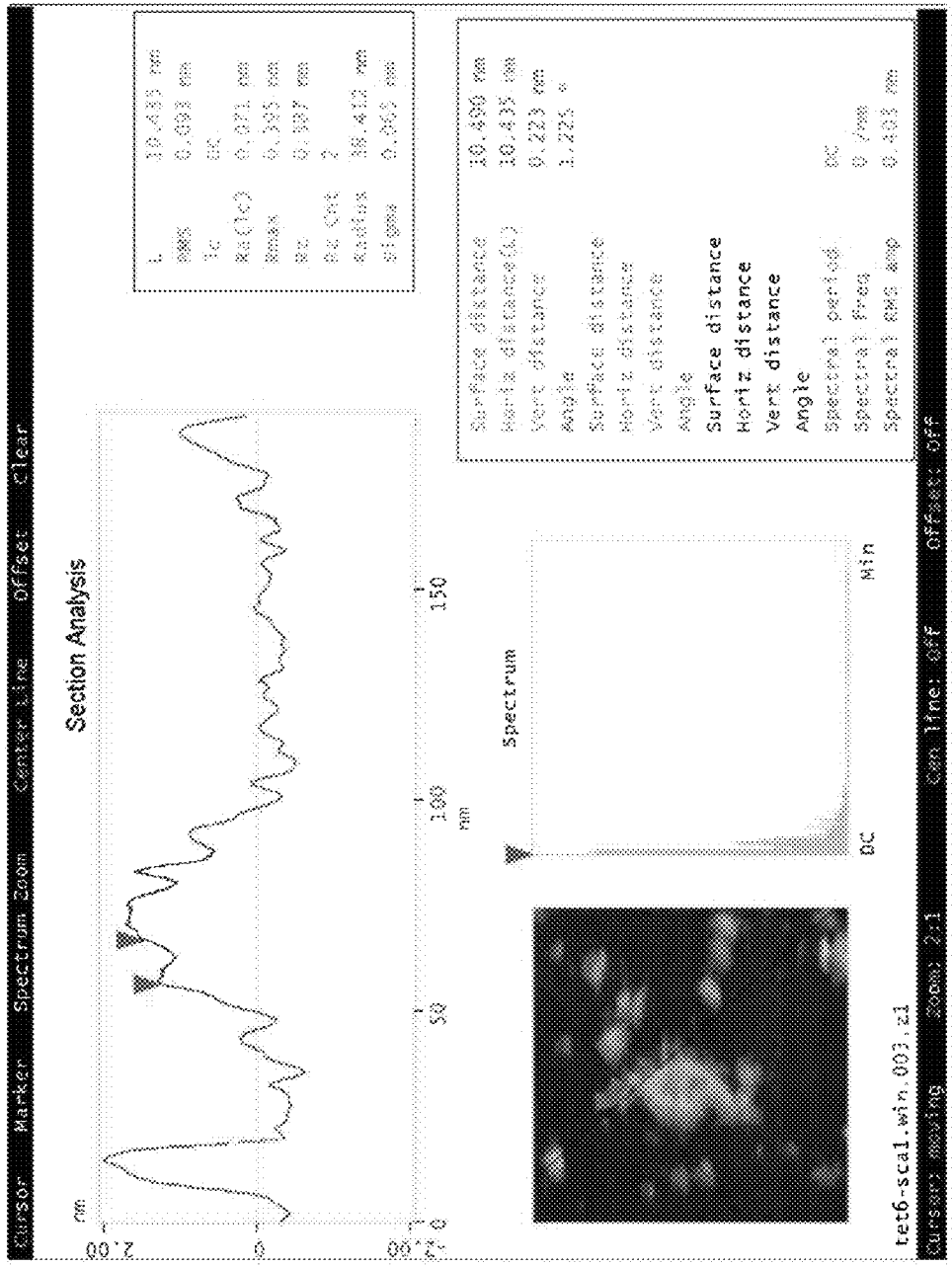
Figure 51:
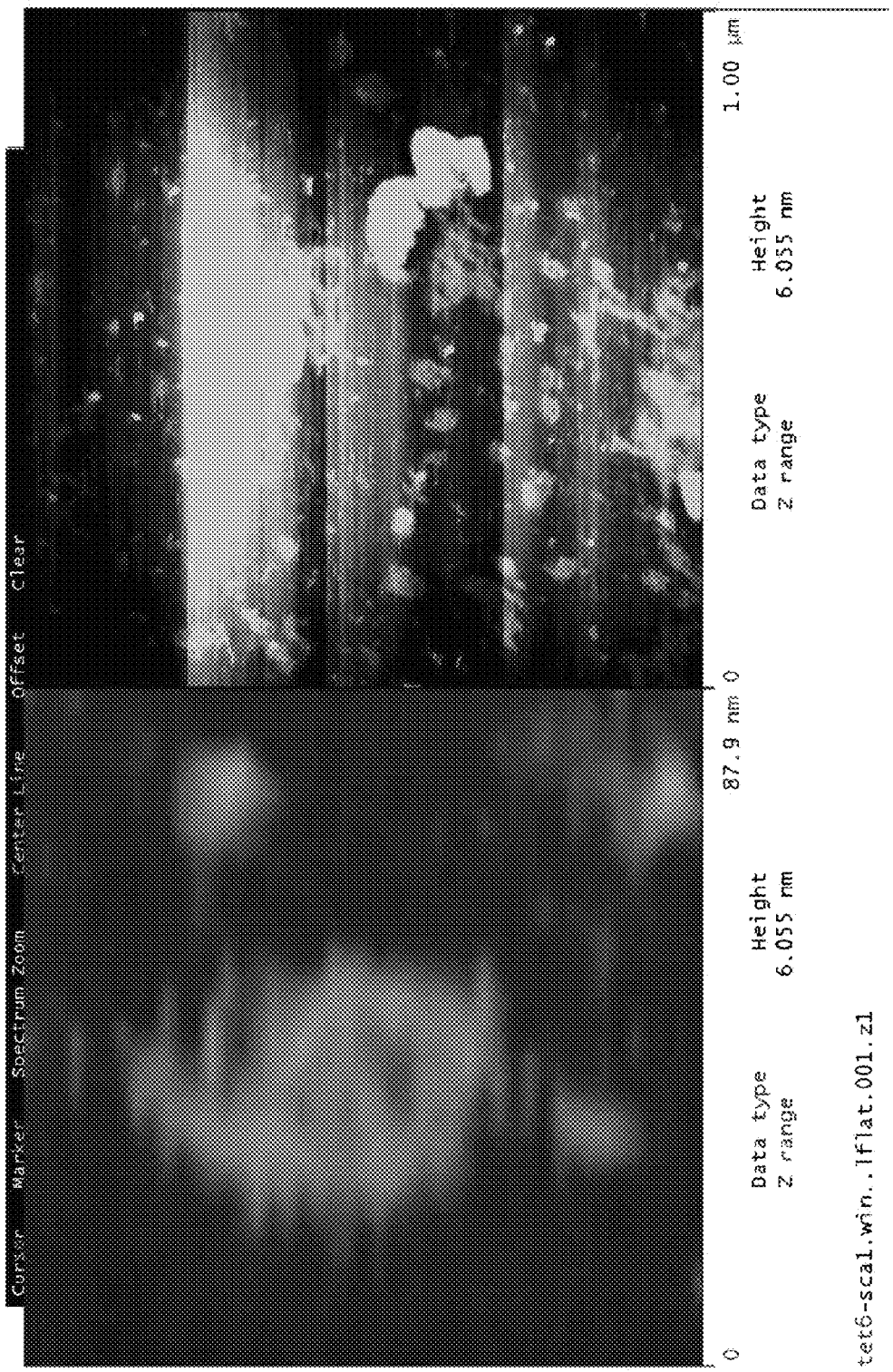
Figure 52:
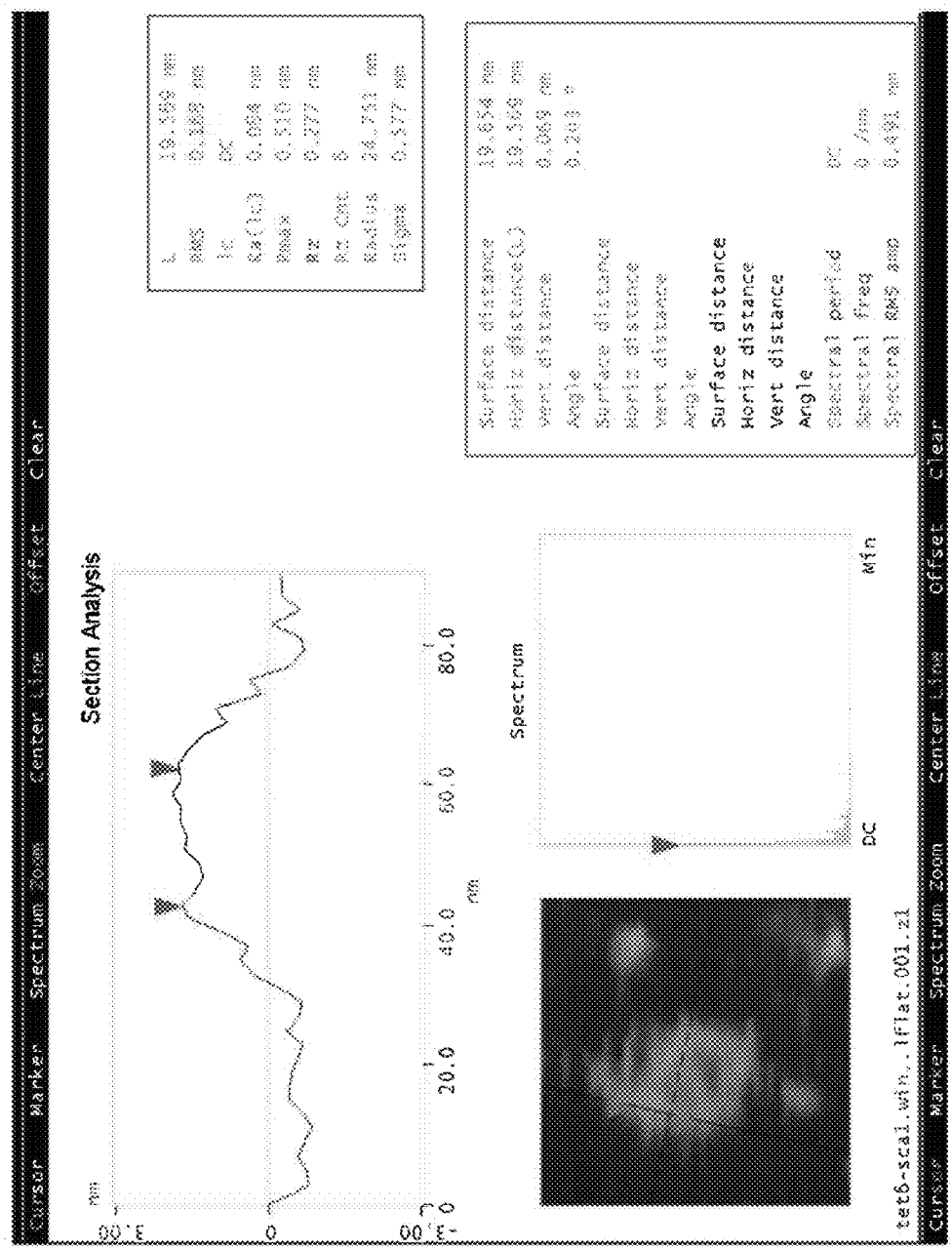
Figure 53:
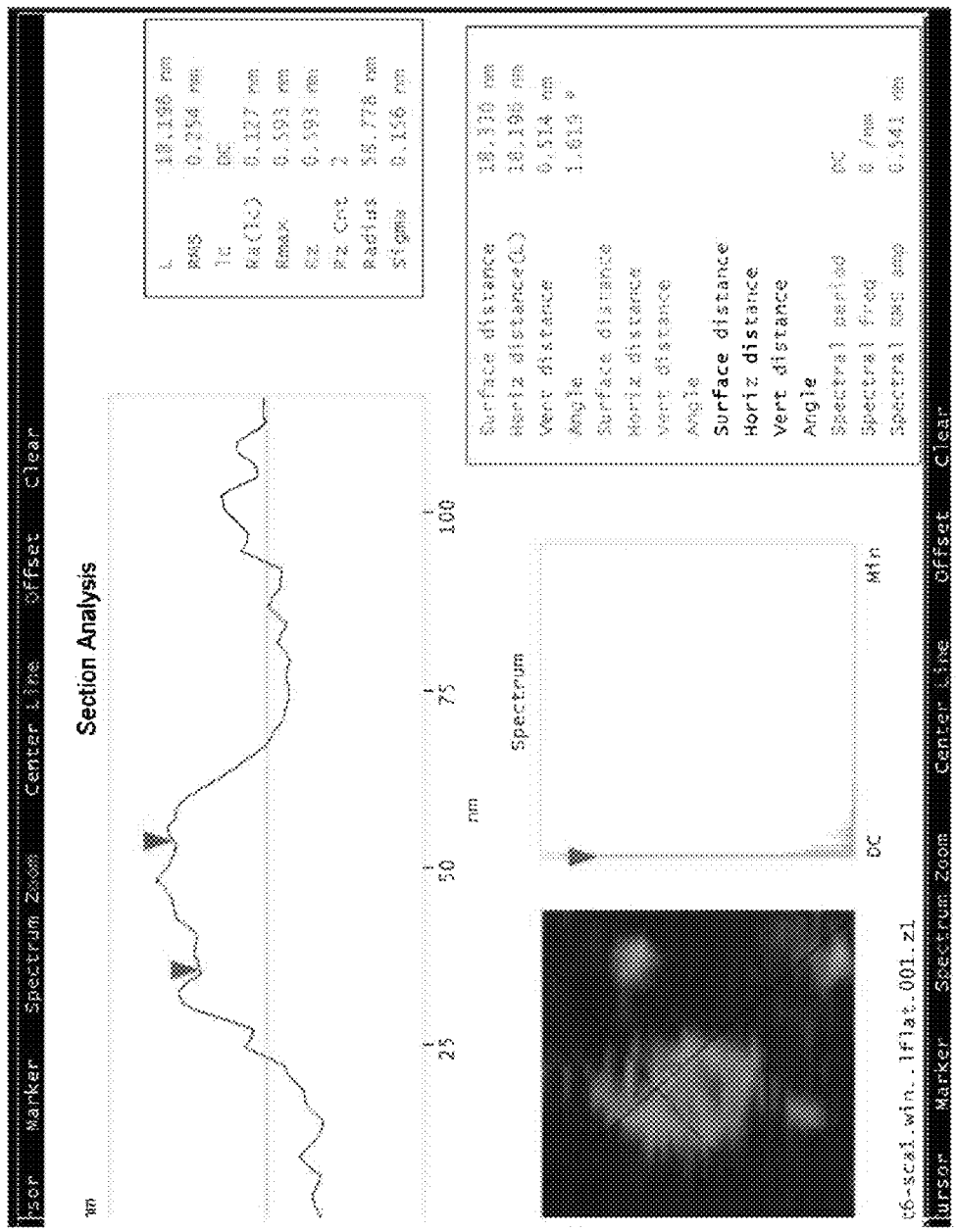
Figure 54:
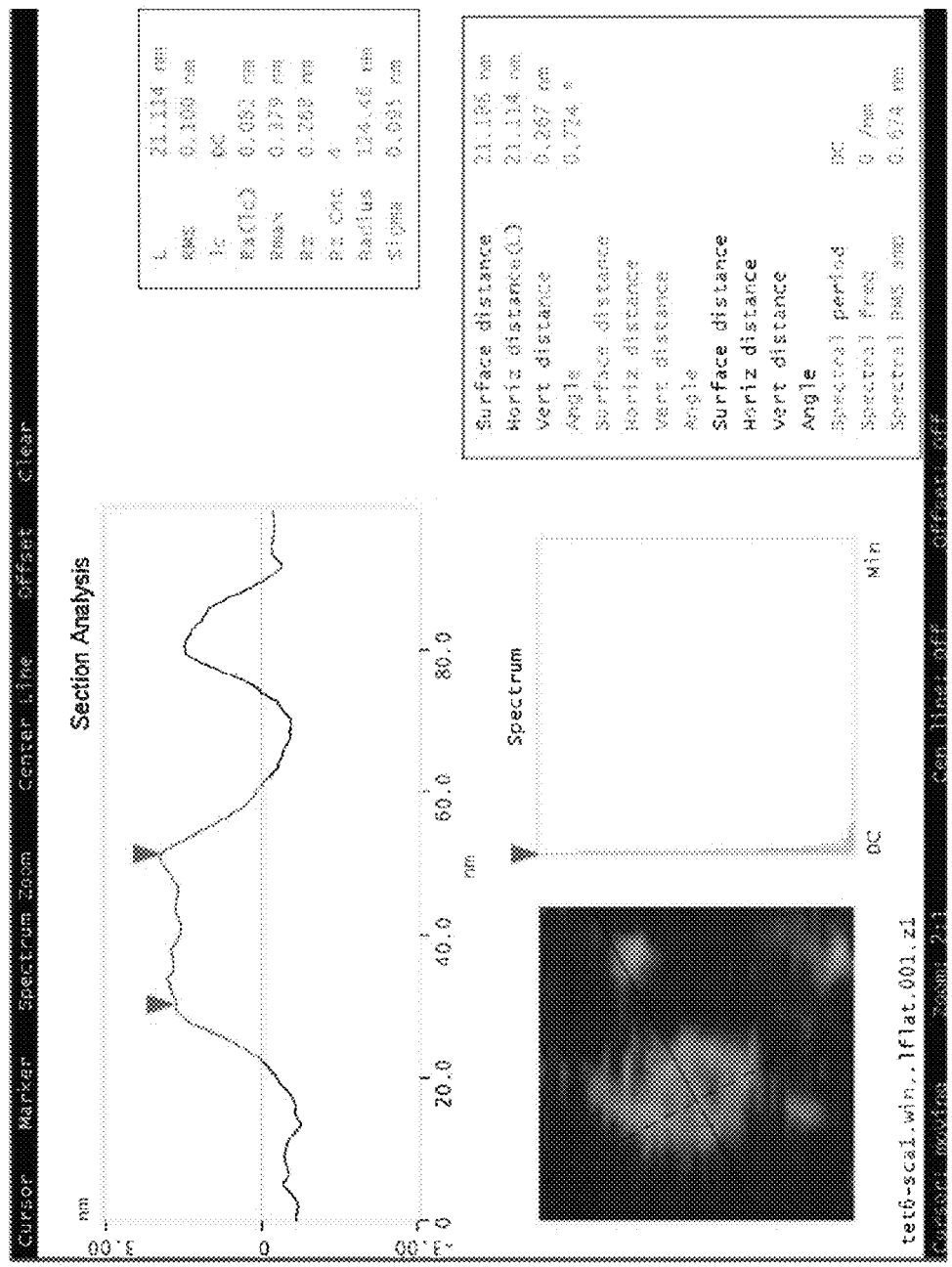
Figure 55:
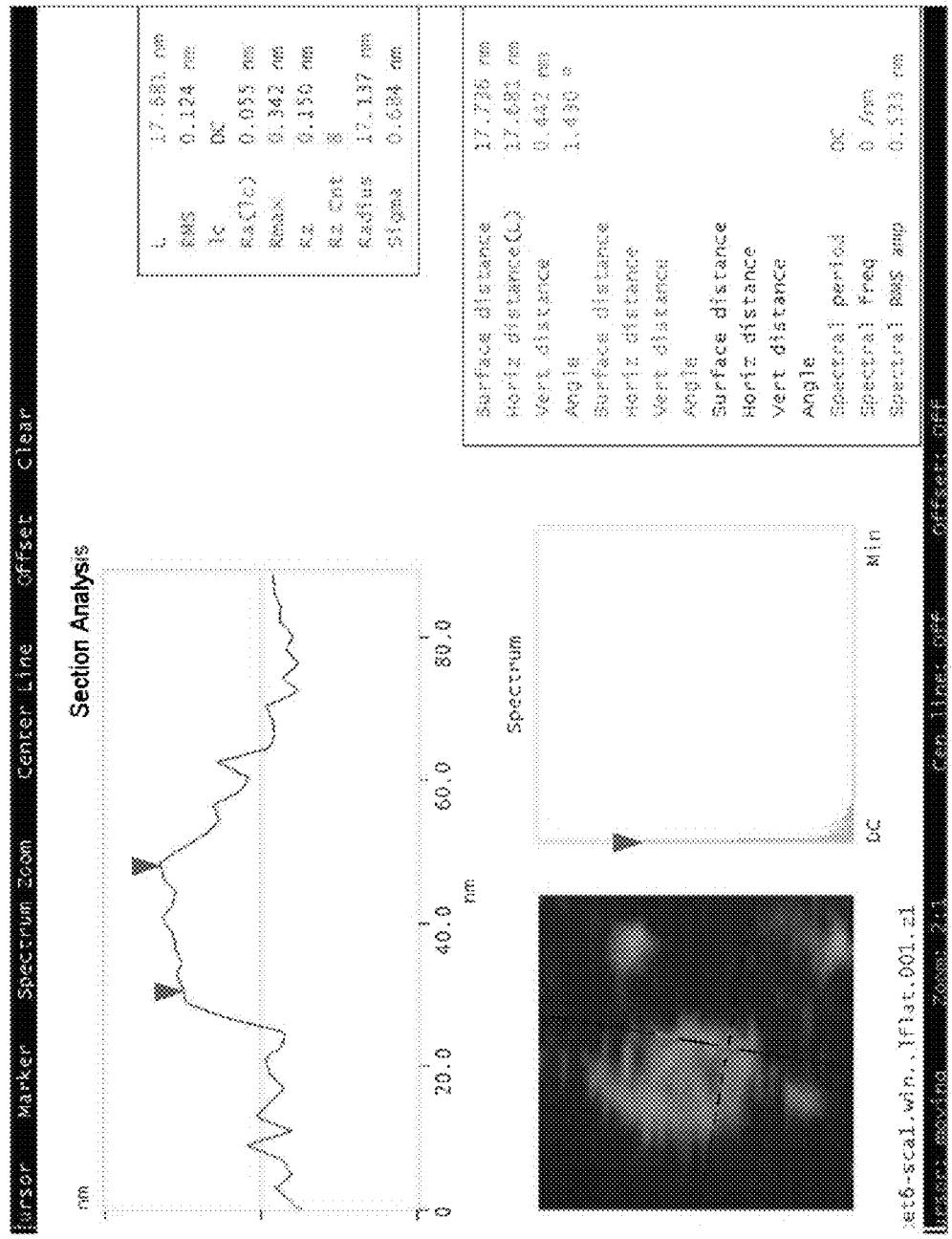
Figure 56:
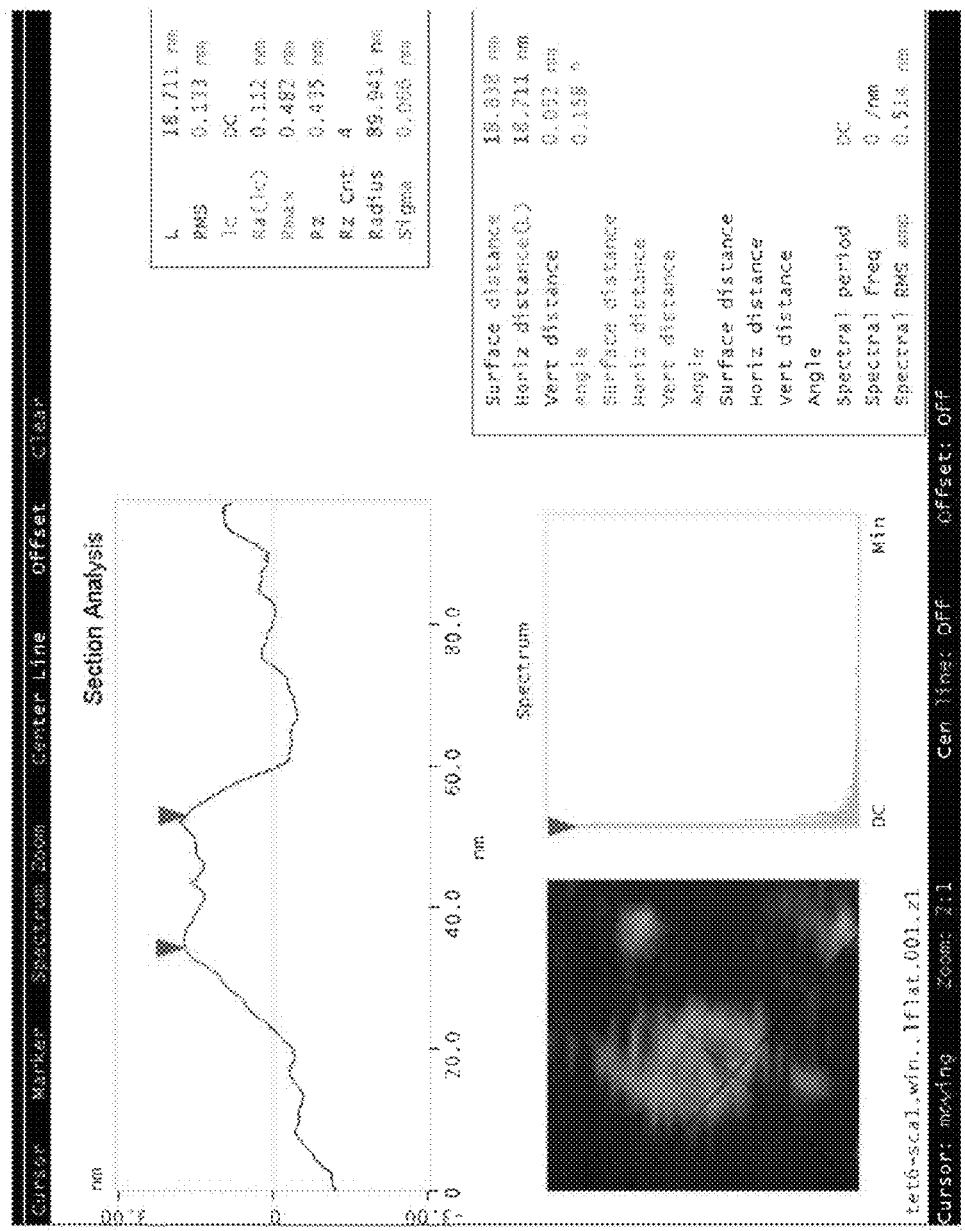
Figure 57:
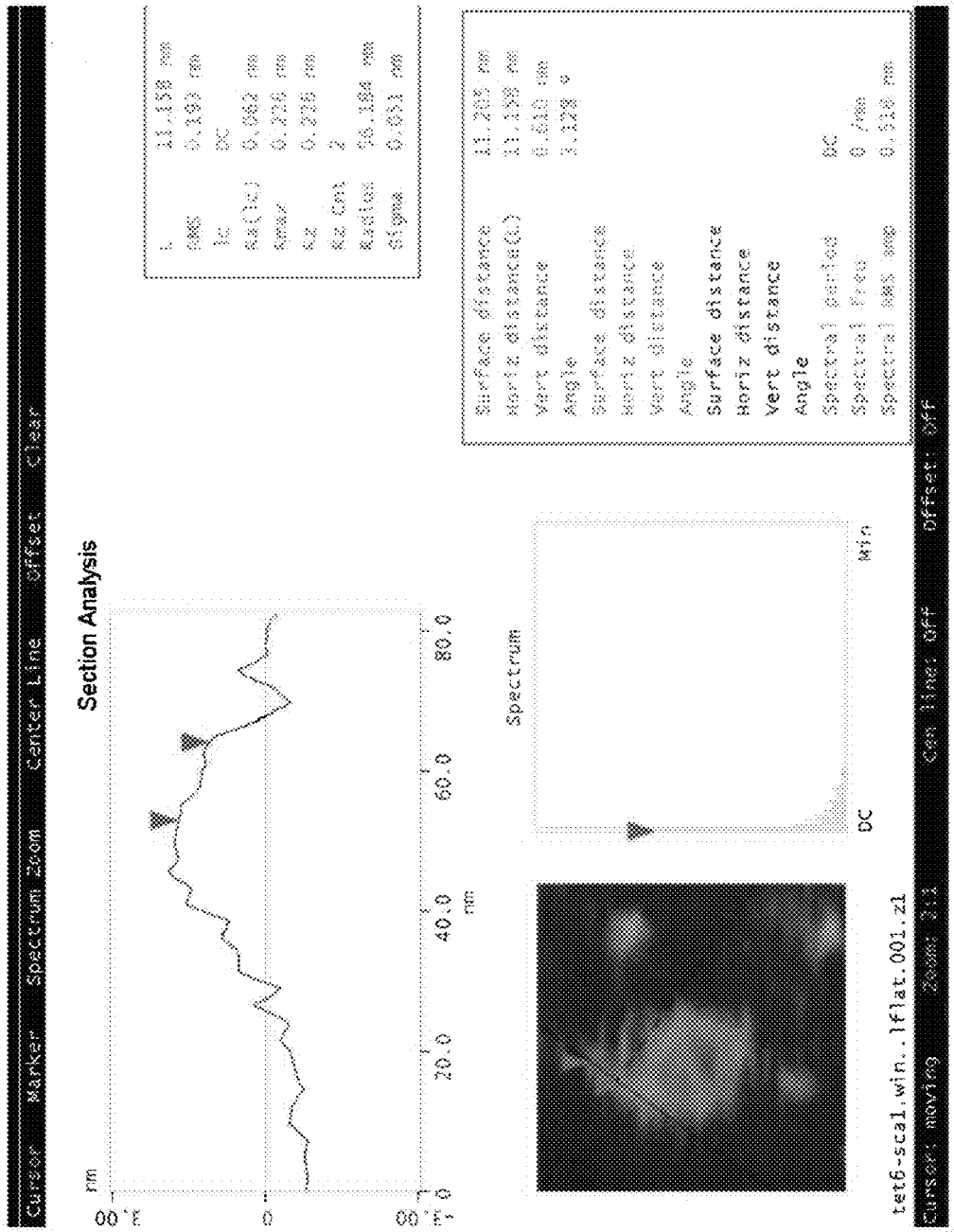

After the triggered formation of the tetrahedron, the system was treated with Sca I, which cut the edge that contained the Sca I restriction site. This produced a dissected and hence flattened tetrahedron, which will facilitate the AFM imaging in FIG. 43-FIG. 70. This is not required for all embodiments. Further, as depicted in the FIG. 40, the strand S2-A2 contained a biotin (depicted as a black dot), which can binds to streptavidin protein, and hence generates a unique dot, which is depicted in FIG. 42 as a red dot with black edge.

Figure 58:
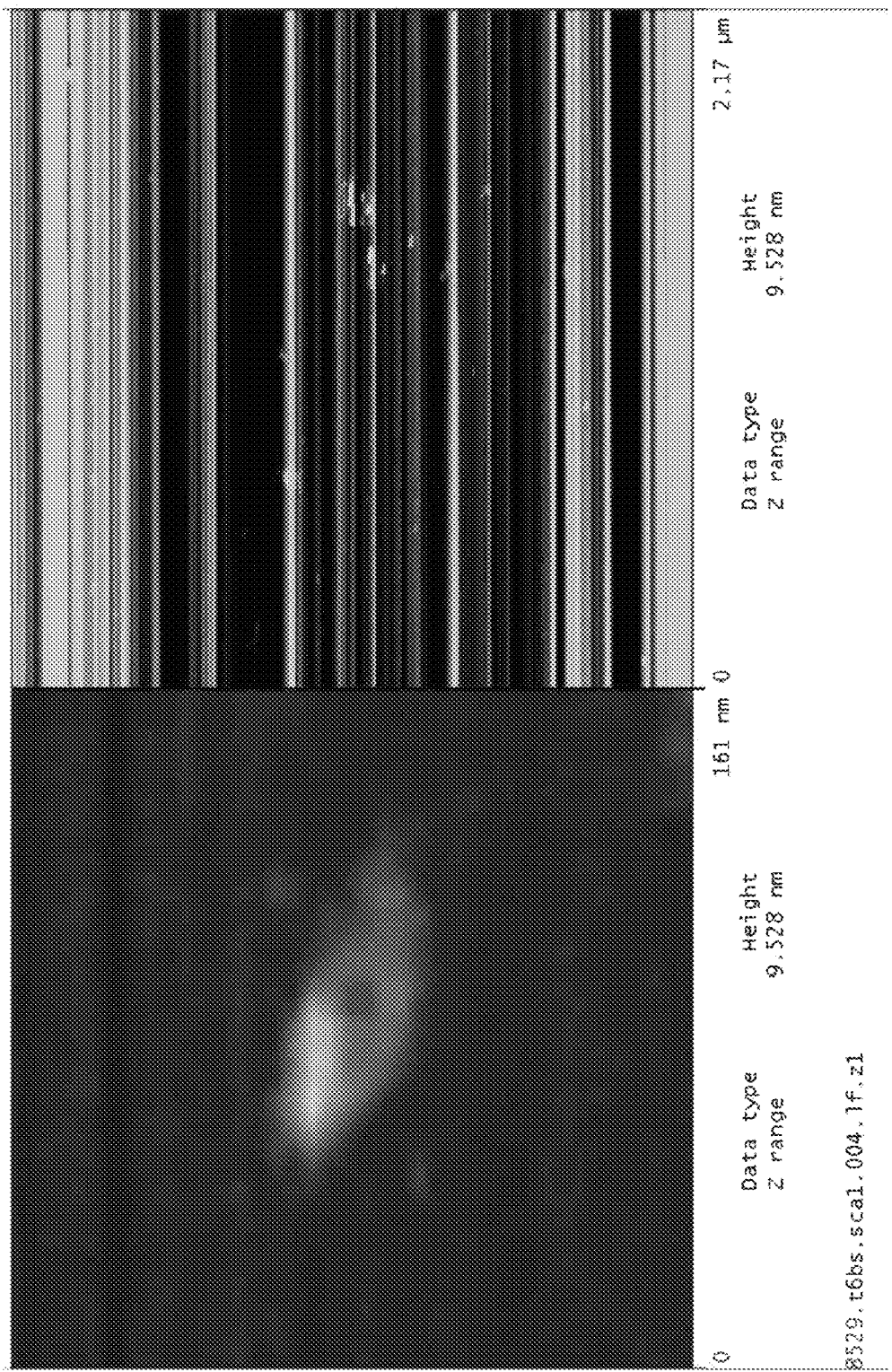
Figure 59:
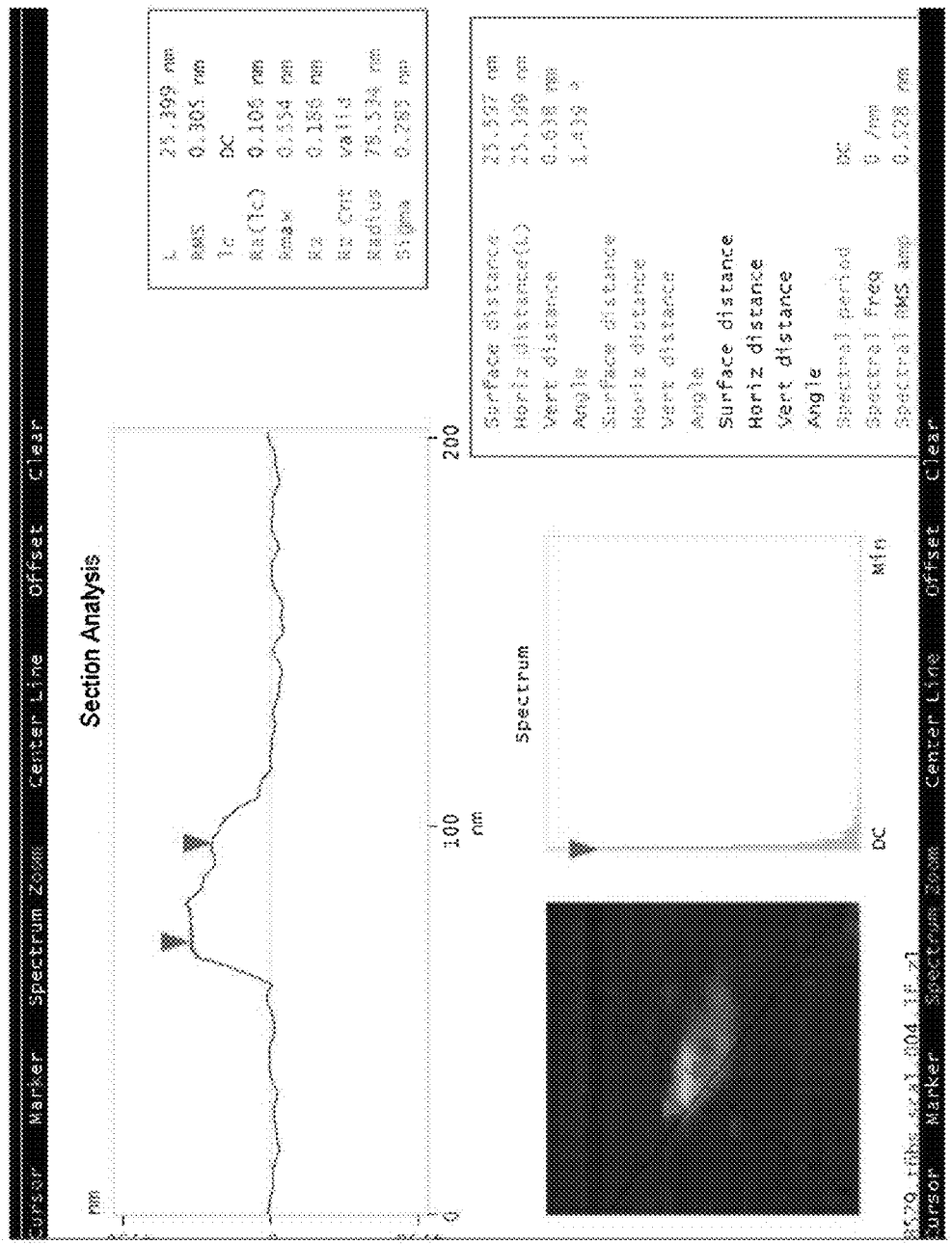
Figure 60:
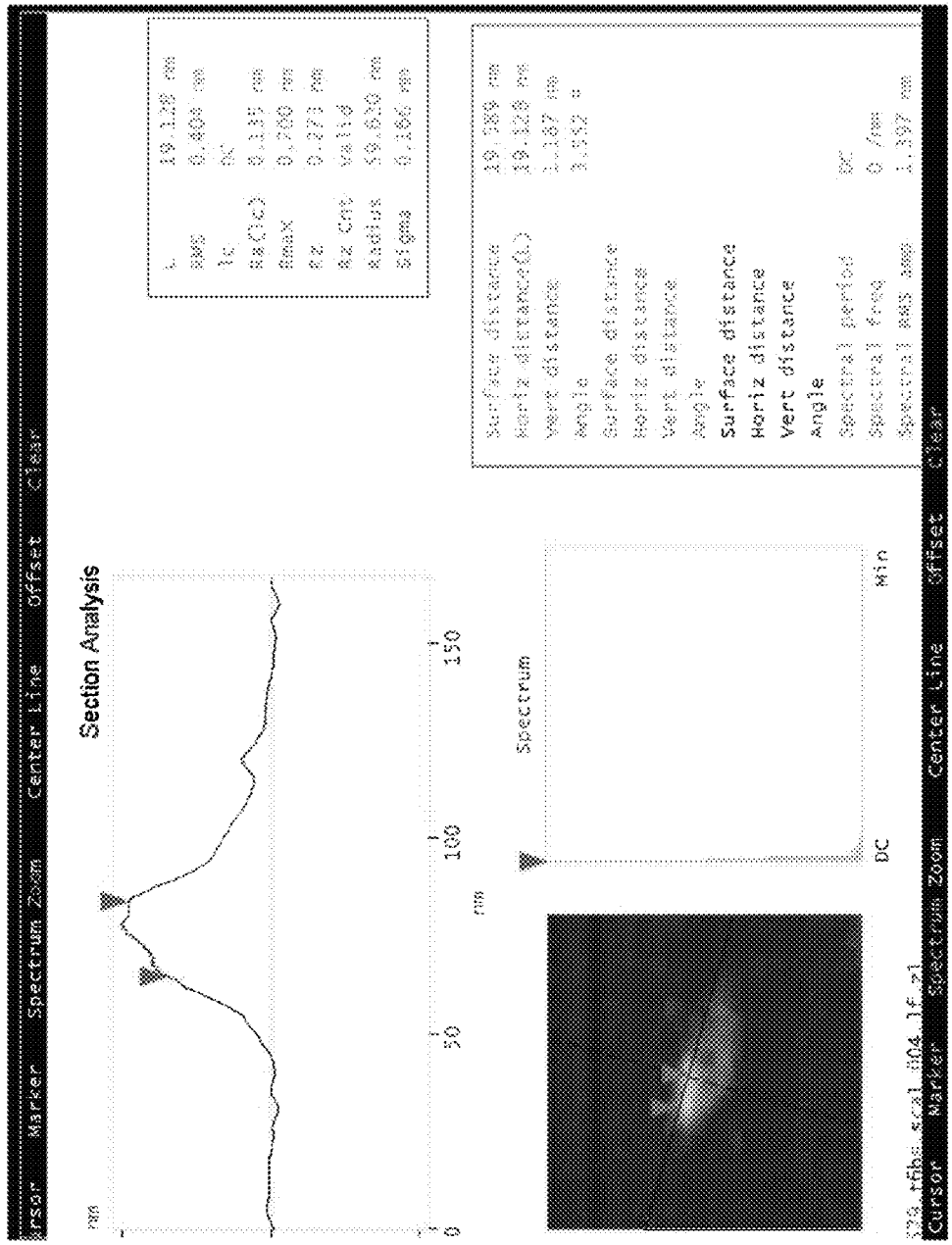
Figure 61:
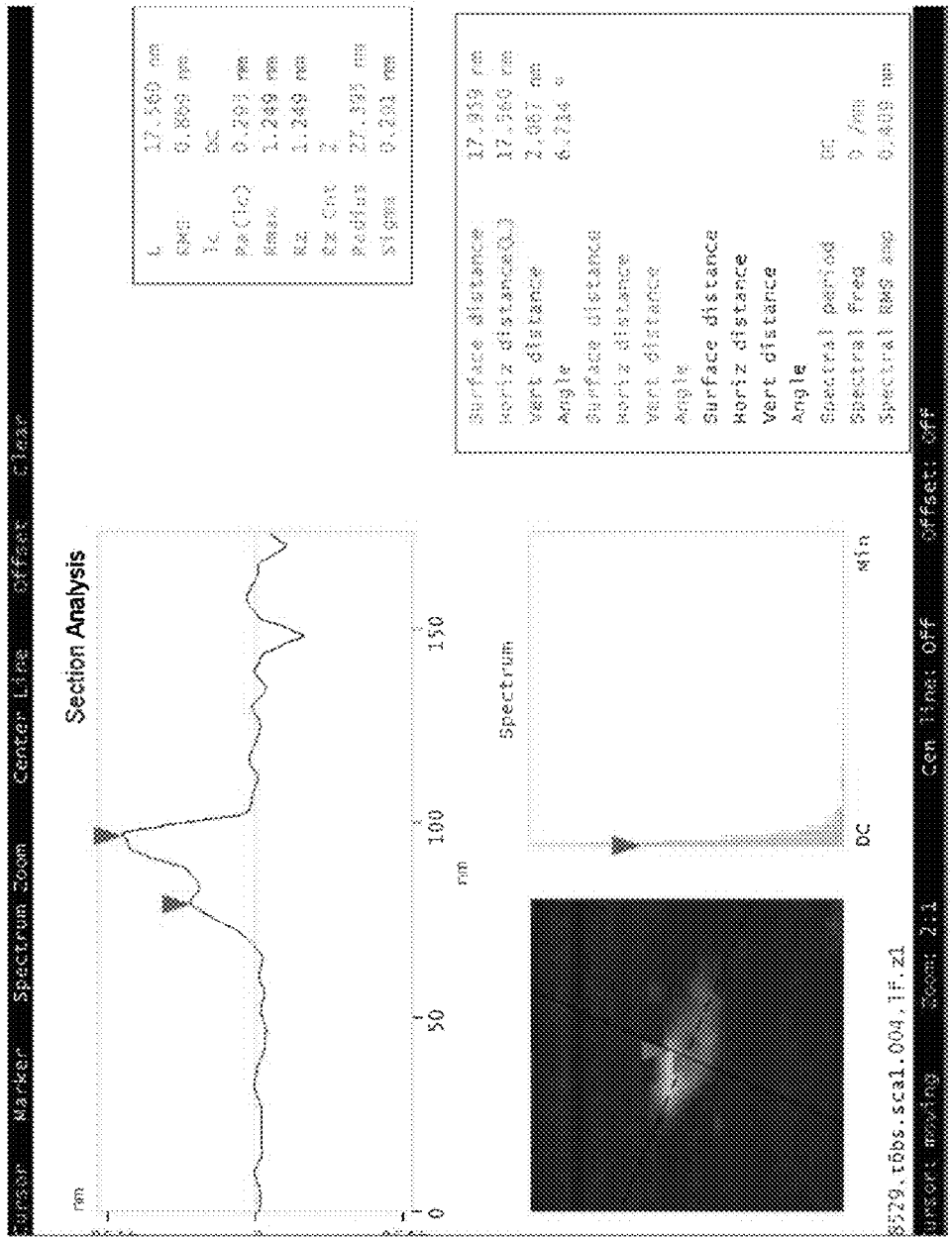
Figure 62:
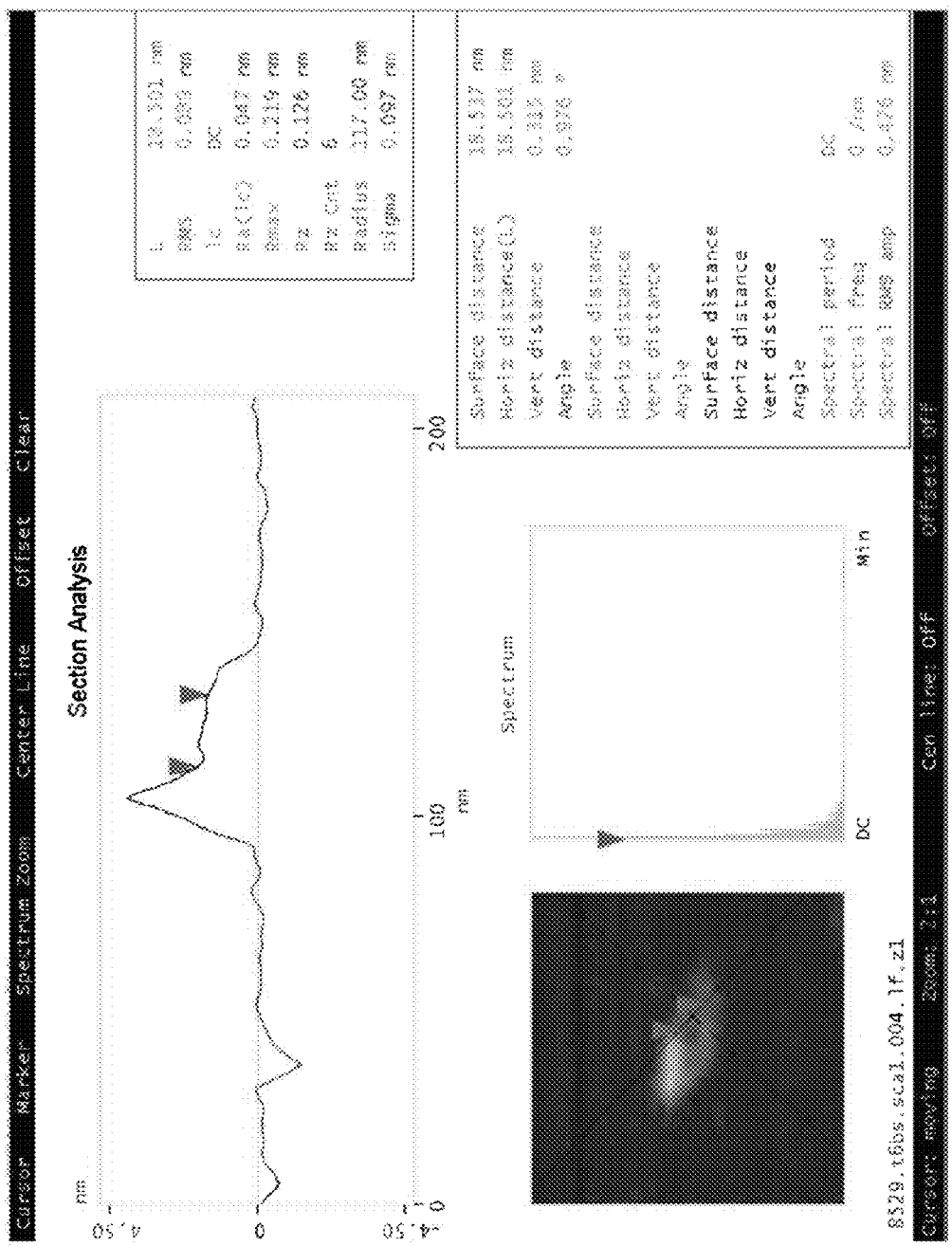
Figure 63:
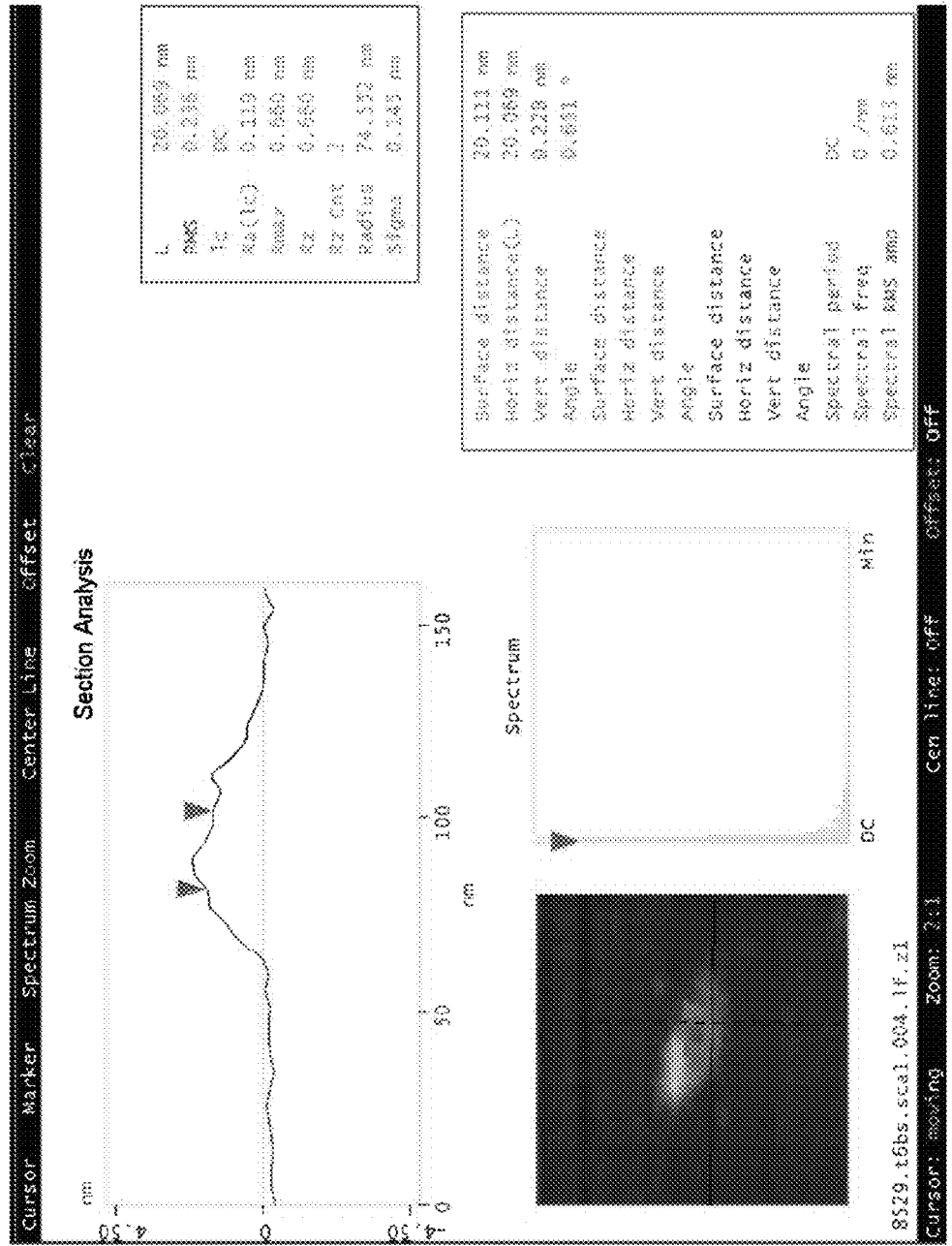
Figure 64:
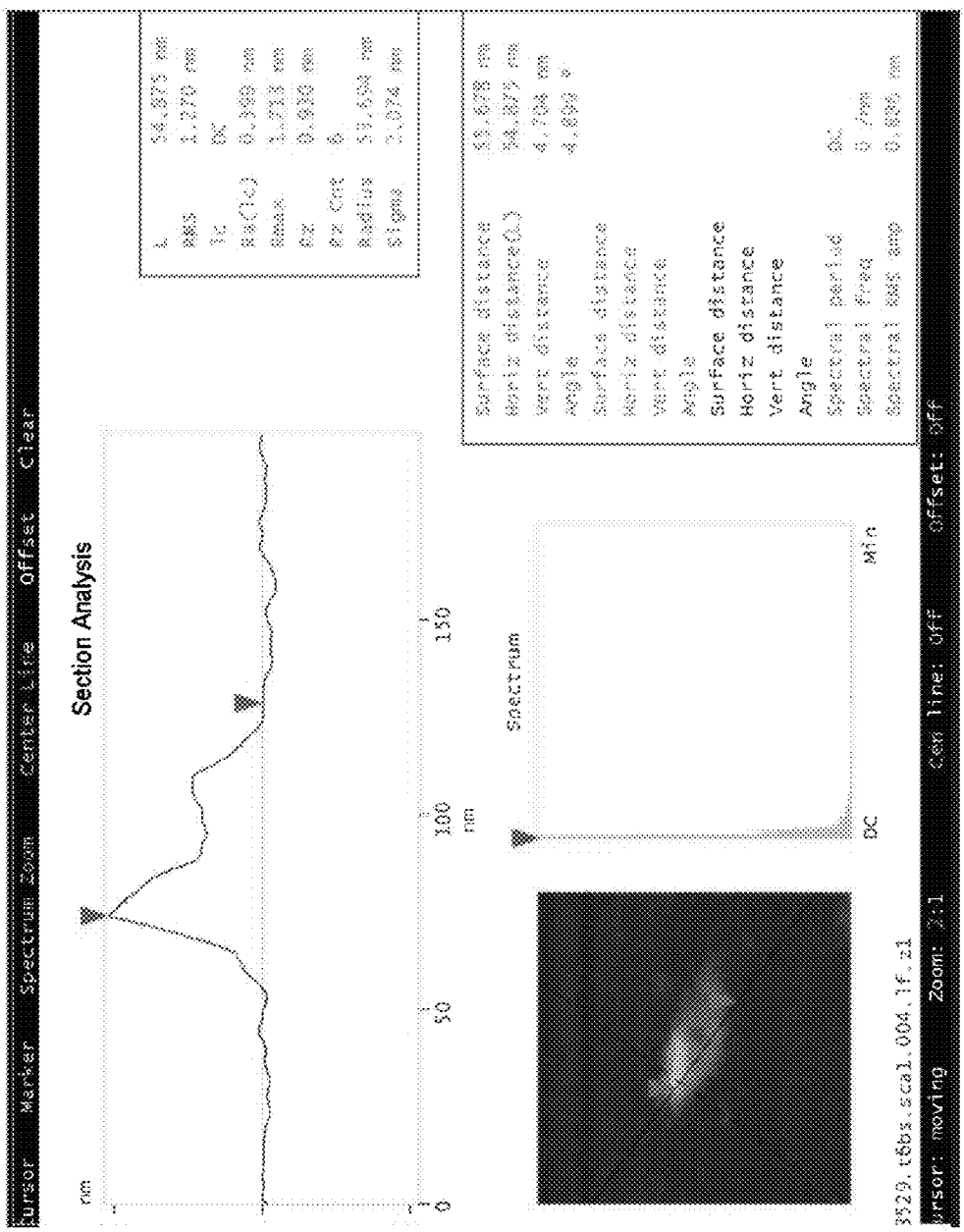
Figure 65:
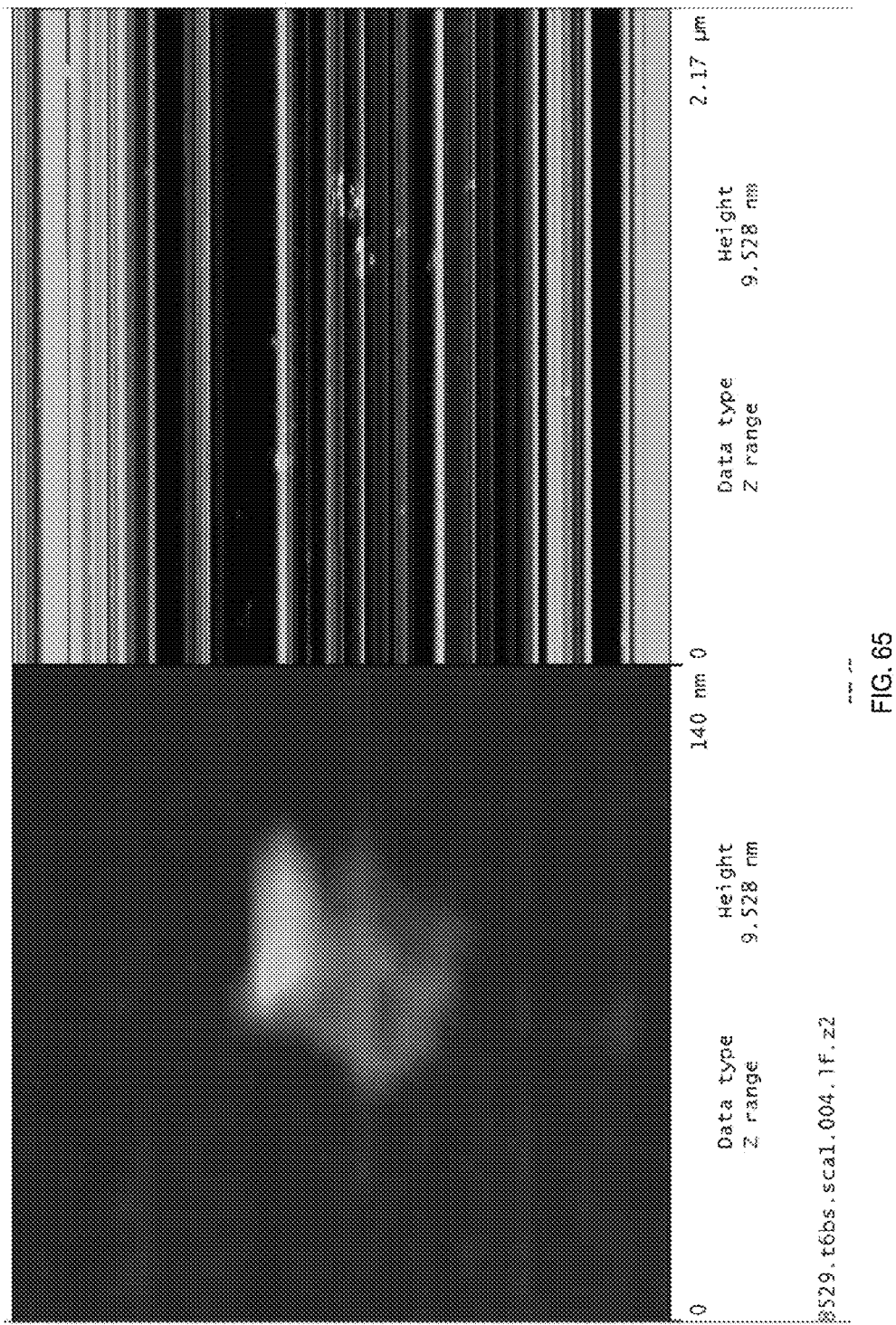
Figure 66:
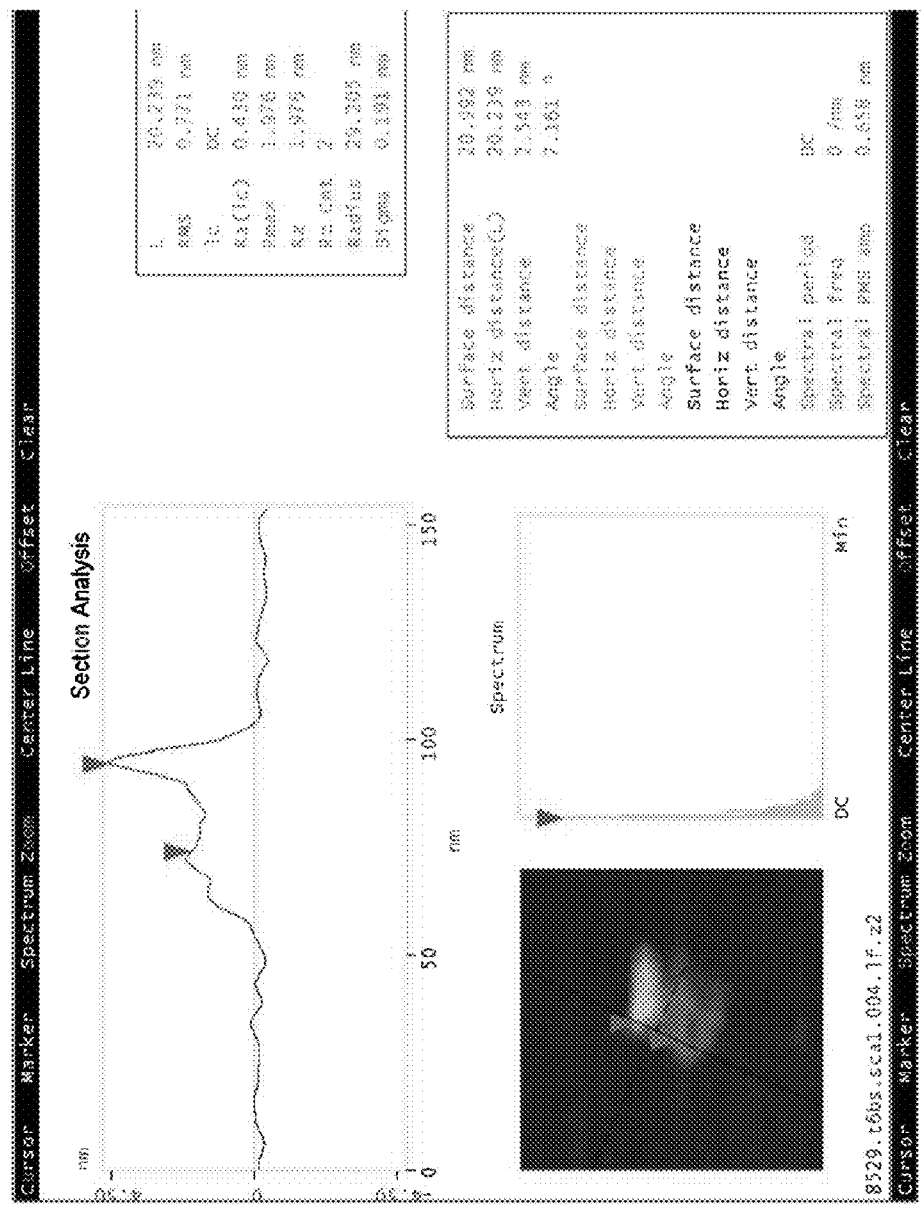
Figure 67:
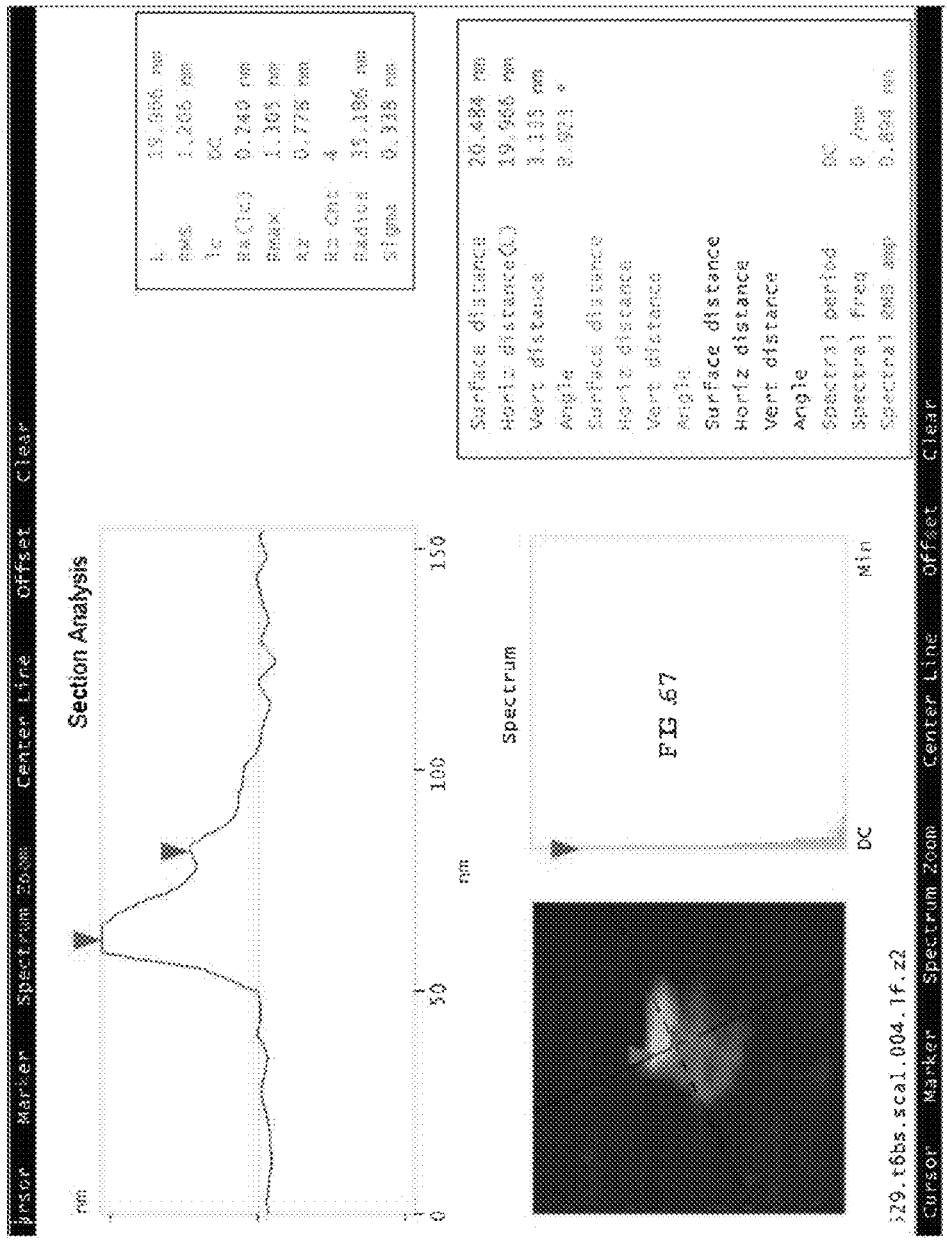
Figure 68:
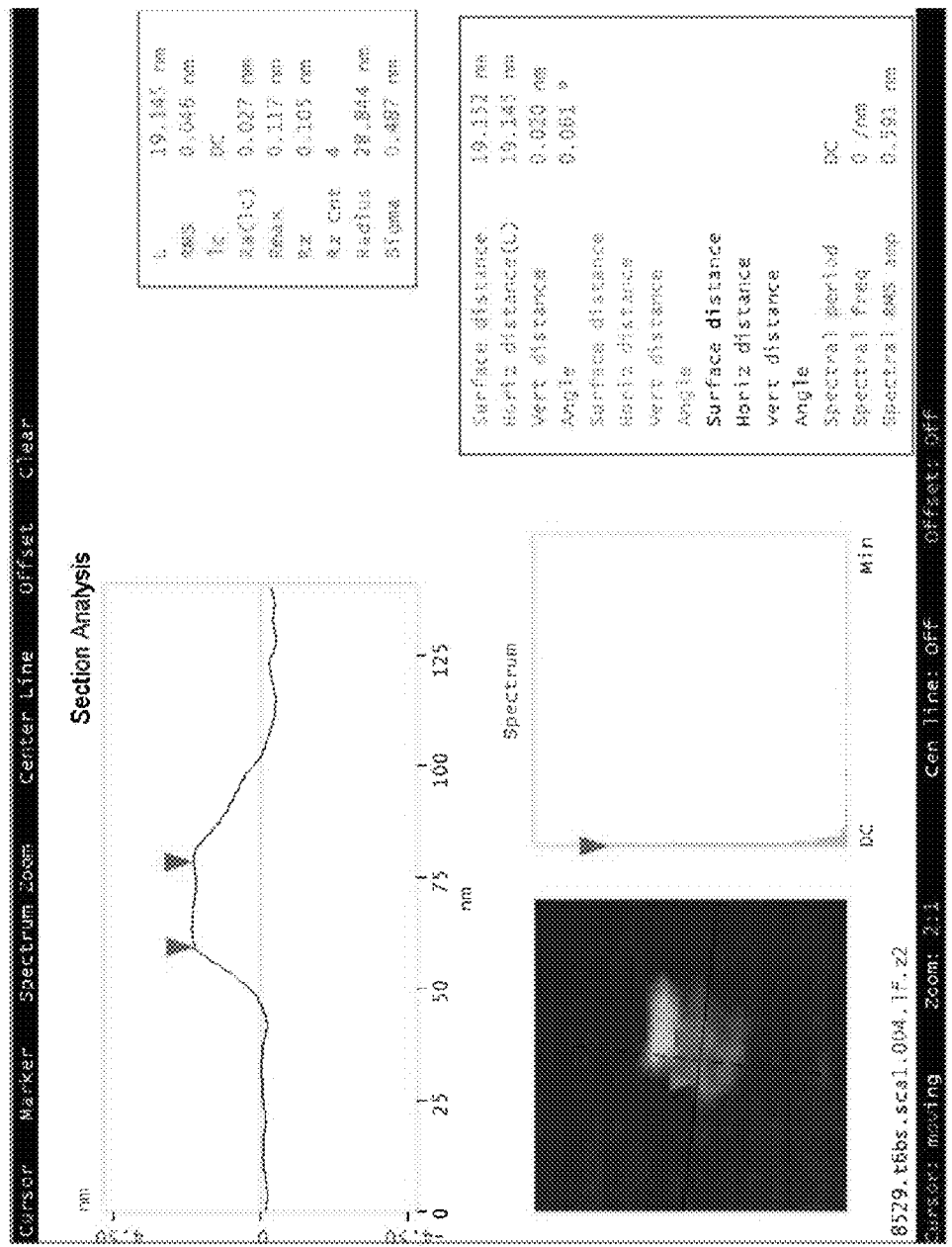
Figure 69:
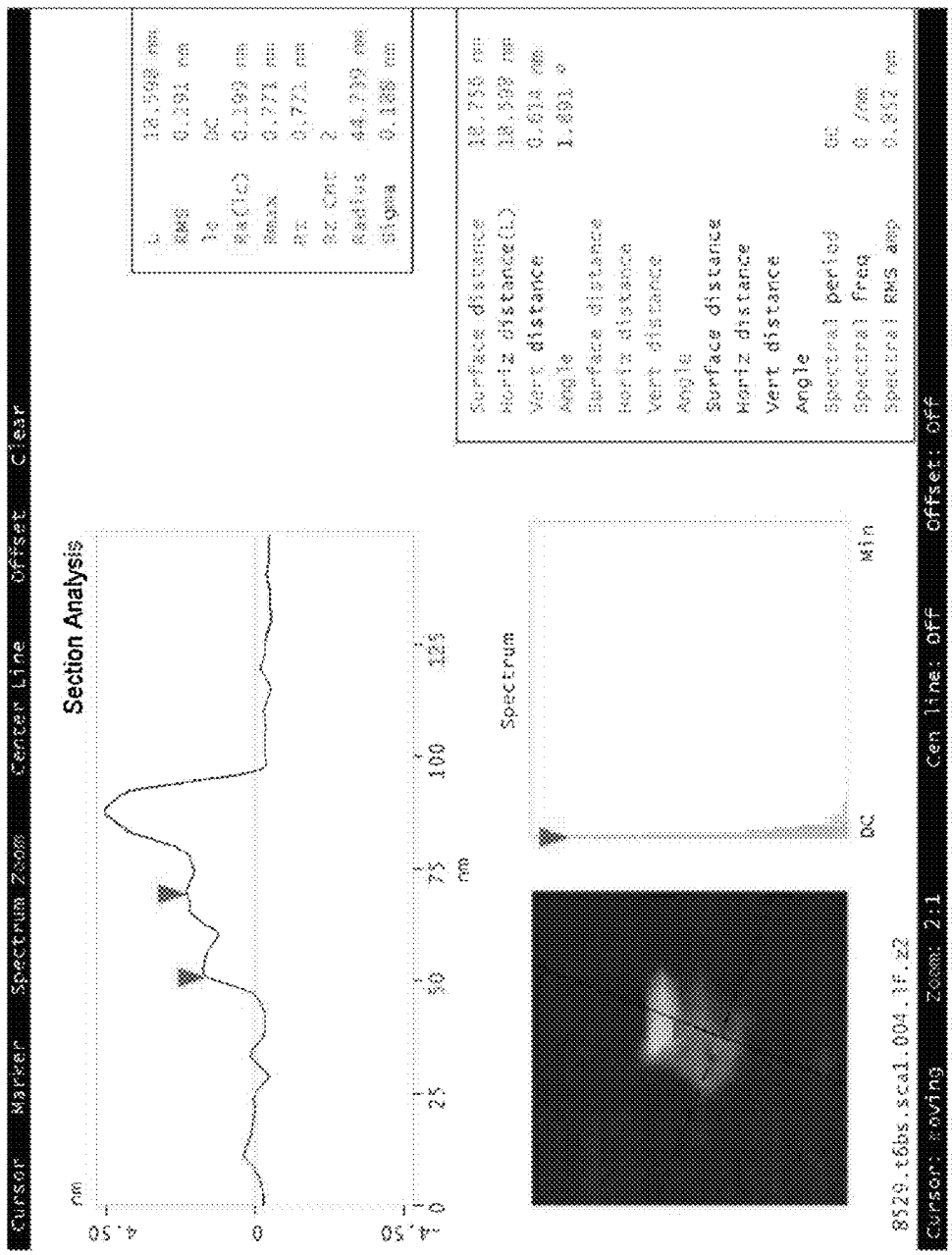
Figure 70:
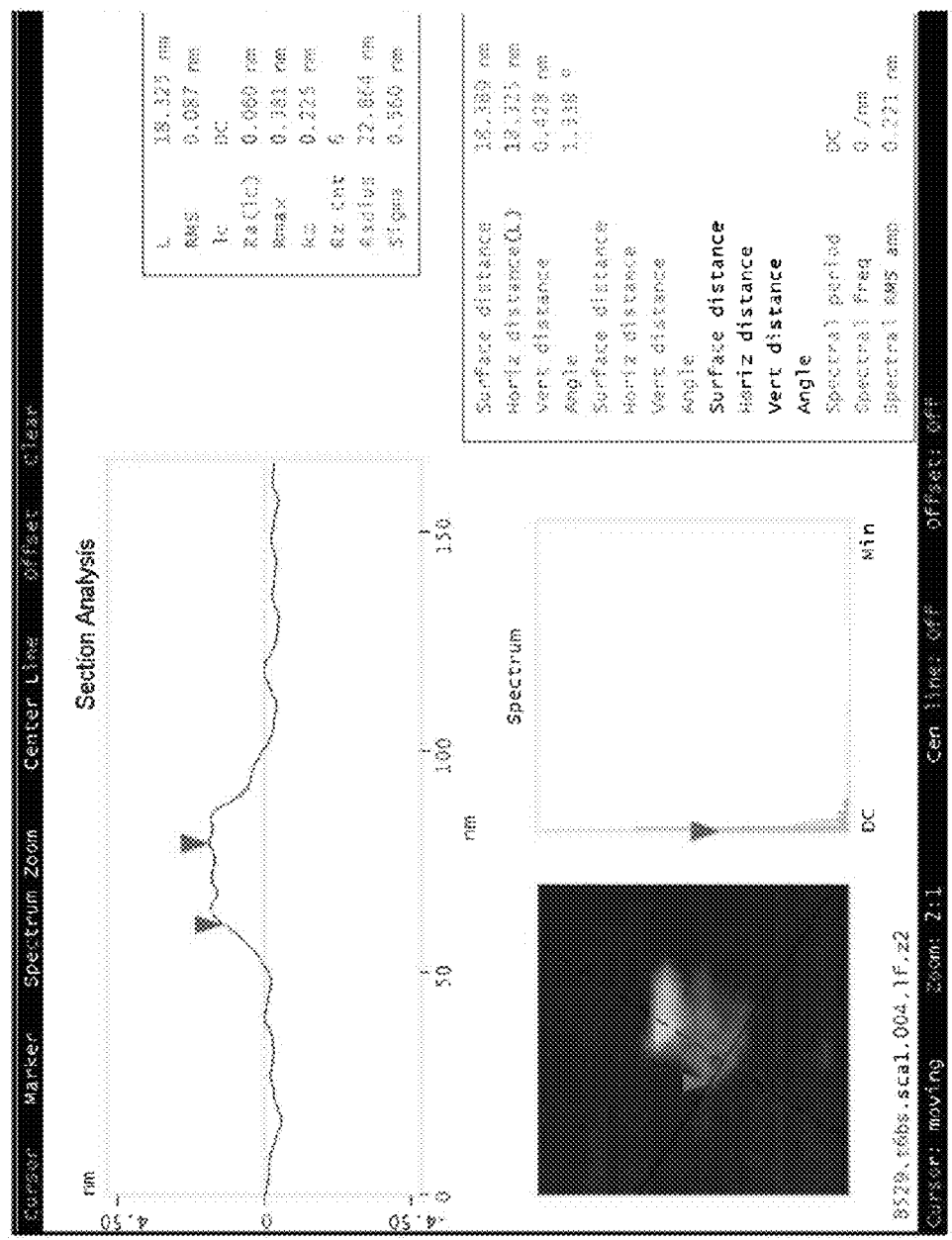
Figure 71:
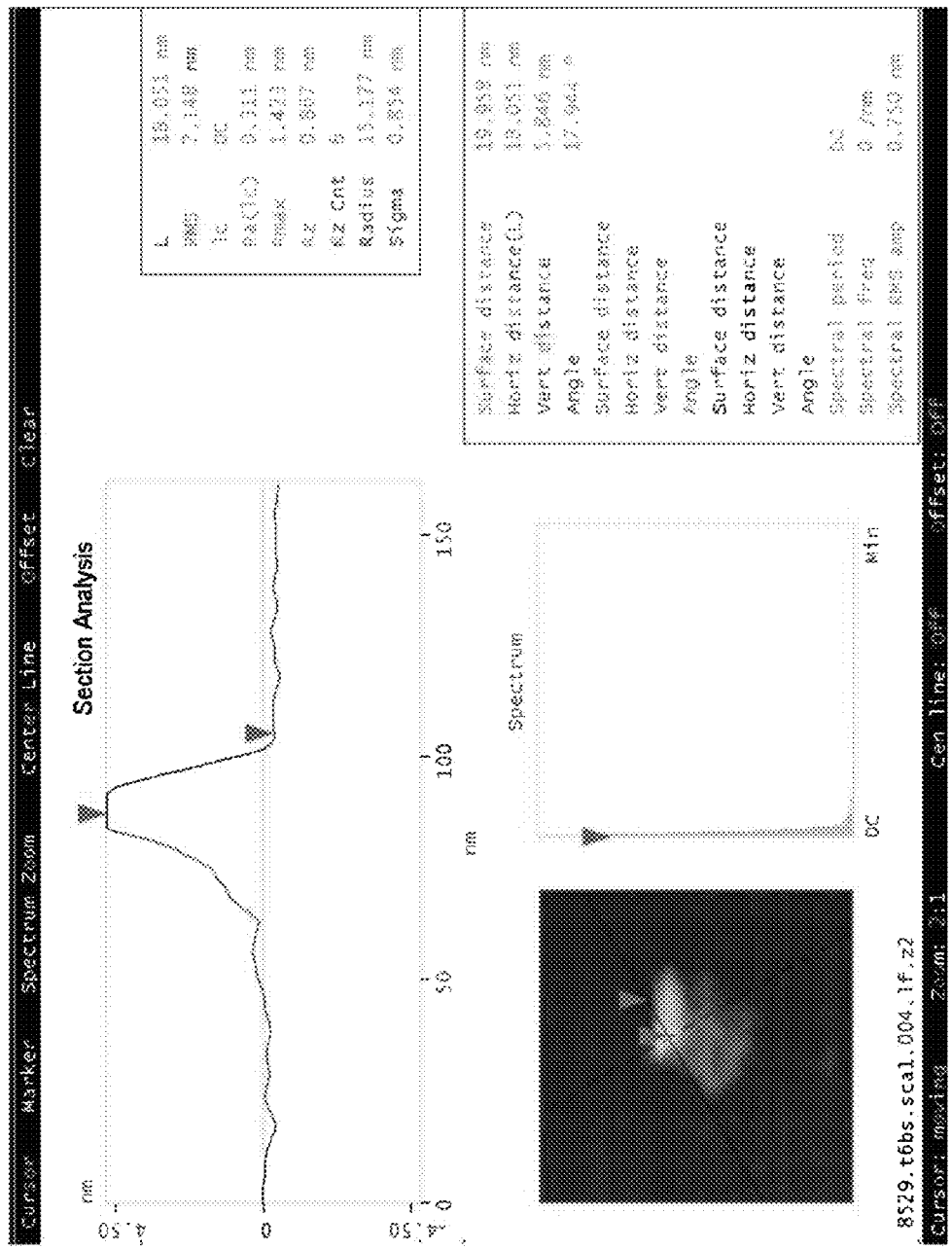

A tetrahedron that was treated with Sca I enzyme and then streptavidin gave an AFM signature which was a DNA bi-triangle with the top vertex of the top triangle labeled with a streptavidin protein, as shown, for example, in the AFM image in FIG. 58, and other AFM images labeled with "sca1" in FIGS. 43-71.

The AFM images were obtained using a multimode scanning probe microscope (Veeco Instruments), equipped with a Q-Control module for analogue AFM systems (Atomic Force F&E). The images were obtained in liquid phase under tapping mode using DNP—S oxide sharpened silicon nitride cantilevers (Veeco). Samples were diluted in 13 TAE/Mg21 buffer to achieve the desired imaging density. A 20 ml drop of 13 TAE/Mg21 and a 5 ml drop of sample were applied to the surface of freshly cleaved mica and allowed to bind for approximately 2 min. Ni21 (15-30 mM) was added to increase the strength of DNA—mica binding32. Before placing the fluid cell on top of the mica puck, an additional 15-20 ml of 13TAE/Mg21 buffer was added to the cavity between the fluid cell and the AFM cantilever chip to avoid bubbles.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

While the present teachings have been described in terms of these exemplary embodiments, the skilled artisan will readily understand that numerous variations and modifications of these exemplary embodiments are possible without undue experimentation. All such variations and modifications are within the scope of the current teachings. The foregoing examples are provided to better illustrate the disclosed teachings and are not intended to limit the scope of the teachings presented herein.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

FIGS. 1-36 are also described in U.S. patent application Ser. No. 12/152,893, which is herein incorporated by reference in its entirety. U.S. patent application Ser. No. 12/152,893 is also incorporated, without limitation, for the purposes of FIGS. 1-36.

What is claimed is:

1. A composition comprising at least nine hairpin monomers, wherein the composition comprises:
a first hairpin monomer;
a second hairpin monomer;
a third hairpin monomer; and
a fourth hairpin monomer, wherein upon binding of the first hairpin monomer to an initiator molecule comprising a nucleic acid, the first hairpin monomer, the second hairpin monomer, the third hairpin monomer, and the fourth hairpin monomer self-assemble in a set order and into a prescribed three-dimensional structure according to a reaction pathway programmed within primary sequences of the hairpin monomers,
wherein the first hairpin monomer comprises:
a first domain comprising a first toehold, a first propagation region, and a seventh toehold, wherein the first toehold is exposed such that it is available to hybridize to a portion of an initiator toehold complementary to the first toehold, and wherein the first toehold is located at an end of the first hairpin monomer, wherein the initiator toehold comprises a portion of the initiator molecule;
a second domain comprising a second toehold and a second propagation region, wherein the second toehold is hybridized to a portion of the first propagation region, and wherein the seventh toehold is hybridized to at least a portion of the second domain; and
an eighth domain comprising an eighth toehold, wherein at least a portion of the eighth toehold is hybridized to the first domain, wherein the second hairpin monomer comprises:
a third domain comprising a third toehold and a third propagation region, wherein the third toehold is exposed such that it is available to hybridize to the second toehold if the second toehold is available for hybridization, and wherein the third toehold is located at an end of the second hairpin monomer;
a fourth domain comprising a fourth toehold and a fourth propagation region, wherein the fourth toehold is hybridized to a portion of the third propagation region; and
a twelfth domain comprising a twelfth toehold, wherein at least a portion of the twelfth toehold is hybridized to the third domain, wherein the third hairpin monomer comprises:
a fifth domain comprising a fifth toehold and a fifth propagation region, wherein the fifth toehold is exposed such that it is available to hybridize to the fourth toehold, if the fourth toehold is available for hybridization, and wherein the fifth toehold is located at an end of the third hairpin monomer;
a sixth domain comprising a sixth toehold and a sixth propagation region, wherein the sixth toehold is hybridized to a portion of the fifth propagation region, wherein the sixth toehold is configured to hybridize to the seventh toehold if the seventh toehold is available for hybridization; and
a sixteenth domain comprising a sixteenth toehold, wherein at least a portion of the sixteenth toehold is hybridized to the fifth domain, wherein the fourth hairpin monomer comprises:
a ninth domain comprising a ninth toehold and a ninth propagation region; and a tenth domain comprising a tenth toehold and a tenth propagation region, wherein the ninth toehold is located at an end of the fourth hairpin monomer, wherein the ninth propagation region is hybridized to at least a portion of the tenth toehold, and wherein the ninth toehold is exposed such that it is available to hybridize to at least portion of the eighth toehold, if the eighth toehold is available for hybridization,
wherein, upon binding of the first hairpin monomer to the initiator molecule, the second toehold is available to hybridize to the third toehold,
wherein, upon hybridization of the second toehold to the third toehold, the third propagation region is available to hybridize to the second propagation region,
wherein, upon hybridization of the third propagation region to the second propagation region, the fourth toehold is available to hybridize to the fifth toehold,
wherein, upon hybridization of the fourth toehold to the fifth toehold, the fifth propagation region is available to hybridize to the fourth propagation region,
wherein, upon hybridization of the fifth propagation region to the fourth propagation region, the sixth toehold is available to hybridize to the seventh toehold,
wherein, upon hybridization of the sixth toehold to the seventh toehold, at least a portion of the first domain is available to hybridize to the sixth propagation region,
wherein the prescribed three-dimensional structure comprises:
a first length of the first hairpin monomer and a first length of the third hairpin monomer that define a first plane;
a length of the second hairpin monomer and a second length of the third hairpin monomer that define a second plane; and
a length of the second hairpin monomer and a second length of the first hairpin monomer that define a third plane, a fifth hairpin monomer, wherein the fifth hairpin monomer comprises:
an eleventh domain comprising a eleventh toehold and an eleventh propagation region; and
a twentieth domain,
wherein the eleventh toehold is located at an end of the fifth hairpin monomer, wherein the eleventh propagation region is hybridized to at least a portion of the twentieth domain, and wherein the eleventh toehold is exposed such that it is available to hybridize to at least a portion of the tenth toehold, if the tenth toehold is available for hybridization;
a sixth hairpin monomer, wherein the sixth hairpin monomer comprises:
a thirteenth domain comprising a thirteenth toehold and a thirteenth propagation region; and
a fourteenth domain comprising a fourteenth toehold and fourteenth propagation region,
wherein the thirteenth toehold is located at an end of the sixth hairpin monomer, wherein the thirteenth propagation region is hybridized to at least a portion of the fourteenth toehold, and wherein the thirteenth toehold is exposed such that it is available to hybridize to at least a portion of the twelfth toehold, if the twelfth toehold is available for hybridization;
a seventh hairpin monomer, wherein the seventh hairpin monomer comprises:
a fifteenth domain comprising a fifteenth toehold and a fifteenth propagation region; and
a twenty-first domain,
wherein the fifteenth toehold is located at an end of the seventh hairpin monomer, wherein the fifteenth propagation region is hybridized to at least a portion of the twenty-first domain, and wherein the fifteenth toehold is exposed such that it is available to hybridize to at least a portion of the fourteenth toehold, if the fourteenth toehold is available for hybridization; and
an eighth hairpin monomer, wherein the eighth hairpin monomer comprises:
a seventeenth domain comprising a seventeenth toehold and a seventeenth propagation region; and
an eighteenth domain comprising an eighteenth toehold and eighteenth propagation region,
wherein the seventeenth toehold is located at an end of the eighth hairpin monomer, wherein the seventeenth propagation region is hybridized to at least a portion of the eighteenth toehold, and wherein the seventeenth toehold is exposed such that it is available to hybridize to at least a portion of the sixteenth toehold, if the sixteenth toehold is available for hybridization;
a ninth hairpin monomer, wherein the ninth hairpin monomer comprises:
a nineteenth domain comprising a nineteenth toehold and a nineteenth propagation region; and
a twenty-second domain,
wherein the nineteenth toehold is located at an end of the ninth hairpin monomer, wherein the nineteenth propagation region is hybridized to at least a portion of the twenty-second domain, and wherein the nineteenth toehold is exposed such that it is available to hybridize to at least a portion of the eighteenth toehold, if the eighteenth toehold is available for hybridization, wherein the eighth toehold becomes available for hybridization following the hybridization of the initiator to the first propagation region, wherein the twelfth toehold becomes available for hybridization following the hybridization of the second propagation region to the third propagation region, and wherein sixteenth toehold becomes available for hybridization following the hybridization of the fourth propagation region to the fifth propagation region,
wherein, following hybridization of the eighth toehold to the ninth toehold, the tenth toehold is available for hybridization,
wherein, following hybridization of the tenth toehold to the eleventh toehold, the tenth propagation region hybridizes to the eleventh propagation region,
wherein, following hybridization of the twelfth toehold to the thirteenth toehold, the fourteenth toehold is available for hybridization,
wherein, following hybridization of the fourteenth toehold to the fifteenth toehold, the fourteenth propagation region hybridizes to the fifteenth propagation region,
wherein, following hybridization of the sixteenth toehold to the seventeenth toehold, the eighteenth toehold is available for hybridization,
wherein, following hybridization of the eighteenth toehold to the nineteenth toehold, the eighteenth propagation region hybridizes to the nineteenth propagation region, and
wherein the prescribed three-dimensional structure comprises a complex polygon, wherein the complex polygon has six edges, and wherein the complex polygon comprises a tetrahedron.

2. The composition of claim 1, where the hairpin monomers comprise nucleic acid sequences such that the first hairpin monomer and the initiator molecule first assemble into a two-dimensional shape.

3. The composition of claim 2, where the second and third hairpin monomers comprise a nucleic acid sequence such that they hybridize to the two-dimensional shape and transform it into a three-dimensional shape.

4. The composition of claim 1, where said second toehold is configured to become available to initiate hybridization of said second propagation region to at least a portion of said third propagation region if at least a portion of the first domain hybridizes to said initiator molecule.

5. The composition of claim 1, where said second propagation region comprises a portion of a single stranded hairpin loop.

6. The composition of claim 1, where a portion of the first propagation region and the second toehold comprise a portion of a duplex stem.

7. The composition of claim 1, where the first toehold is single stranded.

8. The composition of claim 1, further comprising said initiator molecule.

9. A method for assembling a prescribed three-dimensional structure, comprising:
combining an initiator molecule and the composition of claim 1 to form a mixture; and
incubating the mixture under isothermal conditions such that the first hairpin monomer binds to the initiator molecule, which then allows for the second hairpin monomer to hybridize to the first hairpin monomer, which then allows for the third hairpin monomer to hybridize to the second hairpin monomer.

10. A composition comprising at least nine hairpin monomers, wherein the composition comprises:
a first hairpin monomer;
a second hairpin monomer;
a third hairpin monomer; and
a fourth hairpin monomer,
wherein upon binding of the first hairpin monomer to an initiator molecule comprising a nucleic acid, the first hairpin monomer, the second hairpin monomer, the third hairpin monomer, and the fourth hairpin monomer self-assemble in a set order and into a prescribed three-dimensional structure according to a reaction pathway programmed within primary sequences of the hairpin monomers,
wherein the first hairpin monomer comprises:
a first domain comprising a first toehold, a first propagation region, and a seventh toehold, wherein the first toehold is exposed such that it is available to hybridize to a portion of an initiator toehold complementary to the first toehold, and wherein the first toehold is located at an end of the first hairpin monomer, wherein the initiator toehold comprises a portion of the initiator molecule;
a second domain comprising a second toehold and a second propagation region, wherein the second toehold is hybridized to a portion of the first propagation region, and wherein the seventh toehold is hybridized to at least a portion of the second domain; and
an eighth domain comprising an eighth toehold, wherein at least a portion of the eighth toehold is hybridized to the first domain,
wherein the second hairpin monomer comprises:
a third domain comprising a third toehold and a third propagation region, wherein the third toehold is exposed such that it is available to hybridize to the second toehold if the second toehold is available for hybridization, and wherein the third toehold is located at an end of the second hairpin monomer;
a fourth domain comprising a fourth toehold and a fourth propagation region, wherein the fourth toehold is hybridized to a portion of the third propagation region; and
a twelfth domain comprising a twelfth toehold, wherein at least a portion of the twelfth toehold is hybridized to the third domain, wherein the third hairpin monomer comprises:
a fifth domain comprising a fifth toehold and a fifth propagation region, wherein the fifth toehold is exposed such that it is available to hybridize to the fourth toehold, if the fourth toehold is available for hybridization, and wherein the fifth toehold is located at an end of the third hairpin monomer;
a sixth domain comprising a sixth toehold and a sixth propagation region, wherein the sixth toehold is hybridized to a portion of the fifth propagation region, wherein the sixth toehold is configured to hybridize to the seventh toehold if the seventh toehold is available for hybridization, and
a sixteenth domain comprising a sixteenth toehold, wherein at least a portion of the sixteenth toehold is hybridized to the fifth domain,
wherein the fourth hairpin monomer comprises:
a ninth domain comprising a ninth toehold and a ninth propagation region; and a tenth domain comprising a tenth toehold and a tenth propagation region, wherein the ninth toehold is located at an end of the fourth hairpin monomer, wherein the ninth propagation region is hybridized to at least a portion of the tenth toehold, and wherein the ninth toehold is exposed such that it is available to hybridize to at least portion of the eighth toehold, if the eighth toehold is available for hybridization,
wherein, upon binding of the first hairpin monomer to the initiator molecule, the second toehold is available to hybridize to the third toehold,
wherein, upon hybridization of the second toehold to the third toehold, the third propagation region is available to hybridize to the second propagation region,
wherein, upon hybridization of the third propagation region to the second propagation region, the fourth toehold is available to hybridize to the fifth toehold,
wherein, upon hybridization of the fourth toehold to the fifth toehold, the fifth propagation region is available to hybridize to the fourth propagation region,
wherein, upon hybridization of the fifth propagation region to the fourth propagation region, the sixth toehold is available to hybridize to the seventh toehold,
wherein, upon hybridization of the sixth toehold to the seventh toehold, at least a portion of the first domain is available to hybridize to the sixth propagation region,
wherein the prescribed three-dimensional structure comprises:
a prescribed closed structure,
wherein the first length of the first hairpin monomer and the first length of the third hairpin monomer define a first plane of the prescribed closed structure;
wherein a length of the second hairpin monomer and the second length of the third hairpin monomer define the second plane of the prescribed closed structure; and
wherein a length of the second hairpin monomer and the second length of the first hairpin monomer that define the third plane of the prescribed closed structure,
a fifth hairpin monomer, wherein the fifth hairpin monomer comprises:
an eleventh domain comprising a eleventh toehold and an eleventh propagation region; and
a twentieth domain,
wherein the eleventh toehold is located at an end of the fifth hairpin monomer, wherein the eleventh propagation region is hybridized to at least a portion of the twentieth domain, and wherein the eleventh toehold is exposed such that it is available to hybridize to at least a portion of the tenth toehold, if the tenth toehold is available for hybridization;
a sixth hairpin monomer, wherein the sixth hairpin monomer comprises:
a thirteenth domain comprising a thirteenth toehold and a thirteenth propagation region; and
a fourteenth domain comprising a fourteenth toehold and fourteenth propagation region,
wherein the thirteenth toehold is located at an end of the sixth hairpin monomer, wherein the thirteenth propagation region is hybridized to at least a portion of the fourteenth toehold, and wherein the thirteenth toehold is exposed such that it is available to hybridize to at least a portion of the twelfth toehold, if the twelfth toehold is available for hybridization;

a seventh hairpin monomer, wherein the seventh hairpin monomer comprises:
  a fifteenth domain comprising a fifteenth toehold and a fifteenth propagation region; and
  a twenty-first domain,
  wherein the fifteenth toehold is located at an end of the seventh hairpin monomer, wherein the fifteenth propagation region is hybridized to at least a portion of the twenty-first domain, and wherein the fifteenth toehold is exposed such that it is available to hybridize to at least a portion of the fourteenth toehold, if the fourteenth toehold is available for hybridization; and
an eighth hairpin monomer, wherein the eighth hairpin monomer comprises:
  a seventeenth domain comprising a seventeenth toehold and a seventeenth propagation region; and
  an eighteenth domain comprising an eighteenth toehold and eighteenth propagation region,
  wherein the seventeenth toehold is located at an end of the eighth hairpin monomer, wherein the seventeenth propagation region is hybridized to at least a portion of the eighteenth toehold, and wherein the seventeenth toehold is exposed such that it is available to hybridize to at least a portion of the sixteenth toehold, if the sixteenth toehold is available for hybridization;
a ninth hairpin monomer, wherein the ninth hairpin monomer comprises:
  a nineteenth domain comprising a nineteenth toehold and a nineteenth propagation region; and
  a twenty-second domain,
  wherein the nineteenth toehold is located at an end of the ninth hairpin monomer, wherein the nineteenth propagation region is hybridized to at least a portion of the twenty-second domain, and wherein the nineteenth toehold is exposed such that it is available to hybridize to at least a portion of the eighteenth toehold, if the eighteenth toehold is available for hybridization,
  wherein the eighth toehold becomes available for hybridization following the hybridization of the initiator to the first propagation region, wherein the twelfth toehold becomes available for hybridization following the hybridization of the second propagation region to the third propagation region, and wherein sixteenth toehold becomes available for hybridization following the hybridization of the fourth propagation region to the fifth propagation region,
  wherein, following hybridization of the eighth toehold to the ninth toehold, the tenth toehold is available for hybridization,
  wherein, following hybridization of the tenth toehold to the eleventh toehold, the tenth propagation region hybridizes to the eleventh propagation region,
  wherein, following hybridization of the twelfth toehold to the thirteenth toehold, the fourteenth toehold is available for hybridization,
  wherein, following hybridization of the fourteenth toehold to the fifteenth toehold, the fourteenth propagation region hybridizes to the fifteenth propagation region,
  wherein, following hybridization of the sixteenth toehold to the seventeenth toehold, the eighteenth toehold is available for hybridization,
  wherein, following hybridization of the eighteenth toehold to the nineteenth toehold, the eighteenth propagation region hybridizes to the nineteenth propagation region, and
  wherein the prescribed closed structure comprises a complex polygon, wherein the complex polygon has six edges, and wherein the complex polygon comprises a tetrahedron.

11. A method for assembling a prescribed closed structure, comprising:
  combining an initiator molecule and the composition of claim 10 to form a mixture; and
  incubating the mixture under isothermal conditions such that the first hairpin monomer and the initiator molecule hybridize, which then allows for the second hairpin monomer to hybridize to the first hairpin monomer.

12. The method of claim 11, wherein the prescribed closed structure is comprises a complex polygon having six edges and comprises a tetrahedron.

* * * * *

SEQUENCE LISTING

```
<160> NUMBER OF SEQ ID NOS: 117

<210> SEQ ID NO 1
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 1
gcttgagatg ttagggagta gtgctccaat cacaacgcac tactccctaa catc        54

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 2
gcttgagatg ttagg                                                   15

<210> SEQ ID NO 3
<211> LENGTH: 39
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 3
```
gagtagtgct ccaatcacaa cgcactactc cctaacatc                                    39

<210> SEQ ID NO 4
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 4
agggagtagt gcgttgtgat tggaaacatc tcaagctcca atcacaacgc acta                   54

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5
agggagtagt gcgtt                                                              15

<210> SEQ ID NO 6
<211> LENGTH: 39
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 6
gtgattggaa acatctcaag ctccaatcac aacgcacta                                    39

<210> SEQ ID NO 7
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 7
gttgtgattg agcttgaga tgttgcacta ctccctaaca tctcaagctc caat                    54

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
gttgtgattg gagct                                                              15

<210> SEQ ID NO 9
<211> LENGTH: 39
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 9
tgagatgttg cactactccc taacatctca agctccaat                                  39

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
gcactactcc ctaacatctc aagc                                                  24

<210> SEQ ID NO 11
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 11
gcttgagatg ttagggagta gtgctccaat cacaacgcac tactccctaa catcaaccac           60
caccaaccac cc                                                               72

<210> SEQ ID NO 12
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 12
gcttgagatg ttagggagta gtgctccaat cacaacgcac tactcc                          46

<210> SEQ ID NO 13
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 13
ctaacatcaa ccaccaccaa ccaccc                                                26

<210> SEQ ID NO 14
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 14
agggagtagt gcgttgtgat tggaactcat ctaccgtcca atcacaacgc actaacaaca           60
cacacaaacc ac                                                               72

<210> SEQ ID NO 15
<211> LENGTH: 45
<212> TYPE: DNA
<213> ORGANISM: Artificial Sequence
<220> FEATURE:
<223> OTHER INFORMATION: Synthetic oligonucleotide

```
<400> SEQUENCE: 15
agggagtagt gcgttgtgat tggaactcat ctaccgtcca atcac            45

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 16
aacgcactaa caacacacac aaaccac                                27

<210> SEQ ID NO 17
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 17
gttgtgattg gacggtagat gagtaacatc tcaagcactc atctaccgtc caatatcctt   60
cccttcctct cc                                                       72

<210> SEQ ID NO 18
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 18
gttgtgattg gacggtagat gagtaacatc tcaagcactc atctac            46

<210> SEQ ID NO 19
<211> LENGTH: 26
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 19
cgtccaatat ccttcccttc ctctcc                                  26

<210> SEQ ID NO 20
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 20
cggtagatga gtgcttgaga tgttgcacta ctccctaaca tctcaagcac tcattctctt   60
cttctcttct tc                                                       72

<210> SEQ ID NO 21
<211> LENGTH: 46
<212> TYPE: DNA
<213> ORGANISM: Artificial Sequence
<220> FEATURE:
```

<223> OTHER INFORMATION: Synthetic oligonucleotide

<400> SEQUENCE: 21
cggtagatga gtgcttgaga tgttgcacta ctccctaaca tctcaa                46

<210> SEQ ID NO 22
<211> LENGTH: 26
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 22
gcactcattc tcttcttctc ttcttc                26

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
gcactactcc ctaacatctc aagc                24

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gggtggttgg tggtggttga tgtt                24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
gtggtttgtg tgtgttgtta gtgc                24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
ggagaggaag ggaaggatat tgga                24

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 27

```
gaagaagaga agaagagaat gagt                                              24
```

<210> SEQ ID NO 28
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 28

```
acaactgaac acgttagacc acttccatcc tcgcaaatct ccacaactaa gtggtctaac       60
gtgttcagtt gtggagat                                                     78
```

<210> SEQ ID NO 29
<211> LENGTH: 62
<212> TYPE: DNA
<213> ORGANISM: Artificial Sequence
<220> FEATURE:
<221> NAME/KEY: modified_base
<222> LOCATION: 1
<223> OTHER INFORMATION: 5' tetrachlorofluorescein
<220> FEATURE:
<223> OTHER INFORMATION: Synthetic oligonucleotide

<400> SEQUENCE: 29

```
ttacaactga acacgttaga ccacttccat cctcgcaaat ctccacaact aagtggtcta       60
ac                                                                      62
```

<210> SEQ ID NO 30
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<221> NAME/KEY: modified_base
<222> LOCATION: 18
<223> OTHER INFORMATION: 3' black hole quencher-1
<220> FEATURE:
<223> OTHER INFORMATION: Synthetic oligonucleotide

<400> SEQUENCE: 30

```
gtgttcagtt gtggagat                                                     18
```

<210> SEQ ID NO 31
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 31

```
gaacactgct ctccacttcc atcctcgcaa atctccacaa ctgaacacgt tagaccactt       60
agttgtggag atttgcgagg atggaagtgg tctaac                                 96
```

<210> SEQ ID NO 32
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 32

```
gaacactgct ctccacttcc atcctcgcaa atctccacaa ctgaacacgt tagaccactt    60
agttgtggag atttgcga                                                  78
```

<210> SEQ ID NO 33
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 33

```
ggatggaagt ggtctaac                                                  18
```

<210> SEQ ID NO 34
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 34

```
ttgcgaggat ggaagtggag agcagtgttc ccatcctcgc aaatctccac aactgaacac    60
tgctctccac ttccatcc                                                  78
```

<210> SEQ ID NO 35
<211> LENGTH: 68
<212> TYPE: DNA
<213> ORGANISM: Artificial Sequence
<220> FEATURE:
<223> OTHER INFORMATION: Synthetic oligonucleotide

<400> SEQUENCE: 35

```
ttgcgaggat ggaagtggag agcagtgttc ccatcctcgc aaatctccac aactgaacac    60
tgctctcc                                                             68
```

<210> SEQ ID NO 36
<211> LENGTH: 10
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 36

```
acttccatcc                                                           10
```

<210> SEQ ID NO 37
<211> LENGTH: 96
<212> TYPE: DNA
<213> ORGANISM: Artificial Sequence
<220> FEATURE:
<223> OTHER INFORMATION: Synthetic oligonucleotide

<400> SEQUENCE: 37

```
agagcagtgt tcagttgtgg agatttgcga ggatgggaac actgctctcc acttccatcc    60
tcgcaaatct ccacaactga acacgttaga ccactt                              96
```

```
<210> SEQ ID NO 38
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 38
agagcagtgt tcagttgtgg agatttgcga ggatgggaac actgctctcc acttccatcc    60
tcgcaaatct cc                                                        72

<210> SEQ ID NO 39
<211> LENGTH: 24
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 39
acaactgaac acgttagacc actt                                           24

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 40
atctccacaa ctgaacacgt tagaccactt                                     30

<210> SEQ ID NO 41
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 41
caaactctta tctatctctg ccattttaat gcaatgtcac ggtaatggca gagatagata    60
atgcaatgtc acggtaa                                                   77

<210> SEQ ID NO 42
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 42
caaactctta tctatctctg ccattttaat gcaatgtcac ggtaatggca ga            52

<210> SEQ ID NO 43
<211> LENGTH: 25
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide
```

```
<400> SEQUENCE: 43
gatagataat gcaatgtcac ggtaa                                          25

<210> SEQ ID NO 44
<211> LENGTH: 27
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<221> NAME/KEY: modified_base
<222> LOCATION: 27
<223> OTHER INFORMATION: 3' Cy5
<220> FEATURE:
<223> OTHER INFORMATION: Synthetic oligonucleotide

<400> SEQUENCE: 44
gatagataat gcaatgtcac ggtaatt                                        27

<210> SEQ ID NO 45
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 45
tctgccatta ccgtgacatt gcattttaag ctacaggact acgaatgcaa tgtcacggta    60
agctacagga ctacgaa                                                   77

<210> SEQ ID NO 46
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 46
tctgccatta ccgtgacatt gcattttaag ctacaggact acgaatgcaa tg            52

<210> SEQ ID NO 47
<211> LENGTH: 25
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 47
tcacggtaag ctacaggact acgaa                                          25

<210> SEQ ID NO 48
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 48
cattgcattc gtagtcctgt agcttttaag tatcagatcg ccgaagctac aggactacga    60
agtatcagat cgccgaa                                                   77
```

<210> SEQ ID NO 49
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 49
cattgcattc gtagtcctgt agcttttaag tatcagatcg ccgaagctac ag    52

<210> SEQ ID NO 50
<211> LENGTH: 25
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 50
gactacgaag tatcagatcg ccgaa    25

<210> SEQ ID NO 51
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 51
ctgtagcttc ggcgatctga tacttttaat gaccaaacca cctaagtatc agatcgccga    60
atgaccaaac cacctaa    77

<210> SEQ ID NO 52
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 52
ctgtagcttc ggcgatctga tactttaat gaccaaacca cctaagtatc ag    52

<210> SEQ ID NO 53
<211> LENGTH: 25
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 53
atcgccgaat gaccaaacca cctaa    25

<210> SEQ ID NO 54
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 54
ctgatactta ggtggtttgg tcattttaac tccactccta ctcaatgacc aaaccaccta    60
a                                                                    61

<210> SEQ ID NO 55
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 55
ctgatactta ggtggt                                                    16

<210> SEQ ID NO 56
<211> LENGTH: 45
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 56
ttggtcattt taactccact cctactcaat gaccaaacca cctaa                    45

<210> SEQ ID NO 57
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 57
aagctacagg actacgaatg caatgtcacg gtaagctaca ggactacgaa ttttaccgtg    60
acattgcatt atctatc                                                   77

<210> SEQ ID NO 58
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 58
aagctacagg actacgaatg caatg                                          25

<210> SEQ ID NO 59
<211> LENGTH: 52
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 59
tcacggtaag ctacaggact acgaattta ccgtgacatt gcattatcta tc              52

<210> SEQ ID NO 60
<211> LENGTH: 77

```
<212> TYPE: DNA
<213> ORGANISM: Artificial Sequence
<220> FEATURE:
<223> OTHER INFORMATION: Synthetic oligonucleotide

<400> SEQUENCE: 60
aagtatcaga tcgccgaagc tacaggacta cgaagtatca gatcgccgaa ttttcgtagt      60
cctgtagctt accgtga                                                    77

<210> SEQ ID NO 61
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 61
aagtatcaga tcgccgaagc tacag                                           25

<210> SEQ ID NO 62
<211> LENGTH: 52
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 62
gactacgaag tatcagatcg ccgaattttc gtagtcctgt agcttaccgt ga             52

<210> SEQ ID NO 63
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 63
aatgaccaaa ccacctaact ccactcctac tcaatttag gtggtttggt cattcggcga      60
t                                                                     61

<210> SEQ ID NO 64
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 64
aatgaccaaa ccacctaact ccactcctac tcaatttag gtggt                      45

<210> SEQ ID NO 65
<211> LENGTH: 16
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 65
```

```
ttggtcattc ggcgat                                              16
```

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66

```
aatggcagag atagataaga gtttg                                    25
```

<210> SEQ ID NO 67
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 67

```
aagtagtgat tgagcgtgat gaatgtcact acttcaactc gcattcatca cgctcaatc    59
```

<210> SEQ ID NO 68
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 68

```
aagtagtgat tgagcgtgat gaatgtcact acttcaactc gcattcatc              49
```

<210> SEQ ID NO 69
<211> LENGTH: 10
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 69

```
acgctcaatc                                                     10
```

<210> SEQ ID NO 70
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 70

```
tgatgaatgc gagttgaagt agtgacattc atcacgctca atcactactt caactcgca     59
```

<210> SEQ ID NO 71
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 71

```
tgatgaatcc gagttgaagt agtgacattc atcacgctca atcactact               49
```

```
<210> SEQ ID NO 72
<211> LENGTH: 10
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 72
tcaactcgca                                                              10

<210> SEQ ID NO 73
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 73
gacattcatc acgctcaatc actactt                                           27

<210> SEQ ID NO 74
<211> LENGTH: 27
<212> TYPE: DNA
<213> ORGANISM: Artificial Sequence
<220> FEATURE:
<221> NAME/KEY: modified_base
<222> LOCATION: 27
<223> OTHER INFORMATION: 3' 6-carboxyfluorescein
<220> FEATURE:
<223> OTHER INFORMATION: Synthetic oligonucleotide

<400> SEQUENCE: 74
gacattcatc acgctcaatc actactt                                           27

<210> SEQ ID NO 75
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 75
ggtagttcta ggcagctgaa gtagtgattg agcgtgatga atgtcactac ttcaactcgc       60
attcatcacg ctcaatc                                                     77

<210> SEQ ID NO 76
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 76
ggtagttcta ggcagctgaa gtagtgattg agcgt                                  35

<210> SEQ ID NO 77
<211> LENGTH: 42
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
```

<223> OTHER INFORMATION: Synthetic oligonucleotide

<400> SEQUENCE: 77
gatgaatgtc actacttcaa ctcgcattca tcacgctcaa tc                42

<210> SEQ ID NO 78
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 78
tcataggcac cgtcagacag gatagagcag tgcatagata gtcatagcct tggacctgcc    60
tagaactacc                                                           70

<210> SEQ ID NO 79
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 79
gtccaaggct atgactatct atgcact                                 27

<210> SEQ ID NO 80
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 80
gctctatcct gtctgctgaa gtagtgattg agcgtgatga atgtcactac ttcaactcgc    60
attcatcacg ctcaatc                                                   77

<210> SEQ ID NO 81
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 81
gctctatcct gtctgctgaa gtagtgattg agcgt                       35

<210> SEQ ID NO 82
<211> LENGTH: 42
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 82
gatgaatgtc actacttcaa ctcgcattca tcacgctcaa tc                42

<210> SEQ ID NO 83
<211> LENGTH: 27
<212> TYPE: DNA
<213> ORGANISM: Artificial Sequence

```
<220> FEATURE:
<223> OTHER INFORMATION: Synthetic oligonucleotide

<400> SEQUENCE: 83
acggtgccta tgacatggta ctcagct                                              27

<210> SEQ ID NO 84
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 84
gctcgtatct ggtcgctgaa gtagtgattg agcgtgatga atgtcactac ttcaactcgc          60
attcatcacg ctcaatc                                                        77

<210> SEQ ID NO 85
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 85
gctcgtatct ggtcgctgaa gtagtgattg agcgt                                    35

<210> SEQ ID NO 86
<211> LENGTH: 42
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 86
gatgaatgtc actacttcaa ctcgcattca tcacgctcaa tc                             42

<210> SEQ ID NO 87
<211> LENGTH: 128
<212> TYPE: DNA
<213> ORGANISM: Artificial Sequence
<220> FEATURE:
<223> OTHER INFORMATION: Synthetic oligonucleotide

<400> SEQUENCE: 87
cgtaagtcgc agagtatgcc attgcctcat cagcgtagca tcgagatcta agttagtaac          60
tctggcagcc tggtagagcg agcctatcgt cctgatgtac gaccagatac gagcagctga         120
gtaccatg                                                                 128

<210> SEQ ID NO 88
<211> LENGTH: 114
<212> TYPE: DNA
<213> ORGANISM: Artificial Sequence
<220> FEATURE:
<223> OTHER INFORMATION: Synthetic oligonucleotide

<400> SEQUENCE: 88
cgtaagtcgc agagtatgcc attgcctcat cagcgtagca tcgagatcta agttagtaac          60
tctggcagcc tggtagagcg agcctatcgt cctgatgtac gaccagatac gagc              114
```

<210> SEQ ID NO 89
<211> LENGTH: 27
<212> TYPE: DNA
<213> ORGANISM: Artificial Sequence
<220> FEATURE:
<221> NAME/KEY: modified_base
<222> LOCATION: 1
<223> OTHER INFORMATION: 5' carboxytetramethylrhodamine (NHS Ester)
<220> FEATURE:
<223> OTHER INFORMATION: Synthetic oligonucleotide

<400> SEQUENCE: 89
tacatcagga cgataggctc gctctac                                             27

<210> SEQ ID NO 90
<211> LENGTH: 27
<212> TYPE: DNA
<213> ORGANISM: Artificial Sequence
<220> FEATURE:
<221> NAME/KEY: modified_base
<222> LOCATION: 1
<223> OTHER INFORMATION: 5' 6-carboxy-4', 5'dichloro-2',
      7'-dimethoxyfluorescein (NHS Ester)
<220> FEATURE:
<223> OTHER INFORMATION: Synthetic oligonucleotide

<400> SEQUENCE: 90
tacatcagga cgataggctc gctctac                                             27

<210> SEQ ID NO 91
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 91
caggctgcca gagttctgaa gtagtgattg agcgtgatga atgtcatact tcaactcgca         60
ttcatcacgc tcaatc                                                         76

<210> SEQ ID NO 92
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 92
caggctgcca gagttctgaa gtagtgattg agcgt                                    35

<210> SEQ ID NO 93
<211> LENGTH: 42
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 93
gatgaatgtc actacttcaa ctcgcattca tcacgctcaa tc                            42

<210> SEQ ID NO 94
<211> LENGTH: 27
<212> TYPE: DNA

```
<213> ORGANISM: Artificial Sequence
<220> FEATURE:
<221> NAME/KEY: modified_base
<222> LOCATION: 1
<223> OTHER INFORMATION: 5' carboxytetramethylrhodamine (NHS Ester)
<220> FEATURE:
<223> OTHER INFORMATION: Synthetic oligonucleotide

<400> SEQUENCE: 94
actaacttag atctcgatgc tacgctg                                          27

<210> SEQ ID NO 95
<211> LENGTH: 27
<212> TYPE: DNA
<213> ORGANISM: Artificial Sequence
<220> FEATURE:
<221> NAME/KEY: modified_base
<222> LOCATION: 1
<223> OTHER INFORMATION: 5' 6-carboxy-4', 5'dichloro-2',
      7'-dimethoxyfluorescein (NHS Ester)
<220> FEATURE:
<223> OTHER INFORMATION: Synthetic oligonucleotide

<400> SEQUENCE: 95
actaacttag atctcgatgc tacgctg                                          27

<210> SEQ ID NO 96
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 96
atgaggcaat ggcattagaa gtagtgattg agcgtgatga atgtcactac ttcaactcgc      60
attcatcacg ctcaatc                                                    77

<210> SEQ ID NO 97
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 97
atgaggcaat ggcattagaa gtagtgattg agcgt                                 35

<210> SEQ ID NO 98
<211> LENGTH: 42
<212> TYPE: DNA
<213> ORGANISM: Artificial Sequence
<220> FEATURE:
<221> NAME/KEY: modified_base
<222> LOCATION: 1
<223> OTHER INFORMATION: 5' phosphorylation
<220> FEATURE:
<223> OTHER INFORMATION: Synthetic oligonucleotide

<400> SEQUENCE: 98
gatgaatgtc actacttcaa ctcgcattca tcacgctcaa tc                         42

<210> SEQ ID NO 99
<211> LENGTH: 15
<212> TYPE: DNA
<213> ORGANISM: Artificial Sequence
<220> FEATURE:
<221> NAME/KEY: modified_base
<222> LOCATION: 1
```

<223> OTHER INFORMATION: 5' phosphorylation
<220> FEATURE:
<223> OTHER INFORMATION: Synthetic oligonucleotide

<400> SEQUENCE: 99
actctgcgac ttacg                                                          15

<210> SEQ ID NO 100
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 100
ttgcctcgta tcctaaccga acggactcca ggacattcat cacgctcaat cactactt          58

<210> SEQ ID NO 101
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 101
ttgcctcgta tcctaaccga acggactcc                                           29

<210> SEQ ID NO 102
<211> LENGTH: 29
<212> TYPE: DNA
<213> ORGANISM: Artificial Sequence
<220> FEATURE:
<221> NAME/KEY: modified_base
<222> LOCATION: 29
<223> OTHER INFORMATION: 3' black hole quencher-1
<220> FEATURE:
<223> OTHER INFORMATION: Synthetic oligonucleotide

<400> SEQUENCE: 102
aggacattca tcacgctcaa tcactactt                                           29

<210> SEQ ID NO 103
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 103
cgtgatgaat gtcctggagt ccgttcggtt                                          30

<210> SEQ ID NO 104
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 104
gtccgttcgg ttaggatacg aggcaatcca ggacattcat cacgctcaat cactactt          58

<210> SEQ ID NO 105
<211> LENGTH: 29
<212> TYPE: DNA
<213> ORGANISM: Artificial Sequence
<220> FEATURE:
<221> NAME/KEY: modified_base
<222> LOCATION: 29
<223> OTHER INFORMATION: 3' black hole quencher-1
<220> FEATURE:
<223> OTHER INFORMATION: Synthetic oligonucleotide

<400> SEQUENCE: 105
gtccgttcgg ttaggatacg aggcaatcc                                    29

<210> SEQ ID NO 106
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 106
aggacattca tcacgctcaa tcactactt                                    29

<210> SEQ ID NO 107
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 107
cgtgatgaat gtcctggatt gcctcgtatc                                   30

<210> SEQ ID NO 108
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 108
tacttcatcg atcgctccaa atcaca                                       26

<210> SEQ ID NO 109
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 109
atagtctcca caacaatcga tcgctccaaa tcacaaggtc aacaaacagc acatgtgatt   60
tggagcgatc gatgaagta                                               79

<210> SEQ ID NO 110
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 110
tcttctctaa cccaaacaag gtcaacaaac agcacaatct cactacttca tcagtgctgt   60
ttgttgacct tgtgatttg                                               79

<210> SEQ ID NO 111
<211> LENGTH: 79
<212> TYPE: DNA
<213> ORGANISM: Artificial Sequence
<220> FEATURE:

```
<223> OTHER INFORMATION: Synthetic oligonucleotide

<400> SEQUENCE: 111
ttctatactc cttcacacaa tctcactact tcatcgatcg ctccaaatca caagatgaag    60
tagtgagatt gtgctgttt                                                 79

<210> SEQ ID NO 112
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 112
gagcgatcga ttgttgtgga gactatagaa atatagtctc cacaacaatc agtactacaa    60
caaacaaaca ccgagaaga                                                 79

<210> SEQ ID NO 113
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 113
gttgaccttg tttggttag agaagaacta atcttctct aacccaaaca gtataccatc      60
agaaacgata tctatagaa                                                 79

<210> SEQ ID NO 114
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 114
gtgagattgt gtgaaggagt atagaaatgg gcttctatac tccttcacac attaattcgc    60
gaccaaacca acagactat                                                 79

<210> SEQ ID NO 115
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 115
atcagtacta caacaaacaa acaccgagaa gatttagatc ttctcggtgt tgtttgttg     60 tagtactgat tgttgtgg                                                  78

<210> SEQ ID NO 116
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 116
acagtatacc atcagaaacg atatctatag aagcccaatt ctatagatat cgtttctgat    60
ggtatactgt ttgggtta                                                  78
```

```
<210> SEQ ID NO 117
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 117
cacattaatt cgcgaccaaa ccaacagact atatttcaat agtctgttgg tttggtcgcg      60
aattaatgtg tgaaggag                                                   78
```